(12) United States Patent
Donohue et al.

(10) Patent No.: US 11,008,577 B1
(45) Date of Patent: May 18, 2021

(54) OLEAGINOUS MICROORGANISMS AND USES OF SAME

(71) Applicant: WISCONSIN ALUMNI RESEARCH FOUNDATION, Madison, WI (US)

(72) Inventors: Timothy James Donohue, Middleton, WI (US); Kimberly Christensen Lemmer, Madison, WI (US); Daniel Noguera, Madison, WI (US); Weiping Zhang, Beaverton, OR (US)

(73) Assignee: WISCONSIN ALUMNI RESEARCH FOUNDATION, Madison, WI (US)

( * ) Notice: Subject to any disclaimer, the term of this patent is extended or adjusted under 35 U.S.C. 154(b) by 350 days.

(21) Appl. No.: 15/901,676

(22) Filed: Feb. 21, 2018

Related U.S. Application Data

(60) Provisional application No. 62/461,949, filed on Feb. 22, 2017.

(51) Int. Cl.
*C12N 1/20* (2006.01)
*C12P 7/64* (2006.01)
*C12N 15/74* (2006.01)

(52) U.S. Cl.
CPC .............. *C12N 15/74* (2013.01); *C12N 1/20* (2013.01); *C12P 7/6409* (2013.01)

(58) Field of Classification Search
None
See application file for complete search history.

(56) References Cited

PUBLICATIONS

Drepper et al., "Cross-talk towards the response regulator NtrC controlling nitrogen metabolism in Rhodobacter capsulatus", FEMS Microbiology Letters, vol. 258, pp. 250-256, 2006 (Year: 2006).*

Bonato et al., "The NtrY-NtrX two-component system is involved in controlling nitrate assimilation in Herbaspirillum seropedicae strain SmR1", The FEBS Journal, vol. 283, pp. 3919-3930, 2016 (Year: 2016).*

Agler, M.T., B.A. Wrenn, S.H. Zinder and L.T. Angenent, (2011) Waste to bioproduct conversion with undefined mixed cultures: the carboxylate platform. Trends in Biotechnology 29(2): 70-78.

Atack JM, Srikhanta YN, Djoko KY, Welch JP, Hasri NH, Steichen CT, Vanden Hoven RN, Grimmond SM, Othman DS, Kappler U, Apicella MA, Jennings MP, Edwards JL, McEwan AG. Characterization of an ntrX mutant of Neisseria gonorrhoeae reveals a response regulator that controls expression of respiratory enzymes in oxidase-positive proteobacteria. J Bacteriol. Jun. 2013;195(11):2632-41.

Austin, S., W.S. Kontur, A. Ulbrich, J.Z. Oshlag, W. Zhang, A. Higbee, Y. Zhang, J.J. Coon, D.B. Hodge, T.J. Donohue and D.R. Noguera, (2015) Metabolism of Multiple Aromatic Compounds in Corn Stover Hydrolysate by Rhodopseudomonas palustris. Environ Sci Technol 49: 8914-8922.

Bailey TL, Boden M, Buske FA, Frith M, Grant CE, Clementi L, Ren J, Li WW, Noble WS. 2009. MEME SUITE: tools for motif discovery and searching. Nucleic Acids Res 37:W202-W208.

(Continued)

*Primary Examiner* — Richard C Ekstrom
(74) *Attorney, Agent, or Firm* — Daniel A. Blasiole; DeWitt LLP

(57) ABSTRACT

Recombinant microorganisms including one or more modifications that enhance lipid production and uses of same for producing lipid. The modifications alter cell surface functions, envelope functions, and other functions. The modifications are capable of converting non-oleaginous microorganisms into oleaginous microorganisms. The lipids produced by some of the recombinant microorganisms are excreted.

16 Claims, 14 Drawing Sheets
(1 of 14 Drawing Sheet(s) Filed in Color)
Specification includes a Sequence Listing.

(56) References Cited

PUBLICATIONS

Bateman, A. and M. Bycroft, (2000) The structure of a LysM domain from E. coli membrane-bound lytic murein transglycosylase D (MltD). J Mol Biol 299: 1113-1119.

Benjamini Y, Hochberg Y. 1995. Controlling the false discovery rate—a practical and powerful approach to multiple testing. J R Stat Soc B Methodol 57:289-300.

Blatti, J.L., J. Michaud and M.D. Burkart, (2013) Engineering fatty acid biosynthesis in microalgae for sustainable biodiesel. Current opinion in chemical biology 17: 496-505.

Bolstad BM, Irizarry RA, Astrand M, Speed TP. 2003. A comparison of normalization methods for high density oligonucleotide array data based on variance and bias. Bioinformatics 19:185-193.

Carrica, M.d.C., I. Fernandez, M.A. Marti, G. Paris and F.A. Goldbaum, (2012) The NtrY/X two-component system of Brucella spp. acts as a redox sensor and regulates the expression of nitrogen respiration enzymes. Mol Microbiol 85: 39-50.

Carrica, M.d.C., I. Fernandez, R. Sieira, G. Paris and F.A. Goldbaum, (2013) The two-component systems PrrBA and NtrYX coordinately regulate the adaptation of Brucella abortus to an oxygen-limited environment. Mol Microbiol 88: 222-233.

Choi, Y.J. and S.Y. Lee, (2013) Microbial production of short-chain alkanes. Nature 502: 571-574.

Chory, J., T.J. Donohue, A.R. Varga, L.A. Staehelin and S. Kaplan, (1984) Induction of the photosynthetic membranes of Rhodopseudomonas sphaeroides: biochemical and morphological studies. J Bacteriol 159: 540-554.

Choudhary, V. and R. Schneiter, (2012) Pathogen-Related Yeast (PRY) proteins and members of the CAP superfamily are secreted sterol-binding proteins. Proc Natl Acad Sci U S A 109: 16882-16887.

Dangel AW, Tabita FR. 2009. Protein-protein interactions between CbbR and RegA (PrrA), transcriptional regulators of the cbb operons of Rhodobacter sphaeroides. Mol Microbiol71:717-729.

D'Espaux, L., D. Mendez-Perez, R. Li and J.D. Keasling, (2015) Synthetic biology for microbial production of lipid-based biofuels. Current opinion in chemical biology 29: 58-65.

Dufour YS, Landick R, Donohue TJ. 2008. Organization and evolution of the biological response to singlet oxygen stress. J Mol Biol 383:713-730.

Feng, X., J. Lian and H. Zhao, (2015) Metabolic engineering of Saccharomyces cerevisiae to improve 1-hexadecanol production. Metabolic Engineering 27: 10-19.

Gibbs, G.M., K. Roelants and M.K. O'Bryan, (2008) The CAP superfamily: cysteine-rich secretory proteins, antigen 5, and pathogenesis-related 1 proteins—roles in reproduction, cancer, and immune defense. Endocr Rev 29: 865-897.

Goff, M., J. Nikodinovic-Runic and K.E. O'Connor, (2009) Characterization of temperature-sensitive and lipopolysaccharide over-producing transposon mutants of Pseudomonas putida CA-3 affected in PHA accumulation. FEMS microbiology letters 292: 297-305.

Goh, E.B., E.E. Baidoo, J.D. Keasling and H.R. Beller, (2012) Engineering of bacterial methyl ketone synthesis for biofuels. Appl Environ Microbiol 78: 70-80.

Gregor, J., T. Zeller, A. Balzer, K. Haberzettl and G. Klug, (2007) Bacterial regulatory networks include direct contact of response regulator proteins: interaction of RegA and NtrX in Rhodobacter capsulatus. J Mol Microbiol Biotechnol 13: 126-139.

Imam S, Noguera DR, Donohue TJ. 2014. Global analysis of photosynthesis transcriptional regulatory networks. PLoS Genet 10:e1004837.

Imam, S., S. Yilmaz, U. Sohmen, A.S. Gorzalski, J.L. Reed, D.R. Noguera and T.J. Donohue, (2011) iRsp1095: a genome-scale reconstruction of the Rhodobacter sphaeroides metabolic network. BMC systems biology 5: 116.

Ishida, M.L., M.C. Assumpcao, H.B. Machado, E.M. Benelli, E.M. Souza and F.O. Pedrosa, (2002) Identification and characterization of the two-component NtrY/NtrX regulatory system in Azospirillum brasilense. Braz J Med Biol Res 35: 651-661.

Janssen, H.J. and A. Steinbuchel, (2014) Fatty acid synthesis in Escherichia coli and its applications towards the production of fatty acid based biofuels. Biotechnology for biofuels 7: 7.

Javidpour P, Pereira JH, Goh EB, McAndrew RP, Ma SM, Friedland GD, Keasling JD, Chhabra SR, Adams PD, Beller HR. Biochemical and structural studies of NADH-dependent FabG used to increase the bacterial production of fatty acids under anaerobic conditions. Appl Environ Microbiol. Jan. 2014;80(2):497-505.

Kalscheuer, R., T. Stolting and A. Steinbuchel, (2006) Microdiesel: Escherichia coli engineered for fuel production. Microbiology 152: 2529-2536.

Kaltashov, I.A., V. Doroshenko, R.J. Cotter, K. Takayama and N. Qureshi, (1997) Confirmation of the Structure of Lipid A Derived from the Lipopolysaccharide of Rhodobacter sphaeroides by a Combination of MALDI, LSIMS, and Tandem Mass Spectrometry. Analytical Chemistry 69: 2317-2322.

Kien, N.B., I.S. Kong, M.G. Lee and J.K. Kim, (2010) Coenzyme Q10 production in a 150-l reactor by a mutant strain of Rhodobacter sphaeroides. J Ind Microbiol Biotechnol 37: 521-529.

Kiley, P.J. and S. Kaplan, (1988) Molecular genetics of photosynthetic membrane biosynthesis in Rhodobacter sphaeroides. Microbiol Rev 52: 50-69.

Kontur WS, Schackwitz WS, Ivanova N, Martin J, Labutti K, Deshpande S, Tice HN, Pennacchio C, Sodergren E, Weinstock GM, Noguera DR, Donohue TJ. Revised sequence and annotation of the Rhodobacter sphaeroides 2.4.1 genome. J Bacteriol. Dec. 2012;194(24):7016-7.

Kosa, M. and A.J. Ragauskas, (2011) Lipids from heterotrophic microbes: advances in metabolism research. Trends Biotechnol 29: 53-61.

Kuan PF, Chung D, Pan G, Thomson JA, Stewart R, Keleş S. 2011. A statistical framework for the analysis of ChIP-seq data. J Am Stat Assoc 106:891-903.

Kulp, A. and M.J. Kuehn, (2010) Biological functions and biogenesis of secreted bacterial outer membrane vesicles. Annu Rev Microbiol 64: 163-184.

Kumar, P.; Barrett, D. M.; Delwiche, M. J.; Stroeve, P., Methods for Pretreatment of lignocellulosic Biomass for Efficient Hydrolysis and Biofuel Production. Industrial & Engineering Chemistry Research 2009, 48, (8), 3713-3729.

Larsen, R.A., M.M. Wilson, A.M. Guss and W.W. Metcalf, (2002) Genetic analysis of pigment biosynthesis in Xanthobacter autotrophicus Py2 using a new, highly efficient transposon mutagenesis system that is functional in a wide variety of bacteria. Arch Microbiol 178: 193-201.

Lau, M.W., C. Gunawan and B.E. Dale, (2009) The impacts of pretreatment on the fermentability of pretreated lignocellulosic biomass: a comparative evaluation between ammonia fiber expansion and dilute acid pretreatment. Biotechnology for biofuels 2: 30-30.

Ledesma-Amaro, R., R. Dulermo, X. Niehus and J.M. Nicaud, (2016) Combining metabolic engineering and process optimization to improve production and secretion of fatty acids. Metabolic engineering 38: 38-46.

Lemke, R.A., A.C. Peterson, E.C. Ziegelhoffer, M.S. Westphall, H. Tjellstrom, J.J. Coon and T.J. Donohue, (2014) Synthesis and scavenging role of furan fatty acids. Proc Natl Acad Sci U S A 111: E3450-3457.

Lemmer, K.C., A.C. Dohnalkova, D.R. Noguera and T.J. Donohue, (2015) Oxygen-dependent regulation of bacterial lipid production. J Bacteriol 197: 1649-1658.

Lennen, R.M., D.J. Braden, R.A. West, J.A. Dumesic and B.F. Pfleger, (2010) A process for microbial hydrocarbon synthesis: Overproduction of fatty acids in Escherichia coli and catalytic conversion to alkanes. Biotechnol Bioeng 106: 193-202.

Lennen, R.M. and B.F. Pfleger, (2012) Engineering Escherichia coli to synthesize free fatty acids. Trends Biotechnol 30: 659-667.

Lennon, C.W., K.C. Lemmer, J.L. Irons, M.I. Sellman, T.J. Donohue, R.L. Gourse and W. Ross, (2014) A Rhodobacter sphaeroides

(56) References Cited

PUBLICATIONS protein mechanistically similar to *Escherichia coli* DksA regulates photosynthetic growth. mBio 5: e01105-01114.

Levering, J., J. Broddrick and K. Zengler, (2015) Engineering of oleaginous organisms for lipid production. Curr Opin Biotechnol 36: 32-39.

Li R, Yu C, Li Y, Lam TW, Yiu SM, Kristiansen K, Wang J. 2009. SOAP2: an improved ultrafast tool for short read alignment. Bioinformatics 25:1966-1967.

Liang, M.H. and J.G. Jiang, (2013) Advancing oleaginous microorganisms to produce lipid via metabolic engineering technology. Progress in lipid research 52: 395-408.

Lyu, Z.X. and X.S. Zhao, (2015) Periplasmic quality control in biogenesis of outer membrane proteins. Biochem Soc Trans 43: 133-138.

Metcalf, W.W., W. Jiang, L.L. Daniels, S.K. Kim, A. Haldimann and B.L. Wanner, (1996) Conditionally replicative and conjugative plasmids carrying lacZ alpha for cloning, mutagenesis, and allele replacement in bacteria. Plasmid 35: 1-13.

Miller, V.L. and J.J. Mekalanos, (1988) A novel suicide vector and its use in construction of insertion mutations: osmoregulation of outer membrane proteins and virulence determinants in Vibrio cholerae requires toxR. J Bacteriol 170: 2575-2583.

Newman, J.D., M.J. Falkowski, B.A. Schilke, L.C. Anthony and T.J. Donohue, (1999) The Rhodobacter sphaeroides ECF sigma factor, sigma(E), and the target promoters cycA P3 and rpoE P1. J Mol Biol 294: 307-320.

Pawlowski, K., U. Klosse and F.J. de Bruijn, (1991) Characterization of a novel Azorhizobium caulinodans OR971 two-component regulatory system, NtrY/NtrX, involved in nitrogen fixation and metabolism. Mol Gen Genet 231: 124-138.

Rouser, G., S. Fkeischer and A. Yamamoto, (1970) Two dimensional then layer chromatographic separation of polar lipids and determination of phospholipids by phosphorus analysis of spots. Lipids 5: 494-496.

Saldanha, A.J., (2004) Java Treeview—extensible visualization of microarray data. Bioinformatics 203246-3248.

Sangkharak, K. and P. Prasertsan, (2007) Optimization of polyhydroxybutyrate production from a wild type and two mutant strains of Rhodobacter sphaeroides using statistical method. Journal of biotechnology 132: 331-340.

Sawangkeaw, R. and S. Ngamprasertsith, (2013) A review of lipid-based biomasses as feedstocks for biofuels production. Renewable and Sustainable Energy Reviews 25: 97-108.

Schafer, A., A. Tauch, W. Jager, J. Kalinowski, G. Thierbach and A. Puhler, (1994) Small mobilizable multi-purpose cloning vectors derived from the *Escherichia coli* plasmids pK18 and pK19: selection of defined deletions in the chromosome of Corynebacterium glutamicum. Gene 145: 69-73.

Schirmer, A., M.A. Rude, X. Li, E. Popova and S.B. del Cardayre, (2010) Microbial biosynthesis of alkanes. Science 329: 559-562.

Schwalbach, M.S., D.H. Keating, M. Tremaine, W.D. Marner, Y. Zhang, W. Bothfeld, A. Higbee, J.A. Grass, C. Cotten, J.L. Reed, L. da Costa Sousa, M. Jin, V. Balan, J. Ellinger, B. Dale, P.J. Kiley and R. Landick, (2012) Complex physiology and compound stress responses during fermentation of alkali-pretreated corn stover hydrolysate by an *Escherichia coli* ethanologen. Appl Environ Microbiol 78: 3442-3457.

Schwechheimer, C. and M.J. Kuehn, (2015) Outer-membrane vesicles from Gram-negative bacteria: biogenesis and functions. Nat Rev Microbiol 13: 605-619.

Seo, D. Jin, B.H. Chung, Y.D. Hwang and Y.H. Park, (1992) Glucose-limited fed-batch culture of *Escherichia coli* for production of recombinant human interleukin-2 with the DO-stat method. Journal of Fermentation and Bioengineering 74: 196-198.

Shiloach, J. and R. Fass, (2005) Growing *E. coli* to high cell density—a historical perspective on method development. Biotechnology advances 23: 345-357.

Simon, R., U. Priefer and A. Puhler, (1983) A broad host range mobilization system for in vivo genetic engineering: transposon mutagenesis in gram negative bacteria. Biotechnology 1: 748-791.

Sistrom, W.R., (1960) A requirement for sodium in the growth of Rhodopseudomonas spheroides. J Gen Microbiol 22: 778-785.

Song, C., G. Sundqvist, E. Malm, I. de Bruijn, A. Kumar, J. van de Mortel, V. Bulone and J.M. Raaijmakers, (2015) Lipopeptide biosynthesis in Pseudomonas fluorescens is regulated by the protease complex ClpAP. BMC Microbiol 15: 29.

Sperisen, P., C.D. Schmid, P. Bucher and O. Zilian, (2005) Stealth proteins: in silico identification of a novel protein family rendering bacterial pathogens invisible to host immune defense. PLoS Comput Biol 1: e63.

Steen, E.J., Y. Kang, G. Bokinsky, Z. Hu, A. Schirmer, A. McClure, S.B. Del Cardayre and J.D. Keasling, (2010) Microbial production of fatty-acid-derived fuels and chemicals from plant biomass. Nature 463: 559-562.

Tavano, C.L. and T.J. Donohue, (2006) Development of the bacterial photosynthetic apparatus. Curr Opin Microbiol 9: 625-631.

Tavano CL, Podevels AM, Donohue TJ. 2005. Identification of genes required for recycling reducing power during photosynthetic growth. J Bacteriol 187:5249-5258.

Torella JP, Ford TJ, Kim SN, Chen AM, Way JC, Silver PA. Tailored fatty acid synthesis via dynamic control of fatty acid elongation. Proc Natl Acad Sci U S A. Jul. 9, 2013;110(28):11290-5.

Vaara, M., (1993) Outer membrane permeability barrier to azithromycin, clarithromycin, and roxithromycin in gram-negative enteric bacteria. Antimicrobial agents and chemotherapy 37: 354-356.

Van Galen, J., B.W. Van Balkom, R.L. Serrano, D. Kaloyanova, R. Eerland, E. Stuven and J.B. Helms, (2010) Binding of GAPR-1 to negatively charged phospholipid membranes: unusual binding characteristics to phosphatidylinositol. Mol Membr Biol 27: 81-91.

Van Niel, C.B., (1944) The culture, general physiology, morphology, and classification of the non-sulfur purple and brown bacteria. Bacteriol Rev 8: 1-118.

Waltermann, M., A. Hinz, H. Robenek, D. Troyer, R. Reichelt, U. Malkus, H.J. Galla, R. Kalscheuer, T. Stoveken, P. von Landenberg and A. Steinbuchel, (2005) Mechanism of lipid-body formation in prokaryotes: how bacteria fatten up. Mol Microbiol 55: 750-763.

Wang, D., H. Xue, Y. Wang, R. Yin, F. Xie and L. Luo, (2013) The Sinorhizobium meliloti ntrX gene is involved in succinoglycan production, motility, and symbiotic nodulation on alfalfa. Appl Environ Microbiol 79: 7150-7159.

Yen, H.W., C.Y. Feng and J.L. Kang, (2010) Cultivation of Rhodobacter sphaeroides in the stirred bioreactor with different feeding strategies for CoQ(10) production. Appl Biochem Biotechnol 160: 1441-1449.

Yilmaz, L., W. Kontur, A. Sanders, U. Sohmen, T. Donohue and D. Noguera, (2010) Electron Partitioning During Light- and Nutrient-Powered Hydrogen Production by Rhodobacter sphaeroides. BioEnergy Research 3:55-66.

Zeiger, L. and H. Grammel, (2010) Model-based high cell density cultivation of Rhodospirillum rubrum under respiratory dark conditions. Biotechnology and Bioengineering 105: 729-739.

Zhang, L., J. Song, G. Cavigiolio, B.Y. Ishida, S. Zhang, J.P. Kane, K.H. Weisgraber, M.N. Oda, K.A. Rye, H.J. Pownall and G. Ren, (2011) Morphology and structure of lipoproteins revealed by an optimized negative-staining protocol of electron microscopy. J Lipid Res 52: 175-184.

Zhang, Y.M. and C.O. Rock, (2010) A rainbow coalition of lipid transcriptional regulators. Molecular Microbiology 78: 5-8.

\* cited by examiner

OLEAGINOUS MICROORGANISMS AND USES OF SAME

STATEMENT REGARDING FEDERALLY SPONSORED RESEARCH

This invention was made with government support under DE-FC02-07ER64494 awarded by the U.S. Department of Energy. The government has certain rights in the invention.

FIELD OF THE INVENTION

The invention is directed to modified microorganisms configured for enhanced production of lipid and lipid-associated bioproducts and methods of using same.

BACKGROUND

Lipids derived from bacteria, yeast, and microalgae offer a promising source of renewable fuels and chemicals. These sources can offset petroleum usage and reduce $CO_2$ emissions (Liang et al. 2013, Sawangkeaw et al. 2013). A major challenge to producing microbial replacements for oils that are cost-competitive with petroleum products is increasing the yield of these lipids, which are energetically expensive for cells to produce and thus tightly regulated (Zhang et al. 2010, Levering et al. 2015). One approach for microbial oil production is the use of oleaginous microorganisms, defined as those accumulating over 20% of their dry cell weight (DCW) as lipid (Liang et al. 2013). However, even though very high oil content (up to 90%) can be observed under some experimental conditions, lipid content is usually not high under nutrient replete conditions (Levering et al. 2015, Kosa et al. 2011). Genetic and process engineering strategies are being investigated to further increase the biomass lipid content and yield of oleaginous microorganisms (Liang et al. 2013, Kosa et al. 2011). However, although biosynthetic pathways for fatty acids and lipids are well understood in some microorganisms, identifying and bypassing the mechanisms regulating lipid accumulation in oleaginous strains remains a challenge (Blatti et al. 2013, Levering et al. 2015, Liang et al. 2013).

An alternative approach to increasing lipid production in microorganisms is transgenically engineering lipogenic pathways into non-oleaginous, but robust and genetically tractable hosts (d'Espaux et al. 2015). Many enzymes that convert fatty acids, or pathway intermediates, into products with desirable fuel properties have been investigated for their potential use in non-oleaginous microorganisms (Steen et al. 2010, Schirmer et al. 2010, Goh et al. 2012, Kalscheuer et al. 2006, Choi et al. 2013, Feng et al. 2015). However, achieving industrially relevant lipid production levels and yields can require genetic and metabolic engineering steps that are not feasible in many hosts (d'Espaux et al. 2015).

Mechanisms for increasing production of lipids and lipid-associated bioproducts in microorganisms, particularly in non-oleaginous microorganisms, are needed.

SUMMARY OF THE INVENTION

One aspect of the invention is directed to microorganisms with modifications that exhibit enhanced lipid production with respect to corresponding microorganisms that do not contain the modifications.

Some versions are directed to a recombinant microorganism. The recombinant microorganism comprises one or more modifications with respect to a corresponding microorganism not comprising the one or more modifications. The one or more modifications are selected from the group consisting of: a modification that reduces the activity of RSP2839 or a homolog thereof with respect to the corresponding microorganism; a modification that reduces the activity of RSP2840 or a homolog thereof with respect to the corresponding microorganism; a modification that reduces the activity of RSP3218 or a homolog thereof with respect to the corresponding microorganism; a modification that reduces the activity of RSP1056 or a homolog thereof with respect to the corresponding microorganism; a modification that reduces the activity of RSP1200 or a homolog thereof with respect to the corresponding microorganism; a modification that reduces the activity of RSP1422 or a homolog thereof with respect to the corresponding microorganism; a modification that reduces the activity of RSP0355 or a homolog thereof with respect to the corresponding microorganism; a modification that reduces the activity of RSP2545 or a homolog thereof with respect to the corresponding microorganism; a modification that reduces the activity of RSP2544 or a homolog thereof with respect to the corresponding microorganism; a modification that reduces the activity of RSP2543 or a homolog thereof with respect to the corresponding microorganism; a modification that reduces the activity of RSP2745 or a homolog thereof with respect to the corresponding microorganism; a modification that reduces the activity of RSP2293 or a homolog thereof with respect to the corresponding microorganism; a modification that reduces the activity of RSP2839 or a homolog thereof with respect to the corresponding microorganism; a modification that reduces the activity of RSP0334 or a homolog thereof with respect to the corresponding microorganism; a modification that reduces the activity of RSP0333 or a homolog thereof with respect to the corresponding microorganism; a modification that reduces the activity of RSP0332 or a homolog thereof with respect to the corresponding microorganism; a modification that reduces the activity of RSP0331 or a homolog thereof with respect to the corresponding microorganism; a modification that reduces the activity of RSP0330 or a homolog thereof with respect to the corresponding microorganism; a modification that reduces the activity of RSP0335 or a homolog thereof with respect to the corresponding microorganism; a modification that reduces the activity of RSP3540 or a homolog thereof with respect to the corresponding microorganism; a modification that reduces the activity of RSP3539 or a homolog thereof with respect to the corresponding microorganism; a modification that reduces the activity of RSP3538 or a homolog thereof with respect to the corresponding microorganism; a modification that reduces the activity of RSP2095 or a homolog thereof with respect to the corresponding microorganism; a modification that reduces the activity of RSP6038 or a homolog thereof with respect to the corresponding microorganism; a modification that reduces the activity of RSP2097 or a homolog thereof with respect to the corresponding microorganism; a modification that reduces the activity of RSP2098 or a homolog thereof with respect to the corresponding microorganism; a modification that reduces the activity of RSP2099 or a homolog thereof with respect to the corresponding microorganism; a modification that reduces the activity of RSP2100 or a homolog thereof with respect to the corresponding microorganism; a modification that reduces the activity of RSP2101 or a homolog thereof with respect to the corresponding microorganism; a modification that reduces the activity of RSP2111 or a homolog thereof with respect to the corresponding microorganism; a modification that reduces the activity of RSP2112 or a homolog thereof with respect to the corresponding microorganism; a modification that reduces the activity of RSP2113 or a homolog thereof with respect to the corresponding microorganism; a modification that reduces the activity of RSP2916 or a homolog thereof with respect to the corresponding microorganism; and a modification that increases the activity of RSP1860 or a homolog thereof with respect to with respect to the corresponding microorganism. The microorganism may comprise two or more of the one or more modifications. The microorganism may comprise three or more of the one or more modifications. The one or more modifications can be combined in any combination.

In some versions, the homolog of each of RSP2839, RSP2840, RSP3218, RSP1056, RSP1200, RSP1422, RSP0355, RSP2545, RSP2544, RSP2543, RSP2745, RSP2293, RSP2839, RSP0334, RSP0333, RSP0332, RSP0331, RSP0330, RSP0335, RSP3540, RSP3539, RSP3538, RSP2095, RSP6038, RSP2097, RSP2098, RSP2099, RSP2100, RSP2101, RSP2111, RSP2112, RSP2113, RSP2916, and RSP1860 is an ortholog thereof, and the homolog of RSP1860 is an ortholog of RSP1860, comprises or encodes a sequence at least 95% identical to the amino acid sequence of RSP1860, or comprises or encodes a sequence at least 95% identical to the amino acid sequence of the ortholog of RSP1860.

In some versions, the recombinant microorganism exhibits enhanced lipid secretion with respect to the corresponding microorganism.

In some versions, the one or more modifications comprise a modification selected from the group consisting of the modification that reduces the activity of the RSP2839 or homolog thereof, the modification that reduces the activity of the RSP2840 or homolog thereof, and the modification that reduces the activity of the RSP1200 or homolog thereof.

In some versions, the one or more modifications comprise the modification that reduces the activity of the RSP2839 or homolog thereof and the modification that reduces the activity of the RSP2840 or homolog thereof.

In some versions, the homolog of RSP2839 is an NtrY and the homolog of RSP2840 is an NtrX.

In some versions, the recombinant microorganism further comprises one or more modifications that reduce the activity of one or more of an acyl-CoA dehydrogenase, an enoyl-CoA hydratase, a 3-hydroxyacyl-CoA dehydrogenase, and a 3-ketoacyl-CoA thiolase and/or increase the activity of one or more of an acyl-CoA synthetase, an acetyl-CoA carboxylase, an acetyl CoA:ACP transacylase, a malonyl CoA:ACP transacylase, a (3-ketoacyl-ACP synthase, a 3-ketoacyl-ACP reductase, a 3-hydroxyacyl-ACP dehydrase, an enoyl-ACP reductase, a glycerol-3-phosphate acyltransferase, and a 1-acylglycerol-3-phosphate acyltransferase with respect to the corresponding microorganism.

In some versions, the recombinant microorganism comprises one or more modifications that reduce the activity of RSP0382 or a homolog thereof with respect to the corresponding microorganism.

In some versions, the recombinant microorganism further comprises a recombinant gene configured to express a lipid-associated protein.

In some versions, the one or more modifications comprises one or more recombinant genes configured to express one or more of RSP2144 or a homolog thereof, RSP1091 or a homolog thereof, and RSP1090 or a homolog thereof; a modification that disrupts binding between ChrR and $\sigma^E$ or homologs thereof; a modification that increases expression of $\sigma^E$ or a homolog thereof; and/or a modification that eliminates from the microorganism a native ChrR or homolog thereof.

In some versions, the corresponding microorganism is a non-oleaginous microorganism.

In some versions, the recombinant microorganism is a bacterium, such as a microorganism from the genus *Rhodobacter*.

In some versions, the recombinant microorganism exhibits at least a 2-fold enhanced lipid production with respect to the corresponding microorganism when the recombinant microorganism and the corresponding organism are grown under aerobic conditions, is capable of producing at least 1 g/L lipid, and/or is capable of producing lipids in an amount of at least 20% (w/w) dry cell weight.

Another aspect of the invention is directed to methods for producing bioproducts such as lipids, proteins, or other classes of lipid-associated organic compounds.

Some methods comprise culturing a recombinant microorganism of the invention in a medium for a time sufficient to consume nutrients present in the medium and produce the bioproduct.

In some versions, the culturing comprises periodically adding fresh nutrients to the medium during the culturing.

In some versions, the culturing comprises culturing the microorganism at a first level of dissolved oxygen in the medium and adding nutrients to the medium upon detecting an increase in the dissolved oxygen from the first level to a second level in an amount sufficient to reduce the dissolved oxygen from the second level to a third level.

In some versions, the medium comprises biomass hydrolysate.

In some versions, the nutrients comprise at least one of glucose, xylose, succinate, lactate, and acetate.

In some versions, the bioproduct is selected from the group consisting of a lipid, a protein, and an organic compound.

In some versions, the organic compound comprises a quinone.

In some versions, the culturing is conducted at least until the microorganism produces 1 g/L lipid.

In some versions, the culturing is conducted at least until the microorganism produces lipids in an amount of at least 20% (w/w) dry cell weight.

In some versions, the culturing is conducted under aerobic conditions.

The objects and advantages of the invention will appear more fully from the following detailed description of the preferred embodiment of the invention made in conjunction with the accompanying drawings.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION OF THE INVENTION

Figure 1:
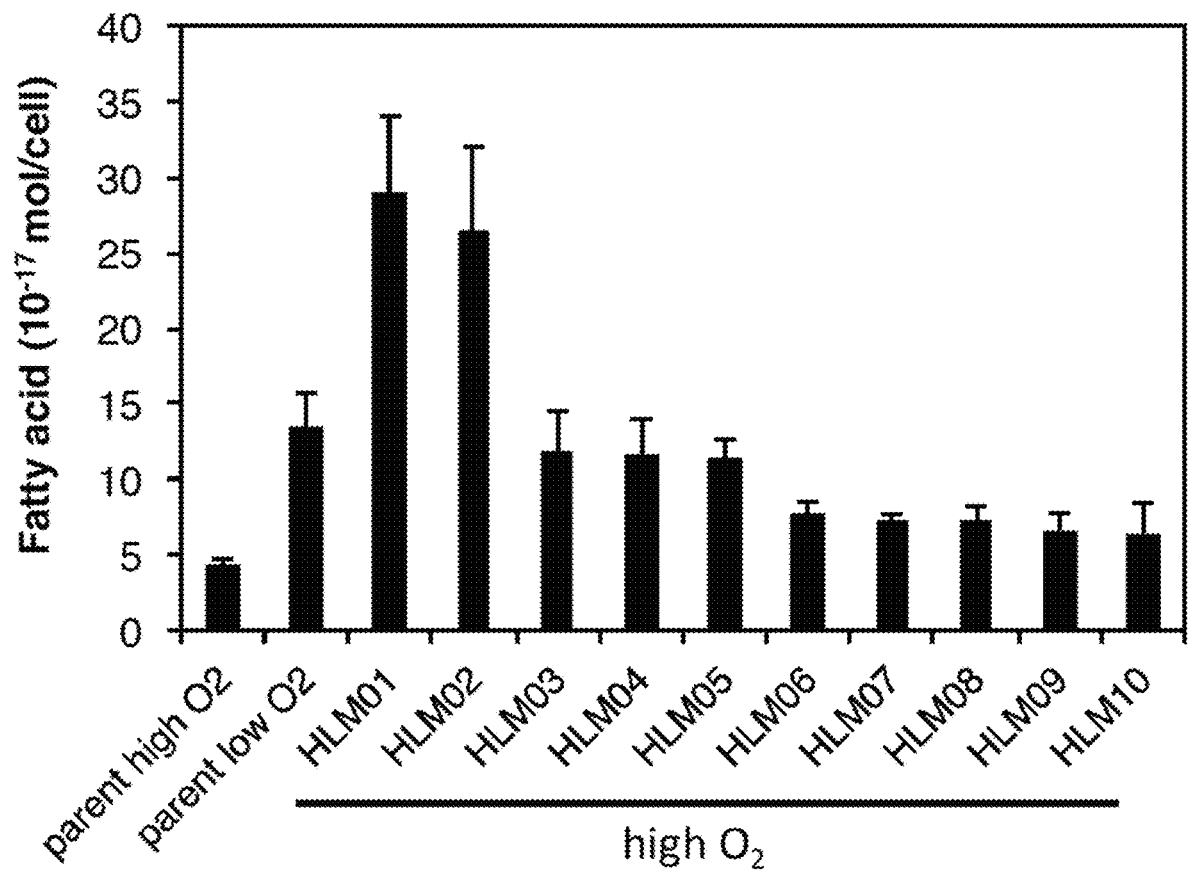
FIG. 1. Fatty acid content of parent *Rhodobacter sphaeroides* strain grown at high and low $O_2$ compared to high-lipid (HL) mutants grown at high $O_2$. Data shown represents the mean of three or more independent cultures ±standard deviation.

One aspect of the invention is directed to recombinant microorganisms configured for enhanced lipid production. The recombinant microorganisms of the invention comprise one or more modifications that reduce the activity of one or more genes or gene products, increase the activity of one or more genes or gene products, or reduce the activity of one or more genes or gene products and increase the activity of one or more genes or gene products. The recombinant microorganisms with the modifications exhibit enhanced lipid production with respect to corresponding microorganisms not comprising the modifications.

"Modifications that reduce the activity of one or more genes or gene products" refers to any modification to a microorganism that decreases or ablates expression of the gene and thus production of the gene product or decreases or ablates the functioning of the gene product. Decreasing or ablating the functioning of a gene product may comprise decreasing or ablating the specific activity of a gene product. Exemplary modifications that reduce the activity of one or more genes or gene products include genetic modifications. The genetic modifications include mutations to a gene that decrease or ablate expression of the gene in producing the gene product. Such mutations may include mutations to the coding sequence, the promoter, an enhancer, or any other part of the gene. The genetic mutations also include mutations to the coding sequence of a gene that decrease or ablate the functioning of a gene product expressed from the gene. The genetic mutations also include recombinant nucleotide sequences configured to express antisense RNAs or other molecules that decrease or ablate production of a gene product. The genetic modifications also include mutations to a first gene (such as a transcription factor or an inhibitor of a transcription factor) that affects the expression of a second gene. Other genetic modifications are described elsewhere herein.

"Modifications that increase the activity of one or more genes or gene products" refers to any modification to microorganism that increases expression of a gene in producing its gene product or increases the functioning of the gene product. "Increase" in this context refers to increasing beyond a positive baseline activity or increasing beyond null activity and thereby introducing a new activity. Exemplary modifications that increase the activity of one or more genes or gene products include genetic modifications. The genetic modifications include genetic modifications to a gene in a manner that increases expression of the gene in producing the gene product. Such modifications include operationally connecting the coding sequence to a stronger promoter or enhancer, etc., and/or introducing additional copies of the gene (whether the native gene or a recombinant version). The genetic modifications also include mutations to a first gene (such as a transcription factor or an inhibitor of a transcription factor) that affects the expression of a second gene. The genetic modifications also include one or more copies of a gene introduced into the microorganism. Other genetic modifications are described herein. Any modifications described herein can comprise recombinant genes.

"Corresponding microorganism" refers to a microorganism of the same species having the same or substantially same genetic and proteomic composition as a recombinant microorganism of the invention, with the exception of genetic and proteomic differences resulting from the modifications described herein for the recombinant microorganisms of the invention. In some versions, the corresponding microorganism is the native version of the recombinant microorganism of the invention, i.e., the unmodified microorganism as found in nature. The terms "microorganism" and "microbe" are used interchangeably herein.

Unless explicitly stated otherwise or indicated from the context, the designations beginning with the prefix "RSP" (e.g., "RSP2839," "RSP2840," "RSP3218," "RSP1056," etc.) and the term "homologs" are used herein to refer to both a gene coding sequence and products (such as proteins) encoded by the coding sequence. The gene coding sequences and products encoded thereby are collectively referred herein to "molecular elements." The sequences corresponding to the designations beginning with the prefix "RSP" are all publicly available and readily accessible. See Kontur 2012. An exemplary database in which the sequences can be found is accessible via the web at img.jgi.doe.gov. The following SEQ ID NOS correspond to the following molecular elements in which "NT" refers to the DNA coding sequence and "PRT" refers to the protein sequence:

SEQ ID NO:1: RSP0190—NT;
SEQ ID NO:2: RSP0190—PRT;
SEQ ID NO:3: RSP0191—NT;
SEQ ID NO:4: RSP0191—PRT;
SEQ ID NO:5: RSP0330—NT;
SEQ ID NO:6: RSP0330—PRT;
SEQ ID NO:7: RSP0331—NT;
SEQ ID NO:8: RSP0331—PRT;
SEQ ID NO:9: RSP0332—NT;
SEQ ID NO:10: RSP0332—PRT;
SEQ ID NO:11: RSP0333—NT;
SEQ ID NO:12: RSP0333—PRT;
SEQ ID NO:13: RSP0334—NT;
SEQ ID NO:14: RSP0334—PRT;
SEQ ID NO:15: RSP0335—NT;
SEQ ID NO:16: RSP0335—PRT;
SEQ ID NO:17: RSP0339—NT;
SEQ ID NO:18: RSP0339—PRT;
SEQ ID NO:19: RSP0355—NT;
SEQ ID NO:20: RSP0355—PRT;
SEQ ID NO:21: RSP0382—NT;
SEQ ID NO:22: RSP0382—PRT;
SEQ ID NO:23: RSP0579—NT;
SEQ ID NO:24: RSP0579—PRT;
SEQ ID NO:25: RSP0735—NT;
SEQ ID NO:26: RSP0735—PRT;
SEQ ID NO:27: RSP0747—NT;
SEQ ID NO:28: RSP0747—PRT;
SEQ ID NO:29: RSP0892—NT;
SEQ ID NO:30: RSP0892—PRT;
SEQ ID NO:31: RSP1004—NT;
SEQ ID NO:32: RSP1004—PRT;
SEQ ID NO:33: RSP1056—NT;
SEQ ID NO:34: RSP1056—PRT;
SEQ ID NO:35: RSP1090—NT;
SEQ ID NO:36: RSP1090—PRT;
SEQ ID NO:37: RSP1091—NT;
SEQ ID NO:38: RSP1091—PRT;
SEQ ID NO:39: RSP1200—NT;
SEQ ID NO:40: RSP1200—PRT;
SEQ ID NO:41: RSP1256—NT;
SEQ ID NO:42: RSP1256—PRT;
SEQ ID NO:43: RSP1293—NT;
SEQ ID NO:44: RSP1293—PRT;
SEQ ID NO:45: RSP1354—NT;
SEQ ID NO:46: RSP1354—PRT;
SEQ ID NO:47: RSP1422—NT;
SEQ ID NO:48: RSP1422—PRT;
SEQ ID NO:49: RSP1687—NT;
SEQ ID NO:50: RSP1687—PRT;
SEQ ID NO:51: RSP1772—NT;
SEQ ID NO:52: RSP1772—PRT;
SEQ ID NO:53: RSP1860—NT;
SEQ ID NO:54: RSP1860—PRT;
SEQ ID NO:55: RSP2095—NT;
SEQ ID NO:56: RSP2095—PRT;
SEQ ID NO:57: RSP2097—NT;
SEQ ID NO:58: RSP2097—PRT;
SEQ ID NO:59: RSP2098—NT;
SEQ ID NO:60: RSP2098—PRT;
SEQ ID NO:61: RSP2099—NT;
SEQ ID NO:62: RSP2099—PRT;
SEQ ID NO:63: RSP2100—NT;
SEQ ID NO:64: RSP2100—PRT;
SEQ ID NO:65: RSP2101—NT;
SEQ ID NO:66: RSP2101—PRT;
SEQ ID NO:67: RSP2111—NT;
SEQ ID NO:68: RSP2111—PRT;
SEQ ID NO:69: RSP2112—NT;
SEQ ID NO:70: RSP2112—PRT;
SEQ ID NO:71: RSP2113—NT;
SEQ ID NO:72: RSP2113—PRT;
SEQ ID NO:73: RSP2144—NT;
SEQ ID NO:74: RSP2144—PRT;
SEQ ID NO:75: RSP2196—NT;
SEQ ID NO:76: RSP2196—PRT;
SEQ ID NO:77: RSP2197—NT;
SEQ ID NO:78: RSP2197—PRT;
SEQ ID NO:79: RSP2293—NT;
SEQ ID NO:80: RSP2293—PRT;
SEQ ID NO:81: RSP2344—NT;
SEQ ID NO:82: RSP2344—PRT;
SEQ ID NO:83: RSP2371—NT;
SEQ ID NO:84: RSP2371—PRT;
SEQ ID NO:85: RSP2461—NT;
SEQ ID NO:86: RSP2461—PRT;
SEQ ID NO:87: RSP2464—NT;
SEQ ID NO:88: RSP2464—PRT;
SEQ ID NO:89: RSP2538—NT;
SEQ ID NO:90: RSP2538—PRT;
SEQ ID NO:91: RSP2543—NT;
SEQ ID NO:92: RSP2543—PRT;
SEQ ID NO:93: RSP2544—NT;

SEQ ID NO:94: RSP2544—PRT;
SEQ ID NO:95: RSP2545—NT;
SEQ ID NO:96: RSP2545—PRT;
SEQ ID NO:97: RSP2612—NT;
SEQ ID NO:98: RSP2612—PRT;
SEQ ID NO:99: RSP2712—NT;
SEQ ID NO:100: RSP2712—PRT;
SEQ ID NO:101: RSP2745—NT;
SEQ ID NO:102: RSP2745—PRT;
SEQ ID NO:103: RSP2839—NT;
SEQ ID NO:104: RSP2839—PRT;
SEQ ID NO:105: RSP2840—NT;
SEQ ID NO:106: RSP2840—PRT;
SEQ ID NO:107: RSP2915—NT;
SEQ ID NO:108: RSP2915—PRT;
SEQ ID NO:109: RSP2916—NT;
SEQ ID NO:110: RSP2916—PRT;
SEQ ID NO:111: RSP2974—NT;
SEQ ID NO:112: RSP2974—PRT;
SEQ ID NO:113: RSP3018—NT;
SEQ ID NO:114: RSP3018—PRT;
SEQ ID NO:115: RSP3062—NT;
SEQ ID NO:116: RSP3062—PRT;
SEQ ID NO:117: RSP3177—NT;
SEQ ID NO:118: RSP3177—PRT;
SEQ ID NO:119: RSP3178—NT;
SEQ ID NO:120: RSP3178—PRT;
SEQ ID NO:121: RSP3184—NT;
SEQ ID NO:122: RSP3184—PRT;
SEQ ID NO:123: RSP3218—NT;
SEQ ID NO:124: RSP3218—PRT;
SEQ ID NO:125: RSP3440—NT;
SEQ ID NO:126: RSP3440—PRT;
SEQ ID NO:127: RSP3468—NT;
SEQ ID NO:128: RSP3468—PRT;
SEQ ID NO:129: RSP3535—NT;
SEQ ID NO:130: RSP3535—PRT;
SEQ ID NO:131: RSP3538—NT;
SEQ ID NO:132: RSP3538—PRT;
SEQ ID NO:133: RSP3539—NT;
SEQ ID NO:134: RSP3539—PRT;
SEQ ID NO:135: RSP3540—NT;
SEQ ID NO:136: RSP3540—PRT;
SEQ ID NO:137: RSP3888—NT;
SEQ ID NO:138: RSP3888—PRT;
SEQ ID NO:139: RSP3970—NT;
SEQ ID NO:140: RSP3970—PRT;
SEQ ID NO:141: RSP6005—NT;
SEQ ID NO:142: RSP6005—PRT;
SEQ ID NO:143: RSP6038—NT;
SEQ ID NO:144: RSP6038—PRT;
SEQ ID NO:145: RSP7370—NT;
SEQ ID NO:146: RSP7370—PRT;
SEQ ID NO:147: RSP7647—NT; and
SEQ ID NO:148: RSP7647—PRT.

In some versions, the recombinant microorganisms comprise one or more modifications that reduce the activity of one or more of RSP2839 or a homolog thereof, RSP2840 or a homolog thereof, RSP3218 or a homolog thereof, RSP1056 or a homolog thereof, RSP1200 or a homolog thereof, RSP1422 or a homolog thereof, RSP0355 or a homolog thereof, RSP2545 or a homolog thereof, RSP2544 or a homolog thereof, RSP2543 or a homolog thereof, RSP2745 or a homolog thereof, and RSP2293 or a homolog thereof, and/or one or more modifications that increase the activity of RSP1056 or homolog thereof, with respect to a corresponding microorganism not comprising the one or more modifications. The recombinant microorganisms may include modifications that reduce the activity of two or more, three or more, four or more, five or more, six or more, or seven or more of the above-referenced molecular elements. The recombinant microorganisms may include modifications that reduce the activity any of the above-referenced molecular elements in any combination. Exemplary combinations include modifications that reduce the activity of RSP2839 and RSP2840 or homologs thereof or of RSP2545, RSP2544 and RSP2543 or homologs thereof.

The RSP2839 and RSP2840 are parts of the NtrXY two-component signaling system, wherein RSP2839 is a sensor histidine kinase referred to as "NtrY" and RSP2840 is the response regulator referred to as "NtrX." The NtrXY system is involved with regulating a set of genes upon activation. An alternative or additional modification to reducing the activity of RSP2839 and/or RSP2840 or any other modification described herein is directly modifying the expression or activity of the NtrXY target genes or products. Accordingly, in some versions of the invention, the recombinant microorganisms comprise one or more modifications that reduce the activity of one or more of RSP2839 or a homolog thereof, RSP0334 or a homolog thereof, RSP0333 or a homolog thereof, RSP0332 or a homolog thereof, RSP0331 or a homolog thereof, RSP0330 or a homolog thereof, RSP0335 or a homolog thereof, RSP3540 or a homolog thereof, RSP3539 or a homolog thereof, RSP3538 or a homolog thereof, RSP2095 or a homolog thereof, RSP6038 or a homolog thereof, RSP2097 or a homolog thereof, RSP2098 or a homolog thereof, RSP2099 or a homolog thereof, RSP2100 or a homolog thereof, RSP2101 or a homolog thereof, RSP2111 or a homolog thereof, RSP2112 or a homolog thereof, RSP2113 or a homolog thereof, and RSP2916 or a homolog thereof; one or more modifications that increase the activity of RSP1860 or a homolog thereof, with respect to a corresponding microorganism not comprising the one or more modifications; and/or one or more modifications that either increase or reduce the activity of one or more of RSP0339 or a homolog thereof, RSP2974 or a homolog thereof, RSP0892 or a homolog thereof, and RSP2915 or a homolog thereof. Two or more, three or more, four or more, or five or more of the above-referenced molecular elements may be modified for ablated, reduced, or increased activity in the recombinant microorganisms. The above-referenced molecular elements may be modified in any combination within the group itself or any other modification described herein.

The recombinant microorganisms in preferred versions of the invention are configured to exhibit enhanced lipid secretion with respect to a corresponding microorganism. The recombinant microorganisms in such versions may include any one or more of the modifications described herein. Modifications that confer a remarkable enhancement in lipid secretion include those that reduce the activity of any one or more of RSP2839 or a homolog thereof, RSP2840 or a homolog thereof, and RSP1200 or a homolog thereof. An exemplary combination of the above-referenced modifications includes modifications that reduce the activity of RSP2839 or a homolog thereof and RSP2840 or a homolog thereof. Other combinations are within the scope of the present invention.

Any of the above-referenced modifications may be combined with modifications that inhibit the β-oxidation of fatty acids. Exemplary modifications that inhibit the β-oxidation of fatty acids include modifications that reduce the activity of any one or more of an acyl-CoA dehydrogenase, an enoyl-CoA hydratase, a 3-hydroxyacyl-CoA dehydrogenase, and a 3-ketoacyl-CoA thiolase. Acyl-CoA dehydrogenases, enoyl-CoA hydratases, 3-hydroxyacyl-CoA dehydrogenases, and 3-ketoacyl-CoA thiolases are well known in the art and are readily identified in any given microorganism. Exemplary acyl-CoA dehydrogenases, enoyl-CoA hydratases, 3-hydroxyacyl-CoA dehydrogenases, and 3-ketoacyl-CoA thiolases (acetyl-CoA C-acyltransferases) include RSP7647, RSP3018, RSP3535, RSP3970, RSP2196, RSP1687, RSP2197, RSP1354, and RSP3184.

Any of the above-referenced modifications may also or alternatively be combined with modifications that promote lipid synthesis. Exemplary modifications that promote lipid synthesis include modifications that increase expression or activity of any one or more of an acetyl-CoA synthetase, an acetyl-CoA carboxylase, an acetyl CoA:ACP transacylase, a malonyl CoA:ACP transacylase, a 3-ketoacyl-ACP synthase, a 3-ketoacyl-ACP reductase, a 3-hydroxyacyl-ACP dehydrase, an enoyl-ACP reductase, a glycerol-3-phosphate acyltransferase, and a 1-acylglycerol-3-phosphate acyltransferase. Acyl-CoA synthetases, acetyl-CoA carboxylases, acetyl CoA:ACP transacylases, malonyl CoA:ACP transacylases, 3-ketoacyl-ACP synthases, 3-ketoacyl-ACP reductases, 3-hydroxyacyl-ACP dehydrases, enoyl-ACP reductases, glycerol-3-phosphate acyltransferases, and 1-acylglycerol-3-phosphate acyltransferases are well known in the art and are readily identified in any given microorganism. Exemplary acetyl-CoA synthetases, acetyl-CoA carboxylases, acetyl CoA:ACP transacylases, malonyl CoA: ACP transacylases, 3-ketoacyl-ACP synthases (3-oxoacyl-ACP synthases), 3-ketoacyl-ACP reductases (3-oxoacyl-ACP reductases), (3-hydroxyacyl-ACP dehydrases, enoyl-ACP reductases, glycerol-3-phosphate acyltransferases, and 1-acylglycerol-3-phosphate acyltransferases include RSP0579, RSP1772, RSP0190, RSP0191, RSP1293, RSP2464, RSP2612, RSP3177, RSP3468, RSP6005, RSP2371, RSP2461, RSP2538, RSP0747, RSP3062, RSP3440, RSP3888, RSP2712, RSP7370, RSP3178, RSP1256, RSP2344, RSP1004, and RSP0735. Additional modifications may include those that increase expression or activity of homologues of FabG that have been engineered to improve the supply of reduced pyridine nucleotides needed for fatty acid synthesis (RSP2461) (Javidpour et al. 2014) or homologues of FabF (RSP2464) that have been engineered to produce fatty acids of shorter chain lengths (Torella et al. 2013).

Any of the above-referenced modifications may also or alternatively be combined with modifications that reduce the production of polyhydroxybutyrate. An exemplary modification that reduces the production of polyhydroxybutyrate is a modification that reduces the activity of RSP0382 or a homolog thereof.

The recombinant microorganisms of the invention may be configured for the novel production or enhanced production of specific lipids. Examples of such lipids include certain straight-chain fatty acids or non-straight-chain fatty acids. Examples of straight-chain fatty acids include omega-3 fatty acids such as docosahexaenoic acid and omega-6 fatty acids such as arachidonic acid. Examples of non-straight-chain fatty acids include branched-chain fatty acids, furan-containing fatty acids, and cyclic fatty acids. To make certain non-straight-chain fatty acids, the microorganisms may comprise any one or more of the modifications described in US 2015/0376659 to Lemke et al., which is incorporated herein by reference. Accordingly, the recombinant microorganism may comprise one or more modifications that increase the activity of one or more of RSP2144 or a homolog thereof, RSP1091 or a homolog thereof, and RSP1090 or a homolog thereof, with respect to the corresponding microorganism. Such microorganisms may comprise one or more recombinant genes configured to express or overexpress one or more of the RSP2144 or homolog thereof, the RSP1091 or homolog thereof, and the RSP1090 or homolog thereof; a modification that disrupts binding between ChrR and $\sigma^E$ or homologs thereof; a modification that increases expression of $\sigma^E$ or a homolog thereof; and/or a modification that eliminates from the microorganism a native ChrR or homolog thereof.

The recombinant microorganisms of the invention may be configured for the novel production or enhanced production of lipid-associated bioproducts. "Lipid-associated bioproducts" refer to products produced by microorganisms that integrate in or associate with cellular lipids, such as membranes. Examples of lipid-associates bioproducts include certain proteins, organic compounds (such as quinones, isoprenoids, etc.), non-organic compounds, or other products. The lipid-associated bioproducts may be lipid-soluble or have lipid-soluble moieties. Lipid-associated bioproducts that are proteins are referred to herein as "lipid-associated proteins." Examples of lipid-associated proteins include various membrane proteins, such as integral membrane proteins and peripheral membrane proteins, as well as soluble proteins contained inside lipid-vesicles. Accordingly, some microorganisms of the invention comprise one or more recombinant genes configured to express lipid-associated proteins. Other microorganisms of the invention comprise one or more recombinant genes configured to express enzymes responsible for producing lipid-associated bioproducts.

Modifications that reduce the activity of a gene or gene product includes any modification to a microorganism that ablates, reduces, inhibits, or otherwise disrupts production of a gene product, renders a produced gene product non-functional, or otherwise reduces or ablates a produced gene product's activity. Accordingly, in some instances, production of a gene product may be completely shut down. "Gene product" refers to products such as an mRNA or a polypeptide encoded and produced by a particular gene. "Gene" refers to a nucleic acid sequence capable of producing a gene product and may include such genetic elements as a coding sequence together with any other genetic elements required for transcription and/or translation of the coding sequence. Such genetic elements may include a promoter, an enhancer, and/or a ribosome binding site (RBS), among others.

There are many well-known ways to reduce the activity of a gene or gene product. This can be accomplished, for example, by introducing one or more genetic modifications. As used herein, "genetic modifications" refer to any differences in the nucleic acid composition of a cell, whether in the cell's native chromosome or in endogenous or exogenous non-chromosomal plasmids harbored within the cell. Examples of genetic modifications that reduce the activity of a gene or gene product include but are not limited to substitutions, partial or complete deletions, insertions, or other variations to a coding sequence or a sequence controlling the transcription or translation of a coding sequence, such as placing a coding sequence under the control of a less active promoter, etc. In some versions, a gene or coding sequence can be replaced with a selection marker or screenable marker. In some versions, the genetic modifications can include the introduction of constructs that express ribozymes or antisense sequences that target the mRNA of the gene of interest. Various other genetic modifications that reduce the activity of a gene or gene product are described elsewhere herein. Various methods for introducing genetic modifications are well known in the art and include homologous recombination, among other mechanisms. See, e.g., Green et al., *Molecular Cloning: A laboratory manual*, 4$^{th}$ ed., Cold Spring Harbor Laboratory Press (2012) and Sambrook et al., *Molecular Cloning: A Laboratory Manual*, 3$^{rd}$ ed., Cold Spring Harbor Laboratory Press (2001). In some instances, reducing the activity of a gene or gene product can be accomplished by chemically inhibiting the activity of a gene product with a small-molecule inhibitor, by expressing a protein that interferes with the activity of the gene product, or by other means.

"Increasing expression" or grammatical variants thereof may refer to expressing a gene product not made by the corresponding microorganism or expressing more of a gene product already made by the corresponding microorganism. Modifying the recombinant microorganisms to increase expression of the gene products described herein can be performed using any methods currently known in the art or discovered in the future. Examples include genetically modifying the microorganism and culturing the microorganism in the presence of factors that increase expression of the gene product. Suitable methods for genetic modification include but are not limited to placing the coding sequence under the control of a more active promoter, increasing the copy number of genes comprising the coding sequence, introducing a translational enhancer on a gene comprising the coding sequence (see, e.g., Olins et al. 1989), and/or modifying factors (e.g., transcription factors or genes therefor) that control expression of a gene comprising the coding sequence. Increasing the copy number of genes comprising a coding sequence can be performed by introducing one or more additional copies of the native gene to the microorganism, introducing one or more a heterologous homologs to the microorganism, introducing one or more copies of recombinant versions of the native gene or heterologous homolog to the microorganism, etc. Genes expressing a given coding sequence may be incorporated into the microbial genome or included on an extrachromosomal genetic construct such as a plasmid. "Exogenous" used in reference to a genetic element means the genetic element is a non-native genetic element. "Heterologous" used in reference to a genetic element means that the genetic element is derived from a different species. A genetic element, such as a promoter, that controls or affects the activity of another genetic element, such as a coding sequence, is herein described as being "operationally connected" thereto.

Some of the microorganisms of the invention may include at least one recombinant nucleic acid configured to express or overexpress a particular product. "Recombinant" as used herein with reference to a nucleic acid molecule or polypeptide is one that has a sequence that is not naturally occurring, has a sequence that is made by an artificial combination of two otherwise separated segments of sequence, or both. This artificial combination can be achieved, for example, by chemical synthesis or by the artificial manipulation of isolated segments of nucleic acid molecules or polypeptides using genetic engineering techniques. A recombinant cell or microorganism is one that contains a recombinant nucleic acid molecule or polypeptide. "Overexpress" as used herein means that a particular gene product is produced at a higher level in one cell, such as a recombinant cell, than in a corresponding cell. For example, a microorganism that includes a recombinant nucleic acid configured to overexpress a gene product produces the gene product at a greater amount than a microorganism of the same species that does not include the recombinant nucleic acid.

In general, proteins and/or protein sequences are "homologous" when they are derived, naturally or artificially, from a common ancestral protein or protein sequence. Similarly, nucleic acids and/or nucleic acid sequences are homologous when they are derived, naturally or artificially, from a common ancestral nucleic acid or nucleic acid sequence. Homology is generally inferred from sequence similarity between two or more nucleic acids or proteins (or sequences thereof). The precise percentage of similarity between sequences that is useful in establishing homology varies with the nucleic acid and protein at issue, but as little as 25% sequence similarity (e.g., identity) over 50, 100, 150 or more residues (nucleotides or amino acids) is routinely used to establish homology (e.g., over the full length of the two sequences to be compared). Higher levels of sequence similarity (e.g., identity), e.g., 30%, 35% 40%, 45% 50%, 55%, 60%, 65%, 70%, 75%, 80%, 85%, 90%, 95%, or 99% or more, can also be used to establish homology. Accordingly, homologous sequences of the sequences described herein include coding sequences, genes, or gene products (e.g., proteins), respectively, having at least about 30%, 35%, 40%, 45%, 50%, 55%, 60%, 65%, 70%, 75%, 80%, 85%, 90%, 95%, or 99% identity to the sequences described herein. Methods for determining sequence similarity percentages (e.g., BLASTP and BLASTN using default parameters) are described herein and are generally available. The homologous proteins should demonstrate comparable activities and, if an enzyme, participate in the same or analogous pathways. "Orthologs" are genes or coding sequences thereof in different species that evolved from a common ancestral gene by speciation. Normally, orthologs retain the same or similar function in the course of evolution. As used herein "orthologs" are included in the term "homologs." Homologs also include sequences at least 90%, 95%, or 97% or more identical to the orthologs.

For sequence comparison and homology determination, one sequence typically acts as a reference sequence to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence based on the designated program parameters. A typical reference sequence of the invention is any nucleic acid or amino acid sequence described herein.

Optimal alignment of sequences for comparison can be conducted, e.g., by the local homology algorithm of Smith & Waterman, Adv. Appl. Math. 2:482 (1981), by the homology alignment algorithm of Needleman & Wunsch, J. Mol. Biol. 48:443 (1970), by the search for similarity method of Pearson & Lipman, Proc. Nat'l. Acad. Sci. USA 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see Current Protocols in Molecular Biology, F. M. Ausubel et al., eds., Current Protocols, a joint venture between Greene Publishing Associates, Inc. and John Wiley & Sons, Inc., (supplemented through 2008)).

One example of an algorithm that is suitable for determining percent sequence identity and sequence similarity for purposes of defining homologs is the BLAST algorithm, which is described in Altschul et al., *J. Mol. Biol.* 215:403-410 (1990). Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always>0) and N (penalty score for mismatching residues; always<0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, a cutoff of 100, M=5, N=−4, and a comparison of both strands. For amino acid sequences, the BLASTP program uses as defaults a wordlength (W) of 3, an expectation (E) of 10, and the BLOSUM62 scoring matrix (see Henikoff & Henikoff (1989) Proc. Natl. Acad. Sci. USA 89:10915).

In addition to calculating percent sequence identity, the BLAST algorithm also performs a statistical analysis of the similarity between two sequences (see, e.g., Karlin & Altschul, Proc. Natl. Acad. Sci. USA 90:5873-5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.1, more preferably less than about 0.01, and most preferably less than about 0.001. The above-described techniques are useful in identifying homologous sequences for use in the methods described herein.

The terms "identical" or "percent identity", in the context of two or more nucleic acid or polypeptide sequences, refer to two or more sequences or subsequences that are the same or have a specified percentage of amino acid residues or nucleotides that are the same, when compared and aligned for maximum correspondence, as measured using one of the sequence comparison algorithms described above (or other algorithms available to persons of skill) or by visual inspection.

The phrase "substantially identical", in the context of two nucleic acids or polypeptides refers to two or more sequences or subsequences that have at least about 60%, about 65%, about 70%, about 75%, about 80%, about 85%, about 90, about 95%, about 98%, or about 99% or more nucleotide or amino acid residue identity, when compared and aligned for maximum correspondence, as measured using a sequence comparison algorithm or by visual inspection. Such "substantially identical" sequences are typically considered to be "homologous" without reference to actual ancestry. Preferably, the "substantial identity" exists over a region of the sequences that is at least about 50 residues in length, more preferably over a region of at least about 100 residues, and most preferably, the sequences are substantially identical over at least about 150 residues, at least about 250 residues, or over the full length of the two sequences to be compared.

Exogenous, heterologous nucleic acids encoding products to be expressed in the microorganism are preferably codon-optimized for the particular microorganism in which they are introduced. Codon optimization can be performed for any nucleic acid by a number of programs, including "GENEGPS"-brand expression optimization algorithm by DNA 2.0 (Menlo Park, Calif.), "GENEOPTIMIZER"-brand gene optimization software by Life Technologies (Grand Island, N.Y.), and "OPTIMUMGENE"-brand gene design system by GenScript (Piscataway, N.J.). Other codon optimization programs or services are well known and commercially available.

Notwithstanding the above discussion, homologs of RSP2839 may also or alternatively include genes identified by the designation "ntrY" or corresponding designations and proteins identified by the designation "NtrY" or corresponding designations. Homologs of RSP2840 include genes identified by the designation "ntrX" or corresponding designations and proteins identified by the designation "NtrX" or corresponding designations. See Atack et al. 2013.

The recombinant microorganisms of the invention may comprise any type of microorganism. The microorganism may be prokaryotic or eukaryotic. Suitable prokaryotes include bacteria and archaea. Suitable types of bacteria include α- and γ-proteobacteria, gram-positive bacteria, gram-negative bacteria, ungrouped bacteria, phototrophs, lithotrophs, and organotrophs. Suitable eukaryotes include yeast and other fungi. Exemplary microorganisms include those from the genus *Rhodobacter*, such as *Rhodobacter sphaeroides*, and those from the genus *Rhodopseudomonas*, such as *Rhodopseudomonas palustris*. In some versions of the invention, the corresponding organism to the recombinant microorganisms of the invention is a non-oleaginous microorganism.

The recombinant microorganisms of the invention preferably exhibit enhanced lipid production with respect to the corresponding microorganism when the recombinant microorganism and the corresponding organism are grown under aerobic conditions. The lipid production may be enhanced by a factor of at least about 1.1, at least about 1.5, at least about 2, at least about 2.5, at least about 3, at least about 3.5, at least about 4, at least about 4.5, at least about 5, at least about 5.5, at least about 6, or at least about 6.5 and/or up to about 6.5, up to about 7, or more. Such increases may reflect an increase by mass.

The recombinant microorganisms of the invention may be configured to be capable of producing lipid in culture in an amount of at least about 0.5 g/L, at least about 0.75 g/L, at least about 1 g/L, or at least about 1.5 g/L and/or up to about 1.7 g/L, up to about 2 g/L, up to about 2.5 g/L or more. Such amounts may reflect the total lipid produced in culture (both intracellular and secreted).

The recombinant microorganisms of the invention may be configured to be capable of secreting lipid in culture in an amount of at least about 0.4 g/L, at least about 0.6 g/L, at least about 0.8 g/L, at least about 1 g/L, at least about 1.2 g/L, or at least about 1.4 g/L, and/or up to about 1.6 g/L or more.

The recombinant microorganisms of the invention may be configured to be capable of secreting an amount of at least about 10% (w/w), at least about 20% (w/w), at least about 30% (w/w), at least about 40% (w/w), at least about 50%

(w/w), at least about 60% (w/w), and/or up to about 60% (w/w), up to about 70% (w/w) or more of total produced lipids.

The recombinant microorganisms of the invention may be configured to be capable of producing lipid in culture in an amount of at least about 15% (w/w) dry cell weight, at least about 20% (w/w) dry cell weight, at least about 25% (w/w) dry cell weight, at least about 30% (w/w) dry cell weight, and/or up to about 30% (w/w) dry cell weight, up to about 35% (w/w) dry cell weight, or more. Such amounts may reflect the total lipid produced in culture (both intracellular and secreted).

The recombinant microorganisms of the invention can be used in methods for producing bioproducts. The bioproducts may include any bioproduct, including those described elsewhere herein such as lipids, proteins, and/or organic compounds. The methods may include culturing the recombinant microorganism as described herein in a medium comprising for a time sufficient to consume nutrients present in the medium and produce the bioproduct.

As shown in the examples, high production of the bioproducts can be obtained through fed-batch culturing, wherein nutrients are freshly added periodically throughout the culturing. In preferred versions, the fed-batch culturing comprises culturing the microorganism at a first level of dissolved oxygen in the medium and adding nutrients to the medium upon detecting an increase in the dissolved oxygen from the first level to a second level of the dissolved oxygen. The nutrients are added in an amount sufficient to reduce the dissolved oxygen from the second level to a third level of dissolved oxygen. The third level may or may not be equivalent to the first level. Such a process may be repeated with 1-500 or more additional iterations, such as 1-200, 110-150, 20-100, or about 60 additional iterations, with the first, second, and third levels in each additional iteration being the same or different as the respective levels in the first iteration.

The medium may comprise a defined set of chemicals or comprise a more complex set of chemicals such as a biomass hydrolysate. The biomass hydrolysate may be included in an amount of at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, or more.

Biomass is biological material derived from living or once-living organisms. Biomass can be from plant, animal, or other organic material. Biomass is carbon based and is composed of a mixture of organic molecules containing hydrogen atoms, usually including atoms of oxygen, often nitrogen and also small quantities of other atoms, including alkali, alkaline earth and heavy metals.

The biomass hydrolysate for use in the present invention can be produced from any biomass feedstock. Exemplary types of biomass feedstocks include sucrose-rich feedstocks such as sugar cane; starchy materials, such as corn grain; and lignocellulosic biomass, such as costal Bermuda grass, corn cobs, corn stover, cotton seed hairs, grasses, hardwood stems, leaves, newspaper, nut shells, paper, primary wastewater solids, softwood stems, solid cattle manure, sorted refuse, swine waste, switchgrass, waste papers from chemical pulps, wheat straw, wood, and woody residues.

Prior to hydrolysis, the biomass feedstock may be pretreated or non-pretreated. Pretreatment of biomass feedstock removes a large proportion of the lignin and other materials and enhances the porosity of the biomass prior to hydrolysis. The biomass feedstock may be pretreated by any method. Exemplary methods to pretreat or dissolve biomass can include chipping, grinding, milling, steam pretreatment, ammonia fiber expansion (AFEX, also referred to as ammonia fiber explosion), ammonia recycle percolation (ARP), $CO_2$ explosion, steam explosion, ozonolysis, wet oxidation, acid hydrolysis, dilute-acid hydrolysis, alkaline hydrolysis, organosolv, ionic liquids, gamma-valerolactone, and pulsed electrical field treatment, among others. See, e.g., Kumar et al. 2009.

The pretreated or non-pretreated biomass may be hydrolyzed by any suitable method. Hydrolysis converts biomass polymers to fermentable sugars, such as glucose and xylose, and other monomeric or oligomeric components. Exemplary hydrolysis methods include enzymatic hydrolysis (e.g., with cellulases or other enzymes) and acid hydrolysis (e.g., with sulfurous, sulfuric, hydrochloric, hydrofluoric, phosphoric, nitric, and/or formic acids), among other methods.

The biomass hydrolysate included in the medium may comprise residual organic solutions (often referred to as conversion residue) from distillation of fermentation products or other downstream products of biomass processing. Exemplary instances include the use of conversion residue from microbial biomass ethanol fermentations or others.

The recombinant microorganisms may be cultured for a time of at least about 20 hours, at least about 40 hours, at least about 60 hours, at least about 80 hours, at least about 100 hours, at least about 120 hours, at least about 140 hours, and/or up to about 120 hours, up to about 140 hours, up to about 160 hours or more.

The nutrients included in the medium and consumed by the recombinant microorganism may include any of a number of carbon sources such as organic acids, sugars, or others. Exemplary nutrients include sugars (such as glucose, xylose), organic acids (such as succinate, lactate, and acetate) amino acids or other organic materials present that are used as nutrients for the lipid-producing microorganism.

The culturing may be conducted until recombinant microorganism produces lipid in an amount of at least about 0.5 g/L, at least about 0.75 g/L, at least about 1 g/L, or at least about 1.5 g/L and/or up to about 1.7 g/L, up to about 2 g/L, up to about 2.5 g/L or more. Such amounts may reflect the total lipid produced in culture (both intracellular and secreted). The culturing may be conducted until recombinant microorganism secretes lipid in an amount of at least about 0.4 g/L, at least about 0.6 g/L, at least about 0.8 g/L, at least about 1 g/L, at least about 1.2 g/L, or at least about 1.4 g/L, and/or up to about 1.6 g/L or more.

The culturing may be conducted until recombinant microorganism produces lipid in an amount of at least about 15% (w/w) dry cell weight, at least about 20% (w/w) dry cell weight, at least about 25% (w/w) dry cell weight, at least about 30% (w/w) dry cell weight, and/or up to about 30% (w/w) dry cell weight, up to about 35% (w/w) dry cell weight, or more. Such amounts may reflect the total lipid produced in culture (both intracellular and secreted).

The culturing may be conducted under aerobic or anaerobic conditions.

The methods may further comprise harvesting a bioproduct secreted from the microorganism into the media. The harvesting may comprise centrifuging the microorganism and medium to obtain a supernatant and separating the supernatant from the microorganism.

The elements and method steps described herein can be used in any combination whether explicitly described or not.

All combinations of method steps as used herein can be performed in any order, unless otherwise specified or clearly implied to the contrary by the context in which the referenced combination is made.

As used herein, the singular forms "a," "an," and "the" include plural referents unless the content clearly dictates otherwise.

Numerical ranges as used herein are intended to include every number and subset of numbers contained within that range, whether specifically disclosed or not. Further, these numerical ranges should be construed as providing support for a claim directed to any number or subset of numbers in that range. For example, a disclosure of from 1 to 10 should be construed as supporting a range of from 2 to 8, from 3 to 7, from 5 to 6, from 1 to 9, from 3.6 to 4.6, from 3.5 to 9.9, and so forth.

All patents, patent publications, and peer-reviewed publications (i.e., "references") cited herein are expressly incorporated by reference to the same extent as if each individual reference were specifically and individually indicated as being incorporated by reference. In case of conflict between the present disclosure and the incorporated references, the present disclosure controls.

It is understood that the invention is not confined to the particular construction and arrangement of parts herein illustrated and described, but embraces such modified forms thereof as come within the scope of the claims.

EXAMPLES

Background

Lipids from microbes offer a promising source of renewable alternatives to petroleum-derived compounds. In particular, oleaginous microbes are of interest because they accumulate a large fraction of their biomass as lipids. We investigated whether it is possible to exploit the native metabolic and regulatory pathways of non-oleaginous bacteria, as an example of a prokaryotic microbe, to increase lipid production to oleaginous levels.

We evaluated the possibility of increasing lipid production by rewiring the native metabolic and regulatory pathways of *Rhodobacter sphaeroides*, a non-oleaginous facultative purple non-sulfur bacterium. Unlike many well-studied facultative bacteria, changes in $O_2$ tension cause significant morphological changes in the cell envelope of this Gram-negative bacterium (Chory et al. 1984, Tavano et al. 2006, Kiley et al. 1988). In response to low $O_2$ tension, *R. sphaeroides* increases its intracellular membrane surface area, developing specialized intracytoplasmic membrane (ICM) invaginations that protrude into the cytoplasm (Chory et al. 1984, Tavano et al. 2006, Kiley et al. 1988). This remodeling of the cell envelope under low $O_2$ conditions increases the cellular phospholipid content ~3-fold (Lemmer et al. 2015).

Since *R. sphaeroides* contains regulatory mechanisms to increase lipid production at low $O_2$, we hypothesized that it could be possible to generate mutants with increased lipid production at high $O_2$.

We screened a *Rhodobacter sphaeroides* Tn5-mutant library for insertions that increased fatty acid content and identified ten high-lipid mutants for further characterization. These high-lipid mutants exhibited increased sensitivity to drugs that target the bacterial cell envelope, exhibited changes in shape, and, in some cases, secreted lipids. Two high-lipid mutants accumulated ~60% of their total lipids extracellularly. We used one of the highest lipid secreting strains to grow high-density cultures in a fed-batch bioreactor. The strain produced 1.3 g/L fatty acids, corresponding to 33% of dry cell weight (DCW). This lipid content is comparable to that of oleaginous microbes.

Thus, by genetically altering cell surface or envelope functions with single genetic alterations, we have converted *R. sphaeroides* into an oleaginous bacterium. Unlike in native oleaginous microbes, however, the majority of the lipids produced by some of the high-lipid mutants are advantageously excreted. Based on the properties of these high-lipid mutants, we conclude that genetically altering the cell envelope can be used as a previously unreported approach to increase microbial lipid production and secretion, and we propose that this approach can be used to increase production of lipids and additional bioproducts in other microbes.

Materials and Methods

Bacterial Strains and Growth Conditions

Bacterial strains used in the present examples are described in Table 1. *R. sphaeroides* strains were grown in Sistrom's minimal medium (SIS) (Sistrom 1960), with 4 g/L succinate as a carbon source, unless otherwise noted when 4 g/L glucose, xylose, lactate, or acetate was used as the carbon source. For batch culture growth in the presence of $O_2$, 10-20 ml cultures were grown in 125 ml flasks with shaking at 200 rpm, at 30° C. in the dark. For low $O_2$ growth, cells were grown by anaerobic photosynthesis; Screw-cap tubes of liquid culture were incubated at room temperature in front of an incandescent light box with a light intensity of 10 W/m$^2$ measured through a red glass filter. Cultures were grown to a density of 0.5-1.5 $OD_{600}$ for analysis. *Escherichia coli* strains were grown at 37° C. in LB broth-Miller (Atlas et al. 1993). When necessary, media were supplemented with 50 µg/ml kanamycin.

TABLE 1

Strains and plasmids.

| Strain | Relevant properties | Source or Reference |
|---|---|---|
| *E. coli* | | |
| DH5α | Host for cloning and plasmid amplification | Bethesda Research Laboratories |
| DH5α/λpir | Host for cloning Tn5 insertion sites; Φ80dlacZΔM15 Δ(lacZYA-argF) U169 recA1 hsdR17 deoR thi-1 supE44 gyrA96 relA1/λpir | Miller et al. 1988 |
| S17-1 | Donor for conjugation; C600::RP-4 2-(Tc::Mu) (Kn::Tn7) thi pro hsdR recA Tra⁺ | Simon et al. 1983 |
| BW20767 | Donor for conjugation; RP-2-Tc::Mu-1 kan::Tn7 integrant leu-63::I20 recA1 zbf-5 creB510 hsdR17 endAl thi uidA (ΔMluI)::pir+ | Metcalf et al. 1996 |

TABLE 1-continued

Strains and plasmids.

| Strain | Relevant properties | Source or Reference |
|---|---|---|
| *R. sphaeroides* | | |
| 2.4.1 | Wild-type strain | van Niel 1944 |
| Δ0382 (parent strain) | ΔRSP0382 in 2.4.1 | Yilmaz et al. 2010 |
| HLM01 | Δ0382 with Tn5 insertion at Chr1: 1,471,645; Km$^R$ | Present examples |
| HLM02 | Δ0382 with Tn5 insertion at Chr1: 1,469,665; Km$^R$ | Present examples |
| HLM03 | Δ0382 with Tn5 insertion at Chr2: 274,987; Km$^R$ | Present examples |
| HLM04 | Δ0382 with Tn5 insertion at Chr1: 2,814,885; Km$^R$ | Present examples |
| HLM05 | Δ0382 with Tn5 insertion at Chr1: 2,970,757; Km$^R$ | Present examples |
| HLM06 | Δ0382 with Tn5 insertion at Chr2: 938,456; Km$^R$ | Present examples |
| HLM07 | Δ0382 with Tn5 insertion at Chr1: 2,086,261; Km$^R$ | Present examples |
| HLM08 | Δ0382 with Tn5 insertion at Chr1: 1,189,239; Km$^R$ | Present examples |
| HLM08b | Same as HLM08, isolated independently from screen | Present examples |
| HLM09 | Δ0382 with Tn5 insertion at Chr1: 1,395,725; Km$^R$ | Present examples |
| HLM10 | Δ0382 with Tn5 insertion at Chr1: 916,649; Km$^R$ | Present examples |
| ΔNrtXYΔ0382 | ΔRSP2839, ΔRSP2840, ΔRSP0382 in 2.4.1 | Present examples |
| ΔChrRANrtXY Δ0382 | ΔchrR-1::dfr, ΔRSP2839, ΔRSP2840, ΔRSP0382 in 2.4.1. | Present examples |
| Δ1200Δ0382 | ΔRSP1200, ΔRSP0382 in 2.4.1 | Present examples |
| KL116 | HLM02 carrying plasmid pKCL22 to express Myc-tagged NtrX | Present examples |
| Plasmids | | |
| pRL27 | Tn5-RL27 delivery vector (Km$^R$-oriR6 K) | Larsen et al. 2002 |
| pK18mobsacb | Broad host range mobilizable vector; Km$^R$ oriV oriT mob sacB | Schafer et al. 1994 |
| pKCL20 | 5,939-bp *R. sphaeroides* genomic region containing RSP2839 and RSP2840 cloned into the XbaI and HindIII sites of pK18mobsacB; Km$^R$ | Present examples |
| pKCL21 | pKCL20 with RSP2839 and RSP2840 deleted; Km$^R$ | Present examples |
| pJDN27 | pSUP202-derived suicide plasmid that creates an insertion of Tp$^R$ gene into a deletion of chrR gene | Newman et al. 1999 |
| pIND5-myc | Expression vector with IPTG-inducible promoter, includes 3X myc tag; Km$^R$ | Imam et al. 2014 |
| pKCL22 | N-terminally 3X myc tagged ntrX (RSP 2840) cloned into BamHI and HindIII sites of pIND5-myc | Present examples |

Transposon Mutagenesis and Nile Red Screening

The transposon delivery plasmid pRL27 (Larsen et al. 2002) was conjugated into *R. sphaeroides* Δ0382 using *E. coli* donor strain BW20767. Individual exconjugant colonies were inoculated into 200 μl SIS plus kanamycin in 96-well plates, grown in a humidified incubator with shaking at 30° C. to saturation (3 days), and then subcultured into fresh SIS containing 5 mg/ml Nile Red in Nunc™ 96-well black optical-bottom plates (Thermo Scientific). After ~14 hours of incubation, fluorescence (excitation 530 nm/emission 580 nm) and absorbance (650 nm and 850 nm) were measured in an Infinite® M1000 plate reader (Tecan). For candidate strains with fluorescence/OD$_{650}$ that was 60% or more higher than the plate average, Nile Red staining was repeated with replicates before cellular fatty acid analysis. Transposon insertion sites were identified by cloning transposon-containing fragments, from BamHI-digested genomic DNA, as pir-dependent plasmids as previously described (Larsen et al. 2002). Sequencing was performed on the Tn5-containing plasmids with primers tpnRL13-2 and tpnRL17-1 (Table 2).

TABLE 2

Oligonucleotides.

| ID Number | Sequence | Purpose |
|---|---|---|
| tpnRL13-2 | CAGCAACACCTTCTTCACGA (SEQ ID NO: 149) | Sequence out from Tn5 insertion site |
| tpnRL17-1 | AACAAGCCAGGGATGTAACG (SEQ ID NO: 150) | Sequence out from Tn5 insertion site |
| KCL58 | GCATTCTAGACGAGGCCTACG ATTATCTGC (SEQ ID NO: 151) | Amplify R5P2839 and R5P2840 from R. sphaeroides DNA (R) |
| KCL59 | CGATAAGCTTGTCGGGTCGTT TACCAGAAC (SEQ ID NO: 152) | Amplify R5P2839 and R5P2840 from R. sphaeroides DNA (R) |
| KCL60 | CGGACCGTTCTGCGAAGCA (SEQ ID NO: 153) | Delete R5P2839 and R5P2840 from pKCL20 to make pKCL21 (F) |
| KCL63 | TTCAGGCGCCGACCGGGACT (SEQ ID NO: 154) | Delete RSP2839 and RSP2840 from pKCL20 to make pKCL21 (R) |
| KCL72 | TATCTCTTCGATTTCGAGCAG CCC (SEQ ID NO: 155) | Sequencing primer (F) |
| KCL84 | ATGTTGACCTCGTCGGAATG (SEQ ID NO: 156) | Sequencing primer (R) |
| KCL85 | GCAAGAAGATCACCGACCTC (SEQ ID NO: 157) | Sequencing primer (F) |
| KCL86 | TCCTTGAGCCAGATGTCGAGG AT (SEQ ID NO: 158) | Sequencing primer (R) |
| KCL87 | AGGCCTTGACCAACCTGATGA AGA (SEQ ID NO: 159) | Sequencing primer (F) |
| KCL88 | TTCCAGCTGATGATAGAGCAC CAC (SEQ ID NO: 160) | Sequencing primer (R) |
| KCL89 | TCACCTTCGGCGCTATTTCGAT CT (SEQ ID NO: 161) | Sequencing primer (F) |
| KCL116 | GCCTTTGTCGGGATGGAAC (SEQ ID NO: 162) | Sequencing primer (F) |
| ChrR-UP1 | GCGCCAGCATATGAGTTGAGT GAG (SEQ ID NO: 163) | Sequencing primer (F) |
| ChrR-DS1 | CGTGAATGACAGGGGTCGCC (SEQ ID NO: 164) | Sequencing primer (F) |

Chemical Sensitivity Analysis

Selected compounds (Tables 4A and 4B) were tested for their effects on growth of the parent strain to determine the highest doses that cause <30% growth reduction. Parent and high-lipid mutant strains were grown in the presence of the chemicals, or DMSO as a control, in 96-well plates at 30° C. with shaking for 48 hours. Final ODs were read at 595 nm on an Infinite® F500 microplate reader (Tecan). For each strain, final ODs for each drug treatment were first divided by the OD of the DMSO control for that strain to determine relative cell growth, and then the growth value for each treated culture was normalized by the parent strain growth under the same condition. Two-way clustering was performed with Cluster 3.0 and visualized with Java TreeView software (Saldanha 2004).

Fed-Batch Bioreactor Cultures

High-density fed-batch cultures were grown in an Applikon biofermenter (3 L Autoclavable Microbial BioBundle, Applikon Biotechnology). An adapted SIS medium (ASIS) was used as a feeding medium. ASIS used 20-fold higher concentrations of the carbon source, 25-fold higher ammonium sulfate, 2-fold higher dipotassium phosphate, and 5-fold higher of all other SIS components. For inoculation of each experiment, 1 L SIS was mixed with 50-ml of succinate grown culture. During operation, pH, dissolved oxygen, and temperature were monitored and controlled by external programmable logic controllers (ez-Control, Applikon Biotechnology). The pH was maintained between 6.95 and 7.05 with additions of 1 M $H_2SO_4$ or 10 M KOH; compressed air was used to provide aeration; temperature was maintained at 30° C. and ASIS medium was used to replenish consumed nutrients. Dissolved oxygen was maintained below 5% of saturated air by fixed aeration rate and feeding of ASIS medium.

Analytical Procedures

Analysis was performed on whole culture, or when noted, the culture was separated into cell and media fractions by centrifugation at 10,000×g for 15 min at 4° C. For analysis of samples from the fed-batch reactor, the samples were diluted with deionized water before lipid extraction. Lipid extraction with chloroform-methanol, esterification, gas chromatography-mass spectrometry (GC-MS) analysis and quantification were performed as previously described (Lennon et al. 2014) using 2.5 ml samples. For lipid phosphorus measurements, dried lipid extracts from 2.5 ml samples were digested with perchloric acid and assayed for phosphorus content (Rouser et al. 1970). Organic acids and sugars were analyzed by high performance liquid chromatography (HPLC) as described previously (Austin et al. 2015, Schwalbach et al. 2012). Samples were prepared by filtering aliquots of the culture with 0.22 µm filter before injection into the HPLC. Dry cell weight (DCW) was calculated by measuring chemical oxygen demand (COD) per liter and using the conversion factor of 1.47 gCOD/gDCW, which was determined from the composition of R. sphaeroides 2.4.1 biomass (Imam et al. 2011), adjusted for the lack of polyhydroxybutyrate in the parent and high-lipid mutant strains, $C_5H_{9.49}O_{2.23}N_{0.76}S_{0.01}P_{0.24}$. COD was analyzed using High Range COD Test Kits (HACH) according to the manufacturer's protocols. Media fractions were stained with 5 µg/ml Nile Red and fluorescence measured as described above. Lipopolysaccharide was measured using Pierce® LAL Chromogenic Endotoxin Quantitation Kit (Thermo Scientific) according to the manufacturer's protocol. To estimate lipopolysaccharide-associated fatty acid levels, the following conversion factors were used: 1 EU lipopolysaccharide=100 pg, 1 mol lipopolysaccharide=10,000 g, and R. sphaeroides lipopolysaccharide contains 5 acyl chains per molecule (Kaltashov et al. 1997). P-values for statistical significance were calculated by unpaired t test using Graph Pad QuickCalcs. For Coenzyme Q10 measurements, 500 µL of supernatant was mixed with either 500 µL ethanol or 500 µL 2 µM Coenzyme Q10 (Sigma Aldrich) and analyzed by LC-MS. The resulting LC-MS data were processed using TraceFinder 4.0 (Thermo Fisher Scientific).

Microscopy

For transmission electron microscopy whole mounts, 5 µL of cell suspension was applied to a transmission electron microscopy grid, post-stained with a negative stain (NanoW, Nanoprobes), blotted after 30 s, and let air dry. Transmission electron microscopy samples were examined using a Tecnai T-12 transmission electron microscope (FEI) operating at 120 kV with a LaB6 filament. Images were collected digitally with a 2x2K Ultrascan 1000 CCD (Gatan).

For structured illumination microscopy, cell culture was fixed by adding to an equal volume 4% paraformaldehyde, incubating for 45 min., and then washing two times with PBS. For staining, 2.5 µl cell suspension, 42.5 µl PBS buffer, and 5 µl Nile Red stock solution (1 mg/ml in ethanol) were mixed, incubated for 10 min, centrifuged, and resuspended in PBS. Samples were dropped onto polylysine coated glass coverslip. Super resolution fluorescence images were collected with a Zeiss Elyra 2 structured illumination microscope. The 63X oil immersion objective, 488 nm wavelength laser fluorescence excitation source, and emission 495-550 nm band pass filter were used. 75 or more cells per sample were measured by custom MATLAB scripts.

Strain Construction

Deletion of the ntrX and ntrY genes (RSP2839 and RSP2840) was carried out to create strain ΔNtrXYΔ0382 using the nonreplicable integration vector pK18mobsacB (Schafer et al. 1994). Both ORFs plus ~1 kb of flanking DNA sequences on either side were amplified from R. sphaeroides genomic DNA with primers containing XbaI and HindIII restriction sites. This PCR product was inserted into pK18mobsacB to create plasmid pKCL20. The entire coding regions of RSP2839 and RSP2840 were deleted from the plasmid by performing PCR with primers facing outward from the upstream end of RSP2839 and the downstream end of RSP2840 and ligation of the resulting fragment with T4 DNA ligase (Promega) to create pKCL21. E. coli S17-1 was used for conjugation of pKCL21 into R. sphaeroides Δ0382 (Yilmaz et al. 2010). Single crossovers were selected by kanamycin resistance, and double crossovers by loss of sucrose sensitivity. Strain ΔChrRΔNtrXYΔ0382 was created by deleting chrR using plasmid pJDN27, as described previously (Newman et al. 1999). Oligonucleotides used in these procedures are listed in Table 2. Deletion of RSP1200 to create strain 4120040382 was performed as described for strain ΔNtrXYΔ0382.

RNA Extraction, qRT-PCR, and Microarray Analyses

RNA extraction and microarray analysis were conducted as previously described (Dangel et al. 2009, Tavano et al. 2005). Briefly, RNA was isolated from exponential-phase R. sphaeroides cultures of Δ0382 and ΔNtrXYΔ0382. RNA isolation, cDNA synthesis, labeling, and hybridization to R. sphaeroides GeneChip microarrays (Affymetrix) were performed as previously described (Tavano et al. 2005). Microarray datasets were normalized by robust multichip average (RMA) to the $log_2$ scale with background adjustment and quantile normalization (Bolstad et al. 2003). Statistical analysis of normalized data to identify differentially expressed genes was done using the Limma package (Smyth 2004). Correction for multiple testing was done using Benjamini-Hochberg correction (Benjamini et al. 1995). All analyses were conducted in the R statistical programming environment (http://www.R-project.org).

Chromatin Immunoprecipitation Analysis

Chromatin immunoprecipitation was conducted as previously described (Imam et al. 2014). Briefly, R. sphaeroides cells (KL116) were grown aerobically in 500-ml cultures with bubbling, as described above. Cells were treated with 3 µM IPTG at inoculation and harvested at an $OD_{600}$ of ~0.35. Chromatin immunoprecipitation was conducted (Dufour et al. 2008) using polyclonal antibodies against the Myc epitope tag (ab9132; Abcam PLC). Immunoprecipitated DNA samples were PCR amplified, gel purified (size selection of ~200 bp), and sequenced at the UW Biotechnology Center sequencing facility, using the HiSeq 2500 sequencing system (I lumina, Inc.). The 50-bp sequence tags were mapped to the *R. sphaeroides* 2.4.1 genome (ftp://ftp.ncbi.nih.gov/genomes/Bacteria/Rhodobacter_sphaeroides_2_4_1_uid57653/) using SOAP version 2.21 (Li et al. 2009), allowing a maximum of 2 mismatches and no gaps.

Peaks were identified using MOSAiCS (Kuan et al. 2011) at a false discovery rate of 0.05. The MOSAiCS analysis was conducted as a two-sample analysis involving a pairwise comparison between with ChIP-seq data obtained from cells with Myc-tagged NtrX and ChIP-seq data obtained from WT cells (with no Myc-tagged proteins) immunoprecipitated using anti-Myc antibodies (used as the control). Motifs were identified from sequences under the peak regions using MEME (Bailey et al. 2009). Genomic locations with both a significant ChIP-seq peak and shared motifs were considered true binding sites.

Results

Identification of High-Lipid Mutants

*R. sphaeroides* has a native ability to increase its fatty acid content under low $O_2$ conditions (Lemmer et al. 2015). We sought to identify mutant strains that contain increased lipid levels at high $O_2$. We used a parent strain (Δ0382) that is unable to make the hydrophobic polymer polyhydroxybutyrate (Yilmaz et al. 2010) so we could use the fluorescence intensity of Nile Red-stained cells as a proxy of lipid content.

To identify potential high-lipid mutants, we screened a library of ~11,400 strains generated by Tn5-transposon mutagenesis. When fatty acid content of the top 30 Nile Red-staining mutants was quantified by GC-MS, we found ten strains (named HML01-10) that had a ≥1.5 increase in fatty acid content per cell when grown at high $O_2$ (FIG. 1). Two mutants (HML01 and HLM02) had a ~6-fold increase in fatty acids compared to the parent strain grown at high $O_2$ (FIG. 1); an increase twice that observed when the parent strain was grown at low $O_2$ (FIG. 1).

Genes and Processes Disrupted in High-Lipid Mutants

The transposon insertion sites identified in these ten high-lipid mutants (Table 3) did not reveal disruption of genes typically targeted for increasing lipid accumulation, such as central carbon metabolism or fatty acid biosynthesis and degradation (Janssen et al. 2014, Lennen et al. 2012). Instead, the genes inactivated in the high-lipid mutants encoded a diverse group of proteins, including a transcription factor, a chaperone, proteases, and putative secreted and cell envelope proteins.

TABLE 3

Transposon-insertion sites in high-lipid mutants.

| Strain | FA inc. | Insertion site | | ORF(s) disrupted with annotation | Sig. pep. | TM helix |
|---|---|---|---|---|---|---|
| HLM01 | 6.7 | Chr1: 1,471,645 | RSP2839 | NtrY sensor signal transduction histidine kinase | no | 5 |
|  |  |  | RSP2840 | NtrX response regulator | no | none |
| HLM02 | 6.1 | Chr1: 1,469,665 | RSP2840 | NtrX response regulator | no | none |
| HLM03 | 2.7 | Chr2: 274,987 | RSP3218 | Cob(II)yrinic acid a,c-diamide reductase/ 5,6-dimethylbenzimidazole synthase | no | none |
| HLM04 | 2.7 | Chr1: 2,814,885 | RSP1056 | Signal transduction histidine kinase | no | 2 |
| HLM05 | 2.6 | Chr1: 2,970,757 | RSP1200 | Uncharacterized conserved protein YkwD | yes | none |
| HLM06 | 1.8 | Chr1 938,456 | RSP1422 | Chromosome partitioning protein, ParB family | no | none |
| HLM07 | 1.7 | Chr1: 2,086,261 | RSP0355 | Periplasmic serine protease DegP | no | 1 |
| HLM08 | 1.7 | Chr1: 1,189,239 | RSP2545 | Stationary phase survival protein SurE | no | none |
|  |  |  | RSP2544 | Protein-L-isoaspartate O-methyltransferase (pcm) | no | none |
|  |  |  | RSP2543 | Peptidoglycan DD-endopeptidase | yes | none |
| HLM09 | 1.5 | Chr1: 1,395,725 | RSP2745 | Stealth protein | no | none |
| HLM10 | 1.5 | Chr1: 916,649 | RSP2293 | ClpA, ATP-dependent Clp protease ATP-binding subunit | no | none |

Strains are sorted from highest to lowest fold increase in total fatty acid (FA inc.) compared to the parent strain. The presence of a signal peptide (Sig. pep.) was predicted by SignalP 4.1 http://www.cbs.dtu.dk/services/SignalP/, and the number of predicted transmembrane helixes (TM helix) was determined by TMHMM Server v. 2.0 http://www.cbs.dtu.dk/services/TMHMM/.

Figure 2:
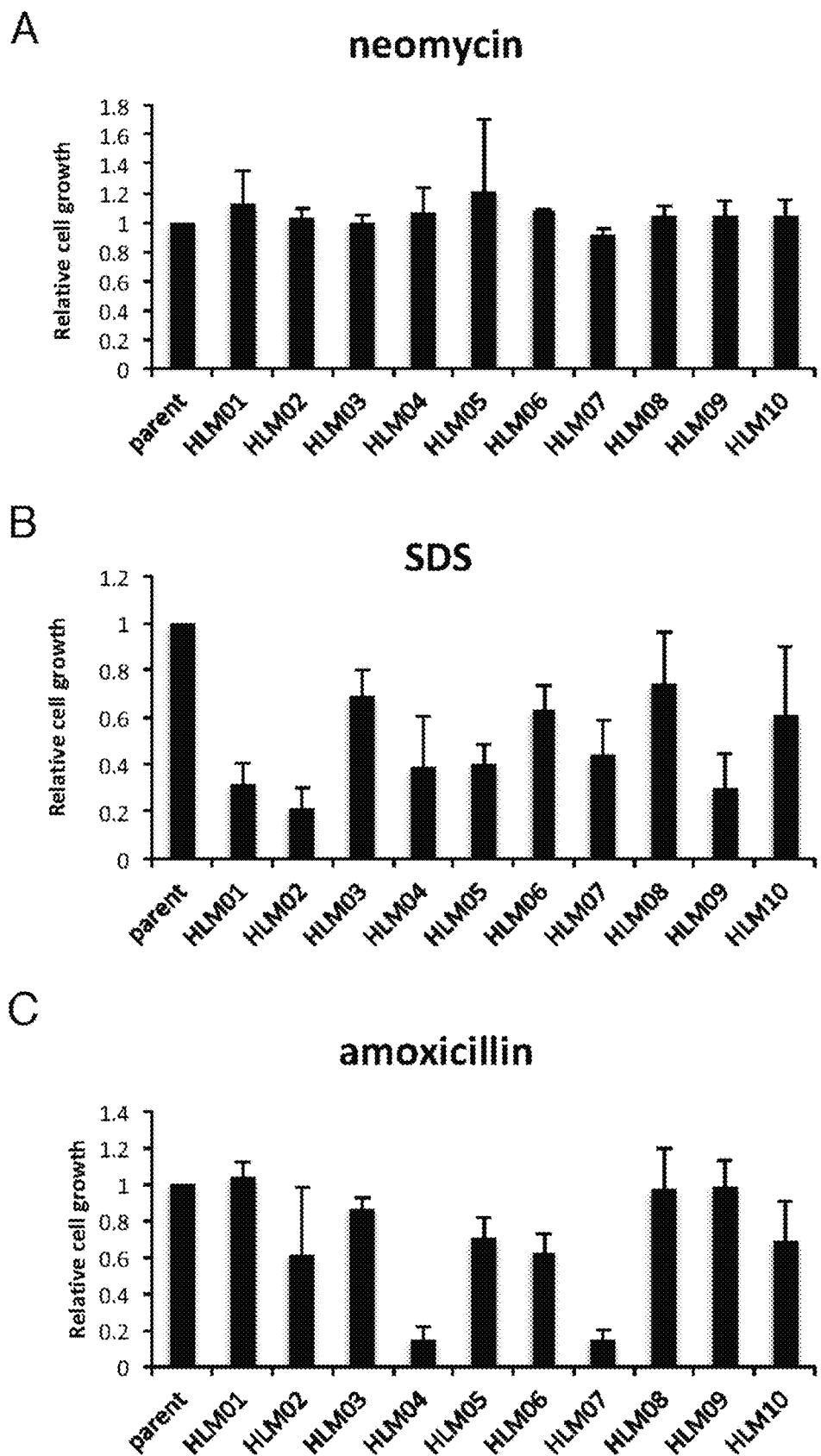
FIG. 2. Relative fitness of high-lipid (HL) mutants in the presence of indicated compounds (A, neomycin; B, sodium dodecyl sulfate (SDS); C, amoxicillin) compared to the parent strain. Data shown represents the mean of three cultures ±standard deviation.

We used chemical sensitivity analysis to characterize what cellular processes were affected in the high-lipid strains. To do this, we tested the impact on growth of a set of compounds that affect protein synthesis, folic acid biosynthesis, membrane integrity, peptidoglycan biosynthesis, and DNA integrity (Tables 4A and 4B). For some compounds, such as the protein synthesis inhibitor neomycin, we saw no growth difference of the high-lipid mutants compared to the parent strain (FIG. 2, panel A). For other compounds, including the detergent sodium dodecyl sulfate (SDS), many or all of the high-lipid mutants showed increased sensitivity (FIG. 2, panel B); while for others, such as the peptidoglycan-active antibiotic amoxicillin, we saw increased sensitivity in one or more high-lipid mutants compared to the parent strain (FIG. 2, panel C). By analyzing the relative growth of all the high-lipid mutants treated with compounds having common cellular targets, we observed that these strains were most sensitive to compounds active on the cell or outer membranes (62% of the parent cell growth).

TABLE 4A

Compounds used in chemical sensitivity analysis and characterstics thereof.

| Drug | Family | Group | General Target |
|---|---|---|---|
| Clotrimazole | azoles | imidizoles | cell envelope |
| Deoxycholate | detergents | anionic detergent | cell envelope |
| Monensin | ionophores | polyether | cell envelope |
| Polymyxin b | peptides | cationic detergent | cell envelope |
| SDS | detergents | detergents | cell envelope |
| Triton X-100 | detergents | detergents | cell envelope |
| Valinomycin | ionophores | dodecadepsipeptide | cell envelope |
| Amoxicillin | beta-lactams | penicillins | cell envelope |
| Ampicillin | beta-lactams | penicillins | cell envelope |
| Aztreonam | beta-lactams | monobactams | cell envelope |
| Bacitracin | peptides | peptides | cell envelope |
| Ceftriaxone | beta-lactams | cephalosporine | cell envelope |
| Cephalexin hydrate | beta-lactams | cephalosporine | cell envelope |
| D-cycloserine | amino acid derivative | amino acid derivative | cell envelope |
| Meropenem | beta-lactam | carbapenem | cell envelope |
| Furazolidone | furans | furans | DNA |
| MMS | alkylating agents | alkylating agents | DNA |
| Ciprofloxacin | quinilones | quinilones | DNA |
| Levofloxacin | quinilones | quinilones | DNA |
| Nalidixic acid | quinilones | quinilones | DNA |
| Ofloxacin | quinilones | quinilones | DNA |
| Hydroxyurea | chemotherapeutics | deoxyribonucleotide | DNA |
| Nitrofurantoin | furans | furans | DNA |
| Acrylic acid | organics | organics | fatty acid metabolism |
| Methotrexate | chemotherapeutics | DHFR inhibitor | folic acid biosynthesis |
| Sulfamethoxazole | chemotherapeutics | sulfonamides | folic acid biosynthesis |
| Sulfanilamide | chemotherapeutics | sulfonamides | folic acid biosynthesis |
| Trimethoprim | pyrimidines | DHFR inhibitor | folic acid biosynthesis |
| Doxicycline | tetracycline antibiotics | tetracyclines | protein synthesis |
| Neomycin | aminoglycosides | aminoglycosides | protein synthesis |
| Spectinomycin | aminoglycosides | aminoglycosides | protein synthesis |
| Tetracycline | tetracycline antibiotics | tetracyclines | protein synthesis |
| Tigecycline | tetracycline antibiotics | tetracyclines | protein synthesis |
| Tobramycin | aminoglycosides | aminoglycosides | protein synthesis |
| Azithromycin | MLS | macrolides | protein synthesis |
| Chloramphenicol | Peptidyl transferase | amphenicols | protein synthesis |
| Clarithromycin | MLS | macrolides | protein synthesis |
| Erythromycin | MLS | macrolides | protein synthesis |
| Florfenicol | Peptidyl transferase | amphenicols | protein synthesis |
| Lincomycin | MLS | lincoamides | protein synthesis |
| Thiamphenicol | Peptidyl transferase | amphenicols | protein synthesis |
| Fuscidic acid | fusidanes | fusidanes | protein synthesis |
| Rifampicin | rifamycins | rifamycins | RNAP |
| Rifaximin | rifamycins | rifamycins | RNAP |
| NaCl | stress | osmotic stress | stress |
| Hydrogen peroxide | stress | oxidative stress | stress |
| Plumbagin | quinones | naphthoquinones | stress |
| EDTA | stress | stress | stress |
| Sulbactam | beta-lactams | | beta-lactamase inhibitor |

TABLE 4B

Compounds used in chemical sensitivity analysis and characterstics thereof.

| Drug | Process Target | Function Target | Gene Target | Conc. |
|---|---|---|---|---|
| Clotrimazole | cell membrane | membrane permeability/ sterol biosynthesis | | 4 µg/ml |
| Deoxycholate | cell membrane | membrane permeability | | 0.1 mg/ml |
| Monensin | cell membrane | cation transport | | 100 µg/ml |
| Polymyxin b | cell membrane | membrane permeability | | 0.4 µg/ml |

TABLE 4B-continued

Compounds used in chemical sensitivity analysis and characteristics thereof.

| Drug | Process Target | Function Target | Gene Target | Conc. |
|---|---|---|---|---|
| SDS | cell membrane | membrane permeability | | 25 µg/ml |
| Triton X-100 | cell membrane | membrane permeability | | 0.1% |
| Valinomycin | cell membrane | cation transport | | 10 µg/ml |
| Amoxicillin | peptidoglycan | PG biosynthesis (transpeptidation) | multiple PBPs | 5 µg/ml |
| Ampicillin | peptidoglycan | PG biosynthesis (transpeptidation) | multiple PBPs | 2 µg/ml |
| Aztreonam | peptidoglycan | PG biosynthesis (transpeptidation) | PBP3 (FtsI) | 20 µg/ml |
| Bacitracin | peptidoglycan | C55 PP pyrophosphatases | BacA, YbjG, PgpB and YeiU | 40 µg/ml |
| Ceftriaxone | peptidoglycan | PG biosynthesis (transpeptidation) | multiple PBPs | 2 µg/ml |
| Cephalexin hydrate | peptidoglycan | PG biosynthesis (transpeptidation) | multiple PBPs | 250 µg/ml |
| D-cycloserine | peptidoglycan | PG biosynthesis (Ala racemase + ligase) | Alr, DadX, DdlA/B | 2 µg/ml |
| Meropenem | peptidoglycan | PG biosynthesis (transpeptidation) | multiple PBPs | 0.5 µg/ml |
| Furazolidone | DNA crosslinking | DNA crosslinking | | 5 µg/ml |
| MMS | DNA damage | methylation | | 0.002% |
| Ciprofloxacin | DNA supercoiling | DNA gyrase/topoisomerase | GyrA/TopA | 0.02 µg/ml |
| Levofloxacin | DNA supercoiling | DNA gyrase/topoisomerase | GyrA/TopA | 0.004 µg/ml |
| Nalidixic acid | DNA supercoiling | DNA gyrase/topoisomerase | GyrA/TopA | 0.4 µg/ml |
| Ofloxacin | DNA supercoiling | DNA gyrase/topoisomerase | GyrA/TopA | 0.02 µg/ml |
| Hydroxyurea | DNA synthesis | ribonucleotide reductase | | 5 mM |
| Nitrofurantoin | mulptiple | | | 10 µg/ml |
| Acrylic acid | beta-oxidation | | | 200 µg/ml |
| Methotrexate | folic acid biosynthesis | dihydrofolate reductase | FolA/FolM | 2 µg/ml |
| Sulfamethoxazole | folic acid biosynthesis | dihydropteroate reductase | FolP | 100 µg/ml |
| Sulfanilamide | folic acid biosynthesis | dihydropteroate reductase | FolP | 100 µg/ml |
| Trimethoprim | folic acid biosynthesis | dihydrofolate reductase | FolA/FolM | 2 µg/ml |
| Doxicycline | 30S ribosome | tRNA binding | | 0.01 µg/ml |
| Neomycin | 30S ribosome | translation initiation | | 10 µg/ml |
| Spectinomycin | 30S ribosome | translation initiation | | 1 µg/ml |
| Tetracycline | 30S ribosome | tRNA binding | | 0.02 µg/ml |
| Tigecycline | 30S ribosome | tRNA binding | | 50 µg/ml |
| Tobramycin | 30S ribosome + 50S ribosome | prevents 70S ribosome formation | | 0.4 µg/ml |
| Azithromycin | 50S | ribosome transpeptidation | | 0.02 µg/ml |
| Chloramphenicol | 50S ribosome | peptidyl transferase | | 0.5 µg/ml |
| Clarithromycin | 50S ribosome | transpeptidation | | 2 µg/ml |
| Erythromycin | 50S ribosome | transpeptidation | | 0.5 µg/ml |
| Florfenicol | 50S ribosome | peptidyl transferase | | 0.5 µg/ml |
| Lincomycin | 50S ribosome | transpeptidation | | 20 µg/ml |
| Thiamphenicol | 50S ribosome | peptidyl transferase | | 0.1 µg/ml |
| Fuscidic acid | G factor | ribosome translocation | FusA | 1 µg/ml |
| Rifampicin | RNAP | RNAP exit channel | RpoB | 0.02 µg/ml |
| Rifaximin | RNAP | RNAP exit channel | RpoB | 0.01 µg/ml |
| NaCl | osmotic stress | | | 50 mM |
| Hydrogen peroxide | oxidative stress | | | 5 mM |
| Plumbagin | oxidative stress | | | 0.4 µg/ml |
| EDTA | | | | 0.4 uM |
| Sulbactam | | beta-lactamase | | 5 µg/ml |

Figure 3:
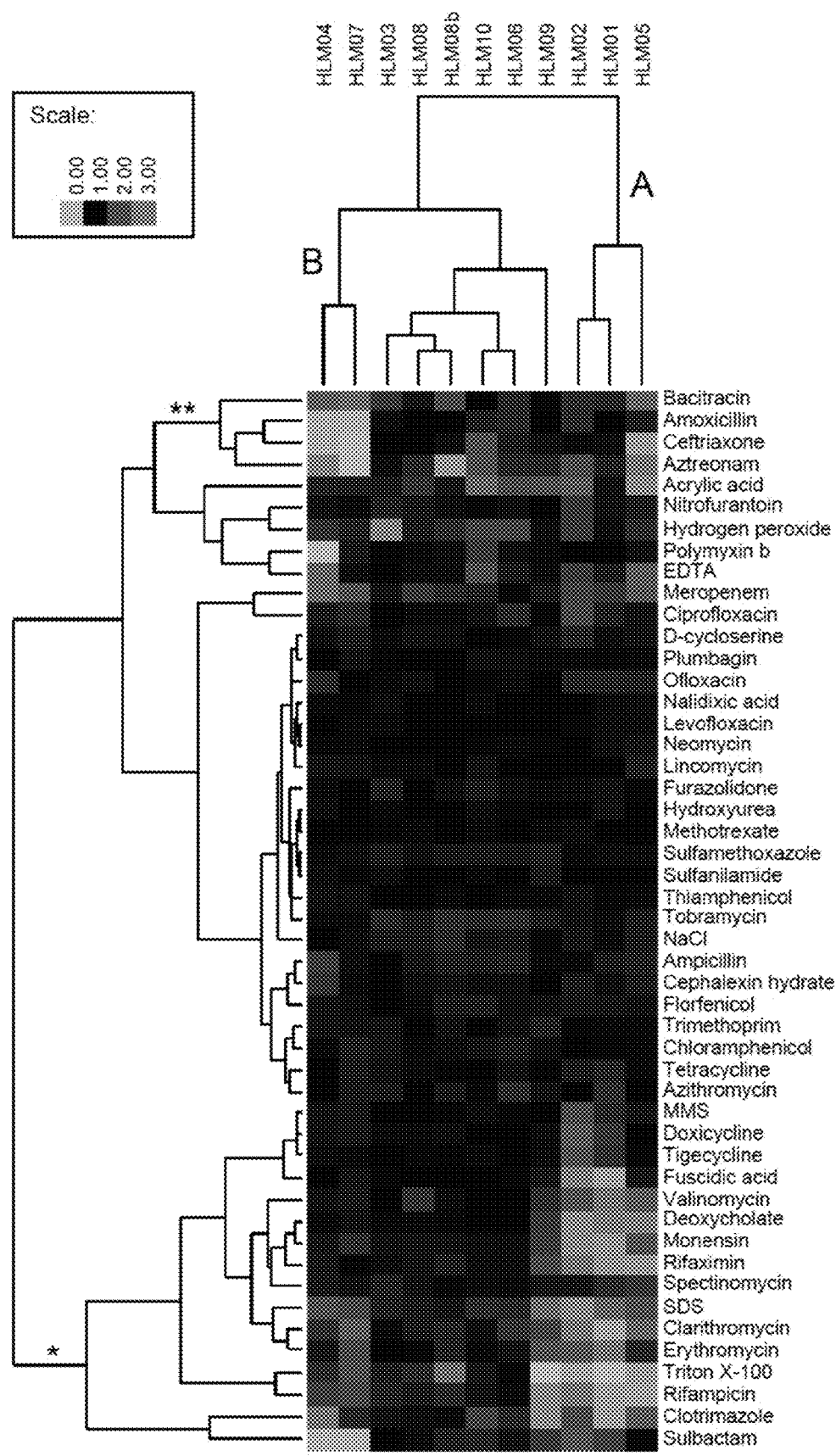
FIG. 3. Chemical sensitivity analysis of high-lipid (HL) mutants. Cluster A shows increased sensitivity to a group of compounds that report on membrane integrity (*). Cluster B shows increased sensitivity to a group of peptidoglycan active compounds (**). The color scale indicates relative fitness compared to the parent strain. A value of 1 (black) indicates no change relative to the parent, <1 (blue) indicates increased sensitivity to the compound, >1 (yellow) indicates increased resistance to the compound.

Clustering the mutants and the compounds based on relative growth (FIG. 3) showed that strains HLM01, HLM02 and HLM05 formed a cluster separate from the other strains (labeled A in FIG. 3). Two of these strains, HLM01 and HLM02, have mutations in genes that are predicted to act in the same pathway (the NtrXY two-component system; Table 3), so it is not surprising that they behave similarly in this analysis. The third strain in this cluster (HLM05) has a mutation in a pathway of no known relation to NtrXY (a conserved uncharacterized membrane protein). These three high-lipid mutants are sensitive to a cluster of compounds (marked * in FIG. 3) containing membrane-targeting detergents and ionophores, as well as the RNA polymerase inhibitors rifampicin and rifaximin, and the protein synthesis inhibitors erythromycin and clarithromycin. The later 4 compounds do not target the membrane, but it is known that decreased membrane integrity can sensitize cells to these hydrophobic drugs (Vaara 1993). Thus, these three high-lipid mutants share increased sensitivity to compounds that are associated with decreased membrane integrity.

A second cluster of high-lipid mutants (HLM04 and HLM07; labeled B in FIG. 3) share increased sensitivity to a group of compounds that inhibit peptidoglycan biosynthesis (amoxicillin, aztreonam, bacitracin, and ceftriaxone; marked ** in FIG. 3). This suggests that the mutations in these two high-lipid strains alter the integrity of the peptidoglycan cell wall.

The appearance of distinct sets of high-lipid mutants with sensitivities to different classes of bioactive compounds suggests that there may be multiple mechanisms causing increased lipid production. While the other high-lipid mutants (HLM03, HLM06 and HLM8-10) showed increased sensitivity to other compounds (e.g., hydrogen peroxide for HLM03), this analysis did not predict specific processes that might be impaired in these strains. In sum, the chemical sensitivity analysis showed that many of the high-lipid mutants had increased sensitivity to compounds that act at the cell envelope, either on the membrane or the cell wall.

Morphological Changes in High-Lipid Mutants

Figure 4:
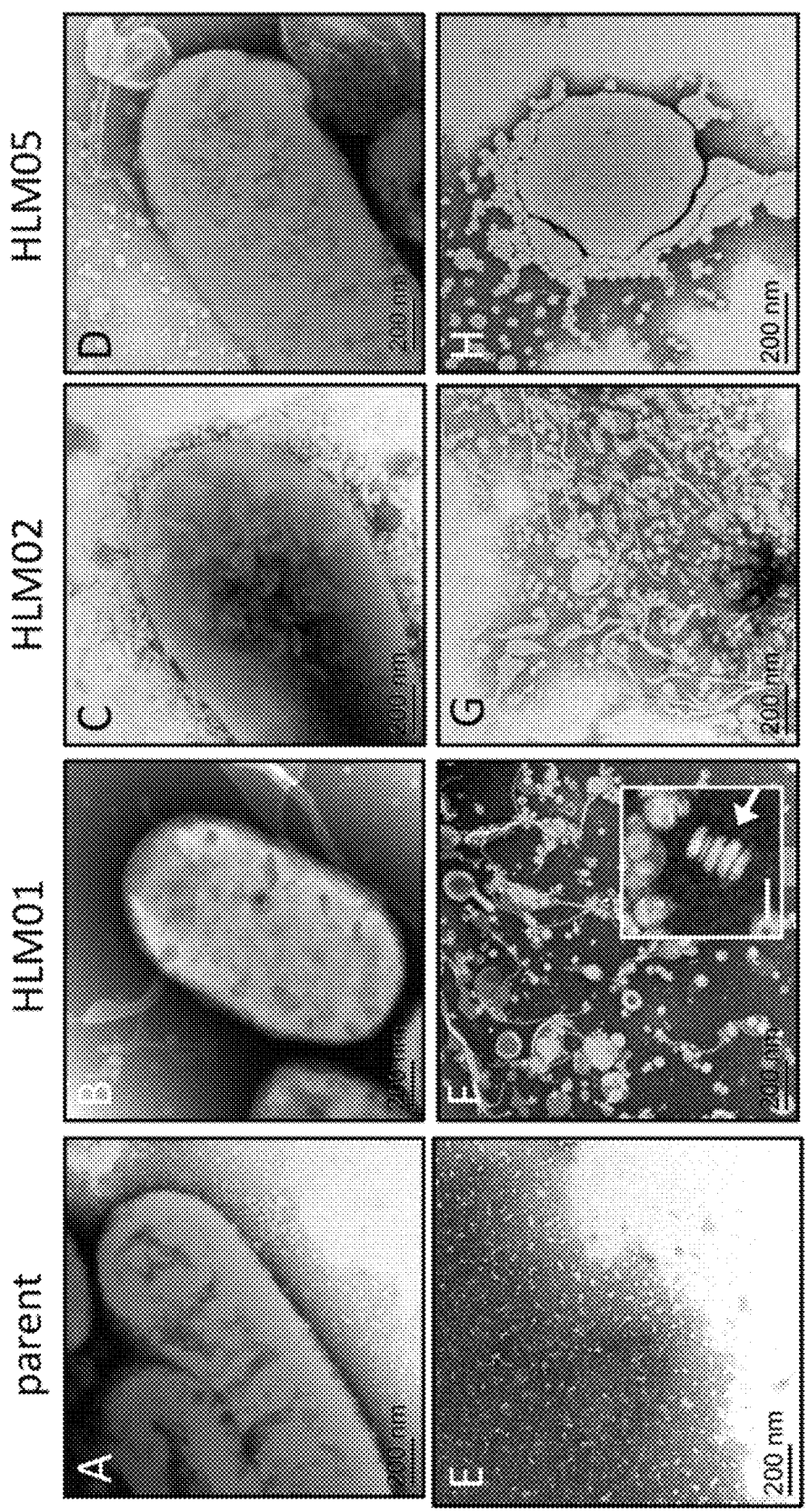
FIG. 4. Transmission electron microscopy micrographs of whole mounts of the parent strain (A, E) and high-lipid (HL) mutants (B-D, F-H). The lower row of panels (E-H) shows views of extracellular material from these strains. Similar micrographs of the parent strain and other HL mutants are shown in FIGS. 5 and 6. Arrow in the inset (F) indicates a stacked structure typical of liposomes; scale bar for this inset panel is 50 nm.
Figure 5:
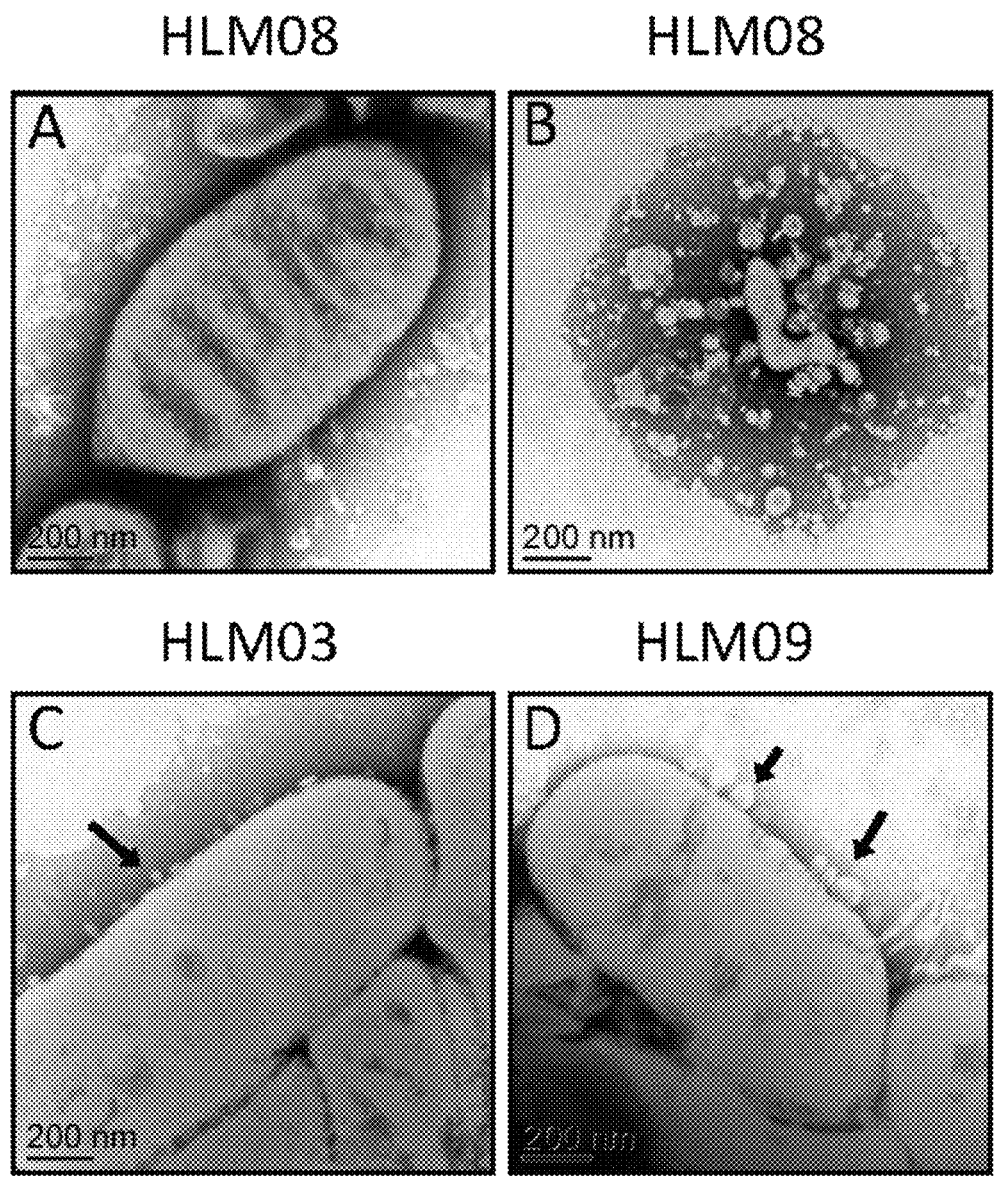
FIG. 5. Transmission electron microscopy micrographs of whole mounts of indicated high-lipid (HL) mutants. A and B) HLM08 has extracellular material, irregular shaped particles of varied sizes as well as stacked structures. C) HLM03 and D) HLM09 have structures extending off the cell surface (arrows).

Based on the above finding, we used transmission electron microscopy of whole mount cells to assess morphologic changes in the cell envelope of the high-lipid strains. This analysis revealed that those high-lipid mutants which are sensitive to membrane-active compounds (Cluster A; HLM01, HLM02, HLM05) produced a large amount of extracellular material (FIG. 4, panels F-H) and irregular shaped particles adjacent to the cells (FIG. 4, panels B-D), that were not seen in the parent strain (FIG. 4, panels A and E). Samples of HLM05 had round extracellular structures in the range of 20-50 nm (FIG. 4, panel H), while samples from HLM01 and HLM02 contained round and irregular structures, as well as stacked structures often observed when liposomes are in aqueous solution (FIG. 4, panels F and G) (Zhang et al. 2011). The mutations in HLM01 and HLM02 are predicted to inactivate proteins in the same two-component (NtrXY) signal transduction pathway, so it is not surprising to find that they have similar morphological changes. One additional high lipid mutant (HLM08) produced extracellular material, some of which was organized in stacked structures (FIG. 5, panels A and B). Two other high-lipid mutants (HLM03 and HLM09) did not have a significant amount of extracellular material, but instead had structures that appeared to bulge off of, but remain attached to, the cell surface (FIG. 5, panels C and D). The membrane protrusions and secretions seen by transmission electron microscopy in HLM01-03, HLM05 and HLM08-09 are consistent with alterations in the cell envelope predicted for some of these strains by chemical sensitivity analysis.

Figure 6:
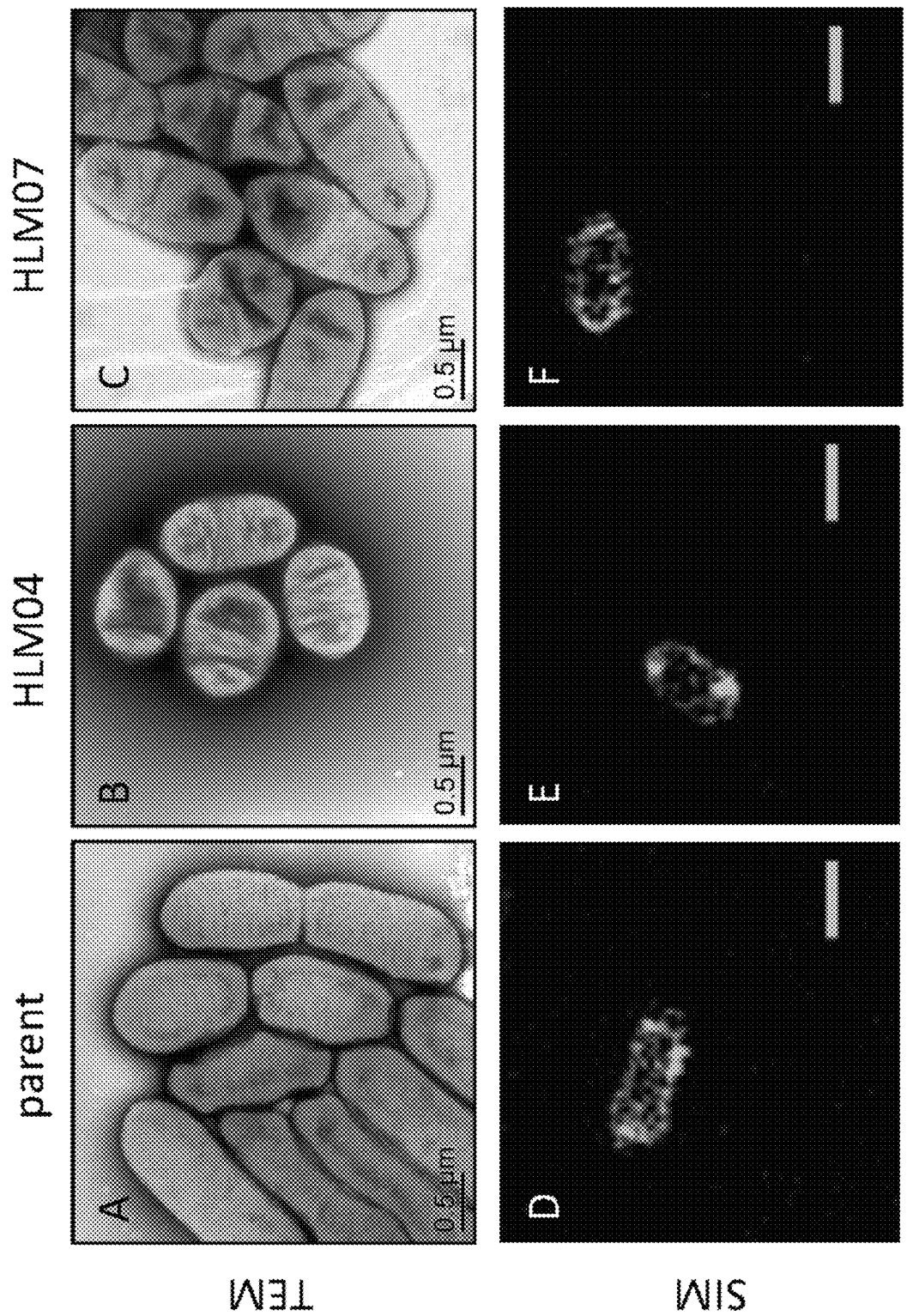
FIG. 6. Cell shape of high-lipid (HL) mutants HLM04 and HLM07 compared to the parent strain. A-C) Transmission electron microscopy micrographs of cell whole mounts. D-F) Super-resolution structured illumination microscopy images of Nile Red-stained cells. Scale bars for (D-F) measure 1 μm.
Figure 7:
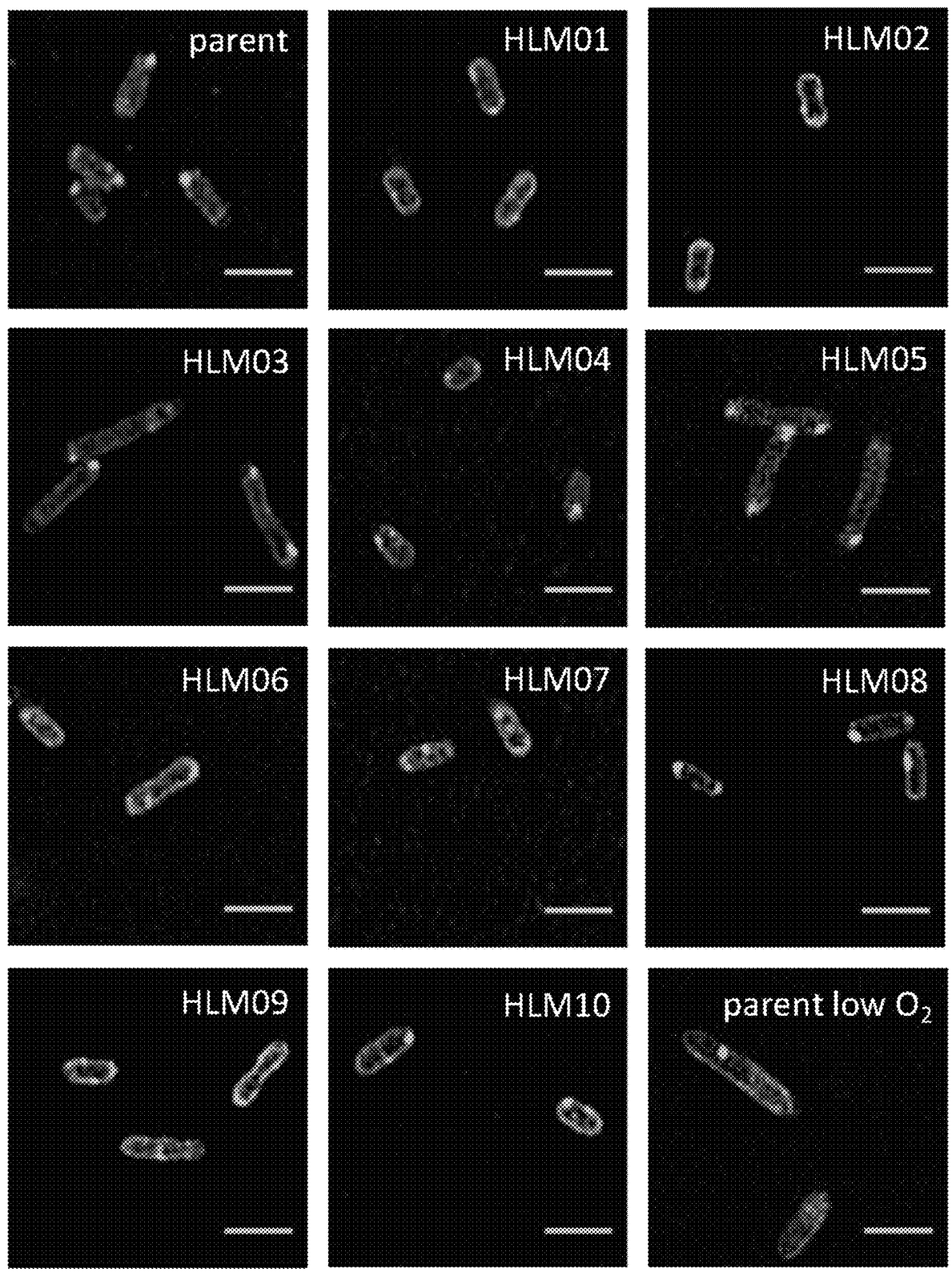
FIG. 7. Super-resolution structured illumination microscopy images of Nile Red-stained parent and high-lipid (HL) mutant cells. Representative fields are shown from images used to measure cell dimensions. Scale bar length=2 μm.

Transmission electron microscopy of the two high-lipid mutants that are sensitive to cell-wall active compounds (Cluster B; HLM04 and HLM07) did not show accumulation of extracellular material, but instead suggested that they had a different shape than the parent strain (FIG. 6, panels A-C). Measurement of cell dimensions of HLM04 and HLM07 by super-resolution structured illumination microscopy (FIG. 6, panels D-F, and FIG. 7) showed that they were shorter than the parent cells but that the cell width was similar (Table 5). Overall, structured illumination microscopy analysis showed that 8 out of the 10 high-lipid mutants had differences in cell length and/or width compared to the parent strain (Table 5), providing additional support for the hypothesis that changes in the cell envelope was a common feature among many of these strains.

TABLE 5

Measurements of cell length and width of Nile Red-stained cells by super resolution fluorescence microscopy.

| Strain | Length (μm) | Width (μm) | N difference |
|---|---|---|---|
| Parent | 1.72 ± 0.38 | 0.72 ± 0.05 | 75 |
| HLM01 | 1.70 ± 0.41 | 0.76 ± 0.06* | 259 wider |
| HLM02 | 1.68 ± 0.46 | 0.73 ± 0.05 | 205 |
| HLM03 | 2.32 ± 0.51* | 0.71 ± 0.05 | 91 longer |
| HLM04 | 1.22 ± 0.22* | 0.73 ± 0.05 | 148 shorter |
| HLM05 | 2.36 ± 0.49* | 0.75 ± 0.06** | 111 longer and wider |
| HLM06 | 1.79 ± 0.36 | 0.73 ± 0.06 | 88 |
| HLM07 | 1.41 ± 0.27* | 0.73 ± 0.06 | 86 shorter |
| HLM08 | 1.73 ± 0.33 | 0.67 ± 0.06* | 102 narrower |
| HLM09 | 1.83 ± 0.46 | 0.70 ± 0.05** | 126 narrower |
| HLM10 | 1.60 ± 0.30*** | 0.74 ± 0.06 | 104 shorter |
| Parent low $O_2$ | 2.27 ± 0.72* | 0.83 ± 0.08* | 83 longer and wider |

Measurements are expressed as mean ± standard deviation, with N = number of cells measured. Significant differences compared to the parent strain are indicated, *$p < 0.0001$, $p < 0.002$, *$p < 0.03$.

Lipid Secretion by High-Lipid Mutants

Figure 8:
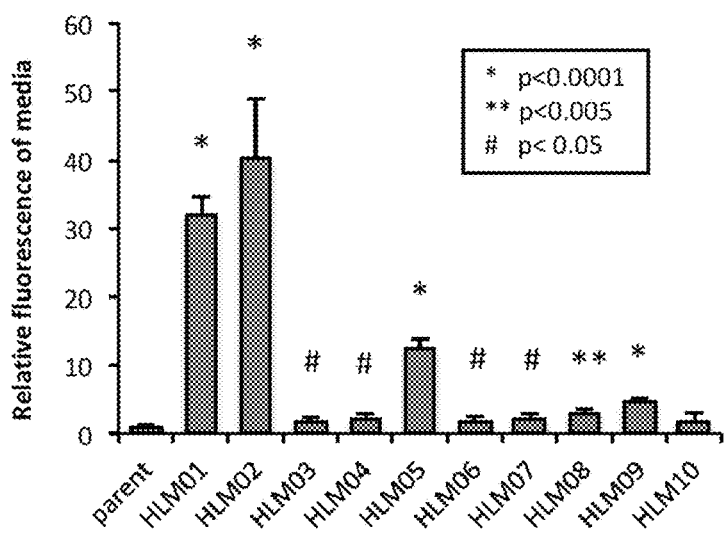
FIG. 8. Analysis of the extracellular material of parent and high-lipid (HL) mutant strains. A) Nile red staining of the media from parent and HL mutant cultures. B) Fatty acid content of cell and media fractions of parent and HL mutant cultures. C) Percent of total fatty acids found in media fraction for data shown in (B). Data shown represents the mean of three or more independent cultures ±standard deviation. P values are for the difference of each HL mutant compared to the parent strain.
Figure 8:
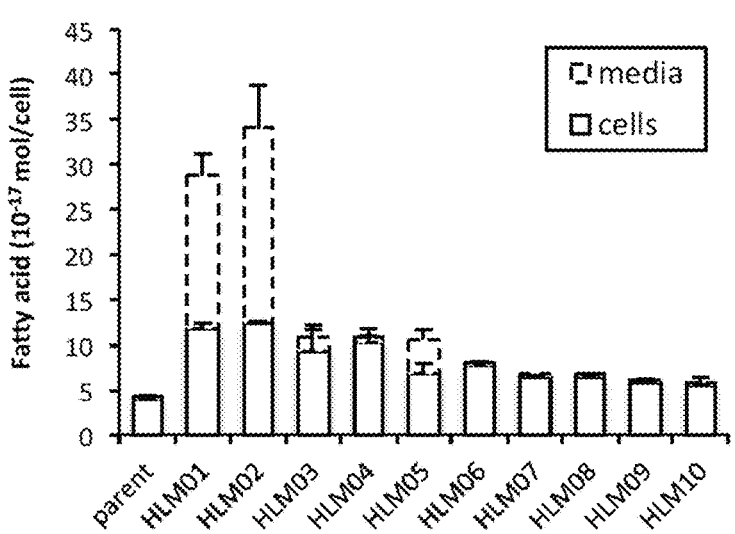
Figure 8:
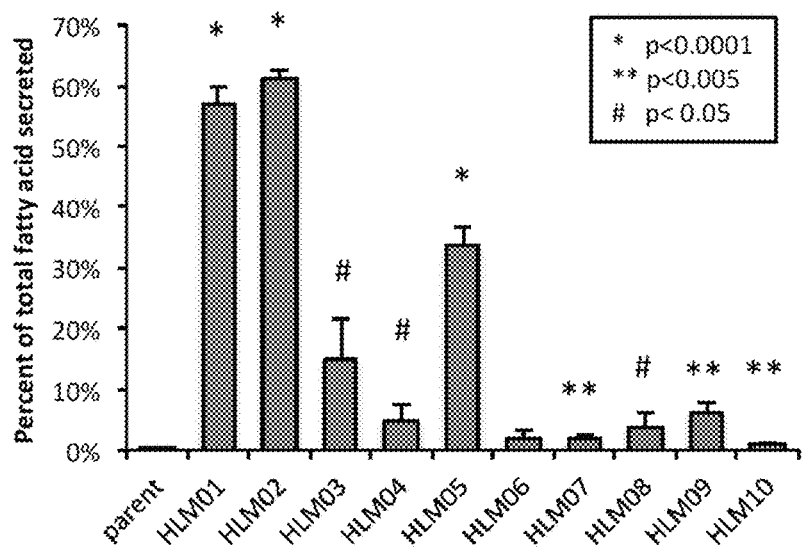

Since we observed materials on the surface or outside of the high-lipid mutants by transmission electron microscopy, we stained the media with Nile Red to test for the presence of hydrophobic compounds. We found that media from all but one of the high-lipid mutants had increased Nile Red staining compared to that of the parent strain (FIG. 8, panel A). In particular, Cluster A strains (HLM01, HLM02, and HLM05) that had the highest amount of extracellular material by transmission electron microscopy had 13-40-fold increases in fluorescence compared to that of the parent strain (FIG. 8, panel A).

We tested if the increased Nile Red staining of the high-lipid mutants was due to the presence of extracellular lipid by quantifying fatty acid levels in the cells and culture supernatant. For the parent strain a small level (0.2%) of the fatty acid in the total culture (cells plus supernatant) was present in the media (FIG. 8, panels B and C), likely representing the background from incomplete separation of cells and media. In contrast, 9 of the 10 high-lipid mutants had a statistically significant increase in fatty acid in the media compared to parent strain. Consistent with the extracellular material observed by transmission electron microscopy, HLM01, HLM02 and HLM05 had the highest percent (≥35%) of the total fatty acid present in the media (FIG. 8, panels B and C).

Figure 9:
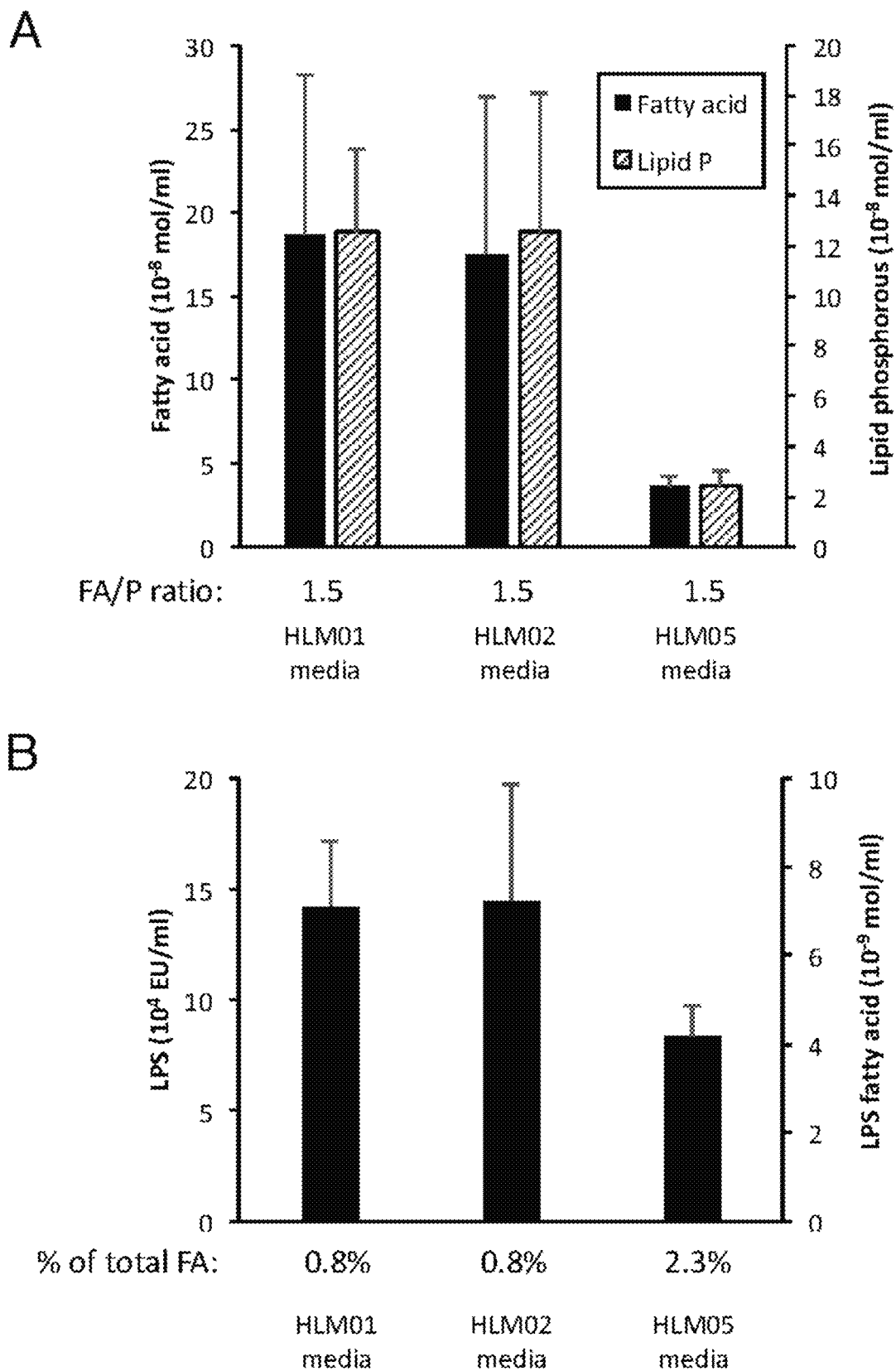
FIG. 9. Analysis of extracellular material of HLM01, HLM02, and HLM05 for phospholipid and lipopolysaccharide (LPS) content. A) Fatty acid and lipid phosphorous levels in the media with molar ratios listed below the graph. B) LPS content of the media, with conversion to estimated LPS-associated fatty acids on the secondary vertical axis. The relative contribution of LPS-associated fatty acids to the total amount of secreted fatty acids is shown below the graph. Data shown represents the mean of four or more independent cultures ±standard deviation.

To further characterize the secreted material, we analyzed fatty acid and lipid phosphorus levels in the culture supernatants of HLM01, HLM02 and HLM05. For all three of these high-lipid mutants, the fatty acid to lipid phosphorus ratio of the supernatants was 1.5, close to the 2:1 ratio expected for phospholipid (FIG. 9, panel A). We also quantified lipopolysaccharide in the supernatants and found that lipopolysaccharide-associated fatty acids accounted for a small amount of the secreted fatty acids, less than 1% for HLM01 and HLM02 (FIG. 9, panel B). Therefore, we conclude that the secreted lipid is composed primarily of phospholipid.

Fatty Acid Productivity of a High-Lipid Secreting Strain

The extracellular accumulation of lipid by some high-lipid mutants could make them attractive for production of biofuels or bioproducts. We chose HLM02, for further characterization since it is one of two high-lipid mutants with the highest level of extracellular lipid.

Figure 10:
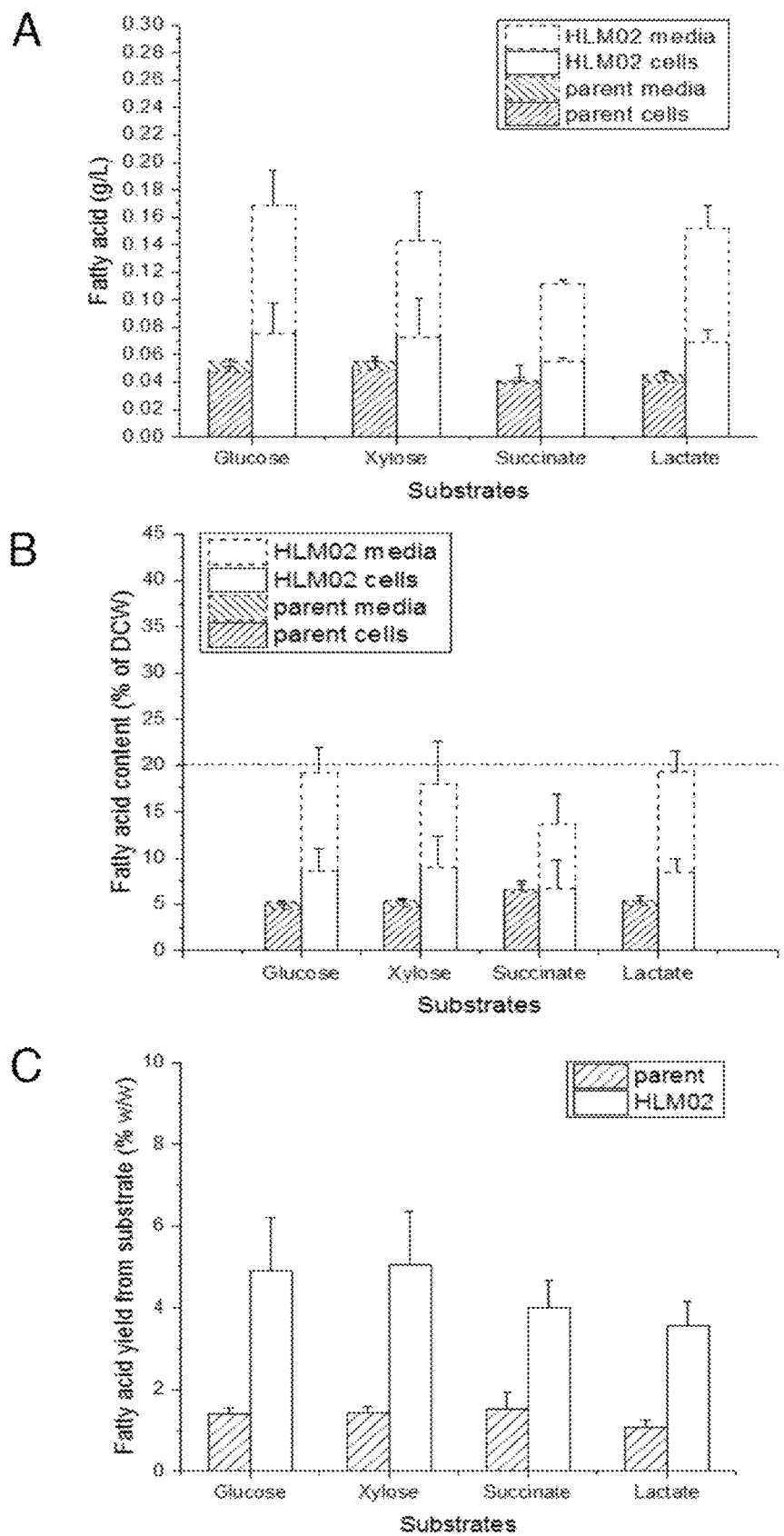
FIG. 10. Fatty acid production by parent and HLM02 strains in batch cultures with one of four different carbon sources. A) Fatty acid productivity per culture volume and B) fatty acid content as a percent of dry cell weight (DCW). C) Fatty acid yield per carbon substrate consumed. Data shown represents the mean of three or more independent cultures ±standard deviation.

When we compared the fatty acid productivity (grams fatty acid per liter) of HLM02 cultures to that of the parent strain, they produced similar amounts of intracellular lipid (FIG. 10, panel A), when grown in batch culture with succinate as a carbon source. However, if one includes cellular and secreted lipids, fatty acid productivity was 2.7-fold higher in the HLM02 culture than the parent strain (FIG. 10, panel A; p<0.001). This increase in culture fatty acid productivity for HLM02 is smaller than the increase observed when measuring fatty acid content per cell (FIG. 1) because in batch cultures HLM02 does not achieve as high a cell density as the parent strain.

R. sphaeroides can metabolize a wide variety of carbon substrates (Imam et al. 2011), so we also tested fatty acid productivity in batch cultures containing a different organic acid (lactate, which is a common fermentation byproduct (Agler et al. 2011)), as well as sugars (glucose and xylose, which are abundant in cellulosic biomass hydrolysates (Lau et al. 2009)). Fatty acid productivity was increased in HLM02 compared to the parent strain when using each of these carbon sources (FIG. 10, panel A), with ~50-55% of the total fatty acid found in the culture supernatant. For each of the carbon sources tested, the cellular fatty acids represented 5-6% of the dry cell weight (DCW) in the parent and HLM02 strain. However, when the secreted lipid was included, the total fatty acid content of HLM02 increased to 15-20% of the DCW (FIG. 10, panel B).

Another common metric is product yield per amount of carbon substrate consumed. For the parent strain, the total fatty acid yield from each of the carbon sources tested was 1.0-1.4% (w/w) (FIG. 10, panel C). For the HLM02 mutant, the fatty acid yield increased 2.9-3.7-fold (p≤0.01 for all substrates) to 3.5-5.0% (w/w) (FIG. 10, panel C). There was no significant difference in fatty acid yield of HLM02 between the different carbon sources tested. The maximum theoretical yield, if all of the carbon substrate were converted into fatty acids by HLM02, is ~35% for glucose, xylose, and succinate, and ~28% percent for lactate. Thus, the fatty acid yields measured for HLM02 in batch culture represent 11-14% of the maximum theoretical yield on these carbon sources.

In addition to the four carbon sources described above, acetate was also tested for the production of fatty acid. After 48 hours cultivation, 0.03 g/L fatty acid was produced by the HLM02 mutant and 55% of the produced fatty acid was in the supernatant. Using acetate as carbon source yielded a slower growth rate and thus a lower amount of fatty acid at the time of harvesting, but the cells excreted a comparable proportion of the fatty acids into media.

Extracellular Production of Novel Fatty Acids

The utility of a lipid-secreting mutant would be increased if one could produce increased levels of novel fatty acids extracellularly. R. sphaeroides has recently been reported to make a furan-containing fatty acid, 10,13-epoxy-11-methyl-octadecadienoic acid (19Fu-FA) that is potentially valuable due to its antioxidant activity (Lemke et al. 2014). Elevated levels of 19Fu-FA are found in a mutant that lacks the ChrR anti-sigma factor (Lemke et al. 2014). In order to test if R. sphaeroides could secrete 19Fu-FA, we constructed a strain that lacked the genes disrupted in HLM01 and HLM02 (ΔNtrXYΔ0382) and chrR (ΔChrRΔNtrXYΔ0382). We found that the ΔChrRΔNtrXYΔ0382 strain made 19Fu-FA as ~3-4% of the total fatty acids in both the cellular and supernatant fractions (Table 6). From this, we conclude that the high-lipid mutants can be used to secrete novel fatty acids as well as those normally present in wild-type cells.

TABLE 6

Relative fatty acid content of R. sphaeroides ΔChrRΔNtrXYΔ0382.

| | Strain | | | | | |
|---|---|---|---|---|---|---|
| | C16:1 | C16:0 | C18:1 | C18:0 | 19M-UFA | 19Fu-FA |
| Cells | 3.2 (0.8) | 11.3 (0.8) | 69.2 (2.2) | 12.5 (0.7) | 0.8 (0.6) | 2.9 (0.5) |
| Supernatant | 0.9 (0.8) | 13.2 (2.1) | 64.5 (6.6) | 15.9 (3.0) | 1.3 (0.3) | 4.2 (1.8) |

Percentage composition of the individual fatty acid species. 11-methyl-octadecanoate (19M-UFA), 10,13-epoxy-11-methyl-octadecadienoic acid (19Fu-FA). Standard deviation in parentheses. N = 7.

Extracellular Production of Non-Lipid Bioproducts

Figure 11:
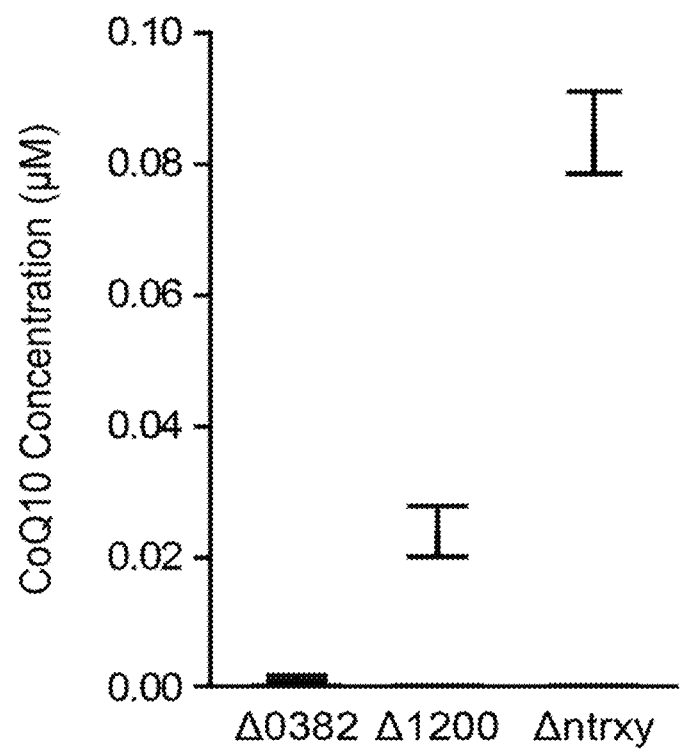
FIG. 11. Coenzyme Q10 (CoQ10) levels in the supernatants from the parent strain (Δ0382), a strain lacking the genes disrupted in HLM05 (Δ1200Δ0382, shown as Δ1200), and a strain lacking the genes disrupted in HLM01 and HLM02 (ΔNtrXYΔ0382, shown as Δntrxy).

The ability of the lipid-secreting high-lipid mutants to secrete bioproducts other than lipids was assessed. Supernatant levels of Coenzyme Q10 (CoQ10, also known as ubiquinone, ubidecarenone, coenzyme Q), a compound commonly found in lipid membranes, were tested in the parent strain (Δ0382), the strain lacking the genes disrupted in HLM01 and HLM02 (ΔNtrXYΔ0382), and a strain lacking the genes disrupted in HLM05 (Δ1200Δ0382). Increased levels of CoQ10 were found in the supernatants of both the ΔNtrXYΔ0382 and Δ1200Δ0382 strains compared to the parent strain (FIG. 11 and Table 7). This shows that extracellular production of membrane-bound or -associated bioproducts, such as small molecules, proteins, etc., is increased in the high-lipid mutants.

TABLE 7

Extracellular production of Coenzyme Q10 in parent and high-lipid mutants.

| | | Spike | | CoQ10 | | |
|---|---|---|---|---|---|---|
| Strain | Replicate | Concentration (μM) | Peak Area | Concentration (μM) | Average | STD Dev |
| Δ1200 | 1 | 0.00 | 1.57E+06 | 0.020 | 0.024 | 0.004 |
| | | 1.00 | 7.97E+07 | | | |
| | 2 | 0.00 | 2.13E+06 | 0.028 | | |
| | | 1.00 | 7.85E+07 | | | |
| | 3 | 0.00 | 1.74E+06 | 0.023 | | |
| | | 1.00 | 7.59E+07 | | | |
| Δ0382 | 1 | 0.00 | 1.94E+05 | 0.003 | 0.002 | 0.000 |
| | | 1.00 | 7.51E+07 | | | |
| | 2 | 0.00 | 1.93E+05 | 0.003 | | |
| | | 1.00 | 7.22E+07 | | | |
| | 3 | 0.00 | 1.32E+05 | 0.002 | | |
| | | 1.00 | 6.41E+07 | | | |
| Δntrxy | 1 | 0.00 | 6.07E+06 | 0.082 | 0.085 | 0.006 |
| | | 1.00 | 8.03E+07 | | | |
| | 2 | 0.00 | 5.32E+06 | 0.080 | | |
| | | 1.00 | 7.15E+07 | | | |
| | 3 | 0.00 | 6.75E+06 | 0.092 | | |
| | | 1.00 | 8.02E+07 | | | |

Δ0382 = parent strain (Δ0382).
Δntrxy = strain lacking the genes disrupted in HLM01 and HLM02 (ΔNtrXYΔ0382).
Δ1200a = strain lacking the genes disrupted in HLM05 (Δ1200Δ0382).

Reactor Engineering to Increase Fatty Acid Yield of a High-Lipid Mutant

Given the properties of high-lipid mutants like HLM02, we reasoned that high-density cultures could be used as a source of extracellular lipid. We opted to use a fed-batch bioreactor (Shiloach et al. 2005, Yen et al. 2010, Zeiger et al. 2010) to obtain high-density cultures since they can bypass the negative impacts of high (toxicity) or low (limitation) nutrient availability in the feedstocks. We reasoned that, if product (fatty acid) formation is tied to cell number, then increasing culture density should increase the reactor productivity.

Figure 12:
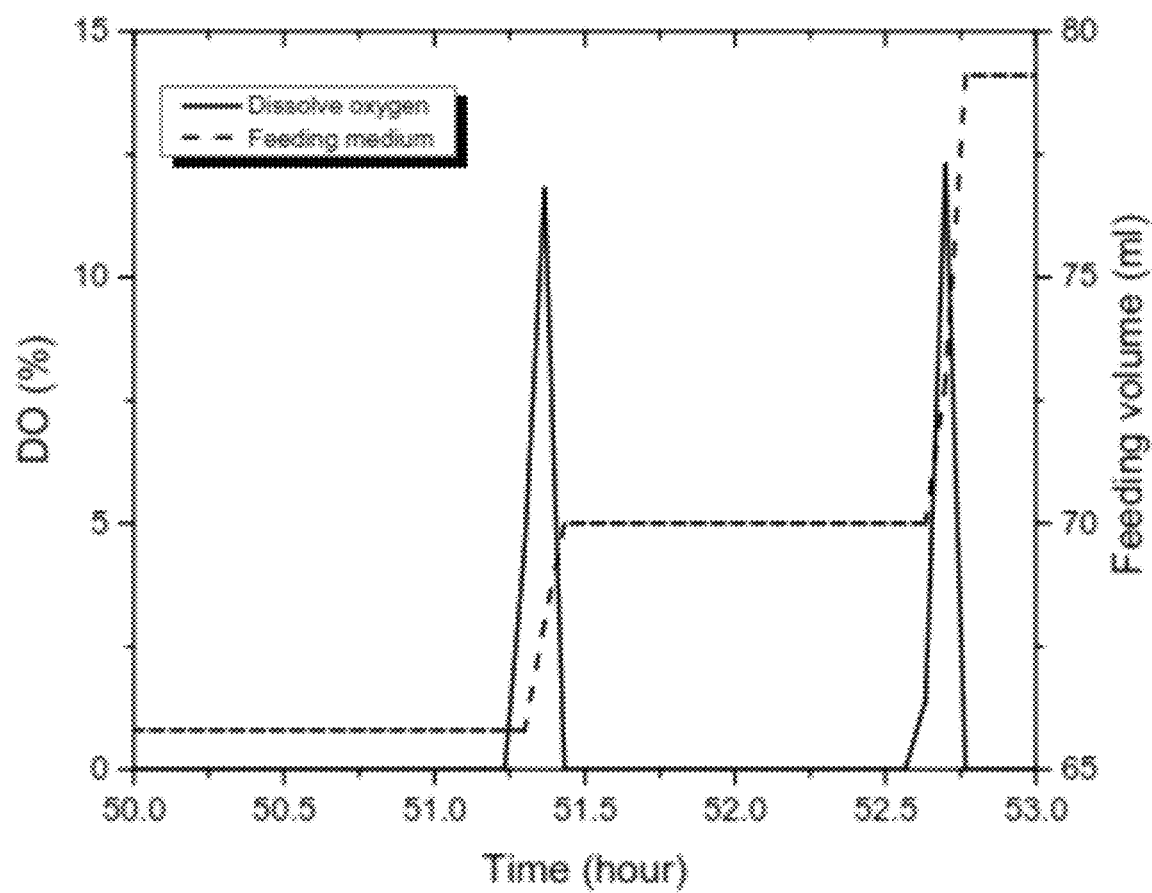
FIG. 12. Feeding protocol for fed-batch high-density cultures. The solid line shows culture dissolved oxygen (DO), which is maintained at a low baseline level by bubbling the reactor with saturated air. Increases in DO (seen at ~51.2 and 52.6 hours) indicate reduced metabolic activity in the reactor, and at these times a bolus of feeding medium is added increasing the total feeding volume (dotted line). After feeding, the culture DO drops to baseline as cellular respiration increases. A three hour period is shown from a 120 hour reactor run, the illustrated process repeats iteratively throughout the reactor incubation.

In our fed-batch reactors, a low level of $O_2$ was provided by bubbling with saturated air. We used real-time measurement of reactor dissolved oxygen as an indicator of substrate limitation (Seo et al. 1992), since decreased cellular respiration should cause an increase in dissolved oxygen. This is illustrated for a *R. sphaeroides* xylose-fed culture in FIG. 12: when the dissolved oxygen increases, nutrients are provided to the reactor causing the dissolved oxygen to decrease again, presumably when cellular respiration increases. This feeding cycle is repeated iteratively throughout the reactor run in order to obtain high density cultures.

Figure 13:
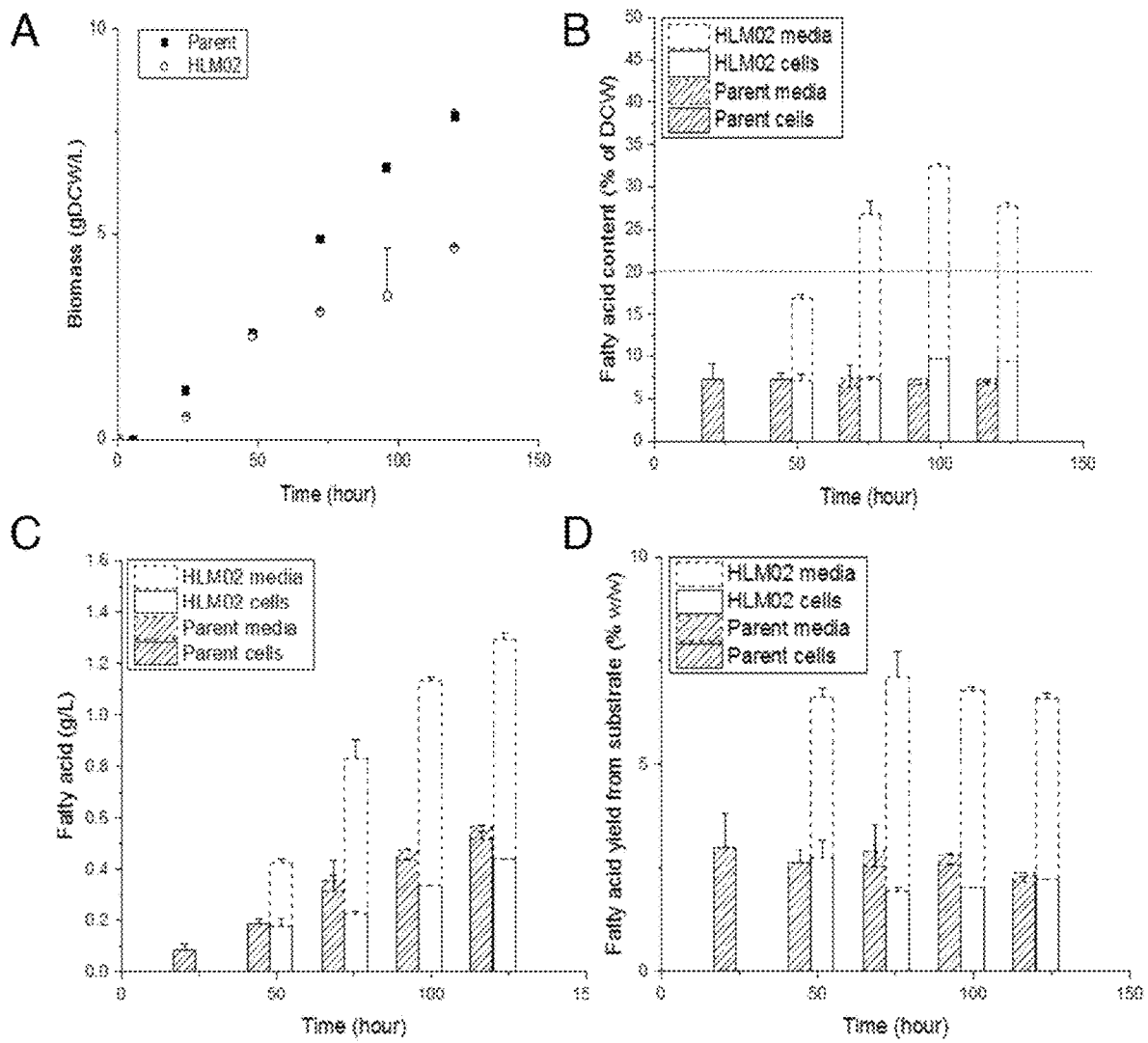
FIG. 13. Fed-batch reactor production of fatty acids by HLM02 mutant compared to the parent strain, grown with xylose as a carbon source. A) Total biomass and B) fatty acid content in the fed-batch reactor. C) Productivity of fatty acids and D) yield of fatty acids per xylose consumed. Data are shown from a representative bioreactor run for each strain; error bars represent standard deviation between technical replicates.

Using this method, we analyzed fatty acid production when cells were grown using xylose as a carbon source. Control experiments indicated that under the feeding regimen described above, cell density increases for ~120 hours and then plateaus. Under these conditions, the parent strain reached a maximal density of 7.9 gDCW/L (FIG. 13, panel A). Fatty acid content of the parent strain was stable in this fed-batch reactor at ~7% of DCW (FIG. 13, panel B), compared to ~5% observed in a xylose fed-batch culture (FIG. 10, panel B). This small increase in fatty acid content of the parent strain likely reflects the low oxygen tension present in the fed-batch reactor. Use of the fed-batch reactor increased total fatty acid productivity 10-fold, from 0.05 g/L in batch culture (FIG. 10, panel A) to 0.50 g/L (FIG. 13, panel C). In addition, the fatty acid yield from xylose increased from 1.4 (w/w) % in batch (FIG. 10. panel C) to a maximum of 3.6% in the high-density cultures (FIG. 13, panel D).

Figure 14:
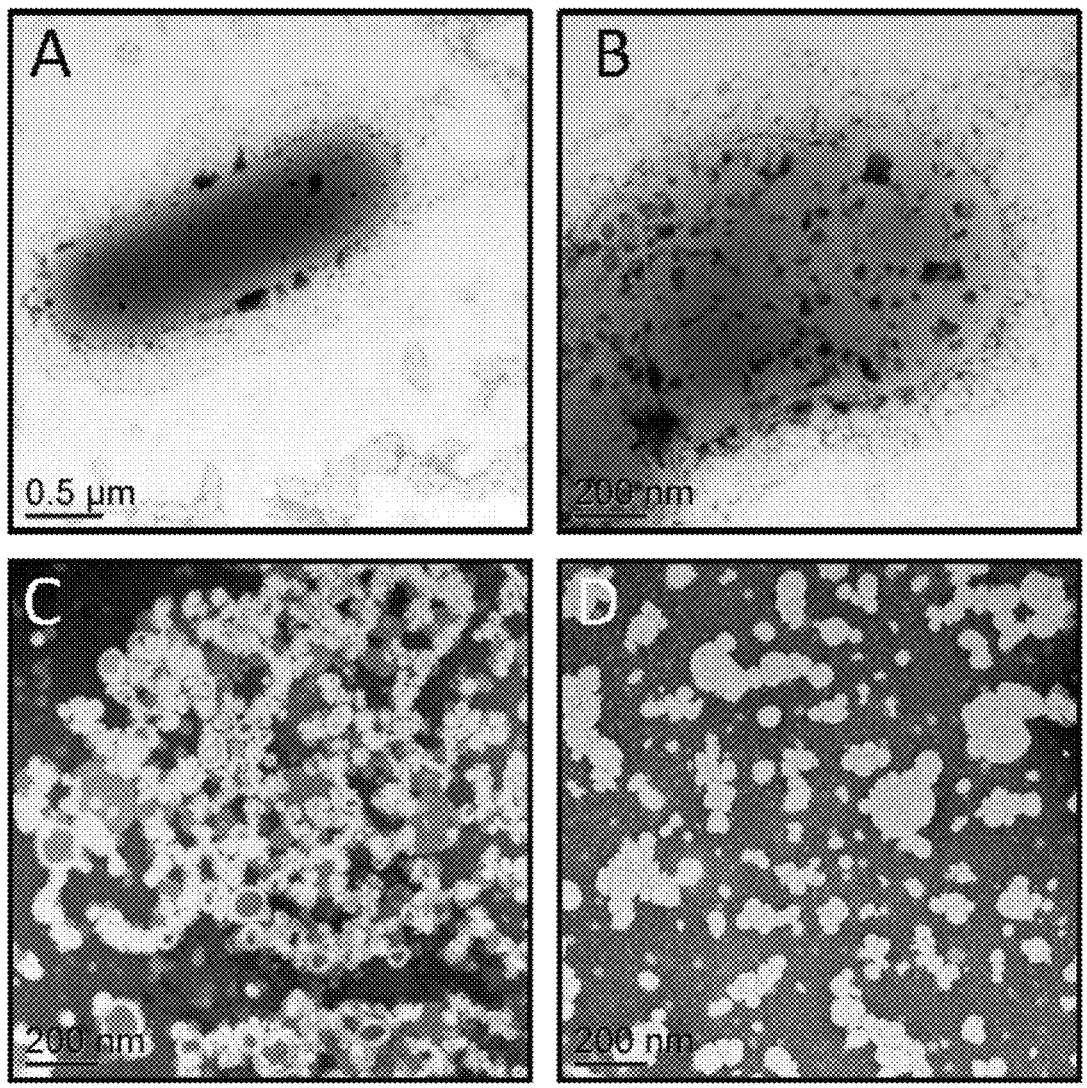
FIG. 14. Transmission electron microscopy of whole mounts of the HLM02 mutant grown in the fed-batch bioreactor. Views are shown of cells surrounded by extracellular structures (A,B), and of extracellular structures only (C,D).

Under identical reactor conditions, the HLM02 mutant grew at a slower rate and to lower final cell density than the parent (4.7 gDCW/L) (FIG. 13, panel A). Despite this, HLM02 produced more than twice the amount of total fatty acids as the parent strain (~1.3 g/L at 120 hours; FIG. 13, panel C). This is 9 times the amount of fatty acid produced by HLM02 in batch culture, demonstrating that growth in a fed-batch bioreactor increased fatty acid productivity. The fatty acid content of the HLM02 mutant increased over time, up to 33% of DCW at 100 hours (FIG. 13, panel B), a ~5-fold increase compared to the parent strain under the same conditions, and an 85% increase compared to the fatty acid content of HLM02 grown on xylose in a batch culture. In addition, a higher percentage of the fatty acids produced by HLM02 were secreted in the high-density culture compared to the batch culture (up to 69% of the total fatty acids) (FIG. 13, panel C). When these cells were examined by transmission electron microscopy, we saw extracellular droplets tightly packed around and away from the cells (FIG. 14), much more so than the same strain grown in batch (FIG. 4, panels C and F).

Finally, fatty acid yield per xylose consumed (% w/w) in the fed-batch bioreactor was more than doubled in HLM02 compared to the parent strain at all time points tested (FIG. 13, panel D). The maximum fatty acid yield observed for HLM02 in the fed batch reactor (8.4%) represents ~24% of the maximum theoretical yield from cells using xylose as a carbon source (35%, see above).

NtrXY Target Genes

The target genes of the NtrXY two-component signaling system were determined by chromatin immunoprecipitation (ChIP), and changes in mRNA expression of the targets were compared between the parental strain and a ΔNtrXY mutant. The results are shown in Table 8.

TABLE 8

NtrX targets as determined by ChIP and changes of expression of the targets.

| ID* | Annotation | CHR | Peak Start | Peak Stop | ChIP Fold Enrichment (Rep1/Rep2)*** | Gene Expression Fold Change** |
|---|---|---|---|---|---|---|
| RSP1860 | Cell wall hydrolase CwlJ, involved in spore germination | chr1 | 458400 | 458999 | 9.5/7.4 | −1.5 |
| RSP2839# | Nitrogen regulation protein NtrY Signal transduction histidine kinase | chr1 | 1472000 | 1472399 | 4.5/3.8 | 1.64 |
| RSP0334# \| RSP0335 | hypothetical protein \| diguanylate cyclase/ phosphodiesterase | chr1 | 2064600 | 2065100 | 2.5/2.5 | 1.8 \| 1.24 |
| RSP3540# | Hemolysin-type calcium-binding region, RTX | chr2 | 630300 | 630600 | 2.5/NA | 1.8 |
| RSP0339 | Methyltransferase domain-containing protein | chr1 | 2069800 | 2070200 | 2.4/NA | 1 |
| RSP2974 | Murein DD-endopeptidase MepM and murein hydrolase activator NlpD, contain LysM domain | chr1 | 1661000 | 1661399 | 2.4/2.7 | 1 |
| RSP0892 | ABC transporter, ATP-binding cassette | chr1 | 2642200 | 2642600 | 2.2/NA | 1 |
| RSP2095# | hypothetical protein | chr1 | 694110 | 695200 | 2/2.2 | 1.4 |
| RSP2111# | D-alanine--D-alanine ligase | chr1 | 711380 | 712030 | 2/3.5 | 2.2 |

TABLE 8-continued

NtrX targets as determined
by ChIP and changes of expression of the targets.

| ID* | Annotation | CHR | Peak Start | Peak Stop | ChIP Fold Enrichment (Rep1/Rep2)*** | Gene Expression Fold Change** |
|---|---|---|---|---|---|---|
| RSP2916 \| RSP2915 | hypothetical protein \| phosphate regulon sensor histidine kinase PhoR | chr1 | 1594600 | 1595000 | 1.5/NA | 1.7 \| 1 |

*The | indicates that the peak was located in an intergenomic region shared by 2 genes (A | B).
**Gene expression is in parental strain relative to the NtrXY mutant, so up genes are upregulated by NtrX.
***NA indicates genes where a ChIP peak was not observed in replicate 2.
The gene listed is followed by additional genes in the same operon, and thus predicted also to be regulated by NtrX in the same direction (increased expression) as the listed gene. The genes in the same operon as RSP2839 include RSP2840. The genes in the same operon as RSP0334 include RSP0333, RSP0332, RSP0331, RSP0330. The genes in the same operon as RSP3540 include RSP3539, RSP3538. The genes in the same operon as RSP2095 include RSP6038, RSP2097, RSP2098, RSP2099, RSP2100, RSP2101. The genes in the same operon as RSP2111 include RSP2112 and RSP2113.

Discussion

Using Native Pathways to Engineer Lipid Accumulation

Microbial lipids are energy dense molecules that have many advantages for use as petroleum replacements (d'Espaux et al. 2015). In order to achieve high enough yields to be cost competitive alternatives, a combination of metabolic engineering and process optimization, tailored to the specific organism and lipid product, is necessary. We took a unique approach to produce high levels of microbial lipids. We sought to use a well-studied non-oleaginous bacterium, R. sphaeroides, that has a native ability to increase its lipid content, to increase synthesis of these molecules. We showed that by combing genetic and reactor engineering, R. sphaeroides can produce and secrete lipids at levels found in oleaginous microbes. Using only a single genetic lesion (disruption of the NtrXY signal transduction pathway), we were able to achieve cells that contain 33% of the DCW as fatty acid, and produce fatty acids at 24% of maximum theoretical yield.

Unique Properties of High-Lipid Mutants

The ten high-lipid mutants that we identified had between a 1.5 to 6.7-fold increase in fatty acid per cell (Table 3), and had increased sensitivity to cell wall and membrane-targeting drugs, changes in cell shape, outer membrane protrusions, and often secreted lipids. These phenotypes suggest that the mutants have cell envelope alterations leading to release of cellular lipids. It is noteworthy that increased lipid production by wild-type R. sphaeroides (at low $O_2$) involves changes in the cell envelope. Specifically, cells increase their inner membrane surface area by creating intracytoplasmic membrane vesicles that protrude into the cytoplasm (Tavano et al. 2006). We are not aware of other reports of changes in the structure of the outer membrane or cell wall leading to increased cellular lipid content. It is also unknown whether any genes disrupted in the high-lipid mutants play a role in increasing lipid content or remodeling the cell envelope that normally occurs at low $O_2$ tensions in this bacterium.

Genetic Links of High-Lipid Mutants to the Cell Envelope

While none of the genes disrupted in the high-lipid mutants had been studied in R. sphaeroides, many of them had predicted functions associated with the cell envelope. The gene product inactivated in HLM05 (RSP1200) encodes an uncharacterized conserved protein that contains a CAP domain. Members of this superfamily are typically secreted, acting extracellularly in signal transduction or protein modification (Gibbs et al. 2008); some family members have been shown to bind lipids (Choudhary et al. 2012, Van Galen et al. 2010). RSP0355 (inactivated in HLM07) encodes one of several periplasmic serine protease (DegP) homologues in this bacterium, a protein that in other bacteria functions in protein quality control, degrading misfolded periplasmic proteins (Lyu et al. 2015). RSP2543 (inactivated in HLM08) encodes a cell wall hydrolase. It contains a signal peptide (Table 3) presumably to target it to the periplasm, a LysM peptidoglycan binding motif (Bateman et al. 2000), and Gly-Gly endopeptidase domain. Thus, RSP2543 could play a previously unreported role in peptidoglycan cell wall remodeling. RSP2745 (inactivated in HLM09) was identified as a Stealth family protein (Sperisen et al. 2005), which in bacteria appear to function in the synthesis of exopolysaccharides (Sperisen et al. 2005). Finally, the gene inactivated in HLM10 (RSP2293) encodes the ClpA subunit of the Clp protease that performs protein quality control in the cell and functions in other regulatory processes. ClpA mutants in some Pseudomonas species have cell envelope-related phenotypes (Song et al. 2015, Goff et al. 2009).

Another group of high-lipid mutants contain disruptions in two-component signaling systems. NtrXY (inactivated in HLM01 and HLM02) encode a sensor histidine kinase and its cognate response regulator that acts as a transcription factor in other bacteria. The NtrXY pathway has been implicated in controlling exopolysaccharide production (Wang et al. 2013), as well as regulating anaerobically induced processes (Ishida et al. 2002, Pawlowski et al. 1991, Carrica et al. 2012, Carrica et al. 2013, Gregor et al. 2007). Future studies to further characterize the transcriptional targets of R. sphaeroides NtrX and determine how they impinge on the cell envelope, lipid accumulation, and secretion has the potential to improve the production of fatty acids and other membrane-associated compounds. RSP1056 (inactivated in HLM04) is an "orphan" histidine kinase whose response regulator is not genetically linked and has not been identified. We suspect that the Tn5 insertion in this mutant causes a gain of function mutation rather than loss of function.

Finally, some high-lipid mutants have insertions in genes whose product does not seem to directly relate to the cell envelope. RSP3218 (inactivated in HLM03) encodes a nitroreductase that is predicted to function in vitamin $B_{12}$ biosynthesis; and RSP1422 (inactivated in HLM06) encodes a chromosome partitioning protein. In these cases, additional experiments are needed to understand how these mutations lead to the high-lipid phenotype of these strains.

Lipid Secretion by High-Lipid Mutants

When R. sphaeroides naturally increases its lipid content it makes additional intracellular membranes, so it was unexpected to find that several of the high-lipid mutants secreted lipids. From analysis of other systems, bacterial lipid secretion often occurs by export of free fatty acids or outer membrane vesicle (OMV) formation (Kulp et al. 2010, Lennen et al. 2010, Ledesma-Amaro et al. 2016). For the high-lipid mutants with the highest levels of secreted lipid (HLM01, HLM02, and HLM05), lipid phosphorus assays indicated the presence of extracellular phospholipid (FIG. 9). The structures observed in the media of HLM01 and HLM02, (FIG. 4, panels B, C, F, and G) do not resemble bacterial outer membrane vesicles, which typically appear as 20-250 nm spherical vesicles (Schwechheimer et al. 2015). However, the media of HLM05 does contain spherical vesicles in the 20-50 nm range (FIG. 4, panel H). Further investigation is needed to determine the cellular source of these lipid secretions (outer membrane, inner membrane, or both), their chemical composition, and the mechanism leading to their production.

R. sphaeroides as an Oleaginous Bacterium

The ability of R. sphaeroides to increase production of hydrophobic compounds at low $O_2$ has led to its use as a source of isoprenoids, quinones and other chemicals (Yen et al. 2010, Kien et al. 2010, Sangkharak et al. 2007). The industrial utility of bacteria as microbial sources of valuable products is often enhanced by the ability to grow cells to high cell density.

By growing HLM02 in a fed-batch bioreactor, total fatty acid productivity increased ~8-fold over what is observed in batch culture. Additionally, in the fed-batch bioreactor, total fatty acid content of HLM02 was ~33% of DCW, classifying this strain as an oleaginous bacterium. We are not aware of any previous examples of microbes accumulating over 20% of its biomass as phospholipid, typically oleaginous organisms accumulate triacylglycerols or wax esters (Waltermann et al. 2005, Liang et al. 2013). Fatty acid yield for HLM02 in the fed-batch bioreactor was 24% of maximum theoretical yield. Considering that, compared to the parent strain, HLM02 had only one genetic lesion, this is a substantial improvement. Further increases in lipid productivity is possible with additional metabolic engineering, e.g., by using other gene disruptions identified herein (Table 3) and/or employing strategies that have been successful in other organisms to either increase flux through fatty acid biosynthesis or decrease β-oxidation (Janssen et al. 2014, Lennen et al. 2012).

Several observations from our studies may be beneficial for increasing the economic feasibility of producing lipid or other bioproducts, either in this or other bacteria that can be engineered to contain similar cell envelope changes. Bioproduct secretion by a microbe has several advantages. First, bioproduct secretion can increase production beyond the amount that can fit within the cell. Second, bioproduct secretion could simplify the ability to harvest, separate and process the product (Caspeta et al. 2013, Arora 2012), as well as minimize intracellular toxicity of this compound. In addition, HLM02 retained its high-lipid phenotype when grown on several different carbon sources, suggesting that the catabolic versatility of R. sphaeroides may be advantageous when cells are grown on more complex media. Finally, we found the HLM02 mutant could over-produce and secrete a novel-furan containing fatty acid that has potential value in biofuel, biochemical, and pharmaceutical industries due to its antioxidant activity.

CONCLUSIONS

By combining genetic and bioreactor engineering, we have created an oleaginous strain of R. sphaeroides, HLM02, that produced fatty acid at ~24% of the maximum theoretical yield. During this process we also isolated and characterized ten different high-lipid strains. We propose that in many of these mutants, alterations in the cell envelope lead to increased lipid content. The novel properties of these high-lipid mutants also suggests that similar changes in cell envelope structure could be used to increase production of lipids or lipid-associated bioproducts in other microbes.

REFERENCES

Agler, M. T., B. A. Wrenn, S. H. Zinder and L. T. Angenent, (2011) Waste to bioproduct conversion with undefined mixed cultures: the carboxylate platform. *Trends in Biotechnology* 29: 70-78.

Arora, R., (2012) *Microbial biotechnology: energy and environment*, p. xiv, 396 pages. Cambridge CAB International, Wallingford, Oxfordshire.

Atack J M, Srikhanta Y N, Djoko K Y, Welch J P, Hasri N H, Steichen C T, Vanden Hoven R N, Grimmond S M, Othman D S, Kappler U, Apicella M A, Jennings M P, Edwards J L, McEwan A G. Characterization of an ntrX mutant of *Neisseria gonorrhoeae* reveals a response regulator that controls expression of respiratory enzymes in oxidase-positive proteobacteria. *J Bacteriol*. 2013 June; 195(11):2632-41.

Atlas, R. M. and L. C. Parks, (1993) *Handbook of microbiological media*, p. v, 1079 pages. CRC Press, Boca Raton.

Austin, S., W. S. Kontur, A. Ulbrich, J. Z. Oshlag, W. Zhang, A. Higbee, Y. Zhang, J. J. Coon, D. B. Hodge, T. J. Donohue and D. R. Noguera, (2015) Metabolism of Multiple Aromatic Compounds in Corn Stover Hydrolysate by *Rhodopseudomonas palustris*. *Environ Sci Technol* 49: 8914-8922.

Bailey T L, Boden M, Buske F A, Frith M, Grant C E, Clementi L, Ren J, Li W W, Noble W S. 2009. MEME SUITE: tools for motif discovery and searching. *Nucleic Acids Res* 37:W202-W208.

Bateman, A. and M. Bycroft, (2000) The structure of a LysM domain from *E. coli* membrane-bound lytic murein transglycosylase D (M1tD). *J Mol Biol* 299: 1113-1119.

Benjamini Y, Hochberg Y. 1995. Controlling the false discovery rate—a practical and powerful approach to multiple testing. J R Stat Soc B Methodol 57:289-300.

Blatti, J. L., J. Michaud and M. D. Burkart, (2013) Engineering fatty acid biosynthesis in microalgae for sustainable biodiesel. *Current opinion in chemical biology* 17: 496-505.

Bolstad B M, Irizarry R A, Astrand M, Speed T P. 2003. A comparison of normalization methods for high density oligonucleotide array data based on variance and bias. Bioinformatics 19:185-193.

Carrica, M.d.C., I. Fernandez, M. A. Marti, G. Paris and F. A. Goldbaum, (2012) The NtrY/X two-component system of *Brucella* spp. acts as a redox sensor and regulates the expression of nitrogen respiration enzymes. *Mol Microbiol* 85: 39-50.

Carrica, M.d.C., I. Fernandez, R. Sieira, G. Paris and F. A. Goldbaum, (2013) The two-component systems PrrBA and NtrYX co-ordinately regulate the adaptation of *Brucella abortus* to an oxygen-limited environment. *Mol Microbiol* 88: 222-233.

Caspeta, L. and J. Nielsen, (2013) Economic and environmental impacts of microbial biodiesel. *Nat Biotechnol* 31: 789-793.

Choi, Y. J. and S. Y. Lee, (2013) Microbial production of short-chain alkanes. *Nature* 502: 571-574.

Chory, J., T. J. Donohue, A. R. Varga, L. A. Staehelin and S. Kaplan, (1984) Induction of the photosynthetic membranes of *Rhodopseudomonas sphaeroides*: biochemical and morphological studies. *J Bacteriol* 159: 540-554.

Choudhary, V. and R. Schneiter, (2012) Pathogen-Related Yeast (PRY) proteins and members of the CAP superfamily are secreted sterol-binding proteins. *Proc Natl Acad Sci USA* 109: 16882-16887.

Dangel A W, Tabita F R. 2009. Protein-protein interactions between CbbR and RegA (PrrA), transcriptional regulators of the cbb operons of *Rhodobacter sphaeroides*. Mol Microbiol 71:717-729.

Dufour Y S, Landick R, Donohue T J. 2008. Organization and evolution of the biological response to singlet oxygen stress. *J Mol Biol* 383:713-730.

d'Espaux, L., D. Mendez-Perez, R. Li and J. D. Keasling, (2015) Synthetic biology for microbial production of lipid-based biofuels. *Current opinion in chemical biology* 29: 58-65.

Feng, X., J. Lian and H. Zhao, (2015) Metabolic engineering of *Saccharomyces cerevisiae* to improve 1-hexadecanol production. *Metabolic engineering* 27: 10-19.

Gibbs, G. M., K. Roelants and M. K. O'Bryan, (2008) The CAP superfamily: cysteine-rich secretory proteins, antigen 5, and pathogenesis-related 1 proteins—roles in reproduction, cancer, and immune defense. *Endocr Rev* 29: 865-897.

Goff, M., J. Nikodinovic-Runic and K. E. O'Connor, (2009) Characterization of temperature-sensitive and lipopolysaccharide overproducing transposon mutants of *Pseudomonas putida* CA-3 affected in PHA accumulation. *FEMS microbiology letters* 292: 297-305.

Goh, E. B., E. E. Baidoo, J. D. Keasling and H. R. Beller, (2012) Engineering of bacterial methyl ketone synthesis for biofuels. *Appl Environ Microbiol* 78: 70-80.

Gregor, J., T. Zeller, A. Balzer, K. Haberzettl and G. Klug, (2007) Bacterial regulatory networks include direct contact of response regulator proteins: interaction of RegA and NtrX in *Rhodobacter capsulatus*. *J Mol Microbiol Biotechnol* 13: 126-139.

Imam S, Noguera D R, Donohue T J. 2014. Global analysis of photosynthesis transcriptional regulatory networks. *PLoS Genet* 10:e1004837.

Imam, S., S. Yilmaz, U. Sohmen, A. S. Gorzalski, J. L. Reed, D. R. Noguera and T. J. Donohue, (2011) iRsp1095: a genome-scale reconstruction of the *Rhodobacter sphaeroides* metabolic network. *BMC systems biology* 5: 116.

Ishida, M. L., M. C. Assumpcao, H. B. Machado, E. M. Benelli, E. M. Souza and F. O. Pedrosa, (2002) Identification and characterization of the two-component NtrY/NtrX regulatory system in *Azospirillum brasilense*. *Braz J Med Biol Res* 35: 651-661.

Javidpour P, Pereira J H, Goh E B, McAndrew R P, Ma S M, Friedland G D, Keasling J D, Chhabra S R, Adams P D, Beller H R. Biochemical and structural studies of NADH-dependent FabG used to increase the bacterial production of fatty acids under anaerobic conditions. *Appl Environ Microbiol.* 2014 January; 80(2):497-505.

Janssen, H. J. and A. Steinbuchel, (2014) Fatty acid synthesis in *Escherichia coli* and its applications towards the production of fatty acid based biofuels. *Biotechnology for biofuels* 7: 7.

Kalscheuer, R., T. Stolting and A. Steinbuchel, (2006) Microdiesel: *Escherichia coli* engineered for fuel production. *Microbiology* 152: 2529-2536.

Kaltashov, I. A., V. Doroshenko, R. J. Cotter, K. Takayama and N. Qureshi, (1997) Confirmation of the Structure of Lipid A Derived from the Lipopolysaccharide of *Rhodobacter sphaeroides* by a Combination of MALDI, LSIMS, and Tandem Mass Spectrometry. *Analytical Chemistry* 69: 2317-2322.

Kontur W S, Schackwitz W S, Ivanova N, Martin J, Labutti K, Deshpande S, Tice H N, Pennacchio C, Sodergren E, Weinstock G M, Noguera D R, Donohue T J. Revised sequence and annotation of the *Rhodobacter sphaeroides* 2.4.1 genome. *J Bacteriol.* 2012 December; 194(24): 7016-7.

Kien, N. B., I. S. Kong, M. G. Lee and J. K. Kim, (2010) *Coenzyme Q10 production in a* 150-1 reactor by a mutant strain of *Rhodobacter sphaeroides*. *J Ind Microbiol Biotechnol* 37: 521-529.

Kiley, P. J. and S. Kaplan, (1988) Molecular genetics of photosynthetic membrane biosynthesis in *Rhodobacter sphaeroides*. *Microbiol Rev* 52: 50-69.

Kosa, M. and A. J. Ragauskas, (2011) Lipids from heterotrophic microbes: advances in metabolism research. *Trends Biotechnol* 29: 53-61.

Kuan P F, Chung D, Pan G, Thomson J A, Stewart R, Kele S. 2011. A statistical framework for the analysis of ChIP-seq data. *J Am Stat Assoc* 106:891-903.

Kulp, A. and M. J. Kuehn, (2010) Biological functions and biogenesis of secreted bacterial outer membrane vesicles. *Annu Rev Microbiol* 64: 163-184.

Kumar, P.; Barrett, D. M.; Delwiche, M. J.; Stroeve, P., Methods for Pretreatment of lignocellulosic Biomass for Efficient Hydrolysis and Biofuel Production. *Industrial & Engineering Chemistry Research* 2009, 48, (8), 3713-3729.

Larsen, R. A., M. M. Wilson, A. M. Guss and W. W. Metcalf, (2002) Genetic analysis of pigment biosynthesis in *Xanthobacter autotrophicus* Py2 using a new, highly efficient transposon mutagenesis system that is functional in a wide variety of bacteria. *Arch Microbiol* 178: 193-201.

Lau, M. W., C. Gunawan and B. E. Dale, (2009) The impacts of pretreatment on the fermentability of pretreated lignocellulosic biomass: a comparative evaluation between ammonia fiber expansion and dilute acid pretreatment. *Biotechnology for biofuels* 2: 30-30.

Ledesma-Amaro, R., R. Dulermo, X. Niehus and J. M. Nicaud, (2016) Combining metabolic engineering and process optimization to improve production and secretion of fatty acids. *Metabolic engineering* 38: 38-46.

Lemke, R. A., A. C. Peterson, E. C. Ziegelhoffer, M. S. Westphall, H. Tjellstrom, J. J. Coon and T. J. Donohue, (2014) Synthesis and scavenging role of furan fatty acids. *Proc Natl Acad Sci USA* 111: E3450-3457.

Lemmer, K. C., A. C. Dohnalkova, D. R. Noguera and T. J. Donohue, (2015) Oxygen-dependent regulation of bacterial lipid production. *J Bacteriol* 197: 1649-1658.

Lennen, R. M., D. J. Braden, R. A. West, J. A. Dumesic and B. F. Pfleger, (2010) A process for microbial hydrocarbon synthesis: Overproduction of fatty acids in *Escherichia coli* and catalytic conversion to alkanes. *Biotechnol Bioeng* 106: 193-202.

Lennen, R. M. and B. F. Pfleger, (2012) Engineering *Escherichia coli* to synthesize free fatty acids. *Trends Biotechnol* 30: 659-667.

Lennon, C. W., K. C. Lemmer, J. L. Irons, M. I. Sellman, T. J. Donohue, R. L. Gourse and W. Ross, (2014) A *Rhodobacter sphaeroides* protein mechanistically similar to *Escherichia coli* DksA regulates photosynthetic growth. *mBio* 5: e01105-01114.

Levering, J., J. Broddrick and K. Zengler, (2015) Engineering of oleaginous organisms for lipid production. *Curr Opin Biotechnol* 36: 32-39.

Li R, Yu C, Li Y, Lam T W, Yiu S M, Kristiansen K, Wang J. 2009. SOAP2: an improved ultrafast tool for short read alignment. *Bioinformatics* 25:1966-1967.

Liang, M. H. and J. G. Jiang, (2013) Advancing oleaginous microorganisms to produce lipid via metabolic engineering technology. *Progress in lipid research* 52: 395-408.

Lyu, Z. X. and X. S. Zhao, (2015) Periplasmic quality control in biogenesis of outer membrane proteins. *Biochem Soc Trans* 43: 133-138.

Metcalf, W. W., W. Jiang, L. L. Daniels, S. K. Kim, A. Haldimann and B. L. Wanner, (1996) Conditionally replicative and conjugative plasmids carrying lacZ alpha for cloning, mutagenesis, and allele replacement in bacteria. *Plasmid* 35: 1-13.

Miller, V. L. and J. J. Mekalanos, (1988) A novel suicide vector and its use in construction of insertion mutations: osmoregulation of outer membrane proteins and virulence determinants in *Vibrio cholerae* requires toxR. *J Bacteriol* 170: 2575-2583.

Newman, J. D., M. J. Falkowski, B. A. Schilke, L. C. Anthony and T. J. Donohue, (1999) The *Rhodobacter sphaeroides* ECF sigma factor, sigma(E), and the target promoters cycA P3 and rpoE P1. *J Mol Biol* 294: 307-320.

Pawlowski, K., U. Klosse and F. J. de Bruijn, (1991) Characterization of a novel *Azorhizobium caulinodans* OR971 two-component regulatory system, NtrY/NtrX, involved in nitrogen fixation and metabolism. *Mol Gen Genet* 231: 124-138.

Rouser, G., S. Fkeischer and A. Yamamoto, (1970) Two dimensional then layer chromatographic separation of polar lipids and determination of phospholipids by phosphorus analysis of spots. *Lipids* 5: 494-496.

Saldanha, A. J., (2004) Java Treeview—extensible visualization of microarray data. *Bioinformatics* 20: 3246-3248.

Sangkharak, K. and P. Prasertsan, (2007) Optimization of polyhydroxybutyrate production from a wild type and two mutant strains of *Rhodobacter sphaeroides* using statistical method. *Journal of biotechnology* 132: 331-340.

Sawangkeaw, R. and S. Ngamprasertsith, (2013) A review of lipid-based biomasses as feedstocks for biofuels production. *Renewable and Sustainable Energy Reviews* 25: 97-108.

Schafer, A., A. Tauch, W. Jager, J. Kalinowski, G. Thierbach and A. Puhler, (1994) Small mobilizable multi-purpose cloning vectors derived from the *Escherichia coli* plasmids pK18 and pK19: selection of defined deletions in the chromosome of *Corynebacterium glutamicum*. *Gene* 145: 69-73.

Schirmer, A., M. A. Rude, X. Li, E. Popova and S. B. del Cardayre, (2010) Microbial biosynthesis of alkanes. *Science* 329: 559-562.

Schwalbach, M. S., D. H. Keating, M. Tremaine, W. D. Marner, Y. Zhang, W. Bothfeld, A. Higbee, J. A. Grass, C. Cotten, J. L. Reed, L. da Costa Sousa, M. Jin, V. Balan, J. Ellinger, B. Dale, P. J. Kiley and R. Landick, (2012) Complex physiology and compound stress responses during fermentation of alkali-pretreated corn stover hydrolysate by an *Escherichia coli* ethanologen. *Appl Environ Microbiol* 78: 3442-3457.

Schwechheimer, C. and M. J. Kuehn, (2015) Outer-membrane vesicles from Gram-negative bacteria: biogenesis and functions. *Nat Rev Microbiol* 13: 605-619.

Seo, D. Jin, B. H. Chung, Y. D. Hwang and Y. H. Park, (1992) Glucose-limited fed-batch culture of *Escherichia coli* for production of recombinant human interleukin-2 with the DO-stat method. *Journal of Fermentation and Bioengineering* 74: 196-198.

Shiloach, J. and R. Fass, (2005) Growing *E. coli* to high cell density—a historical perspective on method development. *Biotechnology advances* 23: 345-357.

Simon, R., U. Priefer and A. Puhler, (1983) A broad host range mobilization system for in vivo genetic engineering: transposon mutagenesis in gram negative bacteria. *Biotechnology* 1: 748-791.

Sistrom, W. R., (1960) A requirement for sodium in the growth of *Rhodopseudomonas spheroides*. *J Gen Microbiol* 22: 778-785.

Smyth G. 2004. Applications in genetics and molecular biology 3. Berkeley Electronic Press, Berkeley, Calif.

Song, C., G. Sundqvist, E. Malm, I. de Bruijn, A. Kumar, J. van de Mortel, V. Bulone and J. M. Raaijmakers, (2015) Lipopeptide biosynthesis in *Pseudomonas fluorescens* is regulated by the protease complex ClpAP. *BMC Microbiol* 15: 29.

Sperisen, P., C. D. Schmid, P. Bucher and O. Zilian, (2005) Stealth proteins: in silico identification of a novel protein family rendering bacterial pathogens invisible to host immune defense. *PLoS Comput Biol* 1: e63.

Steen, E. J., Y. Kang, G. Bokinsky, Z. Hu, A. Schirmer, A. McClure, S. B. Del Cardayre and J. D. Keasling, (2010) Microbial production of fatty-acid-derived fuels and chemicals from plant biomass. *Nature* 463: 559-562.

Tavano, C. L. and T. J. Donohue, (2006) Development of the bacterial photosynthetic apparatus. *Curr Opin Microbiol* 9: 625-631.

Tavano C L, Podevels A M, Donohue T J. 2005. Identification of genes required for recycling reducing power during photosynthetic growth. J Bacteriol 187:5249-5258.

Torella J P, Ford T J, Kim S N, Chen A M, Way J C, Silver P A. Tailored fatty acid synthesis via dynamic control of fatty acid elongation. Proc Natl Acad Sci USA. 2013 Jul. 9; 110(28):11290-5.

Vaara, M., (1993) Outer membrane permeability barrier to azithromycin, clarithromycin, and roxithromycin in gram-negative enteric bacteria. *Antimicrobial agents and chemotherapy* 37: 354-356.

Van Galen, J., B. W. Van Balkom, R. L. Serrano, D. Kaloyanova, R. Eerland, E. Stuven and J. B. Helms, (2010) Binding of GAPR-1 to negatively charged phospholipid membranes: unusual binding characteristics to phosphatidylinositol. *Mol Membr Biol* 27: 81-91.

van Niel, C. B., (1944) The culture, general physiology, morphology, and classification of the non-sulfur purple and brown bacteria. *Bacteriol Rev* 8: 1-118.

Waltermann, M., A. Hinz, H. Robenek, D. Troyer, R. Reichelt, U. Malkus, H. J. Galla, R. Kalscheuer, T. Stoveken, P. von Landenberg and A. Steinbuchel, (2005) Mechanism of lipid-body formation in prokaryotes: how bacteria fatten up. *Mol Microbiol* 55: 750-763.

Wang, D., H. Xue, Y. Wang, R. Yin, F. Xie and L. Luo, (2013) The *Sinorhizobium meliloti* ntrX gene is involved in succinoglycan production, motility, and symbiotic nodulation on alfalfa. *Appl Environ Microbiol* 79: 7150-7159.

Yen, H. W., C. Y. Feng and J. L. Kang, (2010) Cultivation of *Rhodobacter sphaeroides* in the stirred bioreactor with different feeding strategies for CoQ(10) production. *Appl Biochem Biotechnol* 160: 1441-1449.

Yilmaz, L., W. Kontur, A. Sanders, U. Sohmen, T. Donohue and D. Noguera, (2010) Electron Partitioning During Light- and Nutrient-Powered Hydrogen Production by *Rhodobacter sphaeroides*. *BioEnergy Research* 3: 55-66.

Zeiger, L. and H. Grammel, (2010) Model-based high cell density cultivation of *Rhodospirillum rubrum* under respiratory dark conditions. *Biotechnology and Bioengineering* 105: 729-739.

Zhang, L., J. Song, G. Cavigiolio, B. Y. Ishida, S. Zhang, J. P. Kane, K. H. Weisgraber, M. N. Oda, K. A. Rye, H. J. Pownall and G. Ren, (2011) Morphology and structure of lipoproteins revealed by an optimized negative-staining protocol of electron microscopy. *J Lipid Res* 52: 175-184.

Zhang, Y. M. and C. O. Rock, (2010) A rainbow coalition of lipid transcriptional regulators. *Molecular Microbiology* 78: 5-8.

What is claimed is:

1. A recombinant microorganism comprising one or more genetic modifications with respect to a corresponding microorganism not comprising the one or more genetic modifications, wherein:
the one or more genetic modifications comprise at least one of:
a genetic modification that reduces the activity of RSP2839 or a homolog thereof with respect to the corresponding microorganism; and
a genetic modification that reduces the activity of RSP2840 or a homolog thereof with respect to the corresponding microorganism;
the recombinant microorganism exhibits enhanced lipid production with respect to the corresponding microorganism; and
the recombinant microorganism is *Rhodobacter sphaeroides* or a member of the genus *Rhodopseudomonas*.

2. The recombinant microorganism of claim 1, wherein the recombinant microorganism exhibits enhanced lipid secretion with respect to the corresponding microorganism.

3. The recombinant microorganism of claim 1, wherein the one or more genetic modifications comprise the genetic modification that reduces the activity of the RSP2839 or homolog thereof and the genetic modification that reduces the activity of the RSP2840 or homolog thereof.

4. The recombinant microorganism of claim 3, wherein the homolog of RSP2839 is an NtrY and the homolog of RSP2840 is an NtrX.

5. A recombinant microorganism comprising genetic modifications with respect to a corresponding microorganism not comprising the genetic modifications, wherein:
the genetic modifications comprise:
at least one of:
a genetic modification that reduces the activity of RSP2839 or a homolog thereof with respect to the corresponding microorganism; and
a genetic modification that reduces the activity of RSP2840 or a homolog thereof with respect to the corresponding microorganism; and
one or more modifications that reduce the activity of one or more of an acyl-CoA dehydrogenase, an enoyl-CoA hydratase, a 3-hydroxyacyl-CoA dehydrogenase, and a 3-ketoacyl-CoA thiolase and/or increase the activity of one or more of an acyl-CoA synthetase, an acetyl-CoA carboxylase, an acetyl CoA:ACP transacylase, a malonyl CoA:ACP transacylase, a β-ketoacyl-ACP synthase, a β-ketoacyl-ACP reductase, a β-hydroxyacyl-ACP dehydrase, an enoyl-ACP reductase, a glycerol-3-phosphate acyltransferase, and a 1-acylglycerol-3-phosphate acyltransferase with respect to the corresponding microorganism; and
the recombinant microorganism exhibits enhanced lipid production with respect to the corresponding microorganism.

6. A recombinant microorganism comprising genetic modifications with respect to a corresponding microorganism not comprising the genetic modifications, wherein:

the genetic modifications comprise:
at least one of:
a genetic modification that reduces the activity of RSP2839 or a homolog thereof with respect to the corresponding microorganism; and
a genetic modification that reduces the activity of RSP2840 or a homolog thereof with respect to the corresponding microorganism; and
a genetic modification that reduces the activity of RSP0382 or a homolog thereof with respect to the corresponding microorganism; and
the recombinant microorganism exhibits enhanced lipid production with respect to the corresponding microorganism.

7. The recombinant microorganism of claim 1, wherein the one or more genetic modifications further comprise one or more recombinant genes configured to express one or more of RSP2144 or a homolog thereof, RSP1091 or a homolog thereof, and RSP1090 or a homolog thereof; a genetic modification that disrupts binding between ChrR and $\sigma^E$ or homologs thereof; a genetic modification that increases expression of $\sigma^E$ or a homolog thereof; and/or a genetic modification that eliminates from the microorganism a native ChrR or homolog thereof.

8. The recombinant microorganism of claim 5, wherein the corresponding microorganism is a non-oleaginous microorganism.

9. The recombinant microorganism of claim 5, wherein the recombinant microorganism is a bacterium.

10. The recombinant microorganism of claim 5, wherein the recombinant microorganism is from the genus *Rhodobacter* or the genus *Rhodopseudomonas*.

11. The recombinant microorganism of claim 1, wherein the recombinant microorganism exhibits at least 2-fold enhanced lipid production with respect to the corresponding microorganism when the recombinant microorganism and the corresponding organism are grown under aerobic conditions.

12. The recombinant microorganism of claim 1, wherein the recombinant microorganism is capable of producing at least 1 g/L lipid.

13. The recombinant microorganism of claim 1, wherein the recombinant microorganism is capable of producing lipids in an amount of at least 20% (w/w) dry cell weight.

14. A method for producing a bioproduct comprising:
culturing a recombinant microorganism in a medium for a time sufficient to consume nutrients present in the medium and produce the bioproduct, wherein:
the recombinant microorganism comprises one or more genetic modifications with respect to a corresponding microorganism not comprising the one or more genetic modifications;
the one or more genetic modifications comprise at least one of:
a genetic modification that reduces the activity of RSP2839 or a homolog thereof with respect to the corresponding microorganism; and
a genetic modification that reduces the activity of RSP2840 or a homolog thereof with respect to the corresponding microorganism;
the recombinant microorganism exhibits enhanced lipid production with respect to the corresponding microorganism; and
the bioproduct comprises lipid; and
extracting the lipid from the medium.

15. The method of claim 14, wherein the one or more genetic modifications comprise at least one of:
a genetic modification that reduces the activity of RSP2839 or a homolog thereof with respect to the corresponding microorganism, wherein the homolog of RSP2839 is an NtrY; and
a genetic modification that reduces the activity of RSP2840 or a homolog thereof with respect to the corresponding microorganism, wherein the homolog of RSP2840 is an NtrX.

16. The recombinant microorganism of claim 5, wherein the genetic modifications comprise at least one of:
a genetic modification that reduces the activity of RSP2839 or a homolog thereof with respect to the corresponding microorganism, wherein the homolog of RSP2839 is an NtrY; and
a genetic modification that reduces the activity of RSP2840 or a homolog thereof with respect to the corresponding microorganism, wherein the homolog of RSP2840 is an NtrX.

* * * * *

SEQUENCE LISTING

```
<160> NUMBER OF SEQ ID NOS: 164

<210> SEQ ID NO 1
<211> LENGTH: 495
<212> TYPE: DNA
<213> ORGANISM: Rhodobacter sphaeroides

<400> SEQUENCE: 1
atgagcaaga acaacaccga ggccgatgtc gccttcatcc aggcccttgc cgaactgctg      60
aacagcaacg agctcacgga actttcggtc aaacgggaat atggcgagga cgacagcctc     120
gaggtccgcg tggtcaagca ggccaacatc gtgacgaccc aggttgcggc gccgatgatg     180
gccgccgccc ccgcggcgat gccggcggtc ggcggtgccc ccgccgccgc tccggccgcg     240
gtcgaggatc cggcccagca tccggcgcc gtcacctcgc ccatggtggg caccgtctat      300 atcgccccg agccgggcgc ctcgcccttc gtcaccgtgg gcgccaccgt gaccgagggg      360
cagacgctcc tcatcatcga ggcgatgaag accatgaacc acatccccgc ccgcgcgcg     420 ggcacggtga agcgggtcct cgtctcggac ggcacggcgg tcgaatacgg cgcgcccctc     480
atgatcatcg agtga                                                      495

<210> SEQ ID NO 2
<211> LENGTH: 164
<212> TYPE: PRT
<213> ORGANISM: Rhodobacter sphaeroides

<400> SEQUENCE: 2

Met Ser Lys Asn Asn Thr Glu Ala Asp Val Ala Phe Ile Gln Ala Leu
1               5                   10                  15

Ala Glu Leu Leu Asn Ser Asn Glu Leu Thr Glu Leu Ser Val Lys Arg
            20                  25                  30

Glu Tyr Gly Glu Asp Asp Ser Leu Glu Val Arg Val Val Lys Gln Ala
        35                  40                  45

Asn Ile Val Thr Thr Gln Val Ala Ala Pro Met Met Ala Ala Ala Pro
    50                  55                  60

Ala Ala Met Pro Ala Val Gly Gly Ala Pro Ala Ala Pro Ala Ala
65                  70                  75                  80

Val Glu Asp Pro Ala Gln His Pro Gly Ala Val Thr Ser Pro Met Val
                85                  90                  95

Gly Thr Val Tyr Ile Ala Pro Glu Pro Gly Ala Ser Pro Phe Val Thr
            100                 105                 110

Val Gly Ala Thr Val Thr Glu Gly Gln Thr Leu Leu Ile Ile Glu Ala
        115                 120                 125

Met Lys Thr Met Asn His Ile Pro Ala Pro Arg Ala Gly Thr Val Lys
    130                 135                 140

Arg Val Leu Val Ser Asp Gly Thr Ala Val Glu Tyr Gly Ala Pro Leu
145                 150                 155                 160

Met Ile Ile Glu
```

<210> SEQ ID NO 3
<211> LENGTH: 1347
<212> TYPE: DNA
<213> ORGANISM: Rhodobacter sphaeroides

<400> SEQUENCE: 3

| | |
|---|---|
| atgttcgaaa agatcctgat cgccaaccgc ggcgagatcg ccttgcgcgt gatccgcgcc | 60 |
| tgccaggaga tggggatcaa gtcggtcgcc gtccattcga ccgcggacgc cgatgccatg | 120 |
| catgtccgca tggccgatga gagcgtctgc atcggcccgg cctcctcgac cgacagctat | 180 |
| ctcaacaagg cctcgatcat ctcggcctgc gagatcaccg gggccgaggc cgtccatccg | 240 |
| ggttacggct tcctctccga aacgcggcc ttcgcccagg cgctgcagga ccacgggatc | 300 |
| gagttcatcg cccgaccgc ggaccatatc cgcatcatgg cgacaagat caccgccaag | 360 |
| gacacgatga aggctctggg cgtgccctgc gtgcccggct ccgacggcgg cgtgcccgac | 420 |
| tacgagacgg ccatcgccac ggccagagac atcggcttcc cggtcatcat caaggccacg | 480 |
| gcgggcggcg gcgggcgcgg catgaaggtc gcgcggaacg agcaggaact cgagatcgcc | 540 |
| ttccgcaccg cgcgttcgga agccaaggcc gccttcggca acgacgaagt ctatatggag | 600 |
| aaatatctcc agaagccgcg gcacatcgag atccaggtgt cggcgacgg caagggccgc | 660 |
| gcggtccatc tgggcgagcg tgactgctcg ctgcagcggc ggcaccagaa ggtgttcgag | 720 |
| gaagccccgg gtccggtcat cacccccgag atgcgtgcgg agatcggcag gatctgcgcc | 780 |
| gacgcggtgg cgcggatcaa ctacatcggc gcgggcacga tcgaattcct ctacgaggac | 840 |
| ggccagttct acttcatcga gatgaacacc cgcctgcagg tggagcatcc ggtgaccgag | 900 |
| gcgatcttcg cgtcgatct cgtgcgcgag cagatccggg tcgcggcggg cctgccgatg | 960 |
| agcttcaatc aggatgcgct ggagatcaac ggccacgcca tcgaggtgcg gatcaacgcc | 1020 |
| gagaagctgc cgaacttttc gccctgcccc ggcaaggtgc gggtcttcca cgcgccgggc | 1080 |
| ggcctcgggg tgcggatgga ttcggccctc tatggcggct attccatccc gccctattac | 1140 |
| gacagcctga tcggcaagct gatcgtgcac ggccgcgacc ggcccgaggc gctggcgcgc | 1200 |
| ctgcaccgcg ccctgggcga gctgatcgtg gacgggatcg acacgacggt gccgctgttc | 1260 |
| cacgcgcttc tggccgagcc cgacatccag aatggcgact acaatatcca ctggctggaa | 1320 |
| aaatggctcg ccgcccagtt cggctga | 1347 |

<210> SEQ ID NO 4
<211> LENGTH: 448
<212> TYPE: PRT
<213> ORGANISM: Rhodobacter sphaeroides

<400> SEQUENCE: 4

Met Phe Glu Lys Ile Leu Ile Ala Asn Arg Gly Glu Ile Ala Leu Arg
1               5                   10                  15

Val Ile Arg Ala Cys Gln Glu Met Gly Ile Lys Ser Val Ala Val His
                20                  25                  30

Ser Thr Ala Asp Ala Asp Ala Met His Val Arg Met Ala Asp Glu Ser
            35                  40                  45

Val Cys Ile Gly Pro Ala Ser Ser Thr Asp Ser Tyr Leu Asn Lys Ala
        50                  55                  60

Ser Ile Ile Ser Ala Cys Glu Ile Thr Gly Ala Glu Ala Val His Pro
65                  70                  75                  80

Gly Tyr Gly Phe Leu Ser Glu Asn Ala Ala Phe Ala Gln Ala Leu Gln
                85                  90                  95

Asp His Gly Ile Glu Phe Ile Gly Pro Thr Ala Asp His Ile Arg Ile
            100                 105                 110

Met Gly Asp Lys Ile Thr Ala Lys Asp Thr Met Lys Ala Leu Gly Val
        115                 120                 125

Pro Cys Val Pro Gly Ser Asp Gly Val Pro Asp Tyr Glu Thr Ala
    130                 135                 140

Ile Ala Thr Ala Arg Asp Ile Gly Phe Pro Val Ile Lys Ala Thr
145                 150                 155                 160

Ala Gly Gly Gly Arg Gly Met Lys Val Ala Arg Asn Glu Gln Glu
                165                 170                 175

Leu Glu Ile Ala Phe Arg Thr Ala Arg Ser Glu Ala Lys Ala Ala Phe
            180                 185                 190

Gly Asn Asp Glu Val Tyr Met Glu Lys Tyr Leu Gln Lys Pro Arg His
        195                 200                 205

Ile Glu Ile Gln Val Phe Gly Asp Gly Lys Gly Arg Ala Val His Leu
    210                 215                 220

Gly Glu Arg Asp Cys Ser Leu Gln Arg Arg His Gln Lys Val Phe Glu
225                 230                 235                 240

Glu Ala Pro Gly Pro Val Ile Thr Pro Glu Met Arg Ala Glu Ile Gly
                245                 250                 255

Arg Ile Cys Ala Asp Ala Val Ala Arg Ile Asn Tyr Ile Gly Ala Gly
            260                 265                 270

Thr Ile Glu Phe Leu Tyr Glu Asp Gly Gln Phe Tyr Phe Ile Glu Met
        275                 280                 285

Asn Thr Arg Leu Gln Val Glu His Pro Val Thr Glu Ala Ile Phe Gly
    290                 295                 300

Val Asp Leu Val Arg Glu Gln Ile Arg Val Ala Ala Gly Leu Pro Met
305                 310                 315                 320

Ser Phe Asn Gln Asp Ala Leu Glu Ile Asn Gly His Ala Ile Glu Val
                325                 330                 335

Arg Ile Asn Ala Glu Lys Leu Pro Asn Phe Ser Pro Cys Pro Gly Lys
            340                 345                 350

Val Arg Val Phe His Ala Pro Gly Gly Leu Gly Val Arg Met Asp Ser
        355                 360                 365

Ala Leu Tyr Gly Gly Tyr Ser Ile Pro Pro Tyr Tyr Asp Ser Leu Ile
    370                 375                 380

Gly Lys Leu Ile Val His Gly Arg Asp Arg Pro Glu Ala Leu Ala Arg
385                 390                 395                 400

Leu His Arg Ala Leu Gly Glu Leu Ile Val Asp Gly Ile Asp Thr Thr
                405                 410                 415

Val Pro Leu Phe His Ala Leu Leu Ala Glu Pro Asp Ile Gln Asn Gly
            420                 425                 430

Asp Tyr Asn Ile His Trp Leu Glu Lys Trp Leu Ala Ala Gln Phe Gly
        435                 440                 445

<210> SEQ ID NO 5
<211> LENGTH: 1335
<212> TYPE: DNA
<213> ORGANISM: Rhodobacter sphaeroides

<400> SEQUENCE: 5
ttggcgattg cgcccttcg ggtcgtccgg gggcggcgat cccgcccttc gacgcgcgcc    60
aaccgggcgg cggatgccga gctgcggcgc ctccgcgcgc agtttcccga ctgggacgtg   120

-continued

```
ccgtccgacc tcacgacgct gggccagcag cggtctcccg ccgccgagat cgaccggatc    180
taccggcaga tcgcggccgg agacctgacc gaggcccggc aggcgatgga cgagacgtcg    240
cgcaacttcc ccggatggac gccgccgccc gagatggagc gtcttctggc cacggccgag    300
gcacaggccg ccttcgatgc ggccgccagt gcgggcaatg cgggcgcggc aatcgagatc    360
gcgcggcgga cgcccgcgat cctgcgctgc gaccgggtga caacgcctg gcggctggcc     420 gagctgcagg cggcggggg ccagaaggcg ccgcgctgc agagctatcg cggggtgatc      480
gcctcctgct cgggcctgtc cgaggtgacg gcgacgctcg agaaggcgga ggccgtggcc    540
agcgatgcgg agctggtcga gctcttccgg ctggccaatg cgcagcttcc gggctcggga    600
cctgcgctga aggcgctcga gacacggctg agggcgggac gcggcgacac ggcgcccgag    660
gcatcggcgc cggctgccgc agcaacgggc ggagccaagc gcacgccggg ccgcactgcg    720
gtggccgagg cggatctgcc cgcggcgggg cgcccgcgca ctgcgggcgt ggcgcgcagc    780
ggcgaggggg cggggctgtc cgcggtccgc gcggcagcgc aacgcggcga ctggcggacc    840
tgcaccggcc tcaccagcgg cgccaccagc gccgacatgc tctacgagcg ggcctggtgc    900
gtctataatc tcgaccggcc gctcgaggcg ctggcggctt cgagcctgc cgcctcgggg     960 cgcctcgggg cgcaggtcgc gcgggacgcg cgcttcggca agacgctcgc gctgctggcg    1020
ctgaagatga cggaagaggc cgcccggctc gccgccgcga ccgacctgac catccagcag    1080
cggcgcgagg tcgaggccat catcctggat cagcgcgggg tgcgggccta tcagctgaag    1140
gaatatcgcc gcgccatcgc cttcctcacc gcctatgagg atctgacggg ggggctgcgg    1200
cgcgacctcg cgatcatgcg cggctacgcc tacctcaacc tcggcaagcg gaccgaggcc    1260
aagcgcatct tcacggagct gaacaatcag ctcgcgacgc ccgagacccg gcgggcctg    1320 aacgcgagcc gctga                                                    1335
```

<210> SEQ ID NO 6
<211> LENGTH: 444
<212> TYPE: PRT
<213> ORGANISM: Rhodobacter sphaeroides

<400> SEQUENCE: 6

```
Met Ala Ile Ala Pro Phe Arg Val Val Arg Gly Arg Arg Ser Arg Pro
1               5                   10                  15

Ser Thr Arg Ala Asn Arg Ala Ala Asp Ala Glu Leu Arg Arg Leu Arg
            20                  25                  30

Ala Gln Phe Pro Asp Trp Asp Val Pro Ser Asp Leu Thr Thr Leu Gly
        35                  40                  45

Gln Gln Arg Ser Pro Ala Ala Glu Ile Asp Arg Ile Tyr Arg Gln Ile
    50                  55                  60

Ala Ala Gly Asp Leu Thr Glu Ala Arg Gln Ala Met Asp Glu Thr Ser
65                  70                  75                  80

Arg Asn Phe Pro Gly Trp Thr Pro Pro Glu Met Glu Arg Leu Leu
                85                  90                  95

Ala Thr Ala Glu Ala Gln Ala Ala Phe Asp Ala Ala Ala Ser Ala Gly
            100                 105                 110

Asn Ala Gly Ala Ala Ile Glu Ile Ala Arg Arg Thr Pro Ala Ile Leu
        115                 120                 125

Arg Cys Asp Arg Val Asn Asn Ala Trp Arg Leu Ala Glu Leu Gln Ala
    130                 135                 140

Ala Ala Gly Gln Lys Ala Ala Ala Leu Gln Ser Tyr Arg Gly Val Ile
145                 150                 155                 160
```

```
Ala Ser Cys Ser Gly Leu Ser Glu Val Thr Ala Thr Leu Glu Lys Ala
            165                 170                 175

Glu Ala Val Ala Ser Asp Ala Glu Leu Val Glu Leu Phe Arg Leu Ala
        180                 185                 190

Asn Ala Gln Leu Pro Gly Ser Gly Pro Ala Leu Lys Ala Leu Glu Thr
    195                 200                 205

Arg Leu Arg Ala Gly Arg Gly Asp Thr Ala Pro Glu Ala Ser Ala Pro
210                 215                 220

Ala Ala Ala Ala Thr Gly Gly Ala Lys Arg Thr Pro Gly Arg Thr Ala
225                 230                 235                 240

Val Ala Glu Ala Asp Leu Pro Ala Gly Arg Pro Thr Ala Gly
            245                 250                 255

Val Ala Arg Ser Gly Gly Gly Ala Gly Leu Ser Ala Val Arg Ala Ala
        260                 265                 270

Ala Gln Arg Gly Asp Trp Arg Thr Cys Thr Gly Leu Thr Ser Gly Ala
    275                 280                 285

Thr Ser Ala Asp Met Leu Tyr Glu Arg Ala Trp Cys Val Tyr Asn Leu
    290                 295                 300

Asp Arg Pro Leu Glu Ala Leu Ala Phe Glu Pro Ala Ala Ser Gly
305                 310                 315                 320

Arg Leu Gly Ala Gln Val Ala Arg Asp Ala Arg Phe Gly Lys Thr Leu
            325                 330                 335

Ala Leu Leu Ala Leu Lys Met Thr Glu Glu Ala Ala Arg Leu Ala Ala
        340                 345                 350

Ala Thr Asp Leu Thr Ile Gln Gln Arg Arg Glu Val Glu Ala Ile Ile
    355                 360                 365

Leu Asp Gln Arg Gly Val Arg Ala Tyr Gln Leu Lys Glu Tyr Arg Arg
370                 375                 380

Ala Ile Ala Phe Leu Thr Ala Tyr Glu Asp Leu Thr Gly Gly Leu Arg
385                 390                 395                 400

Arg Asp Leu Ala Ile Met Arg Gly Tyr Ala Tyr Leu Asn Leu Gly Lys
            405                 410                 415

Arg Thr Glu Ala Lys Arg Ile Phe Thr Glu Leu Asn Asn Gln Leu Ala
        420                 425                 430

Thr Pro Glu Thr Arg Ala Gly Leu Asn Ala Ser Arg
    435                 440

<210> SEQ ID NO 7
<211> LENGTH: 996
<212> TYPE: DNA
<213> ORGANISM: Rhodobacter sphaeroides

<400> SEQUENCE: 7
atgaggagac ggaccatcct gacatcggcc gccgccgcgc tgatgctggc ccctgcagga      60
cgcctcctcg cgcagtcggg cagagaggct ttgcctgcgg accacccgct ccaggcggcc     120
tggcgcagct ggaaggatgc gttcctgctg cccgccggcc gcatcgtcga cgggccgcag     180
cagaatgcga gccattccga agggcagggc tacggagcca cgctcgccgc gatcttcggc     240
gacgaggagg ccctgcggcg catcgtcgac tggaccgagg cgaaccttgc gcggcgcgag     300
gacaagcttc tgagctggcg ctggctgccc ggtgtggcgc tggccgtgcc cgacgagaac     360
aacgccaccg acggcgatct cttctacgcc tgggggtctcg ccatggccgc gcagcggttc     420
ggcaaggccg attacgccgg cggggcgacc gaactggcgc gcgccatcgc gctgcattgc     480
```

```
gtgcgtccgc atccggacgg ctccgagcag ctcgtgctgc tgccgggggc cagcggcttc      540
gagacgccgg acggggtggt gctcaacccc tcctactaca tgccccgcgc cctgaccgag      600
ctcgccgcct tcagcggcca ggaccggctg gcgcgctgtg cccgcgacgg ggcggactgg      660
atcgcgtcgc tcgggcttcc gccggactgg gcgctggtca cgcccttcgg cacacagccg      720
gcgccgggcc tgtcccacaa cagcggctac gatgcgctgc gggtgcccct gttcctgctc      780
tggtccgggc tgaccgccaa tcccgcgctg cgccgcgcgg tggaggcggc cggggacgcc      840
gcagccggcg acacgccggt gaggttcgac cgcgacacgg gggcggtgct ggaacggtcc      900
gccgatccgg gcttccgcgc cgtgctcgcg cttggcgatt gcgcccttc gggtcgtccg       960 ggggcggcga tcccgccctt cgacgcgcgc caaccg                                996
```

<210> SEQ ID NO 8
<211> LENGTH: 332
<212> TYPE: PRT
<213> ORGANISM: Rhodobacter sphaeroides

<400> SEQUENCE: 8

```
Met Arg Arg Arg Thr Ile Leu Thr Ser Ala Ala Ala Leu Met Leu
1               5                   10                  15

Ala Pro Ala Gly Arg Leu Leu Ala Gln Ser Gly Arg Glu Ala Leu Pro
            20                  25                  30

Ala Asp His Pro Leu Gln Ala Ala Trp Arg Ser Trp Lys Asp Ala Phe
        35                  40                  45

Leu Leu Pro Ala Gly Arg Ile Val Asp Gly Pro Gln Gln Asn Ala Ser
    50                  55                  60

His Ser Glu Gly Gln Gly Tyr Gly Ala Thr Leu Ala Ala Ile Phe Gly
65                  70                  75                  80

Asp Glu Glu Ala Leu Arg Arg Ile Val Asp Trp Thr Glu Ala Asn Leu
                85                  90                  95

Ala Arg Arg Glu Asp Lys Leu Leu Ser Trp Arg Trp Leu Pro Gly Val
            100                 105                 110

Ala Leu Ala Val Pro Asp Glu Asn Asn Ala Thr Asp Gly Asp Leu Phe
        115                 120                 125

Tyr Ala Trp Gly Leu Ala Met Ala Ala Gln Arg Phe Gly Lys Ala Asp
    130                 135                 140

Tyr Ala Gly Arg Ala Thr Glu Leu Ala Arg Ala Ile Ala Leu His Cys
145                 150                 155                 160

Val Arg Pro His Pro Asp Gly Ser Glu Gln Leu Val Leu Leu Pro Gly
                165                 170                 175

Ala Ser Gly Phe Glu Thr Pro Asp Gly Val Val Leu Asn Pro Ser Tyr
            180                 185                 190

Tyr Met Pro Arg Ala Leu Thr Glu Leu Ala Ala Phe Ser Gly Gln Asp
        195                 200                 205

Arg Leu Ala Arg Cys Ala Arg Asp Gly Ala Asp Trp Ile Ala Ser Leu
    210                 215                 220

Gly Leu Pro Pro Asp Trp Ala Leu Val Thr Pro Phe Gly Thr Gln Pro
225                 230                 235                 240

Ala Pro Gly Leu Ser His Asn Ser Gly Tyr Asp Ala Leu Arg Val Pro
                245                 250                 255

Leu Phe Leu Leu Trp Ser Gly Leu Thr Ala Asn Pro Ala Leu Arg Arg
            260                 265                 270

Ala Val Glu Ala Ala Gly Asp Ala Ala Gly Asp Thr Pro Val Arg
        275                 280                 285
```

```
Phe Asp Arg Asp Thr Gly Ala Val Leu Glu Arg Ser Ala Asp Pro Gly
    290                 295                 300

Phe Arg Ala Val Leu Ala Leu Gly Asp Cys Ala Leu Ser Gly Arg Pro
305                 310                 315                 320

Gly Ala Ala Ile Pro Pro Phe Asp Ala Arg Gln Pro
                325                 330

<210> SEQ ID NO 9
<211> LENGTH: 2178
<212> TYPE: DNA
<213> ORGANISM: Rhodobacter sphaeroides

<400> SEQUENCE: 9
```

| | | | | | |
|---|---|---|---|---|---|
| atggacatgc | gactgctgcc | tttccttttc | ctcgggacgc | tggcgtcgat | ggccgcggcg | 60 |
| caggacgcgc | cgatgatcgt | gatcgagggc | ctcacctccg | aagagccgca | ggcgtccccc | 120 |
| gatgcggtcg | cggaagcggt | gccggcggcg | gaggtcgccc | cctggatcat | tccgctgcgc | 180 |
| cctctggccg | agaccgcgca | ggtcgggccg | ctcttccgcc | tgcagggtca | gcaggcgcgc | 240 |
| gcggccttcc | gcctcttcct | gccgaccgaa | gcggtcggcg | gcacgctcac | gctcgcgcag | 300 |
| cgcagcagca | tcgacatcct | gcccgaaagc | tcacagatca | tcgtgcggat | gaacgatcag | 360 |
| gagatcggcc | gcttcacccc | cgccagttc | ggcgctctgg | gggccgtcac | catgccgctc | 420 |
| ggcgaagccg | tgcgggcggg | cgacaatctc | gtgacgatcg | aggcgcagca | ccggcaccgc | 480 |
| atctactgcg | gtgcggatgc | ggagttcgat | ctctggaccg | aggtcgatct | gagccagagc | 540 |
| ggcgtggcgc | ttcccgccgc | ggcgatcggc | accgaacta | cctcgttcat | cgcggccctc | 600 |
| actgcacagg | cggagtcggg | ccggccggtc | gagatccgca | cacccacccc | gcccgacgag | 660 |
| gcgacgctgc | gcaccctcgc | ccaggctctc | ggcggccat | tgcctgacga | ggcgctgccg | 720 |
| ctcgcgctga | gcaagccgtg | gtcggccgag | accggcccca | cctatgcgcg | gatcacgctt | 780 |
| cttccgtccg | acgccgaccg | cgtttccata | cgccggggcg | gggacggggc | cgtggttctg | 840 |
| gtcctcgaac | atccgcccga | aggctcaccc | aacgcgtcgc | tcgtcgccga | tcttctggga | 900 |
| gcgaccccga | cgctgccgcc | tccgacgcta | ccgcagatcc | cgcccggccg | cgtcgtcacg | 960 |
| ctggccgaca | tgggcgtcga | caccattctc | accgacaacc | gctacttcaa | ccgcgatatc | 1020 |
| gacttccagc | tgccggacga | ctggctgctg | ctggcgagcc | agaaggcgca | gatcggcatc | 1080 |
| gactacggct | tgccggcgg | gctgcccgag | ggcgcgctgc | tgctcgtgaa | ggtcaatggc | 1140 |
| acgacggtgc | gcatgctgcc | gctcgaccgc | gacgccgccc | ccgtcaagcc | ccggctcgac | 1200 |
| atccgctttc | cggcgcggct | cctgcatccc | ggcccgaacc | ggctgtcgtt | cgaatcggtc | 1260 |
| atcccgggca | atccgcccga | ccagccctgt | cctgcctccg | ccggcgacct | gatgcaggtg | 1320 |
| ctgagctcga | ccgatctcga | ggtgccgccg | tcgccccgga | tgcagatggc | ggacatggcg | 1380 |
| cgggatctgg | cgcaggtgac | gccggcatcg | gtgcatcctg | ccacgccgga | cggtctggcg | 1440 |
| cggacgctgc | ccttcatggc | ggccttccgc | gaggtgcccg | acgcggcacc | cgtggatctg | 1500 |
| acggtggcgg | gtctgcacga | catcgccacg | gttcccctga | cgaggaagg | cctgacgccg | 1560 |
| cgccttctcg | ccctgacgct | gctaccctcc | accgtctccc | ggctggtgga | gcgtccggcg | 1620 |
| acgcccgcgg | gtccgccggc | caacgccctc | gccccgctgg | gcgccgcgcc | gggcgagggg | 1680 |
| gtgatgccgc | cgctggtcga | gtcgaactgg | tcggaccgcg | cccagaccct | tcgtgcaggcc | 1740 |
| acgctgcagc | ccgtgatcca | gacggtccgg | cggatgctgc | gaccggggga | cggcaacctc | 1800 |
| gccgagtggc | tcgccacgcg | caagggcacg | gccatgctgc | tcgcgcccga | accgggcaag | 1860 |

```
ctctgggtca tcctcgggcc cgaggccgag ccggcccggg ttgcggaagc cctcgccatg    1920
gcgccgcgct cgcccggcgg gccccgcggt caggtggccg ttctcggctc tgacggacgc    1980
tggtcgagct ggtcgaagcc cggcctcctg ccggagttgc gcgaacccgt gagccttgac    2040
aatgtgcgca gcgtggtggg caacgtcgcg tcggcgcggc cgcccctgct gctcggcggg    2100
atgctgggcc tcgcctggat cagcgctgca atcgccgtgg gcttcgtgct ccgcacccgg    2160
aggaagggcc tgaaatga                                                  2178
```

<210> SEQ ID NO 10
<211> LENGTH: 725
<212> TYPE: PRT
<213> ORGANISM: Rhodobacter sphaeroides

<400> SEQUENCE: 10

```
Met Asp Met Arg Leu Leu Pro Phe Leu Phe Leu Gly Thr Leu Ala Ser
1               5                   10                  15

Met Ala Ala Gln Asp Ala Pro Met Ile Val Ile Glu Gly Leu Thr
            20                  25                  30

Ser Glu Glu Pro Gln Ala Ser Pro Asp Ala Val Ala Glu Val Pro
        35                  40                  45

Ala Ala Glu Val Ala Pro Trp Ile Ile Pro Leu Arg Pro Leu Ala Glu
    50                  55                  60

Thr Ala Gln Val Gly Pro Leu Phe Arg Leu Gln Gly Gln Ala Arg
65                  70                  75                  80

Ala Ala Phe Arg Leu Phe Leu Pro Thr Glu Ala Val Gly Gly Thr Leu
                85                  90                  95

Thr Leu Ala Gln Arg Ser Ser Ile Asp Ile Leu Pro Glu Ser Ser Gln
            100                 105                 110

Ile Ile Val Arg Met Asn Asp Gln Glu Ile Gly Arg Phe Thr Pro Arg
        115                 120                 125

Gln Phe Gly Ala Leu Gly Ala Val Thr Met Pro Leu Gly Glu Ala Val
    130                 135                 140

Arg Ala Gly Asp Asn Leu Val Thr Ile Glu Ala Gln His Arg His Arg
145                 150                 155                 160

Ile Tyr Cys Gly Ala Asp Ala Glu Phe Asp Leu Trp Thr Glu Val Asp
                165                 170                 175

Leu Ser Gln Ser Gly Val Ala Leu Pro Ala Ala Ile Gly Thr Glu
            180                 185                 190

Pro Thr Ser Phe Ile Ala Ala Leu Thr Ala Gln Ala Glu Ser Gly Arg
        195                 200                 205

Pro Val Glu Ile Arg Thr Pro Thr Pro Pro Asp Glu Ala Thr Leu Arg
    210                 215                 220

Thr Leu Ala Gln Ala Leu Gly Arg Pro Leu Pro Asp Glu Ala Leu Pro
225                 230                 235                 240

Leu Ala Leu Ser Lys Pro Trp Ser Ala Glu Thr Gly Pro Thr Tyr Ala
                245                 250                 255

Arg Ile Thr Leu Leu Pro Ser Asp Ala Asp Arg Val Ser Ile Arg Arg
            260                 265                 270

Gly Gly Asp Gly Ala Val Val Leu Val Leu Glu His Pro Glu Gly
        275                 280                 285

Ser Pro Asn Ala Ser Leu Val Ala Asp Leu Leu Gly Ala Thr Pro Thr
    290                 295                 300

Leu Pro Pro Pro Thr Leu Pro Gln Ile Pro Pro Gly Arg Val Val Thr
```

```
            305                 310                 315                 320
Leu Ala Asp Met Gly Val Asp Thr Ile Leu Thr Asp Asn Arg Tyr Phe
                325                 330                 335

Asn Arg Asp Ile Asp Phe Gln Leu Pro Asp Asp Trp Leu Leu Leu Ala
                340                 345                 350

Ser Gln Lys Ala Gln Ile Gly Ile Asp Tyr Gly Phe Ala Gly Gly Leu
                355                 360                 365

Pro Glu Gly Ala Leu Leu Leu Val Lys Val Asn Gly Thr Thr Val Arg
                370                 375                 380

Met Leu Pro Leu Asp Arg Asp Ala Ala Pro Val Lys Pro Arg Leu Asp
385                 390                 395                 400

Ile Arg Phe Pro Ala Arg Leu Leu His Pro Gly Pro Asn Arg Leu Ser
                405                 410                 415

Phe Glu Ser Val Ile Pro Gly Asn Pro Asp Gln Pro Cys Pro Ala
                420                 425                 430

Ser Ala Gly Asp Leu Met Gln Val Leu Ser Ser Thr Asp Leu Glu Val
                435                 440                 445

Pro Pro Ser Pro Arg Met Gln Met Ala Asp Met Ala Arg Asp Leu Ala
                450                 455                 460

Gln Val Thr Pro Ala Ser Val His Pro Ala Thr Pro Asp Gly Leu Ala
465                 470                 475                 480

Arg Thr Leu Pro Phe Met Ala Ala Phe Arg Glu Val Pro Asp Ala Ala
                485                 490                 495

Pro Val Asp Leu Thr Val Ala Gly Leu His Asp Ile Ala Thr Val Pro
                500                 505                 510

Leu Asn Glu Glu Gly Leu Thr Pro Arg Leu Leu Ala Leu Thr Leu Leu
                515                 520                 525

Pro Ser Thr Val Ser Arg Leu Val Glu Arg Pro Thr Pro Ala Gly
                530                 535                 540

Pro Pro Ala Asn Ala Leu Ala Pro Leu Gly Ala Ala Pro Gly Glu Gly
545                 550                 555                 560

Val Met Pro Pro Leu Val Glu Ser Asn Trp Ser Asp Arg Ala Gln Thr
                565                 570                 575

Phe Val Gln Ala Thr Leu Gln Pro Val Ile Gln Thr Val Arg Arg Met
                580                 585                 590

Leu Arg Pro Gly Asp Gly Asn Leu Ala Glu Trp Leu Ala Thr Arg Lys
                595                 600                 605

Gly Thr Ala Met Leu Leu Ala Pro Glu Pro Gly Lys Leu Trp Val Ile
                610                 615                 620

Leu Gly Pro Glu Ala Glu Pro Ala Arg Val Ala Glu Ala Leu Ala Met
625                 630                 635                 640

Ala Pro Arg Ser Pro Gly Gly Pro Arg Gly Gln Val Ala Val Leu Gly
                645                 650                 655

Ser Asp Gly Arg Trp Ser Ser Trp Ser Lys Pro Gly Leu Leu Pro Glu
                660                 665                 670

Leu Arg Glu Pro Val Ser Leu Asp Asn Val Arg Ser Val Val Gly Asn
                675                 680                 685

Val Ala Ser Ala Arg Pro Pro Leu Leu Leu Gly Met Leu Gly Leu
                690                 695                 700

Ala Trp Ile Ser Ala Ala Ile Ala Val Gly Phe Val Leu Arg Thr Arg
705                 710                 715                 720

Arg Lys Gly Leu Lys
                725
```

<210> SEQ ID NO 11
<211> LENGTH: 2367
<212> TYPE: DNA
<213> ORGANISM: Rhodobacter sphaeroides

<400> SEQUENCE: 11

| | | | | | | |
|---|---|---|---|---|---|---|
| atgaccgttc | gagccaaggc | ccgctccccg | ctaagggtcg | ttcccgtcct | gctgttcctg | 60 |
| ctgtgggtgg | ctctcctcgt | gccgttcggg | ctgctggccg | ccgcgccggt | cgcgccctcg | 120 |
| gcgcagggcc | tcatcgcttt | gtcggcggtg | gtgctggtgg | cgctgctcaa | gcccttcgcc | 180 |
| gacaagatgg | tgccgcgctt | cctgcttctg | tccgcggcct | cgatgctggt | gatgcgctac | 240 |
| tggttctggc | gcctgttcga | aacgctgccg | ccgcccgcgc | tcgacgcctc | gttcctcttc | 300 |
| gctctgctgc | tcttcgcggt | cgagaccttc | tcgatctcca | tcttcttcct | caacggcttt | 360 |
| ctcagcgccg | acccgaccga | ccggcccttc | ccgcggccgc | tgcagcccga | ggagctgccg | 420 |
| acggtcgaca | ttctcgtgcc | ctcctacaac | gagcccgccg | acatgctgag | cgtgacgctc | 480 |
| gcggcggcca | agaacatgat | ctatccggcg | cggctgcgca | cggtggtgct | ctgcgacgac | 540 |
| gggggcaccg | accagcgctg | catgtcgccc | gaccccgagc | ttgcgcagaa | ggcgcaggag | 600 |
| cggcggcgcg | agttgcagca | gctctgccgc | gagctgggcg | tggtctattc | gacgcgcgag | 660 |
| cggaacgaac | atgccaaggc | gggcaacatg | tcggccgcgc | tcgagcggct | gaagggcgag | 720 |
| ctcgtggtgg | tgttcgatgc | cgaccacgtc | ccgagccgcg | acttccttgc | ccggacggtg | 780 |
| ggctatttcg | tcgaggatcc | tgacctcttc | ctcgtccaga | cgccgcactt | cttcatcaac | 840 |
| cccgacccga | tccagcgcaa | cctcgcgctc | ggcgaccgct | gcccgcccga | gaacgagatg | 900 |
| ttctacggca | agatccaccg | cggcctcgac | cgctggggcg | gggccttctt | ctgcggatcg | 960 |
| gccgcggtcc | tgccgccgcc | cgccctcgac | gaggcgggcg | gctttgccgg | cgagaccatc | 1020 |
| accgaggatg | ccgagaccgc | gctcgagatc | cattcccgcg | gctggaagag | cctctatatc | 1080 |
| gaccgcgcca | tgatcgcggg | gctccagccc | gagaccttcg | cctccttcat | ccagcagcgc | 1140 |
| ggccgctggg | ccaccggcat | gatgcagatg | ctgctgctga | gaacccgct | cttccgccgc | 1200 |
| ggtctcggga | tcgcgcagcg | cctgtgctac | ctcaactcga | tgagcttctg | gttcttcccg | 1260 |
| ctggtgcgga | tgatgttcct | cgtggcgccg | ctcatctatc | tgttcttcgg | catcgagatc | 1320 |
| ttcgtcgcca | ccttcgagga | ggtgctggcc | tacatgccgg | gctatctggc | ggtgagcttc | 1380 |
| ctcgtgcaga | acgcgctgtt | tgcgcggcag | cgatggccgc | tcgtctccga | agtctacgag | 1440 |
| gtggcacagg | cgccctatct | ggcgcgcgcc | atcgtgacca | cgctgctgcg | gccgcgcagt | 1500 |
| gcccgcttcg | cggtgaccgc | gaaggacgag | acgctgagcg | agaactacat | ttcgcccatc | 1560 |
| taccgtccgc | tcctcttcac | cttcctgctc | tgcctgtccg | gggtgctcgc | cacgctggtg | 1620 |
| cgctgggtgg | ccttccccgg | cgaccggtcg | gtcctcctcg | tcgtgggcgg | ctgggcggtg | 1680 |
| ctcaacgtgc | ttctcgtggg | cttcgctttg | cgggcggtgg | ccgagaagca | gcagcggcgc | 1740 |
| gcggccccc | gtgtgcagat | ggaggtgccg | gccgaggcgc | agatccctgc | cttcggcaac | 1800 |
| cgctcgctga | ccgcgaccgt | gctcgacgcc | tcgaccagcg | gcgtgcgcct | tctggtccgg | 1860 |
| ctgcccggcg | tgggcgatcc | gcacccgcg | ctcgaggcg | agggctcat | ccagttccag | 1920 |
| ccgaagttcc | ccgacgcgcc | gcagctcgag | cgcatggtgc | gcggccgcat | ccgctcggcg | 1980 |
| cgccgcgagg | gcgaacggt | gatggtgggc | gtgatcttcg | aggcgggcca | accgatcgcg | 2040 |
| gtgcgcgaga | cggtggccta | tctcatcttc | ggcgagagcg | cgcactggcg | cacgatgcgc | 2100 |

```
gaggccacga tgcggcccat cgggctcctg cacgggatgg cgcgaatcct gtggatggcg    2160
gccgccagcc tgcccaagac cgcgcgcgac ttcatggacg aaccggcccg ccgccggcgc    2220
cgccacgagg aaccgaagga gaagcaggcg catcttctgg ccttcggcac cgacttcagc    2280
accgaacccg actgggcggg cgagctgctc gatccgacgg cgcaggtctc cgcgcgtccc    2340
aacacggtcg cctgggggtc gaactga                                        2367
```

<210> SEQ ID NO 12
<211> LENGTH: 788
<212> TYPE: PRT
<213> ORGANISM: Rhodobacter sphaeroides

<400> SEQUENCE: 12

```
Met Thr Val Arg Ala Lys Ala Arg Ser Pro Leu Arg Val Pro Val
1               5                  10                  15

Leu Leu Phe Leu Leu Trp Val Ala Leu Leu Val Pro Phe Gly Leu Leu
                20                  25                  30

Ala Ala Ala Pro Val Ala Pro Ser Ala Gln Gly Leu Ile Ala Leu Ser
            35                  40                  45

Ala Val Val Leu Val Ala Leu Leu Lys Pro Phe Ala Asp Lys Met Val
        50                  55                  60

Pro Arg Phe Leu Leu Leu Ser Ala Ala Ser Met Leu Val Met Arg Tyr
65                  70                  75                  80

Trp Phe Trp Arg Leu Phe Glu Thr Leu Pro Pro Ala Leu Asp Ala
                85                  90                  95

Ser Phe Leu Phe Ala Leu Leu Leu Phe Ala Val Glu Thr Phe Ser Ile
            100                 105                 110

Ser Ile Phe Phe Leu Asn Gly Phe Leu Ser Ala Asp Pro Thr Asp Arg
        115                 120                 125

Pro Phe Pro Arg Pro Leu Gln Pro Glu Glu Leu Pro Thr Val Asp Ile
    130                 135                 140

Leu Val Pro Ser Tyr Asn Glu Pro Ala Asp Met Leu Ser Val Thr Leu
145                 150                 155                 160

Ala Ala Ala Lys Asn Met Ile Tyr Pro Ala Arg Leu Arg Thr Val Val
                165                 170                 175

Leu Cys Asp Asp Gly Gly Thr Asp Gln Arg Cys Met Ser Pro Asp Pro
            180                 185                 190

Glu Leu Ala Gln Lys Ala Gln Glu Arg Arg Glu Leu Gln Gln Leu
        195                 200                 205

Cys Arg Glu Leu Gly Val Val Tyr Ser Thr Arg Glu Arg Asn Glu His
    210                 215                 220

Ala Lys Ala Gly Asn Met Ser Ala Ala Leu Glu Arg Leu Lys Gly Glu
225                 230                 235                 240

Leu Val Val Val Phe Asp Ala Asp His Val Pro Ser Arg Asp Phe Leu
                245                 250                 255

Ala Arg Thr Val Gly Tyr Phe Val Glu Asp Pro Asp Leu Phe Leu Val
            260                 265                 270

Gln Thr Pro His Phe Phe Ile Asn Pro Asp Pro Ile Gln Arg Asn Leu
        275                 280                 285

Ala Leu Gly Asp Arg Cys Pro Pro Glu Asn Glu Met Phe Tyr Gly Lys
    290                 295                 300

Ile His Arg Gly Leu Asp Arg Trp Gly Gly Ala Phe Phe Cys Gly Ser
305                 310                 315                 320

Ala Ala Val Leu Arg Arg Arg Ala Leu Asp Glu Ala Gly Gly Phe Ala
```

```
                    325                 330                 335
Gly Glu Thr Ile Thr Glu Asp Ala Glu Thr Ala Leu Glu Ile His Ser
                340                 345                 350
Arg Gly Trp Lys Ser Leu Tyr Ile Asp Arg Ala Met Ile Ala Gly Leu
            355                 360                 365
Gln Pro Glu Thr Phe Ala Ser Phe Ile Gln Gln Arg Gly Arg Trp Ala
        370                 375                 380
Thr Gly Met Met Gln Met Leu Leu Leu Lys Asn Pro Leu Phe Arg Arg
385                 390                 395                 400
Gly Leu Gly Ile Ala Gln Arg Leu Cys Tyr Leu Asn Ser Met Ser Phe
                405                 410                 415
Trp Phe Phe Pro Leu Val Arg Met Met Phe Leu Val Ala Pro Leu Ile
                420                 425                 430
Tyr Leu Phe Phe Gly Ile Glu Ile Phe Val Ala Thr Phe Glu Glu Val
            435                 440                 445
Leu Ala Tyr Met Pro Gly Tyr Leu Ala Val Ser Phe Leu Val Gln Asn
450                 455                 460
Ala Leu Phe Ala Arg Gln Arg Trp Pro Leu Val Ser Glu Val Tyr Glu
465                 470                 475                 480
Val Ala Gln Ala Pro Tyr Leu Ala Arg Ala Ile Val Thr Thr Leu Leu
                485                 490                 495
Arg Pro Arg Ser Ala Arg Phe Ala Val Thr Ala Lys Asp Glu Thr Leu
            500                 505                 510
Ser Glu Asn Tyr Ile Ser Pro Ile Tyr Arg Pro Leu Leu Phe Thr Phe
            515                 520                 525
Leu Leu Cys Leu Ser Gly Val Leu Ala Thr Leu Val Arg Trp Val Ala
530                 535                 540
Phe Pro Gly Asp Arg Ser Val Leu Leu Val Val Gly Gly Trp Ala Val
545                 550                 555                 560
Leu Asn Val Leu Leu Val Gly Phe Ala Leu Arg Ala Val Ala Glu Lys
                565                 570                 575
Gln Gln Arg Arg Ala Ala Pro Arg Val Gln Met Glu Val Pro Ala Glu
            580                 585                 590
Ala Gln Ile Pro Ala Phe Gly Asn Arg Ser Leu Thr Ala Thr Val Leu
        595                 600                 605
Asp Ala Ser Thr Ser Gly Val Arg Leu Leu Val Arg Leu Pro Gly Val
610                 615                 620
Gly Asp Pro His Pro Ala Leu Glu Ala Gly Gly Leu Ile Gln Phe Gln
625                 630                 635                 640
Pro Lys Phe Pro Asp Ala Pro Gln Leu Glu Arg Met Val Arg Gly Arg
                645                 650                 655
Ile Arg Ser Ala Arg Arg Glu Gly Gly Thr Val Met Val Gly Val Ile
            660                 665                 670
Phe Glu Ala Gly Gln Pro Ile Ala Val Arg Glu Thr Val Ala Tyr Leu
        675                 680                 685
Ile Phe Gly Glu Ser Ala His Trp Arg Thr Met Arg Glu Ala Thr Met
690                 695                 700
Arg Pro Ile Gly Leu Leu His Gly Met Ala Arg Ile Leu Trp Met Ala
705                 710                 715                 720
Ala Ala Ser Leu Pro Lys Thr Ala Arg Asp Phe Met Asp Glu Pro Ala
                725                 730                 735
Arg Arg Arg Arg Arg His Glu Glu Pro Lys Glu Lys Gln Ala His Leu
            740                 745                 750
```

```
Leu Ala Phe Gly Thr Asp Phe Ser Thr Glu Pro Asp Trp Ala Gly Glu
        755                 760                 765

Leu Leu Asp Pro Thr Ala Gln Val Ser Ala Arg Pro Asn Thr Val Ala
    770                 775                 780

Trp Gly Ser Asn
785

<210> SEQ ID NO 13
<211> LENGTH: 672
<212> TYPE: DNA
<213> ORGANISM: Rhodobacter sphaeroides

<400> SEQUENCE: 13
atgacacagg catcgaaatg gtacgcccgg ctaaggcccg gccttccgct ggcggcgctt    60
ctgctgcttc tggcctgcga gtcgacctcc attcccggca ggcccgcgct ctcgatccgc   120
gaggagacgg cgcagttccg caccgtcccc gccagccggg cctgggtcgc cgtgcccggg   180
gcgctcctcg tgcaggagcg ggatctgggc ggcgacctcg agcagcggat cgcgctgccg   240
aacgccacga cgctcgaagg cgacaatatg atcatcttgc gaggccgggc gccgggcgga   300
ccgattctcg agcggctcca gctgcagagc ttcgccgatg ccgatggcgc gctgcccaag   360
cccttcggcc gggtgagcga cagcgctctc agcacgcgcg aggatgtgct cggcaccgtg   420
gtctttgccg aggagcggct ggcgtggac acggtctgcg ttctggccat gcgccggatg   480
ccgcccacgg cccggccggt tccggcgcgg atcgaggcgc tggacgtgat gctgcgcaac   540
tgcacgcgca acggcacgga ggaggcgctg cggcccatcg cgcggccag cctcggcttc   600 gccccgcccg aagcggtggc cggtacgggg gcagggcgca ccctctcgcc cctcgccgcc   660
ccgatgccct ga                                                      672

<210> SEQ ID NO 14
<211> LENGTH: 223
<212> TYPE: PRT
<213> ORGANISM: Rhodobacter sphaeroides

<400> SEQUENCE: 14

Met Thr Gln Ala Ser Lys Trp Tyr Ala Arg Leu Arg Pro Gly Leu Pro
1               5                   10                  15

Leu Ala Ala Leu Leu Leu Leu Ala Cys Glu Ser Thr Ser Ile Pro
            20                  25                  30

Gly Arg Pro Ala Leu Ser Ile Arg Glu Glu Thr Ala Gln Phe Arg Thr
        35                  40                  45

Val Pro Ala Ser Arg Ala Trp Val Ala Val Pro Gly Ala Leu Leu Val
    50                  55                  60

Gln Glu Arg Asp Leu Gly Asp Leu Glu Gln Arg Ile Ala Leu Pro
65                  70                  75                  80

Asn Ala Thr Thr Leu Glu Gly Asp Asn Met Ile Ile Leu Arg Gly Arg
                85                  90                  95

Ala Pro Gly Gly Pro Ile Leu Glu Arg Leu Gln Leu Gln Ser Phe Ala
            100                 105                 110

Asp Ala Asp Gly Ala Leu Pro Lys Pro Phe Gly Arg Val Ser Asp Ser
        115                 120                 125

Ala Leu Ser Thr Arg Glu Asp Val Leu Gly Thr Val Phe Ala Glu
    130                 135                 140

Glu Arg Leu Gly Val Asp Thr Val Cys Val Leu Ala Met Arg Arg Met
145                 150                 155                 160
```

```
          Pro Pro Thr Ala Arg Pro Val Pro Ala Arg Ile Glu Ala Leu Asp Val
                          165                 170                 175

Met Leu Arg Asn Cys Thr Arg Asn Gly Thr Glu Glu Ala Leu Arg Pro
                      180                 185                 190

Ile Gly Ala Ala Ser Leu Gly Phe Ala Pro Pro Glu Ala Val Ala Gly
                  195                 200                 205

Thr Gly Ala Gly Arg Thr Leu Ser Pro Leu Ala Ala Pro Met Pro
              210                 215                 220

<210> SEQ ID NO 15
<211> LENGTH: 2370
<212> TYPE: DNA
<213> ORGANISM: Rhodobacter sphaeroides

<400> SEQUENCE: 15
atgacgggca agggacaggg tggatcttgg gtgccggggg tcgtttccgc gaccgaccgc      60
ggcaatttcc atgcaagccc caccaccgcc acggtgcttg acatcatcgg ccgcatcctg     120
cgcgccccgc tctctgccac cgacaccgag atcgagaccg ccctcgcgca ggtggcggac     180
gcctgcagcg cggatgtcgc gcaggtctgc cgtgcgggga ccacgggccc tctcgagccg     240
atccacagct gggtgcgtga cggccatatc gtcttgaaca tccaagactt gtgcaaattc     300
tgcccggggt cggaccagac cgggcccgtc atgctgcgcg acctgaagga ccttcccgag     360
gggccggccc gcgatcggct cgcggggatg gagttgcggt cgctcgtcgc ggtgccgatg     420
ctacggcacg gggtgctggc gggccgggtg cttctgggct ggcagacggc gagcagcgac     480
ctgcgccccg aggatctcgc cgcgctgcag tccctcgccg aggccatgca tgcggccgcg     540
gagcgacgcg aaagcgagcg gctcacgacg gaggcggcag cggcgctgca ggaggaccgg     600
cttcttctcg aatcgatcct gcggaccagc acctcggcca tcctcgcctt cgatgccgat     660
gcccgcatcg tcttcgccaa cgatgaggcg gcggccctcc tcggaacgga cgcgaaccgt     720
ctgccgggat gcaccctcga gggcgtgggc tgccgccttc tgtcgcgcga gggcgagccc     780
ctcccgcccg aggccctgcc ggtcgcgcgc gccattgctg aggggcagac gctccgcgac     840
ctgcaccatg tgctgatggc cgccgacggc cgacagagga tcctgtcgat caacgcggcc     900
cccgtggcgg ccggcgcggc gacagcggtg cgcgtcgtcg ccaccatcga cgacgtgacc     960
ggtcaggtct cggccgacag cgcgctgcgc acggcgctcg ccgaagcgca tcagctcgcc    1020
ttcttcgacc ctctgacggg gctttacaac cgccggggca tcgtcgaggt gctgcgcgac    1080
tgcctccaga cctgcgcccg cgagaaggcc ttcctctcgc ttctctatat cgatctggac    1140
gggatgcggc aggtgaacgg cacccgcggg cactggctgg cgaccgggt cctgcaggcg     1200 ctgggcgcgc ggctggacaa cctgcggcag acggcggcg acctcggccg gatctcggcc     1260
gacgaattcg tgctgacctg cggcgagacc catcccgacg ccgccggcgc ggtcgccgcc    1320
gccgaggccg aggcccagcg catcctcgag tcgctgcggg agccgttcgt ggtggatggc    1380
ctcacgctcg aggtcaccgc ctcgatcggc cttgccgcca tttcggccga ggattcggtc    1440
gaggggctgc tgaagggcgt cgatctggcc gtcatggccg ccaaggccgc gggcggcgac    1500
agggcctgtg cctaccgggc cgacatggag caggacatgg tgggtcgcgt ggccctcgcg    1560
caggagttgc gcgaggcgat ccgccgcgac gagttccgca tctacttcga accgatggtc    1620
agcctcggcg agaccgggct cgagatcgtg ggtcaggagg cgctgatccg ctgggagcat    1680
ccgcagcgcg ggcttctggc gcccatcgcc ttcatcccct tcgccgagga gaccggcttc    1740
```

```
atccgcgaca tcgaccgctg ggtgctgcgc gcggcggcac aggagctcgc ccgctgggcc    1800
gaggatcccg cgcgccgcca tctcggggtc tcgatcaaca tcagctcggc gcagttcctg    1860
tccgaggagt tcggccagat ggtgcgcgag gtgctggacg agaccggcgt cgatcccacc    1920
cggatcgagc tggaggtcac cgagggcacg ctcctgtcca atctcggcct cgcgcggacc    1980
acgatgatgg acctgcgctc gctcggcatc tccatcgcgc tggacgattt cggcaccggc    2040
ttctcctcgc tcagctatct gcgggacctg cccgtggacg tgttgaagat cgaccgcagc    2100
ttcttgggcg gcctgtcgga ctcgaaggcg aaccggacca tcctcgaagg gatcatcgga    2160
cttgcctcgg gctcggcgt ggcgctggtg gccgaggggg tggagacgcc ggcgcagttc    2220
gcctggctgc gggccaaggg atgccggacc ttccagggct acctcttcgg ccgcccggtc    2280
gatgaggcgc agacgcagct cgcgcccgag gtgtccgcgc tcggcggcca cggaggcgac    2340
cgtgcggttt cgggccagat caagggctga                                     2370
```

<210> SEQ ID NO 16
<211> LENGTH: 789
<212> TYPE: PRT
<213> ORGANISM: Rhodobacter sphaeroides

<400> SEQUENCE: 16

```
Met Thr Gly Lys Gly Gln Gly Gly Ser Trp Val Pro Gly Val Val Ser
1               5                  10                  15

Ala Thr Asp Arg Gly Asn Phe His Ala Ser Pro Thr Thr Ala Thr Val
                20                  25                  30

Leu Asp Ile Ile Gly Arg Ile Leu Arg Ala Pro Leu Ser Ala Thr Asp
            35                  40                  45

Thr Glu Ile Glu Thr Ala Leu Ala Gln Val Ala Asp Ala Cys Ser Ala
        50                  55                  60

Asp Val Ala Gln Val Cys Arg Ala Gly Thr Thr Gly Pro Leu Glu Pro
65                  70                  75                  80

Ile His Ser Trp Val Arg Asp Gly His Ile Val Leu Asn Ile Gln Asp
                85                  90                  95

Leu Cys Lys Phe Cys Pro Gly Ser Asp Gln Thr Gly Pro Val Met Leu
            100                 105                 110

Arg Asp Leu Lys Asp Leu Pro Glu Gly Pro Ala Arg Asp Arg Leu Ala
        115                 120                 125

Gly Met Glu Leu Arg Ser Leu Val Ala Val Pro Met Leu Arg His Gly
    130                 135                 140

Val Leu Ala Gly Arg Val Leu Leu Gly Trp Gln Thr Ala Ser Ser Asp
145                 150                 155                 160

Leu Arg Pro Glu Asp Leu Ala Ala Leu Gln Ser Leu Ala Glu Ala Met
                165                 170                 175

His Ala Ala Ala Glu Arg Arg Glu Ser Glu Arg Leu Thr Thr Glu Ala
            180                 185                 190

Ala Ala Ala Leu Gln Glu Asp Arg Leu Leu Glu Ser Ile Leu Arg
        195                 200                 205

Thr Ser Thr Ser Ala Ile Leu Ala Phe Asp Ala Asp Ala Arg Ile Val
    210                 215                 220

Phe Ala Asn Asp Glu Ala Ala Leu Leu Gly Thr Asp Ala Asn Arg
225                 230                 235                 240

Leu Pro Gly Cys Thr Leu Glu Gly Val Gly Cys Arg Leu Leu Ser Arg
                245                 250                 255

Glu Gly Glu Pro Leu Pro Pro Glu Ala Leu Pro Val Ala Arg Ala Ile
```

```
            260                 265                 270
Ala Glu Gly Gln Thr Leu Arg Asp Leu His His Val Leu Met Ala Ala
            275                 280                 285

Asp Gly Arg Gln Arg Ile Leu Ser Ile Asn Ala Ala Pro Val Ala Ala
            290                 295                 300

Gly Ala Ala Thr Ala Val Arg Val Val Ala Thr Ile Asp Asp Val Thr
305                 310                 315                 320

Gly Gln Val Ser Ala Asp Ser Ala Leu Arg Thr Ala Leu Ala Glu Ala
                325                 330                 335

His Gln Leu Ala Phe Phe Asp Pro Leu Thr Gly Leu Tyr Asn Arg Arg
            340                 345                 350

Gly Ile Val Glu Val Leu Arg Asp Cys Leu Gln Thr Cys Ala Arg Glu
            355                 360                 365

Lys Ala Phe Leu Ser Leu Leu Tyr Ile Asp Leu Asp Gly Met Arg Gln
            370                 375                 380

Val Asn Gly Thr Arg Gly His Trp Leu Gly Asp Arg Val Leu Gln Ala
385                 390                 395                 400

Leu Gly Ala Arg Leu Asp Asn Leu Arg Gln Asp Gly Gly Asp Leu Gly
                405                 410                 415

Arg Ile Ser Ala Asp Glu Phe Val Leu Thr Cys Gly Glu Thr His Pro
            420                 425                 430

Asp Ala Ala Gly Ala Val Ala Ala Ala Glu Ala Glu Ala Gln Arg Ile
            435                 440                 445

Leu Glu Ser Leu Arg Glu Pro Phe Val Val Asp Gly Leu Thr Leu Glu
            450                 455                 460

Val Thr Ala Ser Ile Gly Leu Ala Ala Ile Ser Ala Glu Asp Ser Val
465                 470                 475                 480

Glu Gly Leu Leu Lys Gly Val Asp Leu Ala Val Met Ala Ala Lys Ala
                485                 490                 495

Ala Gly Gly Asp Arg Ala Cys Ala Tyr Arg Ala Asp Met Glu Gln Asp
            500                 505                 510

Met Val Gly Arg Val Ala Leu Ala Gln Glu Leu Arg Glu Ala Ile Arg
            515                 520                 525

Arg Asp Glu Phe Arg Ile Tyr Phe Glu Pro Met Val Ser Leu Gly Glu
            530                 535                 540

Thr Gly Leu Glu Ile Val Gly Gln Glu Ala Leu Ile Arg Trp Glu His
545                 550                 555                 560

Pro Gln Arg Gly Leu Leu Ala Pro Ile Ala Phe Ile Pro Phe Ala Glu
            565                 570                 575

Glu Thr Gly Phe Ile Arg Asp Ile Asp Arg Trp Val Leu Arg Ala Ala
            580                 585                 590

Ala Gln Glu Leu Ala Arg Trp Ala Glu Asp Pro Ala Arg Arg His Leu
            595                 600                 605

Gly Val Ser Ile Asn Ile Ser Ser Ala Gln Phe Leu Ser Glu Glu Phe
            610                 615                 620

Gly Gln Met Val Arg Glu Val Leu Asp Glu Thr Gly Val Asp Pro Thr
625                 630                 635                 640

Arg Ile Glu Leu Glu Val Thr Glu Gly Thr Leu Leu Ser Asn Leu Gly
                645                 650                 655

Leu Ala Arg Thr Thr Met Met Asp Leu Arg Ser Leu Gly Ile Ser Ile
            660                 665                 670

Ala Leu Asp Asp Phe Gly Thr Gly Phe Ser Ser Leu Ser Tyr Leu Arg
            675                 680                 685
```

```
Asp Leu Pro Val Asp Val Leu Lys Ile Asp Arg Ser Phe Leu Gly Gly
    690             695                 700
Leu Ser Asp Ser Lys Ala Asn Arg Thr Ile Leu Glu Gly Ile Ile Gly
705             710                 715                 720
Leu Ala Ser Gly Leu Gly Val Ala Leu Ala Glu Gly Val Glu Thr
                725                 730                 735
Pro Ala Gln Phe Ala Trp Leu Arg Ala Lys Gly Cys Arg Thr Phe Gln
            740                 745                 750
Gly Tyr Leu Phe Gly Arg Pro Val Asp Glu Ala Gln Thr Gln Leu Ala
        755                 760                 765
Pro Glu Val Ser Ala Leu Gly Gly His Gly Gly Asp Arg Ala Val Ser
    770                 775                 780
Gly Gln Ile Lys Gly
785
```

<210> SEQ ID NO 17
<211> LENGTH: 570
<212> TYPE: DNA
<213> ORGANISM: Rhodobacter sphaeroides

<400> SEQUENCE: 17

```
atgacgctca ccttggccca gaccctggac cgctgcctcg atatcgcagg aaatccgacc      60
gcggcgatca gtttcccgca acggcggatg ctgggtcagg cgctggcgtt cctgccgcgt     120
cagcactacc ggcgtgtgct ggagctcggg tgcgggtcgg gggcgctggc gcgcggtctt     180
tcggcacgct gcgaccatta tgtcggcctc gatgcggacg ccgatgctct ggatgaggcg     240
tccctcatgc cctcgcccta tgcgcagacc gaattccgcc agggccgggt gcccgaggac     300
atccccgagg gtccgttcga tctcgtggtg ctgaacgggg tgctgcagga tctgccggcc     360
gaggcgatcg agcggcttgc ggtgcggttg cgccaggtgg cgcttcggc cgacatcctc      420
tgcctccgca gccttctgtt cgagggtccc gacgaggcgt tccgcccgca ggccgccctg     480
gccgcggccc tcggtcggcc gctcaccgcc tgcaacttcg accggctgtt ccgcatcgac     540
gtgttcgagc cggaacgcgc cgccgcctga                                       570
```

<210> SEQ ID NO 18
<211> LENGTH: 189
<212> TYPE: PRT
<213> ORGANISM: Rhodobacter sphaeroides

<400> SEQUENCE: 18

```
Met Thr Leu Thr Leu Ala Gln Thr Leu Asp Arg Cys Leu Asp Ile Ala
1               5                   10                  15
Gly Asn Pro Thr Ala Ala Ile Ser Phe Pro Gln Arg Arg Met Leu Gly
            20                  25                  30
Gln Ala Leu Ala Phe Leu Pro Arg Gln His Tyr Arg Arg Val Leu Glu
        35                  40                  45
Leu Gly Cys Gly Ser Gly Ala Leu Ala Arg Gly Leu Ser Ala Arg Cys
    50                  55                  60
Asp His Tyr Val Gly Leu Asp Ala Asp Ala Asp Ala Leu Asp Glu Ala
65                  70                  75                  80
Ser Leu Met Pro Ser Pro Tyr Ala Gln Thr Glu Phe Arg Gln Gly Arg
                85                  90                  95
Val Pro Glu Asp Ile Pro Glu Gly Pro Phe Asp Leu Val Val Leu Asn
            100                 105                 110
```

```
Gly Val Leu Gln Asp Leu Pro Ala Glu Ala Ile Glu Arg Leu Ala Val
            115                 120                 125

Arg Leu Arg Gln Val Ala Pro Ser Ala Asp Ile Leu Cys Leu Arg Ser
        130                 135                 140

Leu Leu Phe Glu Gly Pro Asp Glu Ala Phe Arg Pro Gln Ala Ala Leu
145                 150                 155                 160

Ala Ala Ala Leu Gly Arg Pro Leu Thr Ala Cys Asn Phe Asp Arg Leu
                165                 170                 175

Phe Arg Ile Asp Val Phe Glu Pro Glu Arg Ala Ala Ala
            180                 185

<210> SEQ ID NO 19
<211> LENGTH: 1638
<212> TYPE: DNA
<213> ORGANISM: Rhodobacter sphaeroides

<400> SEQUENCE: 19
```

| | | | | | |
|---|---|---|---|---|---|
| gtgacacgat | gcctgtcggc | ggggccctgc | cggcaggctt | cacatgagct | tgacgggcca | 60 |
| agacgccgtt | tgcattgcgg | cgcatcttgc | ccgactgtca | cttcggggcg | gtgcagcttg | 120 |
| cagttggccg | ctcagctatc | tcgaaaggag | tcgggtgtgc | agtctcacgc | cattaccatc | 180 |
| gcccgccgca | tccacccggt | gcccgcgtcg | gtctcgcgtc | tcttcctcgc | gctgatgctc | 240 |
| gggctcgccc | tggcgctggc | gcaggccgtg | gcggtcaagg | cgcagaacgc | tcccgcaagt | 300 |
| ttcgcaggcc | tcgccgagaa | gatcagcccg | gccgtcgtga | acatcacgac | ctcgaccgtc | 360 |
| gtggcggcac | ccacgcagaa | ttcgcccctc | gtgcccgaag | gctcgccctt | cgaggatttc | 420 |
| ttccgtgact | tcatggaccc | gcagaaccgc | ggcgagggcc | cgcgccgctc | cgaggcgctg | 480 |
| ggttcgggct | tcgtgatctc | ggaagacggc | tacatcgtca | ccaacaatca | tgtcatcgaa | 540 |
| ggggccgacg | acatccagat | cgagttcttc | tcgggcaaga | agctcgaggc | gaagctcgtc | 600 |
| ggcaccgatc | cgaagaccga | catcgcgctg | ctgaaggtcg | atgggaacca | gccgctgccc | 660 |
| ttcgtgagct | tcggcaactc | cgacctcgcc | cgcgttggcg | actgggtcgt | ggcgatgggc | 720 |
| aacccgctgg | ggcagggctt | ctcggtctcg | gccggcatcg | tgtcggcgcg | caaccgggcc | 780 |
| ctctccggca | cctacgacga | ttacatccag | accgacgccg | ccatcaaccg | cggcaattcg | 840 |
| ggcggtccgc | tgttcaacat | ggacgggcag | gtgatcggcg | tgaacacggc | gatcctgtcg | 900 |
| ccgaacggcg | gctcgatcgg | catcggcttc | tcgatggcct | cgaacgtggt | ggtgaaggtc | 960 |
| gtgcagcagc | tgcgcgagtt | cggcgagacc | cgccgcggct | ggctcggcgt | gcggatccag | 1020 |
| gacgtgaccc | ccgacgtggc | cgaggcgatg | ggcctcaccg | aggccaaagg | cgccctcgtg | 1080 |
| accgacgtgc | cggaaggccc | cgcgaaagag | gccggcatgc | agtctggcga | cgtgatcgtg | 1140 |
| accttcgata | gcgcgcccgt | ggcggacacc | cgcgatctgg | tgcgccgggt | ggccgatgcg | 1200 |
| cccattggcg | aggcggtgcg | tgtcatcgtg | atgcgcgaag | gcaagacccg | gaccctgtcg | 1260 |
| gtgacgctcg | gcgtcgcga | ggaagccgag | aacgaaggcc | ccgaggcacc | cggcgcgacc | 1320 |
| gagccgacgg | aaccgtcgac | ggccgatctt | ctgggcctga | ccgtggcgcc | gctcacggcc | 1380 |
| gagcaggccg | gagagctggg | cctgccggc | ggcaccgagg | ggcttgccgt | gacggatgtc | 1440 |
| gatccggcct | ccgaggccta | ttccaaggc | ttgcgcgagg | gagacgtgat | caccgaggcc | 1500 |
| ggccagcaga | aagtggtctc | gatcaaggat | ctgcaggacc | gtgtgaccga | ggcgcgggag | 1560 |
| gcggggcgga | aatcgctgct | cctgctgatc | cgccgcggcg | gcgatccgcg | tttcgtggcc | 1620 |
| ctgacggtca | gcgagtag | | | | | 1638 |

```
<210> SEQ ID NO 20
<211> LENGTH: 545
<212> TYPE: PRT
<213> ORGANISM: Rhodobacter sphaeroides

<400> SEQUENCE: 20
```

| | | | | | | | | | | | | | | |
|---|---|---|---|---|---|---|---|---|---|---|---|---|---|---|
| Met | Thr | Arg | Cys | Leu | Ser | Ala | Gly | Pro | Cys | Arg | Gln | Ala | Ser | His | Glu |
| 1 | | | | 5 | | | | | 10 | | | | | 15 | |

| Leu | Asp | Gly | Pro | Arg | Arg | Leu | His | Cys | Gly | Ala | Ser | Cys | Pro | Thr |
|---|---|---|---|---|---|---|---|---|---|---|---|---|---|---|
| | | | 20 | | | | 25 | | | | | 30 | | |

| Val | Thr | Ser | Gly | Arg | Cys | Ser | Leu | Gln | Leu | Ala | Ala | Gln | Leu | Ser | Arg |
|---|---|---|---|---|---|---|---|---|---|---|---|---|---|---|---|
| | | 35 | | | | | 40 | | | | 45 | | | | |

| Lys | Glu | Ser | Gly | Val | Gln | Ser | His | Ala | Ile | Thr | Ile | Ala | Arg | Arg | Ile |
| 50 | | | | | 55 | | | | | 60 | | | | | |

| His | Pro | Val | Pro | Ala | Ser | Val | Ser | Arg | Leu | Phe | Leu | Ala | Leu | Met | Leu |
| 65 | | | | | 70 | | | | | 75 | | | | | 80 |

| Gly | Leu | Ala | Leu | Ala | Leu | Ala | Gln | Ala | Val | Ala | Val | Lys | Ala | Gln | Asn |
| | | | | 85 | | | | | 90 | | | | | 95 | |

| Ala | Pro | Ala | Ser | Phe | Ala | Gly | Leu | Ala | Glu | Lys | Ile | Ser | Pro | Ala | Val |
| | | | 100 | | | | | 105 | | | | | 110 | | |

| Val | Asn | Ile | Thr | Thr | Ser | Thr | Val | Val | Ala | Ala | Pro | Thr | Gln | Asn | Ser |
| | | | 115 | | | | | 120 | | | | | 125 | | |

| Pro | Leu | Val | Pro | Glu | Gly | Ser | Pro | Phe | Glu | Asp | Phe | Phe | Arg | Asp | Phe |
| | 130 | | | | | 135 | | | | | 140 | | | | |

| Met | Asp | Pro | Gln | Asn | Arg | Gly | Glu | Gly | Pro | Arg | Arg | Ser | Glu | Ala | Leu |
| 145 | | | | | 150 | | | | | 155 | | | | | 160 |

| Gly | Ser | Gly | Phe | Val | Ile | Ser | Glu | Asp | Gly | Tyr | Ile | Val | Thr | Asn | Asn |
| | | | | 165 | | | | | 170 | | | | | 175 | |

| His | Val | Ile | Glu | Gly | Ala | Asp | Asp | Ile | Gln | Ile | Glu | Phe | Phe | Ser | Gly |
| | | | 180 | | | | | 185 | | | | | 190 | | |

| Lys | Lys | Leu | Glu | Ala | Lys | Leu | Val | Gly | Thr | Asp | Pro | Lys | Thr | Asp | Ile |
| | | | 195 | | | | | 200 | | | | | 205 | | |

| Ala | Leu | Leu | Lys | Val | Asp | Gly | Asn | Gln | Pro | Leu | Pro | Phe | Val | Ser | Phe |
| | 210 | | | | | 215 | | | | | 220 | | | | |

| Gly | Asn | Ser | Asp | Leu | Ala | Arg | Val | Gly | Asp | Trp | Val | Val | Ala | Met | Gly |
| 225 | | | | | 230 | | | | | 235 | | | | | 240 |

| Asn | Pro | Leu | Gly | Gln | Gly | Phe | Ser | Val | Ser | Ala | Gly | Ile | Val | Ser | Ala |
| | | | | 245 | | | | | 250 | | | | | 255 | |

| Arg | Asn | Arg | Ala | Leu | Ser | Gly | Thr | Tyr | Asp | Asp | Tyr | Ile | Gln | Thr | Asp |
| | | | 260 | | | | | 265 | | | | | 270 | | |

| Ala | Ala | Ile | Asn | Arg | Gly | Asn | Ser | Gly | Gly | Pro | Leu | Phe | Asn | Met | Asp |
| | 275 | | | | | 280 | | | | | 285 | | | | |

| Gly | Gln | Val | Ile | Gly | Val | Asn | Thr | Ala | Ile | Leu | Ser | Pro | Asn | Gly | Gly |
| 290 | | | | | 295 | | | | | 300 | | | | | |

| Ser | Ile | Gly | Ile | Gly | Phe | Ser | Met | Ala | Ser | Asn | Val | Val | Lys | Val |
| 305 | | | | | 310 | | | | | 315 | | | | | 320 |

| Val | Gln | Gln | Leu | Arg | Glu | Phe | Gly | Glu | Thr | Arg | Arg | Gly | Trp | Leu | Gly |
| | | | | 325 | | | | | 330 | | | | | 335 | |

| Val | Arg | Ile | Gln | Asp | Val | Thr | Pro | Asp | Val | Ala | Glu | Ala | Met | Gly | Leu |
| | | | 340 | | | | | 345 | | | | | 350 | | |

| Thr | Glu | Ala | Lys | Gly | Ala | Leu | Val | Thr | Asp | Val | Pro | Glu | Gly | Pro | Ala |
| | 355 | | | | | 360 | | | | | 365 | | | | |

| Lys | Glu | Ala | Gly | Met | Gln | Ser | Gly | Asp | Val | Ile | Val | Thr | Phe | Asp | Ser |
| 370 | | | | | 375 | | | | | 380 | | | | | |

```
Ala Pro Val Ala Asp Thr Arg Asp Leu Val Arg Arg Val Ala Asp Ala
385                 390                 395                 400

Pro Ile Gly Glu Ala Val Arg Val Ile Val Met Arg Glu Gly Lys Thr
                405                 410                 415

Arg Thr Leu Ser Val Thr Leu Gly Arg Arg Glu Glu Ala Glu Asn Glu
            420                 425                 430

Gly Pro Glu Ala Pro Gly Ala Thr Glu Pro Thr Glu Pro Ser Thr Ala
        435                 440                 445

Asp Leu Leu Gly Leu Thr Val Ala Pro Leu Thr Ala Glu Gln Ala Gly
    450                 455                 460

Glu Leu Gly Leu Pro Gly Gly Thr Glu Gly Leu Ala Val Thr Asp Val
465                 470                 475                 480

Asp Pro Ala Ser Glu Ala Tyr Ser Lys Gly Leu Arg Glu Gly Asp Val
                485                 490                 495

Ile Thr Glu Ala Gly Gln Gln Lys Val Val Ser Ile Lys Asp Leu Gln
            500                 505                 510

Asp Arg Val Thr Glu Ala Arg Glu Ala Gly Arg Lys Ser Leu Leu Leu
        515                 520                 525

Leu Ile Arg Arg Gly Gly Asp Pro Arg Phe Val Ala Leu Thr Val Ser
    530                 535                 540

Glu
545

<210> SEQ ID NO 21
<211> LENGTH: 1806
<212> TYPE: DNA
<213> ORGANISM: Rhodobacter sphaeroides

<400> SEQUENCE: 21
atggcaaccg aagagcagtc tccgggttcc ggccgtgacg ctcagttcga gcgtctgaac      60
gcgaatctca cccgcatcga cgagctgtcg aaacggctga cggccgctct cacgaagcgc     120
aaactgtcgg accccgcgct gcacgggccc tcgggcgacg tcttcctgaa ggcgatgacg     180
gcctacatgg ccgagatgat gcagaacccg gccaagatcc tcgagcatca gatcagtttc     240
tggggcaaga gcctgaaaca ttacgtcgag gctcagcacc agctggtgaa gggcgagctg     300
aagccgccgc cggacgtgac gccgaaggac cgccgcttct cgaacccgct ctggcagacg     360
catcccttct tcaactatct caagcagcag tatctgatga acgccgaggc ggtgaatcag     420
gccgtcgagg cgctggagca tatcgagccg tccgacaaga gcgggtcga atatttctcg      480 cgccagatcg tcgatctttt ctcgcccacg aacttcttcg gcaccaatcc cgacgcgctc     540
gaacgcgcca tcgccaccga cggcgagagc ctggtgcagg gctggagaa tctcgtgcgc      600 gacatcgagg ccaacaacgg cgatctgctc gtcacgctgg ccgaccccga ggcctttcag     660
gtggggcaga acctcgccac caccgaaggg tcggtcgtct accgcaaccg catgttcgag     720
ctgatccagt acaagcccac gaccgagacg tccacgaga gccgctgct gatctttccg       780 ccctggatca acaagttcta catcctcgac ctcaagccgc agaattccct gctgaagtgg     840
ctggtggatc agggcttcac ggtcttcgtc gtctcgtggg tgaaccccga caagagctat     900
gccggcatcg gcatggacga ctacatccgc gaaggctaca tgcgcgccat ggccgaggtg     960
cgctcgatca cccggcagaa gcagatcaac gcggtaggct attgcatcgc gggcaccacg    1020
ctcacgctga cgctggcgca cctgcagaag gcgggcgatc cgtccgtacg ctcggccacc    1080
ttcttcacca cgctcaccga cttttcggac ccgggtgagg tggggtgtt cctcaacgac     1140
```

-continued

```
gatttcgtcg acgggatcga gcggcaggtg gcggtggacg ggatcctcga caagaccttc    1200
atgtcgcgca ccttcagcta tctgcggtcg aacgacctga tctatcagcc ggcgatcaag    1260
agctacatga tgggcgaggc gccgccggcc ttcgacctgc tctactggaa cggagacggc    1320
accaacctgc cggcgcagat ggcggtcgaa tacctgcgtg gcctgtgcca gcaggaccgg    1380
ctggcgggcg gcaccttccc ggtgctgggc tcgcccgtgg ggctgaagga tgtgacgctt    1440
cccgtctgcg ccatcgcctg cgagaccgac catatcgcgc cgtggaaaag cagcttcaac    1500
ggcttccgtc agttcggctc gaccgacaag accttcattc tctctcaatc gggccatgtg    1560
gcgggcatcg tgaacccgcc cagccgcaac aaatacggcc attaccaa cgagggcccg      1620 gccggcacgc cggagtcgtt ccgggagggg gccgagttcc acgcgggctc ctggtggccg    1680
cgctggggcg cctggctcgc cgagcgatcg ggcaagcagg tcccggcgcg ccagccgggc    1740
gattcgaaac atcccgagct cgcgccggcg cccggatcct atgtggcggc ggtgggcggg    1800
gcttga                                                               1806
```

<210> SEQ ID NO 22
<211> LENGTH: 601
<212> TYPE: PRT
<213> ORGANISM: Rhodobacter sphaeroides

<400> SEQUENCE: 22

```
Met Ala Thr Glu Glu Gln Ser Pro Gly Ser Gly Arg Asp Ala Gln Phe
1               5                   10                  15

Glu Arg Leu Asn Ala Asn Leu Thr Arg Ile Asp Glu Leu Ser Lys Arg
            20                  25                  30

Leu Thr Ala Ala Leu Thr Lys Arg Lys Leu Ser Asp Pro Ala Leu His
        35                  40                  45

Gly Pro Ser Gly Asp Val Phe Leu Lys Ala Met Thr Ala Tyr Met Ala
    50                  55                  60

Glu Met Met Gln Asn Pro Ala Lys Ile Leu Glu His Gln Ile Ser Phe
65                  70                  75                  80

Trp Gly Lys Ser Leu Lys His Tyr Val Glu Ala Gln His Gln Leu Val
                85                  90                  95

Lys Gly Glu Leu Lys Pro Pro Asp Val Thr Pro Lys Asp Arg Arg
            100                 105                 110

Phe Ser Asn Pro Leu Trp Gln Thr His Pro Phe Phe Asn Tyr Leu Lys
        115                 120                 125

Gln Gln Tyr Leu Met Asn Ala Glu Ala Val Asn Gln Ala Val Glu Ala
    130                 135                 140

Leu Glu His Ile Glu Pro Ser Asp Lys Lys Arg Val Glu Tyr Phe Ser
145                 150                 155                 160

Arg Gln Ile Val Asp Leu Phe Ser Pro Thr Asn Phe Gly Thr Asn
                165                 170                 175

Pro Asp Ala Leu Glu Arg Ala Ile Ala Thr Asp Gly Glu Ser Leu Val
        180                 185                 190

Gln Gly Leu Glu Asn Leu Val Arg Asp Ile Glu Ala Asn Asn Gly Asp
    195                 200                 205

Leu Leu Val Thr Leu Ala Asp Pro Glu Ala Phe Gln Val Gly Gln Asn
210                 215                 220

Leu Ala Thr Thr Glu Gly Ser Val Val Tyr Arg Asn Arg Met Phe Glu
225                 230                 235                 240

Leu Ile Gln Tyr Lys Pro Thr Thr Glu Thr Val His Glu Thr Pro Leu
```

```
            245                 250                 255
Leu Ile Phe Pro Pro Trp Ile Asn Lys Phe Tyr Ile Leu Asp Leu Lys
            260                 265                 270

Pro Gln Asn Ser Leu Leu Lys Trp Leu Val Asp Gln Gly Phe Thr Val
            275                 280                 285

Phe Val Val Ser Trp Val Asn Pro Asp Lys Ser Tyr Ala Gly Ile Gly
            290                 295                 300

Met Asp Asp Tyr Ile Arg Glu Gly Tyr Met Arg Ala Met Ala Glu Val
305                 310                 315                 320

Arg Ser Ile Thr Arg Gln Lys Gln Ile Asn Ala Val Gly Tyr Cys Ile
            325                 330                 335

Ala Gly Thr Thr Leu Thr Leu Thr Leu Ala His Leu Gln Lys Ala Gly
            340                 345                 350

Asp Pro Ser Val Arg Ser Ala Thr Phe Phe Thr Thr Leu Thr Asp Phe
            355                 360                 365

Ser Asp Pro Gly Glu Val Gly Val Phe Leu Asn Asp Asp Phe Val Asp
            370                 375                 380

Gly Ile Glu Arg Gln Val Ala Val Asp Gly Ile Leu Asp Lys Thr Phe
385                 390                 395                 400

Met Ser Arg Thr Phe Ser Tyr Leu Arg Ser Asn Asp Leu Ile Tyr Gln
                405                 410                 415

Pro Ala Ile Lys Ser Tyr Met Met Gly Glu Ala Pro Pro Ala Phe Asp
            420                 425                 430

Leu Leu Tyr Trp Asn Gly Asp Gly Thr Asn Leu Pro Ala Gln Met Ala
            435                 440                 445

Val Glu Tyr Leu Arg Gly Leu Cys Gln Gln Asp Arg Leu Ala Gly Gly
            450                 455                 460

Thr Phe Pro Val Leu Gly Ser Pro Val Gly Leu Lys Asp Val Thr Leu
465                 470                 475                 480

Pro Val Cys Ala Ile Ala Cys Glu Thr Asp His Ile Ala Pro Trp Lys
                485                 490                 495

Ser Ser Phe Asn Gly Phe Arg Gln Phe Gly Ser Thr Asp Lys Thr Phe
            500                 505                 510

Ile Leu Ser Gln Ser Gly His Val Ala Gly Ile Val Asn Pro Pro Ser
            515                 520                 525

Arg Asn Lys Tyr Gly His Tyr Thr Asn Glu Gly Pro Ala Gly Thr Pro
            530                 535                 540

Glu Ser Phe Arg Glu Gly Ala Glu Phe His Ala Gly Ser Trp Trp Pro
545                 550                 555                 560

Arg Trp Gly Ala Trp Leu Ala Glu Arg Ser Gly Lys Gln Val Pro Ala
                565                 570                 575

Arg Gln Pro Gly Asp Ser Lys His Pro Glu Leu Ala Pro Ala Pro Gly
            580                 585                 590

Ser Tyr Val Ala Ala Val Gly Gly Ala
            595                 600

<210> SEQ ID NO 23
<211> LENGTH: 1962
<212> TYPE: DNA
<213> ORGANISM: Rhodobacter sphaeroides

<400> SEQUENCE: 23
atggatcacg ctcaggcgaa tgcggtctat accgcgtcgg cagatttcat tgcgcaagcc      60
catgtcgacg cggccggcta cgagcggatg tatgctgcat ccgtggccga cccggaggcg     120
```

```
ttctggggcg aacagggcaa gcggctcgac tggatcaagc cctacaccaa ggtcaagaac      180
acgaacttcc ggccgggcga ggtctcgatc aagtggttcg aggacggcac gctgaacatc      240
gcctggaact gcatcgaccg gcatctggcg acgcgggcca agcagaccgc gatcatctgg      300
gagccggacg atccgaacgt gccggcccag cacatcagct atcaggagct gcacgacaac      360
gtctgccgca tggccaacgt gctggtgagc cagggcgtgc gcaagggcga ccgggtggtg      420
atgtatctgc gatgatccc cgaggccgcc tatgcgatgc tggcgtgcgc ccggatcggc      480
gccatccatt ccgtcgtctt cgcgggcttc tcgcccgacg cgctggcgaa ccggatcaac      540
gactgtcagg ccaaggtggt catcaccgcc gacacggctc gcgtggcgg ccggcgcacg      600 cccttgaagt cgaacaccga cgcagcccct ctccattgct cggaccgggt gcgctgcctc      660
gtcgtcaagc acacgggcga ccagatccac tggatggacg gccgcgacgt ggacgtgaag      720
gagctgatgc ccacgcctc gcccgactgc ccgatcgagg aggtgaatgc gaggatccg      780 ctcttcatcc tctatacctc gggctcgacc ggcaagccga aggggtcgt gcacacctcg      840 ggcggctatc tgacctatgc cgccatgacc catcagatga ccttcgacta ccatgacggc      900
gacgtcttct ggtgcaccgc ggacgtgggc tgggtcacgg ccacagcta tcgtctac      960 ggcccgctgg cgaacggcgc gaccacgctc atgttcgagg gcgtgccgac ctatcccgat     1020
gcgggccgct tctgggccgt ctgcgagaag cacaaggtga accagttcta caccgcgccc     1080
acggcgatcc gctcgctgat gggcctcggg ccggaatggg tcgacaagta cgacctgtcg     1140
tcgctgaagc cttgggctc ggtgggcgag ccgatcaacc ccgaggcctg gagctggtac     1200
aacacccatg tcggcaaggg ccgctgcccg atcgtcgaca ccttctggca gaccgagacc     1260
ggcggccaca tgatcacgcc gctgccgggc gcgatcccgg tgaagccggg cgcggcctcg     1320
aagcccttct tcgggtgaa gccggtgatc ctcgaccga ccgacgggca cgagctgcac     1380
gaaaccgcga ccgagggggt gctctgcatc gccgacagct ggccggggca gatgcgcacg     1440
ctctggggcg accacgagcg gttcgaagag gcctatttct cgcaatacaa gggctattac     1500
ttcaccggcg acggctgccg ccgcgatgcg gacggctatt actgggtcac gggccggtc     1560 gatgacgtca tcaacgtctc gggccaccgg atgggcaccg ccgaggtgga atccgcgctc     1620
gtcgcccatg cgcaggtcgc cgaagccgcg gtggtgggct atccgcacga catcaagggg     1680
cagggcatct atgcctatgt cacgctgatg aacggggtcc agccgaccga ggagctgcgc     1740
aaggatctgg tgaaatgggt ccgcaccgag atcggcccca tcgcctcgcc ggacgtgatc     1800
cagtgggcgc gggcctgcc caagacccgc tcgggcaaga tcatgcgccg catcctgcgc     1860
aagatcgccg agaacgactt cggctcgctc ggcgacacca cgacgctggc cgatccgtcg     1920
gtggtcgacg acctgatcgc caaccgcaag aaccggggct ga                        1962
```

<210> SEQ ID NO 24
<211> LENGTH: 653
<212> TYPE: PRT
<213> ORGANISM: Rhodobacter sphaeroides

<400> SEQUENCE: 24

Met Asp His Ala Gln Ala Asn Ala Val Tyr Thr Ala Ser Ala Asp Phe
1               5                   10                  15

Ile Ala Gln Ala His Val Asp Ala Ala Gly Tyr Glu Arg Met Tyr Ala
            20                  25                  30

Ala Ser Val Ala Asp Pro Glu Ala Phe Trp Gly Glu Gln Gly Lys Arg
        35                  40                  45

```
Leu Asp Trp Ile Lys Pro Tyr Thr Lys Val Lys Asn Thr Asn Phe Arg
 50                  55                  60

Pro Gly Glu Val Ser Ile Lys Trp Phe Glu Asp Gly Thr Leu Asn Ile
 65                  70                  75                  80

Ala Trp Asn Cys Ile Asp Arg His Leu Ala Thr Arg Ala Lys Gln Thr
                 85                  90                  95

Ala Ile Ile Trp Glu Pro Asp Pro Asn Val Pro Ala Gln His Ile
            100                 105                 110

Ser Tyr Gln Glu Leu His Asp Asn Val Cys Arg Met Ala Asn Val Leu
            115                 120                 125

Val Ser Gln Gly Val Arg Lys Gly Asp Arg Val Val Met Tyr Leu Pro
130                 135                 140

Met Ile Pro Glu Ala Ala Tyr Ala Met Leu Ala Cys Ala Arg Ile Gly
145                 150                 155                 160

Ala Ile His Ser Val Val Phe Ala Gly Phe Ser Pro Asp Ala Leu Ala
                165                 170                 175

Asn Arg Ile Asn Asp Cys Gln Ala Lys Val Val Ile Thr Ala Asp Thr
            180                 185                 190

Ala Pro Arg Gly Arg Arg Thr Pro Leu Lys Ser Asn Thr Asp Ala
    195                 200                 205

Ala Leu Leu His Cys Ser Asp Arg Val Arg Cys Leu Val Val Lys His
    210                 215                 220

Thr Gly Asp Gln Ile His Trp Met Asp Gly Arg Asp Val Asp Val Lys
225                 230                 235                 240

Glu Leu Met Arg His Ala Ser Pro Asp Cys Pro Ile Glu Glu Val Asn
                245                 250                 255

Ala Glu Asp Pro Leu Phe Ile Leu Tyr Thr Ser Gly Ser Thr Gly Lys
            260                 265                 270

Pro Lys Gly Val Val His Thr Ser Gly Gly Tyr Leu Thr Tyr Ala Ala
    275                 280                 285

Met Thr His Gln Met Thr Phe Asp Tyr His Asp Gly Asp Val Phe Trp
290                 295                 300

Cys Thr Ala Asp Val Gly Trp Val Thr Gly His Ser Tyr Ile Val Tyr
305                 310                 315                 320

Gly Pro Leu Ala Asn Gly Ala Thr Thr Leu Met Phe Glu Gly Val Pro
                325                 330                 335

Thr Tyr Pro Asp Ala Gly Arg Phe Trp Ala Val Cys Glu Lys His Lys
            340                 345                 350

Val Asn Gln Phe Tyr Thr Ala Pro Thr Ala Ile Arg Ser Leu Met Gly
    355                 360                 365

Leu Gly Pro Glu Trp Val Asp Lys Tyr Asp Leu Ser Ser Leu Lys Leu
370                 375                 380

Leu Gly Ser Val Gly Glu Pro Ile Asn Pro Glu Ala Trp Ser Trp Tyr
385                 390                 395                 400

Asn Thr His Val Gly Lys Gly Arg Cys Pro Ile Val Asp Thr Phe Trp
                405                 410                 415

Gln Thr Glu Thr Gly Gly His Met Ile Thr Pro Leu Pro Gly Ala Ile
            420                 425                 430

Pro Val Lys Pro Gly Ala Ala Ser Lys Pro Phe Phe Gly Val Lys Pro
    435                 440                 445

Val Ile Leu Asp Pro Thr Asp Gly His Glu Leu His Glu Thr Ala Thr
450                 455                 460
```

Glu Gly Val Leu Cys Ile Ala Asp Ser Trp Pro Gly Gln Met Arg Thr
465                 470                 475                 480

Leu Trp Gly Asp His Glu Arg Phe Glu Glu Ala Tyr Phe Ser Gln Tyr
            485                 490                 495

Lys Gly Tyr Tyr Phe Thr Gly Asp Gly Cys Arg Arg Asp Ala Asp Gly
        500                 505                 510

Tyr Tyr Trp Val Thr Gly Arg Val Asp Asp Val Ile Asn Val Ser Gly
        515                 520                 525

His Arg Met Gly Thr Ala Glu Val Ser Ala Leu Val Ala His Ala
        530                 535                 540

Gln Val Ala Glu Ala Ala Val Val Gly Tyr Pro His Asp Ile Lys Gly
545                 550                 555                 560

Gln Gly Ile Tyr Ala Tyr Val Thr Leu Met Asn Gly Val Gln Pro Thr
                565                 570                 575

Glu Glu Leu Arg Lys Asp Leu Val Lys Trp Val Arg Thr Glu Ile Gly
            580                 585                 590

Pro Ile Ala Ser Pro Asp Val Ile Gln Trp Ala Pro Gly Leu Pro Lys
        595                 600                 605

Thr Arg Ser Gly Lys Ile Met Arg Arg Ile Leu Arg Lys Ile Ala Glu
610                 615                 620

Asn Asp Phe Gly Ser Leu Gly Asp Thr Thr Thr Leu Ala Asp Pro Ser
625                 630                 635                 640

Val Val Asp Asp Leu Ile Ala Asn Arg Lys Asn Arg Gly
                645                 650

<210> SEQ ID NO 25
<211> LENGTH: 726
<212> TYPE: DNA
<213> ORGANISM: Rhodobacter sphaeroides

<400> SEQUENCE: 25
atgcgcaccg cgctgcaatg gatccggtcc atcctcttca acatcgtgat gtatgtctcg      60
atgatcgcca tcgcgctggc cttcacgccg ctcgtgctgg tcgaccgcaa gtgggcgccg     120
gtctggatgc ggatcttcgc gcgctggacg cgcttcacgc tgcgctggat cgcggggctc     180
cggaccgagg tgcggggcga gatccccacg accggcgcgc tcatcgcctc gaagcaccag     240
agcttcctcg attccatcct gctcttctcg gtgctgcccg cgccgcgctt catcatgaag     300
aagcagctgg cctggatccc gctgatgggc tggatggcgc ttcaggcggg cttcattccg     360
gtggaccgcg gcaagcgggg cgcggccatc aagaagatga tggccgatgt cgagaagggc     420
cgcgcgacgc cgggccagct catcatctat ccgcagggca cccgcgtggc tccgggcgcg     480
catctgccct acaagatggg caccgccgcc ctctacggcc agctcgatca gccctgctat     540
ccggtggcgg ccaatgtggg cgtcttctgg ccgcggcacg ggatctatcg ccggcccggc     600
accgccgtgg tggagttcct gccgccgatc cagcccggcc aaacggccgc ggccttcatg     660
gtcgagctgg agaccgcgat cgaggacgcc tcgaaccggc tgatcgccga ggcccggcag     720
ggctga                                                               726

<210> SEQ ID NO 26
<211> LENGTH: 241
<212> TYPE: PRT
<213> ORGANISM: Rhodobacter sphaeroides

<400> SEQUENCE: 26

Met Arg Thr Ala Leu Gln Trp Ile Arg Ser Ile Leu Phe Asn Ile Val

```
 1               5                  10                 15
Met Tyr Val Ser Met Ile Ala Ile Ala Leu Ala Phe Thr Pro Leu Val
             20                 25                 30

Leu Val Asp Arg Lys Trp Ala Pro Val Trp Met Arg Ile Phe Ala Arg
             35                 40                 45

Trp Thr Arg Phe Thr Leu Arg Trp Ile Ala Gly Leu Arg Thr Glu Val
     50                 55                 60

Arg Gly Glu Ile Pro Thr Thr Gly Ala Leu Ile Ala Ser Lys His Gln
 65                 70                 75                 80

Ser Phe Leu Asp Ser Ile Leu Leu Phe Ser Val Leu Pro Ala Pro Arg
             85                 90                 95

Phe Ile Met Lys Lys Gln Leu Ala Trp Ile Pro Leu Met Gly Trp Met
             100                105                110

Ala Leu Gln Ala Gly Phe Ile Pro Val Asp Arg Gly Lys Arg Gly Ala
             115                120                125

Ala Ile Lys Lys Met Met Ala Asp Val Glu Lys Gly Arg Ala Thr Pro
             130                135                140

Gly Gln Leu Ile Ile Tyr Pro Gln Gly Thr Arg Val Ala Pro Gly Ala
145                 150                155                160

His Leu Pro Tyr Lys Met Gly Thr Ala Ala Leu Tyr Gly Gln Leu Asp
             165                170                175

Gln Pro Cys Tyr Pro Val Ala Ala Asn Val Gly Val Phe Trp Pro Arg
             180                185                190

His Gly Ile Tyr Arg Arg Pro Gly Thr Ala Val Val Glu Phe Leu Pro
             195                200                205

Pro Ile Gln Pro Gly Gln Thr Ala Ala Ala Phe Met Val Glu Leu Glu
             210                215                220

Thr Ala Ile Glu Asp Ala Ser Asn Arg Leu Ile Ala Glu Ala Arg Gln
225                 230                235                240

Gly

<210> SEQ ID NO 27
<211> LENGTH: 723
<212> TYPE: DNA
<213> ORGANISM: Rhodobacter sphaeroides

<400> SEQUENCE: 27
atgtccaagg ttgctctggt gacgggcggt tcgcgggca tcggcgccgc catctcggtg     60
gcgctgaaga cgcgggcta cacggtcgcc gcgaactatg cgggcaatga cgaggcggcg    120
cggaagttca ccgaagagac cggcatcaag acctacaaat ggtccgtcgc ggattacgat    180
gcctgcgctg cgggcatcgc gcaggtcgag gccgagctcg gccggtggc tgtgctggtg    240 aacaacgccg gcatcacgcg ggattcgatg ttccacaaga tgacgcgcga ccagtggaaa    300
gaggtgatcg acaccaacct gtcgggcctc ttcaacatga cccacccggt ctggtccggg    360
atgcgggacc gcaagttcgg ccggatcatc aacatctctt cgatcaacgg ccagaagggc    420
caggccgggc aggcgaacta ttccgcggcc aaggcgggcg acctcggctt caccaaggcg    480
ctggcgcagg agggcgcgcg gcggcatc accgtcaatg cgatctgccc cggctatatc    540
gcgaccgaga tggtgatggc cgtgccggaa aaggtgcgcg agtcgatcat cgcccagatc    600
ccgaccggcc gcctcggcga gccggaggag attgcccgct gcgtggtctt cctcgcctcc    660
gacgatgcgg gcttcgtcac cggatcgacc atcacggcga acggcggcca gtatttcgtc    720
tga                                                                 723
```

<210> SEQ ID NO 28
<211> LENGTH: 240
<212> TYPE: PRT
<213> ORGANISM: Rhodobacter sphaeroides

<400> SEQUENCE: 28

```
Met Ser Lys Val Ala Leu Val Thr Gly Gly Ser Arg Gly Ile Gly Ala
1               5                   10                  15
Ala Ile Ser Val Ala Leu Lys Asn Ala Gly Tyr Thr Val Ala Ala Asn
                20                  25                  30
Tyr Ala Gly Asn Asp Glu Ala Ala Arg Lys Phe Thr Glu Glu Thr Gly
            35                  40                  45
Ile Lys Thr Tyr Lys Trp Ser Val Ala Asp Tyr Asp Ala Cys Ala Ala
        50                  55                  60
Gly Ile Ala Gln Val Glu Ala Glu Leu Gly Pro Val Ala Val Leu Val
65                  70                  75                  80
Asn Asn Ala Gly Ile Thr Arg Asp Ser Met Phe His Lys Met Thr Arg
                85                  90                  95
Asp Gln Trp Lys Glu Val Ile Asp Thr Asn Leu Ser Gly Leu Phe Asn
            100                 105                 110
Met Thr His Pro Val Trp Ser Gly Met Arg Asp Arg Lys Phe Gly Arg
        115                 120                 125
Ile Ile Asn Ile Ser Ser Ile Asn Gly Gln Lys Gly Gln Ala Gly Gln
    130                 135                 140
Ala Asn Tyr Ser Ala Ala Lys Ala Gly Asp Leu Gly Phe Thr Lys Ala
145                 150                 155                 160
Leu Ala Gln Glu Gly Ala Arg Ala Gly Ile Thr Val Asn Ala Ile Cys
                165                 170                 175
Pro Gly Tyr Ile Ala Thr Glu Met Val Met Ala Val Pro Glu Lys Val
            180                 185                 190
Arg Glu Ser Ile Ile Ala Gln Ile Pro Thr Gly Arg Leu Gly Glu Pro
        195                 200                 205
Glu Glu Ile Ala Arg Cys Val Val Phe Leu Ala Ser Asp Asp Ala Gly
    210                 215                 220
Phe Val Thr Gly Ser Thr Ile Thr Ala Asn Gly Gly Gln Tyr Phe Val
225                 230                 235                 240
```

<210> SEQ ID NO 29
<211> LENGTH: 1737
<212> TYPE: DNA
<213> ORGANISM: Rhodobacter sphaeroides

<400> SEQUENCE: 29

```
atgacgcgaa gcgacaatcg caagggactg gaggagctgc gcgccgtccg ccgcagcacc    60
atgggcgcgc tgacgtccgt gttcctcttc agcatcttcg tcaatctgct gatgctgacg   120
ggcccgctct acatgctgca ggtctacgac cgggtgctcg gctcgcgctc cgaggagacg   180
ctgctcgcgc tgtccctgct cgtgaccttc ctgttcgtcg ccatgggcgt gctcgaccat   240
gcgcgggcgc gcgtcatggc gcgcgtgggc gcaggctttc aggagaagct cgaccgccgc   300
gtcttcgagg ccgcggtgcg gcggctctcg ctcgcgcccg gcgatccgtc ggccgtggca   360
gcgcagcgcg atctcgaatc ggtgcagcgg ctctgggcct cgccggtgct gatcgcgctc   420
ttcgacattc cctggacccc gttcttcctc gcggccatct tcgtcttcca cccctacatg   480
ggctggctcg ccatcggggg cggcgtcgtc ctcgtgatcg tgacgatcct gaaccagcgc   540
```

```
ctgtccgagg ggccgatgca gaaggccaac atcgtggcgc tgcaggccga ccggtttgcc    600
gagaacctca agtcggaatc cgaggtggtg caggcgctcg gcatggcggg caacggcttc    660
gaccgctggc acaaggcgcg tgccgccgcg ctcgacgcga acatggcggc ggccgacctg    720
acgggcgcct tcggcacgct gaccaagacg ctgcgcctct tcctgcagtc ggcgatgctg    780
gggctcggcg cgtggctcgt cctgcagcag gaactgagcg cgggcgccat gatcgcgggc    840
tcgatcctga tgggccgggc gctcgccccg atcgagagcg ccatcggcca gtgggcgctg    900
gtgcagcgcg cctccgaagg ctggcgacgg ctgggagagc tgctgacccg ccagccggtc    960
gagccgccgc gcatcgccct gccccgcccg cgggcgctga tcgaggcgca gaacctctcc   1020
gtggtgccgc cgggcgaggc ggtcgcggtg ctgcgcggcg tgagcttccg gctggatccg   1080
ggtcaggcgc tcggggtcat cggcccctcc gggtcgggca agtccacgct ggcgcgggcc   1140
ctgatcgggg tctggcgtcc ggccgcgggc aaggtccggc tcgatggcgc cgccctcgac   1200
cagtatgacc cggacgtgct cggcggctat atcggttacc tgccccagcg cgtgacgctg   1260
ttcgagggca ccatcgccga gaatatcgcg cgcctccggg gcgcgcccga tggtgacgcc   1320
gtggtggccg ccgcgcgcaa ggccgccgcg cacgacatga tcgtggcact tccctcgggc   1380
tacgacaccc gcgtctcggc cctgggtggc cggctgtccg gcgggcagat ccagcgcatc   1440
gggctcgcgc gcgccatgta cggcaacccc gtgttcctcg tcctcgacga gccgaactcg   1500
aacctcgaca atgagggctc gcttgcgctg aacgcggcga tccgctcgat gaagcaggcg   1560
ggagggtcgg tgttcatcat ggcccaccgc cccgccgcaa ttcaggagtg cgacctcctc   1620
atggtgatgg agaacggaat gcgcgccgcc ttcggccagc gcgacgccgt gctgcgcgac   1680
atggtgaaga accataccga gatcgtgcga aacgcaggcc ccggaggcgt gacatga      1737
```

<210> SEQ ID NO 30
<211> LENGTH: 578
<212> TYPE: PRT
<213> ORGANISM: Rhodobacter sphaeroides

<400> SEQUENCE: 30

```
Met Thr Arg Ser Asp Asn Arg Lys Gly Leu Glu Glu Leu Arg Ala Val
1               5                   10                  15

Arg Arg Ser Thr Met Gly Ala Leu Thr Ser Val Phe Leu Phe Ser Ile
            20                  25                  30

Phe Val Asn Leu Leu Met Leu Thr Gly Pro Leu Tyr Met Leu Gln Val
        35                  40                  45

Tyr Asp Arg Val Leu Gly Ser Arg Glu Glu Thr Leu Leu Ala Leu
    50                  55                  60

Ser Leu Leu Val Thr Phe Leu Phe Val Ala Met Gly Val Leu Asp His
65                  70                  75                  80

Ala Arg Ala Arg Val Met Ala Arg Val Gly Ala Gly Phe Gln Glu Lys
                85                  90                  95

Leu Asp Arg Arg Val Phe Glu Ala Ala Val Arg Arg Leu Ser Leu Ala
            100                 105                 110

Pro Gly Asp Pro Ser Ala Val Ala Ala Gln Arg Asp Leu Glu Ser Val
        115                 120                 125

Gln Arg Leu Trp Ala Ser Pro Val Leu Ile Ala Leu Phe Asp Ile Pro
    130                 135                 140

Trp Thr Pro Phe Phe Leu Ala Ala Ile Phe Val Phe His Pro Tyr Met
145                 150                 155                 160
```

```
Gly Trp Leu Ala Ile Gly Gly Gly Val Val Leu Val Ile Val Thr Ile
            165                 170                 175
Leu Asn Gln Arg Leu Ser Glu Gly Pro Met Gln Lys Ala Asn Ile Val
        180                 185                 190
Ala Leu Gln Ala Asp Arg Phe Ala Glu Asn Leu Lys Ser Glu Ser Glu
    195                 200                 205
Val Val Gln Ala Leu Gly Met Ala Gly Asn Gly Phe Asp Arg Trp His
    210                 215                 220
Lys Ala Arg Ala Ala Leu Asp Ala Asn Met Ala Ala Ala Asp Leu
225                 230                 235                 240
Thr Gly Ala Phe Gly Thr Leu Thr Lys Thr Leu Arg Leu Phe Leu Gln
                245                 250                 255
Ser Ala Met Leu Gly Leu Gly Ala Trp Leu Val Leu Gln Gln Glu Leu
            260                 265                 270
Ser Ala Gly Ala Met Ile Ala Gly Ser Ile Leu Met Gly Arg Ala Leu
        275                 280                 285
Ala Pro Ile Glu Ser Ala Ile Gly Gln Trp Ala Leu Val Gln Arg Ala
    290                 295                 300
Ser Glu Gly Trp Arg Arg Leu Gly Glu Leu Leu Thr Arg Gln Pro Val
305                 310                 315                 320
Glu Pro Pro Arg Ile Ala Leu Pro Arg Pro Arg Ala Leu Ile Glu Ala
                325                 330                 335
Gln Asn Leu Ser Val Val Pro Pro Gly Glu Ala Val Ala Val Leu Arg
            340                 345                 350
Gly Val Ser Phe Arg Leu Asp Pro Gly Gln Ala Leu Gly Val Ile Gly
        355                 360                 365
Pro Ser Gly Ser Gly Lys Ser Thr Leu Ala Arg Ala Leu Ile Gly Val
    370                 375                 380
Trp Arg Pro Ala Ala Gly Lys Val Arg Leu Asp Gly Ala Ala Leu Asp
385                 390                 395                 400
Gln Tyr Asp Pro Asp Val Leu Gly Gly Tyr Ile Gly Tyr Leu Pro Gln
                405                 410                 415
Arg Val Thr Leu Phe Glu Gly Thr Ile Ala Glu Asn Ile Ala Arg Leu
            420                 425                 430
Arg Gly Ala Pro Asp Gly Asp Ala Val Val Ala Ala Arg Lys Ala
        435                 440                 445
Ala Ala His Asp Met Ile Val Ala Leu Pro Ser Gly Tyr Asp Thr Arg
    450                 455                 460
Val Ser Ala Leu Gly Gly Arg Leu Ser Gly Gln Ile Gln Arg Ile
465                 470                 475                 480
Gly Leu Ala Arg Ala Met Tyr Gly Asn Pro Val Phe Leu Val Leu Asp
                485                 490                 495
Glu Pro Asn Ser Asn Leu Asp Asn Glu Gly Ser Leu Ala Leu Asn Ala
            500                 505                 510
Ala Ile Arg Ser Met Lys Gln Ala Gly Gly Ser Val Phe Ile Met Ala
        515                 520                 525
His Arg Pro Ala Ala Ile Gln Glu Cys Asp Leu Leu Met Val Met Glu
    530                 535                 540
Asn Gly Met Arg Ala Ala Phe Gly Gln Arg Asp Ala Val Leu Arg Asp
545                 550                 555                 560
Met Val Lys Asn His Thr Glu Ile Val Arg Asn Ala Gly Pro Gly Gly
                565                 570                 575
Val Thr
```

<210> SEQ ID NO 31
<211> LENGTH: 606
<212> TYPE: DNA
<213> ORGANISM: Rhodobacter sphaeroides

<400> SEQUENCE: 31

```
atgccggcca tcgaaagcgg cctttgggcg ctgatcctga cgggagtgct gggctatctg    60
ctcggctcga tcccgttcgg catcgtcatc acccgcgcgc tggggctggg cgacctgcgc   120
aagatcggct cgggcaatat cggcgcgacc aacgtgctcc ggacgggcaa caagcccgcg   180
gcgctggcca cgctgctcct cgattcgggc aagggcgcca tcgccgtgct gatcgcgcgc   240
gcggccgtgg gcgaggatgc ggcgcagctt gcggccttca cctcgtttct ggggcacctt   300
ttcccggtct ggctcggctt ccgcggcggc aaggggggtcg cgaccttcct cggcacgctg   360
ctggcactcg catggcccgt ggggctcgcc tgctgcctca cctggctcgc gaccgcggcc   420
ctgggccgga tctcctcgct ctcggccctc gtgctgcgg cgagcggtgt cctctggatg   480
atccttctgg gctacggcca gatggcggcg ctggggcgg tgctcgcggt gctgatcttc   540
atccgccacc atgcgaacat ccgccggatc ctcgccggca ccgagccgcg gatcgggaag   600
aagtaa                                                              606
```

<210> SEQ ID NO 32
<211> LENGTH: 201
<212> TYPE: PRT
<213> ORGANISM: Rhodobacter sphaeroides

<400> SEQUENCE: 32

```
Met Pro Ala Ile Glu Ser Gly Leu Trp Ala Leu Ile Leu Thr Gly Val
1               5                  10                  15

Leu Gly Tyr Leu Leu Gly Ser Ile Pro Phe Gly Ile Val Ile Thr Arg
            20                  25                  30

Ala Leu Gly Leu Gly Asp Leu Arg Lys Ile Gly Ser Gly Asn Ile Gly
        35                  40                  45

Ala Thr Asn Val Leu Arg Thr Gly Asn Lys Pro Ala Ala Leu Ala Thr
    50                  55                  60

Leu Leu Leu Asp Ser Gly Lys Gly Ala Ile Ala Val Leu Ile Ala Arg
65                  70                  75                  80

Ala Ala Val Gly Glu Asp Ala Ala Gln Leu Ala Ala Phe Thr Ser Phe
                85                  90                  95

Leu Gly His Leu Phe Pro Val Trp Leu Gly Phe Arg Gly Gly Lys Gly
            100                 105                 110

Val Ala Thr Phe Leu Gly Thr Leu Leu Ala Leu Ala Trp Pro Val Gly
        115                 120                 125

Leu Ala Cys Cys Leu Thr Trp Leu Ala Thr Ala Ala Leu Gly Arg Ile
    130                 135                 140

Ser Ser Leu Ser Ala Leu Val Ala Ala Ser Gly Val Leu Trp Met
145                 150                 155                 160

Ile Leu Leu Gly Tyr Gly Gln Met Ala Ala Leu Gly Ala Val Leu Ala
                165                 170                 175

Val Leu Ile Phe Ile Arg His His Ala Asn Ile Arg Arg Ile Leu Ala
            180                 185                 190

Gly Thr Glu Pro Arg Ile Gly Lys Lys
        195                 200
```

<210> SEQ ID NO 33
<211> LENGTH: 1401
<212> TYPE: DNA
<213> ORGANISM: Rhodobacter sphaeroides

<400> SEQUENCE: 33

| | | | | | |
|---|---|---|---|---|---|
| ttgcggcggt | tcctgaacac | gctctccggg | cggttcctga | tgctgaccgc | cgccttcgtc | 60 |
| atgctggcgg | aggtgctgat | cctcgtgccc | tcggtggcgc | gcttccgcga | ggattacctc | 120 |
| ctcctccggc | tggagaaggc | gcagatcgcg | tcgctggccc | tgctggcggc | ggacgacatg | 180 |
| atcgcgcccg | acctcgaggc | ggagcttctg | gccaatgcgg | gcgtctacaa | cgtggtgctg | 240 |
| cgccgcgacg | aggtgcgcca | gcttgtgctg | tcctcgccca | ttcccgtgcc | ggtggagcag | 300 |
| acctacgacc | tgcgcttcgc | gggccccctc | gggctgatcc | gcgacacctt | catggatgtg | 360 |
| ctcgacaagc | agggcgtgat | cgggtgatc | ggcgaaccgg | tggagagcgg | cggccagcag | 420 |
| atcgaggtcg | cgctcgaacg | gggccccatg | cgcaaggcca | tgctcgagca | tggggcgcgg | 480 |
| gtgctcgtct | tctcggcgct | gatctcgatg | gtgacggcgc | ttctgctgtt | ccttgcggtg | 540 |
| cggcggcttc | tggtggtgcc | gatccggcgg | gtcgtcaccc | acatgaccgc | ctatgccgaa | 600 |
| gcgcccgagg | atgcgcgccg | cgtgatcgcg | cccaccgcgg | gcatccgcga | gctgcgcgag | 660 |
| gccgaggagg | cgctgcagat | gatgcagacc | cagctcatcg | gcgcgctgcg | ccagaaggag | 720 |
| cggctggccc | agctcggcgg | ggcggtggcc | aagatcagcc | acgacctgcg | caacatcctg | 780 |
| acgacggcgc | agctgtttgc | cgaccggctg | tcggcctccg | acgatccggc | ggtggcccgg | 840 |
| gcggcgccga | gctggtggg | atcgatccgg | cgcgcggtct | cgctttgcga | atcgacgctg | 900 |
| accttcgggc | gcgccgagga | gccgccgccc | cagatcgcgc | gcgtgccgct | cgccggctg | 960 |
| atggaggagg | tggccgaggc | cgaatcgctg | gtggcggatg | ccagcgtggg | ctgcctgatc | 1020 |
| gatgtggcgc | cgaacatggt | gatccgtgcc | gacggcgagc | agctctaccg | cgtgctgggc | 1080 |
| aacctcgtgc | gcaatgcgcg | gcaggcgctg | gagacggcgg | gccggccgg | caccatcgag | 1140 |
| ctctcggcgg | gcgagggcga | ggaagagtgg | tggatcaagg | tgggcgacac | cgggccgggc | 1200 |
| ctgccgccca | aggcgcgcga | acatctcttc | accgccttcc | agggcggggc | gcgcaagggg | 1260 |
| ggctcgggcc | tcgggctcgc | catctcggcc | gagctggtgc | gtggtcacgg | cggacggctc | 1320 |
| gacctgttgc | ggagcgacag | cgacgggacg | gagttcatca | tccgcctgcc | caagggggcc | 1380 |
| ggtctcagcg | ccctcgtctg | a | | | | 1401 |

<210> SEQ ID NO 34
<211> LENGTH: 466
<212> TYPE: PRT
<213> ORGANISM: Rhodobacter sphaeroides

<400> SEQUENCE: 34

Met Arg Arg Phe Leu Asn Thr Leu Ser Gly Arg Phe Leu Met Leu Thr
1               5                   10                  15

Ala Ala Phe Val Met Leu Ala Glu Val Leu Ile Leu Val Pro Ser Val
            20                  25                  30

Ala Arg Phe Arg Glu Asp Tyr Leu Leu Leu Arg Leu Glu Lys Ala Gln
        35                  40                  45

Ile Ala Ser Leu Ala Leu Ala Ala Asp Asp Met Ile Ala Pro Asp
    50                  55                  60

Leu Glu Ala Glu Leu Leu Ala Asn Ala Gly Val Tyr Asn Val Val Leu
65                  70                  75                  80

Arg Arg Asp Glu Val Arg Gln Leu Val Leu Ser Ser Pro Ile Pro Val

```
            85                  90                  95
Pro Val Glu Gln Thr Tyr Asp Leu Arg Phe Ala Gly Pro Leu Gly Leu
            100                 105                 110

Ile Arg Asp Thr Phe Met Asp Val Leu Asp Lys Gln Gly Val Ile Arg
            115                 120                 125

Val Ile Gly Glu Pro Val Ser Gly Gly Gln Gln Ile Glu Val Ala
            130                 135                 140

Leu Glu Arg Gly Pro Met Arg Lys Ala Met Leu Glu His Gly Ala Arg
145                 150                 155                 160

Val Leu Val Phe Ser Ala Leu Ile Ser Met Val Thr Ala Leu Leu Leu
                165                 170                 175

Phe Leu Ala Val Arg Arg Leu Leu Val Val Pro Ile Arg Arg Val Val
                180                 185                 190

Thr His Met Thr Ala Tyr Ala Glu Ala Pro Glu Asp Ala Arg Arg Val
                195                 200                 205

Ile Ala Pro Thr Ala Gly Ile Arg Glu Leu Arg Glu Ala Glu Ala
            210                 215                 220

Leu Gln Met Met Gln Thr Gln Leu Ile Gly Ala Leu Arg Gln Lys Glu
225                 230                 235                 240

Arg Leu Ala Gln Leu Gly Gly Ala Val Ala Lys Ile Ser His Asp Leu
                245                 250                 255

Arg Asn Ile Leu Thr Thr Ala Gln Leu Phe Ala Asp Arg Leu Ser Ala
                260                 265                 270

Ser Asp Asp Pro Ala Val Ala Arg Ala Ala Pro Lys Leu Val Gly Ser
            275                 280                 285

Ile Arg Arg Ala Val Ser Leu Cys Glu Ser Thr Leu Thr Phe Gly Arg
            290                 295                 300

Ala Glu Glu Pro Pro Gln Ile Ala Arg Val Pro Leu Arg Arg Leu
305                 310                 315                 320

Met Glu Glu Val Ala Glu Ala Glu Ser Leu Val Ala Asp Ala Ser Val
                325                 330                 335

Gly Cys Leu Ile Asp Val Ala Pro Asn Met Val Ile Arg Ala Asp Gly
                340                 345                 350

Glu Gln Leu Tyr Arg Val Leu Gly Asn Leu Val Arg Asn Ala Arg Gln
            355                 360                 365

Ala Leu Glu Thr Ala Gly Arg Pro Gly Thr Ile Glu Leu Ser Ala Gly
            370                 375                 380

Glu Gly Glu Glu Glu Trp Trp Ile Lys Val Gly Asp Thr Gly Pro Gly
385                 390                 395                 400

Leu Pro Pro Lys Ala Arg Glu His Leu Phe Thr Ala Phe Gln Gly Gly
                405                 410                 415

Ala Arg Lys Gly Gly Ser Gly Leu Gly Leu Ala Ile Ser Ala Glu Leu
            420                 425                 430

Val Arg Gly His Gly Gly Arg Leu Asp Leu Leu Arg Ser Asp Ser Asp
            435                 440                 445

Gly Thr Glu Phe Ile Ile Arg Leu Pro Lys Gly Ala Gly Leu Ser Ala
            450                 455                 460

Leu Val
465

<210> SEQ ID NO 35
<211> LENGTH: 750
<212> TYPE: DNA
<213> ORGANISM: Rhodobacter sphaeroides
```

<400> SEQUENCE: 35

```
atgtgggtcg atcatgtgca gggcgagacc ttccacgggc gcaaggggc gctcggcaac    60
agctttcgct acggggtgga ttatctgctg atcgatcccg aggcggtgga ggggccggcg   120
ctcttctcgc gcaaccgggc caacctcatc tcgctccacg atcgcgacta cggcggtgcg   180
ccgggcgagg acggggcgc agcgtgggtg cgcgaggtgc tggcggcgca ggggctgccg    240
cccgccgcgc gcatcctgct gctgacccag ccgcgggtgc tgggccatgt gttcaacccg   300
gtcagcttct ggctctgcga ggatgccgcg gcgcgctcc gctgcgtggt ggccgaggtc    360
agcaacacct tcggcgaccg gcactggtat ctctgcgcca gcccgacgg ctccgtcatc    420
gagcggacgg acacgctcga ggcggccaag atcatgcatg tctcgcccct ccagccgatc   480
gagggcggct atcgcttccg cttcgacatc cgcgaggatc gggtgggcgt ctggatcgac   540
tacagctccg ccgagggcgg gctctatgcc acgcttacgg gccggcgagc gcggctgtcg   600
aaccggggga tcctgcgcgc ctgcctccgg cggcccttcg gtcgcgccg cgtgctggcg    660
ctgatccact ggcaggcgct taagctggcg ctgaaggggg cgcgctaccg cagccgcccc   720
gcgccgccgc tgcaagacgt cacgcggtga                                    750
```

<210> SEQ ID NO 36
<211> LENGTH: 249
<212> TYPE: PRT
<213> ORGANISM: Rhodobacter sphaeroides

<400> SEQUENCE: 36

```
Met Trp Val Asp His Val Gln Gly Glu Thr Phe His Gly Arg Lys Gly
1               5                   10                  15
Ala Leu Gly Asn Ser Phe Arg Tyr Gly Val Asp Tyr Leu Leu Ile Asp
            20                  25                  30
Pro Glu Ala Val Glu Gly Pro Ala Leu Phe Ser Arg Asn Arg Ala Asn
        35                  40                  45
Leu Ile Ser Leu His Asp Arg Asp Tyr Gly Gly Ala Pro Gly Glu Gly
    50                  55                  60
Arg Gly Ala Ala Trp Val Arg Glu Val Leu Ala Ala Gln Gly Leu Pro
65                  70                  75                  80
Pro Ala Ala Arg Ile Leu Leu Leu Thr Gln Pro Arg Val Leu Gly His
                85                  90                  95
Val Phe Asn Pro Val Ser Phe Trp Leu Cys Glu Asp Ala Ala Gly Ala
            100                 105                 110
Leu Arg Cys Val Val Ala Glu Val Ser Asn Thr Phe Gly Asp Arg His
        115                 120                 125
Trp Tyr Leu Cys Ala Lys Pro Asp Gly Ser Val Ile Glu Arg Thr Asp
    130                 135                 140
Thr Leu Glu Ala Ala Lys Ile Met His Val Ser Pro Phe Gln Pro Ile
145                 150                 155                 160
Glu Gly Gly Tyr Arg Phe Arg Phe Asp Ile Arg Glu Asp Arg Val Gly
                165                 170                 175
Val Trp Ile Asp Tyr Ser Ser Ala Glu Gly Gly Leu Tyr Ala Thr Leu
            180                 185                 190
Thr Gly Arg Arg Ala Arg Leu Ser Asn Arg Gly Ile Leu Arg Ala Cys
        195                 200                 205
Leu Arg Arg Pro Phe Gly Ser Arg Val Leu Ala Leu Ile His Trp
    210                 215                 220
```

```
Gln Ala Leu Lys Leu Ala Leu Lys Gly Ala Arg Tyr Arg Ser Arg Pro
225                 230                 235                 240

Ala Pro Pro Leu Gln Asp Val Thr Arg
                245
```

<210> SEQ ID NO 37
<211> LENGTH: 1293
<212> TYPE: DNA
<213> ORGANISM: Rhodobacter sphaeroides

<400> SEQUENCE: 37

```
atgccattcg agacgtctga gttcgcgcgg cggcgcgttg cggtgatcgg tgggggcatc      60
tcggggatgg ctgcggcgca tcttctggcc tccgaccatg cggtcgtgct gttcgaggcc     120
gagaagcggc tcgggggca cgcccgcacg gtcctcgcgg gcaagcgcgg cgaccagcct     180
gtcgacacgg gcttcatcgt gttcaacaag gtgaattatc cgcacctcac gcggctcttc     240
gacgagctcg gcgtgccggt ggcgaagagt gacatgagct tcggcgcctc ggttcgcggc     300
gggcggctgg aatacggcct caagaacctg aaatccgtct tcgcgcagaa gcgcaacatg     360
gcggatccgc gcttcctcaa catgatgatg gatgtgctgc gcttcaacgc ccatgcgctc     420
gaccatgcga cgatccggc catgacgatc gcgagctgc tcgcgcggct cgacctcggc     480
gactggttcc gggactatta cctcctgccg atctcggggg cgatctggtc cacgccctcg     540
cgcgggatcc tcgacttccc ggcgcaggca ctgctgcgct tcttccagaa ccatgcgctc     600
ctgtcccata cggggcagca ccagtggttc acggtcgagg cggctcgat cgaatatgtc     660
acccggctga aggccgcgat ggcggcgcgc ggggtggacc tgcgcaccgg ggcgcaggtg     720
gccggcgtgc gccgcgcgga cggcggggtg cgggtgcggg ccgagggcgg cgagtgggag     780
gccttcgacg aggtgatctt cgccacccat tccgacgata cgctgcggct tctgtccgat     840
gcgacggagg ccgagacgag cgcgctcggg gccgtgcgct accagccgaa ccgggcggtg     900
ctgcattccg atccgtcggt catgccgaag cgcaaggccg cctgggcctc ctgggtctat     960
gtcgagcctg acgatccgga ggcgcccatc gacatcacct actggatgaa ctcgctgcag    1020
cccatcccgc aggacgatcc gctgttcgtg acgctgaacg gcacccgccc ggtgcgcgag    1080
gaactggtgc atgatgtggc gaccttccgc cacccggtct acgacctcgc ggcgcagctg    1140
ggcgtggcgg cgctgcggat gatgaacggc cagcgtcaga cctggttcgc gggcgcctgg    1200
atgcgcaacg gcttccacga ggatggcttt gccagcgctg tggatgttgt cgaggcgatg    1260
cgccggcgca ttcccgcctc ggccgcggcc tga                                  1293
```

<210> SEQ ID NO 38
<211> LENGTH: 430
<212> TYPE: PRT
<213> ORGANISM: Rhodobacter sphaeroides

<400> SEQUENCE: 38

```
Met Pro Phe Glu Thr Ser Glu Phe Ala Arg Arg Val Ala Val Ile
1               5                   10                  15

Gly Gly Gly Ile Ser Gly Met Ala Ala Ala His Leu Leu Ala Ser Asp
                20                  25                  30

His Ala Val Val Leu Phe Glu Ala Glu Lys Arg Leu Gly Gly His Ala
            35                  40                  45

Arg Thr Val Leu Ala Gly Lys Arg Gly Asp Gln Pro Val Asp Thr Gly
        50                  55                  60

Phe Ile Val Phe Asn Lys Val Asn Tyr Pro His Leu Thr Arg Leu Phe
```

```
                65                  70                  75                  80
Asp Glu Leu Gly Val Pro Val Ala Lys Ser Asp Met Ser Phe Gly Ala
                    85                  90                  95

Ser Val Arg Gly Gly Arg Leu Glu Tyr Gly Leu Lys Asn Leu Lys Ser
                    100                 105                 110

Val Phe Ala Gln Lys Arg Asn Met Ala Asp Pro Arg Phe Leu Asn Met
                    115                 120                 125

Met Met Asp Val Leu Arg Phe Asn Ala His Ala Leu Asp His Ala Asp
                    130                 135                 140

Asp Pro Ala Met Thr Ile Arg Glu Leu Leu Ala Arg Leu Asp Leu Gly
145                 150                 155                 160

Asp Trp Phe Arg Asp Tyr Tyr Leu Leu Pro Ile Ser Gly Ala Ile Trp
                    165                 170                 175

Ser Thr Pro Ser Arg Gly Ile Leu Asp Phe Pro Ala Gln Ala Leu Leu
                    180                 185                 190

Arg Phe Phe Gln Asn His Ala Leu Leu Ser His Thr Gly Gln His Gln
                    195                 200                 205

Trp Phe Thr Val Glu Gly Gly Ser Ile Glu Tyr Val Thr Arg Leu Gln
                    210                 215                 220

Ala Ala Met Ala Ala Arg Gly Val Asp Leu Arg Thr Gly Ala Gln Val
225                 230                 235                 240

Ala Gly Val Arg Arg Ala Asp Gly Gly Val Arg Val Arg Ala Glu Gly
                    245                 250                 255

Gly Glu Trp Glu Ala Phe Asp Glu Val Ile Phe Ala Thr His Ser Asp
                    260                 265                 270

Asp Thr Leu Arg Leu Leu Ser Asp Ala Thr Glu Ala Glu Thr Ser Ala
                    275                 280                 285

Leu Gly Ala Val Arg Tyr Gln Pro Asn Arg Ala Val Leu His Ser Asp
                    290                 295                 300

Pro Ser Val Met Pro Lys Arg Lys Ala Ala Trp Ala Ser Trp Val Tyr
305                 310                 315                 320

Val Glu Pro Asp Asp Pro Glu Ala Pro Ile Asp Ile Thr Tyr Trp Met
                    325                 330                 335

Asn Ser Leu Gln Pro Ile Pro Gln Asp Asp Pro Leu Phe Val Thr Leu
                    340                 345                 350

Asn Gly Thr Arg Pro Val Arg Glu Glu Leu Val His Asp Val Ala Thr
                    355                 360                 365

Phe Arg His Pro Val Tyr Asp Leu Ala Ala Gln Leu Gly Val Ala Ala
                    370                 375                 380

Leu Arg Met Met Asn Gly Gln Arg Gln Thr Trp Phe Ala Gly Ala Trp
385                 390                 395                 400

Met Arg Asn Gly Phe His Glu Asp Gly Phe Ala Ser Ala Val Asp Val
                    405                 410                 415

Val Glu Ala Met Arg Arg Arg Ile Pro Ala Ser Ala Ala Ala
                    420                 425                 430

<210> SEQ ID NO 39
<211> LENGTH: 540
<212> TYPE: DNA
<213> ORGANISM: Rhodobacter sphaeroides

<400> SEQUENCE: 39
atgaagacta tctccgcgtt cgccctctgt ggcgccctgg tcctttcggc ctgcgcctcg      60
acgacgccga tggcgctggg gcccgacgga aagccgctgc cgcaggtcta caagatcacg     120
```

```
tccgctcagg agggtgaagt cacctaccgg ctgctggatt cggtcaatgc gctgcgccag      180
gcgaaggggg cggctccgct ccagctcaac tcgcagctca ccgccgccgc ggccacccac      240
tcgcgcgaca tgtcggtgca gaaccgcccc tggcacttcg gtcggacgg ctcctcgcct       300 cttctgcggg tgcagcgcgc gggctatcag ggcaagctga agggtgagct gatctcggaa      360
acctaccaga ccgagctcga cgctggcc gtctggatgg agcagaagga cacgcgcgag        420
atcgtgctgg atccgaccgc gaccgacctc ggcttcgcct ggtatcagga gccgcagggc     480
aagatctggt ggaccgtcgt gacgggcagt ccgcgccca tggcggtggc gggtctctga      540
```

<210> SEQ ID NO 40
<211> LENGTH: 179
<212> TYPE: PRT
<213> ORGANISM: Rhodobacter sphaeroides

<400> SEQUENCE: 40

```
Met Lys Thr Ile Ser Ala Phe Ala Leu Cys Gly Ala Leu Val Leu Ser
 1                5                  10                  15

Ala Cys Ala Ser Thr Thr Pro Met Ala Leu Gly Pro Asp Gly Lys Pro
               20                  25                  30

Leu Pro Gln Val Tyr Lys Ile Thr Ser Ala Gln Glu Gly Glu Val Thr
           35                  40                  45

Tyr Arg Leu Leu Asp Ser Val Asn Ala Leu Arg Gln Ala Lys Gly Ala
       50                  55                  60

Ala Pro Leu Gln Leu Asn Ser Gln Leu Thr Ala Ala Ala Thr His
   65                  70                  75                  80

Ser Arg Asp Met Ser Val Gln Asn Arg Pro Trp His Phe Gly Ser Asp
                   85                  90                  95

Gly Ser Ser Pro Leu Leu Arg Val Gln Arg Ala Gly Tyr Gln Gly Lys
               100                 105                 110

Leu Lys Gly Glu Leu Ile Ser Glu Thr Tyr Gln Thr Glu Leu Glu Thr
           115                 120                 125

Leu Ala Val Trp Met Glu Gln Lys Asp Thr Arg Glu Ile Val Leu Asp
       130                 135                 140

Pro Thr Ala Thr Asp Leu Gly Phe Ala Trp Tyr Gln Glu Pro Gln Gly
  145                 150                 155                 160

Lys Ile Trp Trp Thr Val Val Thr Gly Ser Ser Ala Pro Met Ala Val
                   165                 170                 175

Ala Gly Leu
```

<210> SEQ ID NO 41
<211> LENGTH: 759
<212> TYPE: DNA
<213> ORGANISM: Rhodobacter sphaeroides

<400> SEQUENCE: 41

```
atgctgaagg gaaaatatgg ctggtggtg gtgtcgcca acggccagtc gatcgccgcc       60
ggatgcgccc gcgccttcgc gggcgccggg gccgagcttg cgctgaccta tctgaacgag     120
cgcgccctgc ccatgtcca gccggtggcc gaggaggtgg acgccgcggc gctgctgccg     180
ctcgacctgt cgcaggaaga tgcgctggaa gcggtcttcg agagcgtcag gcaacgctgg   240
gggcgtctcg acttcctgct ccattcggtg gccttctgcc cgaaggagga tctgcacggc    300
cgcgtcaccg actgttcggc ccggggcttc gcacaggcca tggacatctc ctgccactcg   360
ttcctgcgga tggcgaagct ggccgaaccg ctgatgagcg cggcggcag cctgatgacg    420
```

```
gtcagctact acggcgccga aaggtggtg gaccattaca acatcatggg tccggtgaag    480
gccgcgctcg aagcctgcac ccgccatgtg gcggccgagc tcgggccgca ggggatccgg    540
gccaacgtgc tctcgcccgg cccgatcgcg acccgcgcag cgagcggcat cgaccatttc    600
gacgcgctga tcgaggatgc caagacccgc tcgcccgagc ggcgtctcgt gaccatcgac    660
gaggtgggtg ccgtggccgc cttcctcgcc tccgatgccg cctcgggcgt caccggaacc    720
gtgacccaca tcgacggagg ccgacatgtt cggatgtga                          759
```

<210> SEQ ID NO 42
<211> LENGTH: 252
<212> TYPE: PRT
<213> ORGANISM: Rhodobacter sphaeroides

<400> SEQUENCE: 42

```
Met Leu Lys Gly Lys Tyr Gly Leu Val Val Gly Val Ala Asn Gly Gln
1               5                   10                  15

Ser Ile Ala Ala Gly Cys Ala Arg Ala Phe Ala Gly Ala Gly Ala Glu
            20                  25                  30

Leu Ala Leu Thr Tyr Leu Asn Glu Arg Ala Leu Pro His Val Gln Pro
        35                  40                  45

Val Ala Glu Val Asp Ala Ala Leu Leu Pro Leu Asp Leu Ser
    50                  55                  60

Gln Glu Asp Ala Leu Glu Ala Val Phe Glu Ser Val Arg Gln Arg Trp
65                  70                  75                  80

Gly Arg Leu Asp Phe Leu Leu His Ser Val Ala Phe Cys Pro Lys Glu
                85                  90                  95

Asp Leu His Gly Arg Val Thr Asp Cys Ser Ala Arg Gly Phe Ala Gln
            100                 105                 110

Ala Met Asp Ile Ser Cys His Ser Phe Leu Arg Met Ala Lys Leu Ala
        115                 120                 125

Glu Pro Leu Met Ser Ala Gly Gly Ser Leu Met Thr Val Ser Tyr Tyr
    130                 135                 140

Gly Ala Glu Lys Val Val Asp His Tyr Asn Ile Met Gly Pro Val Lys
145                 150                 155                 160

Ala Ala Leu Glu Ala Cys Thr Arg His Val Ala Ala Glu Leu Gly Pro
                165                 170                 175

Gln Gly Ile Arg Ala Asn Val Leu Ser Pro Gly Pro Ile Ala Thr Arg
            180                 185                 190

Ala Ala Ser Gly Ile Asp His Phe Asp Ala Leu Ile Glu Asp Ala Lys
        195                 200                 205

Thr Arg Ser Pro Glu Arg Arg Leu Val Thr Ile Asp Glu Val Gly Ala
    210                 215                 220

Val Ala Ala Phe Leu Ala Ser Asp Ala Ala Ser Gly Val Thr Gly Thr
225                 230                 235                 240

Val Thr His Ile Asp Gly Gly Arg His Val Arg Met
                245                 250
```

<210> SEQ ID NO 43
<211> LENGTH: 1035
<212> TYPE: DNA
<213> ORGANISM: Rhodobacter sphaeroides

<400> SEQUENCE: 43

```
atgagggtcg tcgtcgtctg tcccggccgc ggcacctaca ccaaggcaga actgggctct    60
```

-continued

```
ctcggccggc tccatcccga caaggccgcg ctgttcgccc ggttcgatgc ccagcgccgg      120 gtggcgggc aggagacgct ggccgatctc gacggcgaag cgagctattc cgtggcgcgc      180
cacacgcggg gcgacaatgc ctcggcgctg atctatgccg cgggctacgc cgatttcctg      240
tcgctcacgg gcgtcgaggt ggtggccgtc accggcaatt cgatgggctg gtatacggcg      300
ctggcctgcg gcggcgccct tcggccgaa gacggcttcc gggtcgtcaa cacgatgggc       360
acgctgatgc aggaggcgct gatcggcggc cagatcgtcc atccggtcat gggcgaggac      420
tggcggcccg accttgcccg ccgcgcgcaa ctgctggatc aggtggccgg gatcgacgcc      480
cgcccggggc gcatcctcgg cctctccatc gcgctcggcg gatgctcgt gctggcgggc       540 aatgccgaag gtctggccga tttcgaggcc gaagtgccgc ccgaacaggg ccgcttcccg      600
atgcgccttg ccaatcacgc ggccttccac accgcccttc aggcgccggt cgccgcgcgc      660
ggacaggcgg cgctgcccga ggcgctgttc ggtcagccgc ggctgccgct catcgacggg      720
cgcggcgccg tctggtggcc gaaagccacc gacgcggcgg cgctccgggc ctatacgctc      780
ggccatcagg tcacggagcc ctacgatttc acccgcgcca tcgcggtcgc cgcgcgggaa      840
ttcgcgcccg acgccttcgt cgtactcggc cccggcacca cgctgggcgg ggccgtggcg      900
cagagcttga tcctcgccgg ctggcgcggg atgaaggacc gcaaggattt ccagacccgt      960
caggccgaga gcccctgct gatcgcactg gggcgagagg accagcgcgg gcacgtcaca      1020
ggaggaccca gatga                                                      1035
```

<210> SEQ ID NO 44
<211> LENGTH: 344
<212> TYPE: PRT
<213> ORGANISM: Rhodobacter sphaeroides

<400> SEQUENCE: 44

```
Met Arg Val Val Val Cys Pro Gly Arg Gly Thr Tyr Thr Lys Ala
1               5                   10                  15

Glu Leu Gly Ser Leu Gly Arg Leu His Pro Asp Lys Ala Ala Leu Phe
            20                  25                  30

Ala Arg Phe Asp Ala Gln Arg Val Ala Gly Gln Glu Thr Leu Ala
        35                  40                  45

Asp Leu Asp Gly Glu Ala Ser Tyr Ser Val Ala Arg His Thr Arg Gly
    50                  55                  60

Asp Asn Ala Ser Ala Leu Ile Tyr Ala Ala Gly Tyr Ala Asp Phe Leu
65                  70                  75                  80

Ser Leu Thr Gly Val Glu Val Ala Val Thr Gly Asn Ser Met Gly
                85                  90                  95

Trp Tyr Thr Ala Leu Ala Cys Gly Gly Ala Leu Ser Ala Glu Asp Gly
                100                 105                 110

Phe Arg Val Val Asn Thr Met Gly Thr Leu Met Gln Glu Ala Leu Ile
            115                 120                 125

Gly Gly Gln Ile Val His Pro Val Met Gly Glu Asp Trp Arg Pro Asp
        130                 135                 140

Leu Ala Arg Arg Ala Gln Leu Leu Asp Gln Val Ala Gly Ile Asp Ala
145                 150                 155                 160

Arg Pro Gly Arg Ile Leu Gly Leu Ser Ile Ala Leu Gly Gly Met Leu
                165                 170                 175

Val Leu Ala Gly Asn Ala Glu Gly Leu Ala Asp Phe Glu Ala Glu Val
            180                 185                 190

Pro Pro Glu Gln Gly Arg Phe Pro Met Arg Leu Ala Asn His Ala Ala
```

```
            195                 200                 205
Phe His Thr Ala Leu Gln Ala Pro Val Ala Ala Arg Gly Gln Ala Ala
    210                 215                 220

Leu Pro Glu Ala Leu Phe Gly Gln Pro Arg Leu Pro Leu Ile Asp Gly
225                 230                 235                 240

Arg Gly Ala Val Trp Pro Lys Ala Thr Asp Ala Ala Leu Arg
                245                 250                 255

Ala Tyr Thr Leu Gly His Gln Val Thr Glu Pro Tyr Asp Phe Thr Arg
            260                 265                 270

Ala Ile Ala Val Ala Ala Arg Glu Phe Ala Pro Asp Ala Phe Val Val
        275                 280                 285

Leu Gly Pro Gly Thr Thr Leu Gly Gly Ala Val Ala Gln Ser Leu Ile
    290                 295                 300

Leu Ala Gly Trp Arg Gly Met Lys Asp Arg Lys Asp Phe Gln Thr Arg
305                 310                 315                 320

Gln Ala Glu Ser Pro Leu Leu Ile Ala Leu Gly Arg Glu Asp Gln Arg
                325                 330                 335

Gly His Val Thr Gly Gly Pro Arg
            340
```

<210> SEQ ID NO 45
<211> LENGTH: 1170
<212> TYPE: DNA
<213> ORGANISM: Rhodobacter sphaeroides

<400> SEQUENCE: 45

| | | | | | |
|---|---|---|---|---|---|
| atgtccgaca | tcctcgtcct | ctccgccgtc | cgcaccgcca | tcggcggctt | cggcggcgcg | 60 |
| ctcgccgcgg | tcccgccggg | cgatctcgcc | accaccgtca | cccgtgccgc | gctggagcgc | 120 |
| gcaggcgtgg | agcccggccg | cgtggggcat | gtggtcttcg | gccatgtcat | caacaccgaa | 180 |
| ccgcgcgaca | tgtatctctc | gcgcgtggcg | gcgatgcagg | cgggtatccc | gtcggaggtg | 240 |
| ccggcgatga | acgtgaaccg | gctctgcggc | tcgggcgtgc | aggccgtcgt | ctcggccatg | 300 |
| caggcgctga | tgctgggcga | tgccgaggtg | gcgctggcgg | gcggcgcgga | atcgatgagc | 360 |
| cgcgcgccct | atgcgctgac | gacggcgcgg | tggggccaga | agatgggcga | cacgcgcgcg | 420 |
| ctcgacatga | tgacggggggc | gctcaactgc | cccttcggca | ccggccacat | gggcatcacc | 480 |
| gccgagatcg | tggccgagcg | ccacggcatc | agccgcgagg | atcaggacgc | gttcgcgctg | 540 |
| gaaagccaga | cccgcaccgc | ccgcgcgcag | gaggagggcc | gcttcgacgg | ccagatcgtt | 600 |
| ccggtcgaga | tcgcctcgcg | gaaggggccg | gtctccttct | cccgcgacga | acatcccaag | 660 |
| gccaccaccc | tcgaggcgct | cgcggggctg | cgtcccgcct | tccagaaagg | cggcacggtg | 720 |
| accgcaggca | atgcgagcgg | gatcaacgac | ggggccgggg | cgctgatcct | cgcgcgcgag | 780 |
| ggggccgtgc | ccgacgcgcg | tccgctcggc | cggctgatcg | gctatgccca | tgcgggcgtc | 840 |
| gatcccgagg | tgatggggct | ggggccgatc | ccggcggtaa | aggcgctctg | cgcgcgcacc | 900 |
| ggcctctcgg | tcgcggattt | cgacgtgatc | gagtcgaacg | aggccttcgc | ggcacaggcg | 960 |
| ctggccgtgg | cgcgcgcgct | cgatttcgat | ccggccaggg | tgaacccgaa | cggcggcgcc | 1020 |
| atcgcgctcg | gccatccggt | cggcgccacc | ggggcgatca | tcacggtgaa | ggcgctccac | 1080 |
| gagctgcacc | ggacgggcgg | gcgccgggcc | ctcgtcacca | tgtgcatcgg | cggcgggcag | 1140 |
| gggatcgcgc | tggcgctcga | gcgggtctga | | | | 1170 |

<210> SEQ ID NO 46

```
<211> LENGTH: 389
<212> TYPE: PRT
<213> ORGANISM: Rhodobacter sphaeroides

<400> SEQUENCE: 46
```

| | | | | | | | | | | | | | | |
|---|---|---|---|---|---|---|---|---|---|---|---|---|---|---|
| Met | Ser | Asp | Ile | Leu | Val | Leu | Ser | Ala | Val | Arg | Thr | Ala | Ile | Gly | Gly |
| 1 | | | | 5 | | | | | 10 | | | | | 15 | |
| Phe | Gly | Gly | Ala | Leu | Ala | Ala | Val | Pro | Pro | Gly | Asp | Leu | Ala | Thr | Thr |
| | | | 20 | | | | | 25 | | | | | 30 | | |
| Val | Thr | Arg | Ala | Ala | Leu | Glu | Arg | Ala | Gly | Val | Glu | Pro | Gly | Arg | Val |
| | | 35 | | | | | 40 | | | | | 45 | | | |
| Gly | His | Val | Val | Phe | Gly | His | Val | Ile | Asn | Thr | Glu | Pro | Arg | Asp | Met |
| | 50 | | | | | 55 | | | | | 60 | | | | |
| Tyr | Leu | Ser | Arg | Val | Ala | Ala | Met | Gln | Ala | Gly | Ile | Pro | Ser | Glu | Val |
| 65 | | | | | 70 | | | | | 75 | | | | | 80 |
| Pro | Ala | Met | Asn | Val | Asn | Arg | Leu | Cys | Gly | Ser | Val | Gln | Ala | Val | |
| | | | | 85 | | | | | 90 | | | | | 95 | |
| Val | Ser | Ala | Met | Gln | Ala | Leu | Met | Leu | Gly | Asp | Ala | Glu | Val | Ala | Leu |
| | | | 100 | | | | | 105 | | | | | 110 | | |
| Ala | Gly | Gly | Ala | Glu | Ser | Met | Ser | Arg | Ala | Pro | Tyr | Ala | Leu | Thr | Thr |
| | | 115 | | | | | 120 | | | | | 125 | | | |
| Ala | Arg | Trp | Gly | Gln | Lys | Met | Gly | Asp | Thr | Arg | Ala | Leu | Asp | Met | Met |
| | 130 | | | | | 135 | | | | | 140 | | | | |
| Thr | Gly | Ala | Leu | Asn | Cys | Pro | Phe | Gly | Thr | Gly | His | Met | Gly | Ile | Thr |
| 145 | | | | | 150 | | | | | 155 | | | | | 160 |
| Ala | Glu | Ile | Val | Ala | Glu | Arg | His | Gly | Ile | Ser | Arg | Glu | Asp | Gln | Asp |
| | | | | 165 | | | | | 170 | | | | | 175 | |
| Ala | Phe | Ala | Leu | Glu | Ser | Gln | Thr | Arg | Thr | Ala | Arg | Ala | Gln | Glu | Glu |
| | | | 180 | | | | | 185 | | | | | 190 | | |
| Gly | Arg | Phe | Asp | Gly | Gln | Ile | Val | Pro | Val | Glu | Ile | Ala | Ser | Arg | Lys |
| | | 195 | | | | | 200 | | | | | 205 | | | |
| Gly | Pro | Val | Ser | Phe | Ser | Arg | Asp | Glu | His | Pro | Lys | Ala | Thr | Thr | Leu |
| | 210 | | | | | 215 | | | | | 220 | | | | |
| Glu | Ala | Leu | Ala | Gly | Leu | Arg | Pro | Ala | Phe | Gln | Lys | Gly | Gly | Thr | Val |
| 225 | | | | | 230 | | | | | 235 | | | | | 240 |
| Thr | Ala | Gly | Asn | Ala | Ser | Gly | Ile | Asn | Asp | Gly | Ala | Gly | Ala | Leu | Ile |
| | | | | 245 | | | | | 250 | | | | | 255 | |
| Leu | Ala | Arg | Glu | Gly | Ala | Val | Pro | Asp | Ala | Arg | Pro | Leu | Gly | Arg | Leu |
| | | | 260 | | | | | 265 | | | | | 270 | | |
| Ile | Gly | Tyr | Ala | His | Ala | Gly | Val | Asp | Pro | Glu | Val | Met | Gly | Leu | Gly |
| | | 275 | | | | | 280 | | | | | 285 | | | |
| Pro | Ile | Pro | Ala | Val | Lys | Ala | Leu | Cys | Ala | Arg | Thr | Gly | Leu | Ser | Val |
| | 290 | | | | | 295 | | | | | 300 | | | | |
| Ala | Asp | Phe | Asp | Val | Ile | Glu | Ser | Asn | Glu | Ala | Phe | Ala | Ala | Gln | Ala |
| 305 | | | | | 310 | | | | | 315 | | | | | 320 |
| Leu | Ala | Val | Ala | Arg | Ala | Leu | Asp | Phe | Asp | Pro | Ala | Arg | Val | Asn | Pro |
| | | | | 325 | | | | | 330 | | | | | 335 | |
| Asn | Gly | Gly | Ala | Ile | Ala | Leu | Gly | His | Pro | Val | Gly | Ala | Thr | Gly | Ala |
| | | | 340 | | | | | 345 | | | | | 350 | | |
| Ile | Ile | Thr | Val | Lys | Ala | Leu | His | Glu | Leu | His | Arg | Thr | Gly | Gly | Arg |
| | | 355 | | | | | 360 | | | | | 365 | | | |
| Arg | Ala | Leu | Val | Thr | Met | Cys | Ile | Gly | Gly | Gln | Gly | Ile | Ala | Leu | |
| | 370 | | | | | 375 | | | | | 380 | | | | |
| Ala | Leu | Glu | Arg | Val | | | | | | | | | | | |

<210> SEQ ID NO 47
<211> LENGTH: 1086
<212> TYPE: DNA
<213> ORGANISM: Rhodobacter sphaeroides

<400> SEQUENCE: 47

```
atggcgaagc gcagacggct tgaggctccc tcggcggaag aactcgagga gctggagacc        60
ggtttcgccc gcgaaacctc caccagcacg cggccgccca tcgcacaggt ggcggcggat       120
gcggcctcgc tggccatgcc gatgcccacg gccaacgtg ccgcggccgc gaaggacagc        180
gccgatgcca cacggctgag gcaggccgag gccgaagggt tgcttctgct cgagatcccg       240
ctggccgaga tccgcgccga tgatctgacg cgcgaccggc tgaagatcga cggcgaggaa       300
atggacgagc tgcgcgcctc gatccgagcg catgggctgc ggttgccggt cgaggtgttc       360
gagcggccgg aggggcaggg agagcgctac ggtctgatct ccggctggcg gcgtctgtgg       420
gcgctgcgct cgctccatgc cgagacgggc gacgggcgct tcgcccgggt cgtgcgctg        480
gtgcggcggc cgaccgacgt ctcggcagcc tatgtcgcga tggtcgagga aaacgagatc       540
cgctctgacc tctcgcctta cgagcgcggc aggatcgcgg ccctcgctgc ggggcagggg       600
gcgttcgggt cggtcgagga agcggtcgac gtgctgttcg gcgcggcctc gaaggcgaag       660
cggtcgaaga tccgcagctt cgcgcttatc catgaagagc tgggcgatct tctgggtttc       720
gccacgacgc tgggcgagcg gcccggcctg cgtctggccc acgccctgcg gctgggctac       780
gccggagcac tgcgcgaggc gctggcggcg gggcagggcg gcgatgccga ggcggagtgg       840
ctgctgatgg agcccttggt gaaggccgcc gaagggacgg tggcggaccc gtcgcgcggc       900
ggccgccccgc cccgtaaaca ggttcctgtg cagcaacgg tccagatcga gcggtcgggc        960
gacggtccgg gctacctgtt gcggttggag ggtgacgacg tcgacgaagc gctggcgcag      1020
cgtgtcgcgc aggagttgcg aaagctgctg cgtcggggga gggtttcgcc ggcgaaaccc      1080
ggttga                                                                 1086
```

<210> SEQ ID NO 48
<211> LENGTH: 361
<212> TYPE: PRT
<213> ORGANISM: Rhodobacter sphaeroides

<400> SEQUENCE: 48

```
Met Ala Lys Arg Arg Arg Leu Glu Ala Pro Ser Ala Glu Glu Leu Glu
 1               5                  10                  15

Glu Leu Glu Thr Gly Phe Ala Arg Glu Thr Ser Thr Ser Thr Arg Pro
            20                  25                  30

Pro Ile Ala Gln Val Ala Ala Asp Ala Ala Ser Leu Ala Met Pro Met
        35                  40                  45

Pro Thr Ala Glu Arg Ala Ala Ala Lys Asp Ser Ala Asp Ala Thr
    50                  55                  60

Arg Leu Arg Gln Ala Glu Ala Glu Gly Leu Leu Leu Glu Ile Pro
65                  70                  75                  80

Leu Ala Glu Ile Arg Ala Asp Asp Leu Thr Arg Asp Arg Leu Lys Ile
                85                  90                  95

Asp Gly Glu Glu Met Asp Glu Leu Arg Ala Ser Ile Arg Ala His Gly
            100                 105                 110

Leu Arg Leu Pro Val Glu Val Phe Glu Arg Pro Glu Gly Gln Gly Glu
        115                 120                 125
```

Arg Tyr Gly Leu Ile Ser Gly Trp Arg Arg Leu Trp Ala Leu Arg Ser
            130                 135                 140

Leu His Ala Glu Thr Gly Asp Gly Arg Phe Ala Arg Val Arg Ala Leu
145                 150                 155                 160

Val Arg Arg Pro Thr Asp Val Ser Ala Ala Tyr Val Ala Met Val Glu
                165                 170                 175

Glu Asn Glu Ile Arg Ser Asp Leu Ser Pro Tyr Glu Arg Gly Arg Ile
            180                 185                 190

Ala Ala Leu Ala Ala Gly Gln Gly Ala Phe Gly Ser Val Glu Glu Ala
        195                 200                 205

Val Asp Val Leu Phe Gly Ala Ala Ser Lys Ala Lys Arg Ser Lys Ile
210                 215                 220

Arg Ser Phe Ala Leu Ile His Glu Glu Leu Gly Asp Leu Leu Gly Phe
225                 230                 235                 240

Ala Thr Thr Leu Gly Glu Arg Pro Gly Leu Arg Leu Ala His Ala Leu
                245                 250                 255

Arg Leu Gly Tyr Ala Gly Ala Leu Arg Glu Ala Leu Ala Ala Gly Gln
            260                 265                 270

Gly Gly Asp Ala Glu Ala Glu Trp Leu Leu Met Glu Pro Leu Val Lys
        275                 280                 285

Ala Ala Glu Gly Thr Val Ala Asp Pro Ser Arg Gly Gly Arg Pro Pro
290                 295                 300

Arg Lys Gln Val Pro Val Ala Ala Thr Val Gln Ile Glu Arg Ser Gly
305                 310                 315                 320

Asp Gly Pro Gly Tyr Leu Leu Arg Leu Glu Gly Asp Asp Val Asp Glu
                325                 330                 335

Ala Leu Ala Gln Arg Val Ala Gln Glu Leu Arg Lys Leu Leu Ala Ser
            340                 345                 350

Gly Arg Val Ser Pro Ala Lys Pro Gly
        355                 360

<210> SEQ ID NO 49
<211> LENGTH: 876
<212> TYPE: DNA
<213> ORGANISM: Rhodobacter sphaeroides

<400> SEQUENCE: 49
atggagatcc gcaaggtcgg cgtcgtgggc gcgggacaga tgggcagcgg tatcgcgcat      60
gtcttctcgc tcgcgggcta cgaggtgctg ctgaacgaca tcagcgccga agggctgaac     120
aaggcgctct cgaccatcga gcgcaacatg gagcggcagg tctcgcgcgg gaaggtctcg     180
gccgaggaca aggccgcggc gctcgggcgg atccgcacca cccagaccct caccgacatc     240
gccaggagcg acctcgtgat cgaggccgcc accgagcgcg agacggtgaa acaggcgatc     300
ttcgaggatc tggtgccgca tcttctgccg cacacgatcc tgacctcgaa cacctcctcg     360
atctcgatca cacggcttgc ctcgcgcacg gaccggcccg agaaattcat gggctttcac     420
ttcatgaacc cggtgccggt gatgcagctc gtcgagctga tccgcggcat cgcgaccgac     480
gacccgacct atcaggcgct gctcaaggtg gtgcagagcc tcggcaagac gcggccagc      540 gccgaggatt tcccggcctt catcgtcaac cgcatcctcg tgccgatgat caacgaagcg     600
gtctacacgc tctatgaagg cgtgggcctc gtgcgctcga tcgacgagtc gatgaagctc     660
ggggcgaatc atccgatggg gccgctggag ctcgcggatt tcatcgggct cgacacctgc     720
cttgcgatca tgaacgtgct gcacgacggg ctggccgata cgaaataccg gccctgcccg     780

```
cttctggtga aatatgtcga ggcaggatgg ctcggccgga agaccgcccg cggcttctac    840
gattatcgcg gcgagacgcc ggtgccgaca cggtag                              876
```

<210> SEQ ID NO 50
<211> LENGTH: 291
<212> TYPE: PRT
<213> ORGANISM: Rhodobacter sphaeroides

<400> SEQUENCE: 50

```
Met Glu Ile Arg Lys Val Gly Val Gly Ala Gly Gln Met Gly Ser
1               5                  10                  15

Gly Ile Ala His Val Phe Ser Leu Ala Gly Tyr Glu Val Leu Leu Asn
            20                  25                  30

Asp Ile Ser Ala Glu Gly Leu Asn Lys Ala Leu Ser Thr Ile Glu Arg
        35                  40                  45

Asn Met Glu Arg Gln Val Ser Arg Gly Lys Val Ser Ala Glu Asp Lys
    50                  55                  60

Ala Ala Ala Leu Gly Arg Ile Arg Thr Thr Gln Thr Leu Thr Asp Ile
65                  70                  75                  80

Ala Arg Ser Asp Leu Val Ile Glu Ala Ala Thr Glu Arg Glu Thr Val
                85                  90                  95

Lys Gln Ala Ile Phe Glu Asp Leu Val Pro His Leu Leu Pro His Thr
            100                 105                 110

Ile Leu Thr Ser Asn Thr Ser Ser Ile Ser Ile Thr Arg Leu Ala Ser
        115                 120                 125

Arg Thr Asp Arg Pro Glu Lys Phe Met Gly Phe His Phe Met Asn Pro
    130                 135                 140

Val Pro Val Met Gln Leu Val Glu Leu Ile Arg Gly Ile Ala Thr Asp
145                 150                 155                 160

Asp Pro Thr Tyr Gln Ala Leu Leu Lys Val Val Gln Ser Leu Gly Lys
                165                 170                 175

Thr Ala Ala Ser Ala Glu Asp Phe Pro Ala Phe Ile Val Asn Arg Ile
            180                 185                 190

Leu Val Pro Met Ile Asn Glu Ala Val Tyr Thr Leu Tyr Glu Gly Val
        195                 200                 205

Gly Ser Val Arg Ser Ile Asp Glu Ser Met Lys Leu Gly Ala Asn His
    210                 215                 220

Pro Met Gly Pro Leu Glu Leu Ala Asp Phe Ile Gly Leu Asp Thr Cys
225                 230                 235                 240

Leu Ala Ile Met Asn Val Leu His Asp Gly Leu Ala Asp Thr Lys Tyr
                245                 250                 255

Arg Pro Cys Pro Leu Leu Val Lys Tyr Val Glu Ala Gly Trp Leu Gly
            260                 265                 270

Arg Lys Thr Ala Arg Gly Phe Tyr Asp Tyr Arg Gly Glu Thr Pro Val
        275                 280                 285

Pro Thr Arg
    290
```

<210> SEQ ID NO 51
<211> LENGTH: 960
<212> TYPE: DNA
<213> ORGANISM: Rhodobacter sphaeroides

<400> SEQUENCE: 51

```
atgaactatc tcgaattcga aaagccgctg tccgagatcg agggcaaggc cgaggagttg    60
```

-continued

```
cgcgcgctcg cgcggggcaa cagggagatg gacgtcgaga aggaagcgtc ggcgctcgac    120
aagaaggccg agacgctgct gaaggatctc tacaaggacc tgaccccctg gcggaagtgc    180
caggtggcgc gccatcccga ccgcccgcac tgcaaggact atatcgaggg cctcttcacc    240
gaatatacgc cgctcgcggg cgaccggaac ttcgccgacg accatgcgat catgggcggg    300
ctcgcgcggt tcaacgacaa tccggtggtg gtgatcggtc aggagaaggg ccacgacacc    360
aagacccgga tcgagcgcaa cttcggcatg gcccgccccg agggctatcg caaagccatc    420
cggctgatgg agatggcgca ccgcttccgg ctgccggtca tcacgctcgt ggatacgccc    480
ggcgcctatc ccggcaaggg tgcggaagag cgcggccagg ccgaggccat gcgcgggcc    540 acgcagaaat gcctcgagat cggcgtgccg ctggtggcgg tggtgatcgg cgagggcggc    600
tcgggcgggg cggtggcgct ggccacggcg aaccggatcg ccatgctcga acattcggtc    660
tattcggtga tctcgcccga gggctgcgcc tcgatcctgt ggaaggatgc cgagaagatg    720
cgcgaagccg ccgaagccct gcggctgacc gcgcaggatc tccacaagct cggcgtgatc    780
gaccggatca tcaaggagcc gctcggcggg gcgcagcgcg gacgccgcga cggtcgac    840 gccgtgggca aggccatcga gatgatgctg aaggagctgg tgggccgcaa gcccgagtgg    900
ctcgtgaagg atcggcgcaa caagttcctc gacatggggt cgaagggcct cgcggcgtga    960
```

<210> SEQ ID NO 52  
<211> LENGTH: 319  
<212> TYPE: PRT  
<213> ORGANISM: Rhodobacter sphaeroides

<400> SEQUENCE: 52

```
Met Asn Tyr Leu Glu Phe Glu Lys Pro Leu Ser Glu Ile Glu Gly Lys
1               5                   10                  15

Ala Glu Glu Leu Arg Ala Leu Ala Arg Gly Asn Arg Glu Met Asp Val
                20                  25                  30

Glu Lys Glu Ala Ser Ala Leu Asp Lys Lys Ala Glu Thr Leu Leu Lys
            35                  40                  45

Asp Leu Tyr Lys Asp Leu Thr Pro Trp Arg Lys Cys Gln Val Ala Arg
        50                  55                  60

His Pro Asp Arg Pro His Cys Lys Asp Tyr Ile Glu Gly Leu Phe Thr
65                  70                  75                  80

Glu Tyr Thr Pro Leu Ala Gly Asp Arg Asn Phe Ala Asp Asp His Ala
                85                  90                  95

Ile Met Gly Gly Leu Ala Arg Phe Asn Asp Asn Pro Val Val Ile
                100                 105                 110

Gly Gln Glu Lys Gly His Asp Thr Lys Thr Arg Ile Glu Arg Asn Phe
            115                 120                 125

Gly Met Ala Arg Pro Glu Gly Tyr Arg Lys Ala Ile Arg Leu Met Glu
        130                 135                 140

Met Ala His Arg Phe Arg Leu Pro Val Ile Thr Leu Val Asp Thr Pro
145                 150                 155                 160

Gly Ala Tyr Pro Gly Lys Gly Ala Glu Glu Arg Gly Gln Ala Glu Ala
                165                 170                 175

Ile Ala Arg Ala Thr Gln Lys Cys Leu Glu Ile Gly Val Pro Leu Val
            180                 185                 190

Ala Val Val Ile Gly Glu Gly Gly Ser Gly Gly Ala Val Ala Leu Ala
        195                 200                 205

Thr Ala Asn Arg Ile Ala Met Leu Glu His Ser Val Tyr Ser Val Ile
```

```
                     210                 215                 220
Ser Pro Glu Gly Cys Ala Ser Ile Leu Trp Lys Asp Ala Glu Lys Met
225                 230                 235                 240

Arg Glu Ala Ala Glu Ala Leu Arg Leu Thr Ala Gln Asp Leu His Lys
                245                 250                 255

Leu Gly Val Ile Asp Arg Ile Ile Lys Glu Pro Leu Gly Gly Ala Gln
                260                 265                 270

Arg Gly Arg Arg Glu Thr Val Asp Ala Val Gly Lys Ala Ile Glu Met
            275                 280                 285

Met Leu Lys Glu Leu Val Gly Arg Lys Pro Glu Trp Leu Val Lys Asp
        290                 295                 300

Arg Arg Asn Lys Phe Leu Asp Met Gly Ser Lys Gly Leu Ala Ala
305                 310                 315

<210> SEQ ID NO 53
<211> LENGTH: 723
<212> TYPE: DNA
<213> ORGANISM: Rhodobacter sphaeroides

<400> SEQUENCE: 53
atgcgcttgc ttgatatctg gatgcgcagt gccgcggcac tgatgctcct gagcggagcg     60
gccttcgccg atgtgacggt gagccagtcc aacgatccgt ccgtcagtct gggcgggcag    120
ctttcggccc ttctgggcgc cgagcggagc ccctcgggga ccctgccggc ccagcggctc    180
gagcaggtgg cggccgccgt ggcccgcccc gaggcgaagc ccgaggcgcc ggtcaaggcg    240
gtggcgacca aggcaaccg cggcgccaag gccgcggacg acgctccggc cgcgcgctac    300
gacgaggcct ggctcgcctc gcagccggcg accgcgaagg actcggacga gtggaagtgt    360
ctggccacgg cgctctattt cgaggcgcgc ggcgagtcga tccagggcca gttcgcggtg    420
gccgaggtca tcatgaaccg cgtcgaccgc cccggctatc ccgggtccat ctgcggcgtg    480
gtccggcagg gcgggcagtt ctccttcatg ttcgacggca gcccgaaaac gatccgcgag    540
aaggcggcct ccagcgtgc gggcaagatc gcggcgctga tgctggcggg cgctccgcgc    600
cagctcacgc agggcgccac ccacttccac acccgcgccg tccgcccggg ttgggcgcac    660
cgcttcccgc gcacggcggc catcggcgcg catctgttct accgccagcc cggcggctcc    720
tga                                                                  723

<210> SEQ ID NO 54
<211> LENGTH: 240
<212> TYPE: PRT
<213> ORGANISM: Rhodobacter sphaeroides

<400> SEQUENCE: 54

Met Arg Leu Leu Asp Ile Trp Met Arg Ser Ala Ala Leu Met Leu
1               5                   10                  15

Leu Ser Gly Ala Ala Phe Ala Asp Val Thr Val Ser Gln Ser Asn Asp
                20                  25                  30

Pro Ser Val Ser Leu Gly Gly Gln Leu Ser Ala Leu Leu Gly Ala Glu
            35                  40                  45

Arg Ser Ala Leu Gly Thr Leu Pro Ala Gln Arg Leu Glu Gln Val Ala
        50                  55                  60

Ala Ala Val Ala Arg Pro Glu Ala Lys Pro Glu Ala Pro Val Lys Ala
65                  70                  75                  80

Val Ala Thr Lys Gly Asn Arg Gly Ala Lys Ala Ala Asp Asp Ala Pro
                85                  90                  95
```

Ala Pro Arg Tyr Asp Glu Ala Trp Leu Ala Ser Gln Pro Ala Thr Ala
            100                 105                 110

Lys Asp Ser Asp Glu Trp Lys Cys Leu Ala Thr Ala Leu Tyr Phe Glu
            115                 120                 125

Ala Arg Gly Glu Ser Ile Gln Gly Gln Phe Ala Val Ala Glu Val Ile
            130                 135                 140

Met Asn Arg Val Asp Arg Pro Gly Tyr Pro Gly Ser Ile Cys Gly Val
145                 150                 155                 160

Val Arg Gln Gly Gly Gln Phe Ser Phe Met Phe Asp Gly Lys Pro Glu
                165                 170                 175

Thr Ile Arg Glu Lys Ala Ala Phe Gln Arg Ala Gly Lys Ile Ala Ala
            180                 185                 190

Leu Met Leu Ala Gly Ala Pro Arg Gln Leu Thr Gln Gly Ala Thr His
            195                 200                 205

Phe His Thr Arg Ala Val Arg Pro Gly Trp Ala His Arg Phe Pro Arg
            210                 215                 220

Thr Ala Ala Ile Gly Ala His Leu Phe Tyr Arg Gln Pro Gly Gly Ser
225                 230                 235                 240

<210> SEQ ID NO 55
<211> LENGTH: 507
<212> TYPE: DNA
<213> ORGANISM: Rhodobacter sphaeroides

<400> SEQUENCE: 55
gtggcggagg cgttcagagg cgaatacaac cagaaggttg acgccaaggc gcgggtgtcg      60
atcccggccc ccttccgtcg tgtcatcgaa gcggcgatc ccaaattctc cggcggccgg     120
tcgagcttcg tgctcgtcta tggcggcgac cgctcctacg tcgaatgcta caccatttcc     180
gagatggagc ggatcgagga acggatccgc agcctgccca tgggcacgcc caagcggcgc     240
tatctcgaac gcaacatgat caccctcgcg cttaacatgg agctcgacga ggacggccgg     300
atcgtgctgc cgcccaaggg ccgcgagaag ctgggcatct cgcccgacga gctgaagggc     360
ggcaccgaag ccacctttgc gggcacgctc aacaagttcc agatctggaa ggccgacacc     420
tacgcagccg agctcgccgc gaagaggag gtgctcctgc ctccgggcgc cgacatgctc     480
tcgctgctcg aagagacggg gctctga                                         507

<210> SEQ ID NO 56
<211> LENGTH: 168
<212> TYPE: PRT
<213> ORGANISM: Rhodobacter sphaeroides

<400> SEQUENCE: 56

Met Ala Glu Ala Phe Arg Gly Glu Tyr Asn Gln Lys Val Asp Ala Lys
1               5                   10                  15

Ala Arg Val Ser Ile Pro Ala Pro Phe Arg Arg Val Ile Glu Ala Gly
            20                  25                  30

Asp Pro Lys Phe Ser Gly Gly Arg Ser Ser Phe Val Leu Val Tyr Gly
            35                  40                  45

Gly Asp Arg Ser Tyr Val Glu Cys Tyr Thr Ile Ser Glu Met Glu Arg
        50                  55                  60

Ile Glu Glu Arg Ile Arg Ser Leu Pro Met Gly Thr Pro Lys Arg Arg
65                  70                  75                  80

Tyr Leu Glu Arg Asn Met Ile Thr Leu Ala Leu Asn Met Glu Leu Asp
                85                  90                  95

Glu Asp Gly Arg Ile Val Leu Pro Pro Lys Gly Arg Glu Lys Leu Gly
                100                 105                 110

Ile Ser Pro Asp Glu Leu Lys Gly Gly Thr Glu Ala Thr Phe Ala Gly
            115                 120                 125

Thr Leu Asn Lys Phe Gln Ile Trp Lys Ala Asp Thr Tyr Ala Ala Glu
    130                 135                 140

Leu Ala Ala Glu Glu Val Leu Leu Pro Pro Gly Ala Asp Met Leu
145                 150                 155                 160

Ser Leu Leu Glu Glu Thr Gly Leu
                165

<210> SEQ ID NO 57
<211> LENGTH: 360
<212> TYPE: DNA
<213> ORGANISM: Rhodobacter sphaeroides

<400> SEQUENCE: 57 atgcgcccg tgctctatgt cctcaccttc ctcgccgtga tggggctggc cttctgggcc      60
taccgtgaga actatgccac gcagcaggcg ctcaaggatg tctcggcgct caaccgcgag    120
atcgcgaccc tgcgcgagtc gctctcggtg cagcgcgcgg aatgggccta tctgaaccgt    180
cccgaccggc tgcgcgagct ggcggcgctg aacttcgacc gtctgggcct gctgccgctc    240
gaggccgtgc aattcggctc ggccgcgcag gtctcctacc cgccggatcc gcttcaggtg    300
gtcacgccgc aggatctgcg gccgggcgac atctcgggcg aagtgggaga gccgctgtga    360

<210> SEQ ID NO 58
<211> LENGTH: 119
<212> TYPE: PRT
<213> ORGANISM: Rhodobacter sphaeroides

<400> SEQUENCE: 58

Met Arg Pro Val Leu Tyr Val Leu Thr Phe Leu Ala Val Met Gly Leu
1               5                   10                  15

Ala Phe Trp Ala Tyr Arg Glu Asn Tyr Ala Thr Gln Gln Ala Leu Lys
            20                  25                  30

Asp Val Ser Ala Leu Asn Arg Glu Ile Ala Thr Leu Arg Glu Ser Leu
        35                  40                  45

Ser Val Gln Arg Ala Glu Trp Ala Tyr Leu Asn Arg Pro Asp Arg Leu
    50                  55                  60

Arg Glu Leu Ala Ala Leu Asn Phe Asp Arg Leu Gly Leu Leu Pro Leu
65                  70                  75                  80

Glu Ala Val Gln Phe Gly Ser Ala Ala Gln Val Ser Tyr Pro Pro Asp
                85                  90                  95

Pro Leu Gln Val Val Thr Pro Gln Asp Leu Arg Pro Gly Asp Ile Ser
            100                 105                 110

Gly Glu Val Gly Glu Pro Leu
        115

<210> SEQ ID NO 59
<211> LENGTH: 1794
<212> TYPE: DNA
<213> ORGANISM: Rhodobacter sphaeroides

<400> SEQUENCE: 59
gtgatccgca cgccgctgcg tcccctcgcc cggatcctcg acgcccgcgc caagggcgag      60
aatcccgatt ccatcgagcg cgagaaccgc cgcatccgcc acgaggcgat gcgcgacaag    120

```
gcgcgcaacc gcgccgaggg ccggctcctg ctgctcggcc tcagcttctt cctcgccttc    180
tccgtcattg gggcgcgcat ggggcttctg gcctcgaccc agcccatgga gccgcgcgcg    240
gcggcgagcg gggccgagat cctgaaccag cgggccgaca ttaccgaccg ctcgggccgg    300
atcctcgcca cgaacctgct gacccattcg ctctacgccc atccgcagga catggtggat    360
ccctccgggt cgcccgcga gctggcggcg atcttccccg aactgaagga gaggatctc     420 gccaagcgct tcaccgacgg ccgccgcttc tctggatcc gcaagaagct ctcgcccgag    480
cagatgcagc aggtgcatga catcggcgac ccgggcctgc tcttcggccc gcgcgagatg    540
cgcctctatc ccaacggccg gctggcggcc catgtgctcg gcggcaccag cttcggcgcc    600
gagggcgtcc attcggcgga agtgatcggc acggccggca tcgagaaggc gctcgacacg    660
cggctgcgcg atccgcggc ggccggagag ccgctgcagc tctccatcga cctgaccgtg    720
caggcggcca tcaccgaggt tctcggcgcc ggcatgaaga tgatgaacgc caagggcgcg    780
acggcgatcc tgatggaggc gcacagcggc gagatcctcg cgctcgcctc gctgcccgac    840
ttcgatccga cgaccgtcc ggcgcccctc gtcgatcgca cgccgatcc cggcgacagc     900 ccgctcttca accgcgcggt gcagggcgtc tacgaactcg gctcgacctt caagatcttc    960
accgtggctc aggcgatgga gctgggcctc gtgaatgcgc agaccatcgt cgatgccaat   1020
gcgccgatgc gctggggccg gttcctcatc aaggaattca agaaccacaa ttacggcccg   1080
ctcctctcgg tcaccgacgt catcgtgaaa agctcgaacg tgggtgtggc gcggctcgcg   1140
ctccagatcg gggggctgcg ccagcaggcc ttcctgaaat cgctgggctt cttcgatccg   1200
accccggtcg agctggtcga ggcaccctat gcccgcccgc tcgtccccgc gaaatgggcc   1260
gagatcacca cgatcaccac ctcctacggc cacgggctcg ccgcgagccc gctgcatctg   1320
gccgcggcct acggcacgat cgcgaacggc ggcatcaccg tgaaacccac gctccttcat   1380
gggaacgacc gtccgcaggg cgcgcgcgcc atgcgggccg aggtcgcgca cgattcgctc   1440
gcgatgctgc ggcaggtggt gacgcgcggc acggcctcct acggcgacgt cgagggttac   1500
gaggtggcgg gcaagaccgg caccgccgac aagcccaacc cgcgcggcgg ctattatcac   1560
gacaaggtgg tgaacaccct tcgcctccatc ttccccgcct cggaccgcgc ctatgtgctg   1620
atcgtcacgc tcgacgagcc ggtcgagacc tcgggtcccc agccgcgccg gacggccggc   1680
tacaccgccg tccccgtggc cgccgagatc atccgtcgca cggcgccgct cctcggcctg   1740
cgccccaagg ttgaagcccc acccgtggat cggataacag cggtgcgcaa ctga         1794
```

<210> SEQ ID NO 60
<211> LENGTH: 597
<212> TYPE: PRT
<213> ORGANISM: Rhodobacter sphaeroides

<400> SEQUENCE: 60

Met Ile Arg Thr Pro Leu Arg Pro Leu Ala Arg Ile Leu Asp Ala Arg
1               5                   10                  15

Ala Lys Gly Glu Asn Pro Asp Ser Ile Glu Arg Glu Asn Arg Arg Ile
                20                  25                  30

Arg His Glu Ala Met Arg Asp Lys Ala Arg Asn Arg Ala Glu Gly Arg
            35                  40                  45

Leu Leu Leu Leu Gly Leu Ser Phe Phe Leu Ala Phe Ser Val Ile Gly
        50                  55                  60

Ala Arg Met Gly Leu Leu Ala Ser Thr Gln Pro Met Glu Pro Arg Ala
65                  70                  75                  80

```
Ala Ala Ser Gly Ala Glu Ile Leu Asn Gln Arg Ala Asp Ile Thr Asp
            85                  90                  95

Arg Ser Gly Arg Ile Leu Ala Thr Asn Leu Leu Thr His Ser Leu Tyr
        100                 105                 110

Ala His Pro Gln Asp Met Val Asp Pro Leu Arg Val Ala Arg Glu Leu
        115                 120                 125

Ala Ala Ile Phe Pro Glu Leu Lys Glu Glu Asp Leu Ala Lys Arg Phe
    130                 135                 140

Thr Asp Gly Arg Arg Phe Leu Trp Ile Arg Lys Lys Leu Ser Pro Glu
145                 150                 155                 160

Gln Met Gln Gln Val His Asp Ile Gly Asp Pro Gly Leu Leu Phe Gly
                165                 170                 175

Pro Arg Glu Met Arg Leu Tyr Pro Asn Gly Arg Leu Ala Ala His Val
            180                 185                 190

Leu Gly Gly Thr Ser Phe Gly Ala Glu Gly Val His Ser Ala Glu Val
        195                 200                 205

Ile Gly Thr Ala Gly Ile Glu Lys Ala Leu Asp Thr Arg Leu Arg Asp
    210                 215                 220

Pro Ala Ala Ala Gly Glu Pro Leu Gln Leu Ser Ile Asp Leu Thr Val
225                 230                 235                 240

Gln Ala Ala Ile Thr Glu Val Leu Gly Ala Gly Met Lys Met Met Asn
                245                 250                 255

Ala Lys Gly Ala Thr Ala Ile Leu Met Glu Ala His Ser Gly Glu Ile
            260                 265                 270

Leu Ala Leu Ala Ser Leu Pro Asp Phe Asp Pro Asn Asp Arg Pro Ala
        275                 280                 285

Pro Leu Val Asp Arg Asn Ala Asp Pro Gly Asp Ser Pro Leu Phe Asn
    290                 295                 300

Arg Ala Val Gln Gly Val Tyr Glu Leu Gly Ser Thr Phe Lys Ile Phe
305                 310                 315                 320

Thr Val Ala Gln Ala Met Glu Leu Gly Leu Val Asn Ala Gln Thr Ile
                325                 330                 335

Val Asp Ala Asn Ala Pro Met Arg Trp Gly Arg Phe Leu Ile Lys Glu
            340                 345                 350

Phe Lys Asn His Asn Tyr Gly Pro Leu Leu Ser Val Thr Asp Val Ile
        355                 360                 365

Val Lys Ser Ser Asn Val Gly Val Ala Arg Leu Ala Leu Gln Ile Gly
    370                 375                 380

Gly Leu Arg Gln Gln Ala Phe Leu Lys Ser Leu Gly Phe Phe Asp Pro
385                 390                 395                 400

Thr Pro Val Glu Leu Val Glu Ala Pro Tyr Ala Arg Pro Leu Val Pro
                405                 410                 415

Ala Lys Trp Ala Glu Ile Thr Thr Ile Thr Thr Ser Tyr Gly His Gly
            420                 425                 430

Leu Ala Ala Ser Pro Leu His Leu Ala Ala Ala Tyr Gly Thr Ile Ala
        435                 440                 445

Asn Gly Gly Ile Thr Val Lys Pro Thr Leu His Gly Asn Asp Arg
    450                 455                 460

Pro Gln Gly Ala Arg Ala Met Arg Ala Glu Val Ala His Asp Ser Leu
465                 470                 475                 480

Ala Met Leu Arg Gln Val Val Thr Arg Gly Thr Ala Ser Tyr Gly Asp
                485                 490                 495
```

```
Val Glu Gly Tyr Glu Val Ala Gly Lys Thr Gly Thr Ala Asp Lys Pro
            500                 505                 510

Asn Pro Arg Gly Gly Tyr Tyr His Asp Lys Val Val Asn Thr Phe Ala
        515                 520                 525

Ser Ile Phe Pro Ala Ser Asp Pro Arg Tyr Val Leu Ile Val Thr Leu
    530                 535                 540

Asp Glu Pro Val Glu Thr Ser Gly Pro Gln Pro Arg Arg Thr Ala Gly
545                 550                 555                 560

Tyr Thr Ala Val Pro Val Ala Ala Glu Ile Ile Arg Arg Thr Ala Pro
                565                 570                 575

Leu Leu Gly Leu Arg Pro Lys Val Glu Ala Pro Pro Val Asp Arg Ile
            580                 585                 590

Thr Ala Val Arg Asn
        595

<210> SEQ ID NO 61
<211> LENGTH: 1488
<212> TYPE: DNA
<213> ORGANISM: Rhodobacter sphaeroides

<400> SEQUENCE: 61
atggcggatc gcgcagcaac actctcggcg ctcgggctca cgcccgcagg cggccgcgga      60
ggcgacatcg ccgtgaccgg cctcgcggtt gacagccggc aagtgcgccc ggcacccctc     120
ttcgcggcgc tgcccggctc ccgcagccac ggcgcgagct tcgtgccggc ggcgctcgcc     180
gcaggcgcca ccgcgatcct caccgatgcc gccggcgcgg cgctcgcgcg cgaggcgctc     240
gcgggctcgg gcgcggccct cgtcctggcc gaggatcccc gccagaccct cgccggcgcg     300
gccgccctct ggttcggccg ccagcccgcg accgtggtcg ccgtaacggg caccaacggc     360
aagacctcgg tcgcgacctt caccgccag atctgggcgg ccctcggcca tgccgcgatc     420
aacatcggca cgaccggcgt cgagggcgcc ttcgcagccc cctccgccca taccacgccc     480
gagcccatca ccctccaccg gctcctcgcc gaggcggccg aggcgggcgt cacccatgcc     540
gccatggagg cctcctccca cgggctcgag cagcgccgcc tcgacggcgt gcatctcgcg     600
gccgcgggct tcaccaactt cacccaggac catctcgact atcacgagac cttcgaggcc     660
tatttcgccg ccaaggccgg gctcttcacc cgggtcttgc ccgacgaggg cacggcggtc     720
gtcaatctcg acgatccccg cggccccgag atcgcggccc tcgcgcgggc gcgcgcgcaa     780
cgggtgatcg gcacgggctt tcacgccgat gcggacctgc gccttctctc gcagcgcttc     840
gacgcgaccg gcaggaccct ccgcttctcc tggcagggcg aggtgcatct cgcgcgtctg     900
ccgctgatcg gcggcttcca ggcctggaac gtcgcggtcg cggccagcct cgccatcggc     960
gcgggcgacg cccccgagcg ggtcttcgcc accttctccc ggcttcaggg cgtgcgcggg    1020
cggatgcagc tcgccgccac ccgcaagaac ggtgcctcgg tcttcgtcga ttatgcccat    1080
acgcccgacg ccctcgccac cgccctcaag gcgctgcgcc gcatgtgat gggcgcatc     1140 gtcgtcgtct tcggtgccgg cggcgaccgc gaccgcggca agcgcccgct gatgggccgc    1200
gccgcggcag accatgccga cgtgctctat gtcaccgacg acaatccccg caccgaggat    1260
cccgccgcca tccgccgcgc catcctcgag gcctgccccg aggcgcatga ggtgggcgac    1320
cgggccgagg ccatcctgcg cggcgtcgat gcgctcacgc cgggcgacgc gctcctcatc    1380
gcgggcaagg ccacgaatc gggccaggtg gtgggcaccg acatcttccc cttcgacgat    1440
gccgaacagg cgagcatcgc caccgccgcg ctggacgggc tgatatga                1488
```

<210> SEQ ID NO 62
<211> LENGTH: 495
<212> TYPE: PRT
<213> ORGANISM: Rhodobacter sphaeroides

<400> SEQUENCE: 62

```
Met Ala Asp Arg Ala Ala Thr Leu Ser Ala Leu Gly Leu Thr Pro Ala
1               5                   10                  15

Gly Gly Arg Gly Gly Asp Ile Ala Val Thr Gly Leu Ala Val Asp Ser
            20                  25                  30

Arg Gln Val Arg Pro Gly Thr Leu Phe Ala Ala Leu Pro Gly Ser Arg
        35                  40                  45

Ser His Gly Ala Ser Phe Val Pro Ala Ala Leu Ala Ala Gly Ala Thr
    50                  55                  60

Ala Ile Leu Thr Asp Ala Ala Gly Ala Ala Leu Ala Arg Glu Ala Leu
65                  70                  75                  80

Ala Gly Ser Gly Ala Ala Leu Val Leu Ala Glu Asp Pro Arg Gln Thr
                85                  90                  95

Leu Ala Gly Ala Ala Ala Leu Trp Phe Gly Arg Gln Pro Ala Thr Val
            100                 105                 110

Val Ala Val Thr Gly Thr Asn Gly Lys Thr Ser Val Ala Thr Phe Thr
        115                 120                 125

Arg Gln Ile Trp Ala Ala Leu Gly His Ala Ala Ile Asn Ile Gly Thr
    130                 135                 140

Thr Gly Val Glu Gly Ala Phe Ala Ala Pro Ser Ala His Thr Thr Pro
145                 150                 155                 160

Glu Pro Ile Thr Leu His Arg Leu Leu Ala Glu Ala Ala Glu Ala Gly
                165                 170                 175

Val Thr His Ala Ala Met Glu Ala Ser Ser His Gly Leu Glu Gln Arg
            180                 185                 190

Arg Leu Asp Gly Val His Leu Ala Ala Ala Gly Phe Thr Asn Phe Thr
        195                 200                 205

Gln Asp His Leu Asp Tyr His Glu Thr Phe Glu Ala Tyr Phe Ala Ala
    210                 215                 220

Lys Ala Gly Leu Phe Thr Arg Val Leu Pro Asp Glu Gly Thr Ala Val
225                 230                 235                 240

Val Asn Leu Asp Asp Pro Arg Gly Pro Glu Ile Ala Ala Leu Ala Arg
                245                 250                 255

Ala Arg Ala Gln Arg Val Ile Gly Thr Gly Phe His Ala Asp Ala Asp
            260                 265                 270

Leu Arg Leu Leu Ser Gln Arg Phe Asp Ala Thr Gly Gln Asp Leu Arg
        275                 280                 285

Phe Ser Trp Gln Gly Glu Val His Leu Ala Arg Leu Pro Leu Ile Gly
    290                 295                 300

Gly Phe Gln Ala Trp Asn Val Ala Val Ala Ala Ser Leu Ala Ile Gly
305                 310                 315                 320

Ala Gly Asp Ala Pro Glu Arg Val Phe Ala Thr Phe Ser Arg Leu Gln
                325                 330                 335

Gly Val Arg Gly Arg Met Gln Leu Ala Ala Thr Arg Lys Asn Gly Ala
            340                 345                 350

Ser Val Phe Val Asp Tyr Ala His Thr Pro Asp Ala Leu Ala Thr Ala
        355                 360                 365

Leu Lys Ala Leu Arg Pro His Val Met Gly Arg Ile Val Val Val Phe
    370                 375                 380
```

```
Gly Ala Gly Gly Asp Arg Asp Arg Gly Lys Arg Pro Leu Met Gly Arg
385                 390                 395                 400

Ala Ala Ala Asp His Ala Asp Val Leu Tyr Val Thr Asp Asp Asn Pro
            405                 410                 415

Arg Thr Glu Asp Pro Ala Ala Ile Arg Arg Ala Ile Leu Glu Ala Cys
        420                 425                 430

Pro Glu Ala His Glu Val Gly Asp Arg Ala Glu Ala Ile Leu Arg Gly
    435                 440                 445

Val Asp Ala Leu Thr Pro Gly Asp Ala Leu Leu Ile Ala Gly Lys Gly
450                 455                 460

His Glu Ser Gly Gln Val Val Gly Thr Asp Ile Phe Pro Phe Asp Asp
465                 470                 475                 480

Ala Glu Gln Ala Ser Ile Ala Thr Ala Ala Leu Asp Gly Leu Ile
                485                 490                 495
```

<210> SEQ ID NO 63
<211> LENGTH: 1434
<212> TYPE: DNA
<213> ORGANISM: Rhodobacter sphaeroides

<400> SEQUENCE: 63

```
atgaccccc tctggacctc cgacgaggcc gccgccacga cgggcggccg cgccacccgc    60
gccttcgccg ccacaggcgt ctcgatcgac acccgcagcc tcgggccggg cgacctcttc   120
gtggcgctca ccgaccagcg cgacggccac gccttcgtgg ccgaggcgct ggcccgtggc   180
gccgccgcgg cgctggtctc cgccgcccg gaaggcctcc ccgaggatgc gccgctcctt   240
ctcgtgcccg atgtgctgga agggctccgc gcgctcggcc gcgcggcccg cgcccggacc   300
cgcgcccgc tcgtgggcgt gacgggctcg gtcggcaaga cctcgaccaa ggagatgctg   360
cgcgccacgc tcggcgggca gggcaccgtc catgccgccg aggcctccta caacaaccac   420
tggggcgtgc cgctcacgct ggcgcggatg cccgccgacg tggatttcgc cgtcgtcgag   480
atcggcatga accatccggg cgagatcgcc ccgctgtcgc gcctcgcccg ccgcatctg    540
gccctcatca ccaccgtggc cgcggcccat ctcgaggcct tcgacagcct ctccgccatc   600
gccgaggaga aggccgcgat cctcgagggg ctcgagccgg ccgggcgcgc gatcttgccc   660
gccgggctcg aggtgtcgcc ggtgctcgca gcccgcgccg cggcgctggg cgtgccggcc   720
gtgaccttcg ccagacggc cgacgccgac tggcgcctcg ccgacatcca gatcaccccc   780
gaggccaccg tcgcgcgggc gagccatgcc ggcggaacct tcctcttcaa ggtgctgacg   840
ccgggccggc atttcgcctc gaacgcgctc gccactctgg ccgcggccga ggcgctcggg   900
ctcgatctca ccatcgccgc ctgcgacttg gtctctgga cgccgccctc gggccgcggc   960
acgcgcgagc gcatcgcgct cgacccggtg acgaggcag gcttcgacct gatcgacgat   1020
gccttcaacg ccaatcccgc ctcgatggcg gcgagcctcg agcttctggc cgcgatggcg   1080
cccaccgacg gggtcgggcg gatcgccgcc ggccgccgga tcgccatcct cggcgacatg   1140
ctcgaactcg ggcccaccga ggcagagctg catcgtgcgg tggccgacca tcccgccctg   1200
gccgagatcg ccctcgttca ctgccgtggc cccggatgc gggcgctcca cgaggcgctg   1260
ccgcgccgcc agcgcggcga atgggtcgag accgcggccg agctcgtgcc gcgggcccgt   1320
ctgctcgtcg atgcgggcga catcgtgctg gtgaagggct cgaaagggat caaggtcagc   1380
ctggtggttg acgcgctccg caaactgggc cagtcgagcc catccaggac ctga          1434
```

```
<210> SEQ ID NO 64
<211> LENGTH: 477
<212> TYPE: PRT
<213> ORGANISM: Rhodobacter sphaeroides

<400> SEQUENCE: 64

Met Thr Pro Leu Trp Thr Ser Asp Glu Ala Ala Thr Thr Gly Gly
1               5                   10                  15

Arg Ala Thr Arg Ala Phe Ala Ala Thr Gly Val Ser Ile Asp Thr Arg
                20                  25                  30

Ser Leu Gly Pro Gly Asp Leu Phe Val Ala Leu Thr Asp Gln Arg Asp
                35                  40                  45

Gly His Ala Phe Val Ala Glu Ala Leu Ala Arg Gly Ala Ala Ala
    50                  55                  60

Leu Val Ser Arg Arg Pro Glu Gly Leu Pro Glu Asp Ala Pro Leu Leu
65                  70                  75                  80

Leu Val Pro Asp Val Leu Glu Gly Leu Arg Ala Leu Gly Arg Ala Ala
                85                  90                  95

Arg Ala Arg Thr Arg Ala Arg Val Val Gly Val Thr Gly Ser Val Gly
                100                 105                 110

Lys Thr Ser Thr Lys Glu Met Leu Arg Ala Thr Leu Gly Gly Gln Gly
            115                 120                 125

Thr Val His Ala Ala Glu Ala Ser Tyr Asn Asn His Trp Gly Val Pro
    130                 135                 140

Leu Thr Leu Ala Arg Met Pro Ala Asp Val Asp Phe Ala Val Val Glu
145                 150                 155                 160

Ile Gly Met Asn His Pro Gly Glu Ile Ala Pro Leu Ser Arg Leu Ala
                165                 170                 175

Arg Pro His Leu Ala Leu Ile Thr Thr Val Ala Ala His Leu Glu
            180                 185                 190

Ala Phe Asp Ser Leu Ser Ala Ile Ala Glu Glu Lys Ala Ala Ile Leu
                195                 200                 205

Glu Gly Leu Glu Pro Ala Gly Arg Ala Ile Leu Pro Ala Gly Leu Glu
210                 215                 220

Val Ser Pro Val Leu Ala Ala Arg Ala Ala Ala Leu Gly Val Pro Ala
225                 230                 235                 240

Val Thr Phe Gly Gln Thr Ala Asp Ala Asp Trp Arg Leu Ala Asp Ile
                245                 250                 255

Gln Ile Thr Pro Glu Ala Thr Val Ala Arg Ala Ser His Ala Gly Gly
            260                 265                 270

Thr Phe Leu Phe Lys Val Leu Thr Pro Gly Arg His Phe Ala Ser Asn
        275                 280                 285

Ala Leu Ala Thr Leu Ala Ala Ala Glu Ala Leu Gly Leu Asp Leu Thr
    290                 295                 300

Ile Ala Ala Cys Asp Leu Gly Leu Trp Thr Pro Pro Ser Gly Arg Gly
305                 310                 315                 320

Thr Arg Glu Arg Ile Ala Leu Asp Pro Val Asp Glu Ala Gly Phe Asp
                325                 330                 335

Leu Ile Asp Asp Ala Phe Asn Ala Asn Pro Ala Ser Met Ala Ala Ser
            340                 345                 350

Leu Glu Leu Leu Ala Ala Met Ala Pro Thr Asp Gly Val Gly Arg Ile
        355                 360                 365

Ala Ala Gly Arg Arg Ile Ala Ile Leu Gly Asp Met Leu Glu Leu Gly
    370                 375                 380
```

```
Pro Thr Glu Ala Glu Leu His Arg Ala Val Ala Asp His Pro Ala Leu
385                 390                 395                 400

Ala Glu Ile Ala Leu Val His Cys Val Gly Pro Arg Met Arg Ala Leu
            405                 410                 415

His Glu Ala Leu Pro Arg Arg Gln Arg Gly Glu Trp Val Glu Thr Ala
        420                 425                 430

Ala Glu Leu Val Pro Arg Ala Arg Leu Leu Val Asp Ala Gly Asp Ile
    435                 440                 445

Val Leu Val Lys Gly Ser Lys Gly Ile Lys Val Ser Leu Val Val Asp
    450                 455                 460

Ala Leu Arg Lys Leu Gly Gln Ser Ser Pro Ser Arg Thr
465                 470                 475

<210> SEQ ID NO 65
<211> LENGTH: 1083
<212> TYPE: DNA
<213> ORGANISM: Rhodobacter sphaeroides

<400> SEQUENCE: 65
atgctgtatc tcctgaccgc cttctccgac ggcggcgaca ttttcaacct cttccgctac      60
ctgaccttcc gggccggagc cgccttcttc accgcgctga tcttcggctt cctcttcggc     120
cgcccgctga tcgacttcct gcgccgcaag cagggcaagg ccagccgat ccgggacgac     180
gggccgacca cccacttcgc caaggcgggc acccccacca tgggcggcct tctgatcctc     240
tcggcacttg tggtctcgac cctcctctgg gcgcggctcg acaatcctta cgtctggatc     300
gtcctcctcg tgaccgtggc cttcggcctg atcggcttcg ccgacgacta tgccaaggtg     360
aagaagcaga acaccaaggg cgtgccgggc cgggtgcgtt tcctgatcgg gctcctgatc     420
gccgcgctcg cggccatcgc ggccgcctgg tcgcatccgc cggatctgac gctccagctc     480
gccatgccct tcttcaagga tgcgctcatc aatctcggct ggttcttcgt gcccttcgcc     540
atggtggtga tcgtgggcgc ggccaatgcg gtgaacctca ccgacgggct cgacgggctg     600
gccatcatgc cggtgatgat cgcgggcacc accctcggcg tgatcgccta tgtcgtcggc     660
aacttcaatc tgaccgacta tctgggcgtc catttcgtcc ccggcacggg cgagcttctg     720
atcttcagct ccgcgctcgt ggggggcggg ctgggctttc tgtggtacaa cgcgccccg      780
gccgcggtct tcatgggcga cacgggctcg ctcgccctgg gcggcgcgct cggcgccatc     840
gcggtctgca ccaagcacga gatcgtgctc gcgatcgtgg gcggcctctt cgtcaccgag     900
gcgctctcgg tcatcatcca ggttctctat ttcaagcgca ccgggcggcg ggtgttcctg     960
atggcgccga tccaccacca tttcgagaag aagggctggg ccgagccgca gatcgtgatc    1020
cgcttctgga tcatctcgct gatcctcgcc ctgatcggcc tctcgaccct caagctgcgc    1080
tga                                                                 1083

<210> SEQ ID NO 66
<211> LENGTH: 360
<212> TYPE: PRT
<213> ORGANISM: Rhodobacter sphaeroides

<400> SEQUENCE: 66

Met Leu Tyr Leu Leu Thr Ala Phe Ser Asp Gly Gly Asp Ile Phe Asn
1               5                   10                  15

Leu Phe Arg Tyr Leu Thr Phe Arg Ala Gly Ala Ala Phe Phe Thr Ala
            20                  25                  30

Leu Ile Phe Gly Phe Leu Phe Gly Arg Pro Leu Ile Asp Phe Leu Arg
```

```
            35                  40                  45
Arg Lys Gln Gly Lys Gly Gln Pro Ile Arg Asp Asp Gly Pro Thr Thr
 50                  55                  60

His Phe Ala Lys Ala Gly Thr Pro Thr Met Gly Gly Leu Leu Ile Leu
 65                  70                  75                  80

Ser Ala Leu Val Val Ser Thr Leu Leu Trp Ala Arg Leu Asp Asn Pro
                 85                  90                  95

Tyr Val Trp Ile Val Leu Leu Val Thr Val Ala Phe Gly Leu Ile Gly
                100                 105                 110

Phe Ala Asp Asp Tyr Ala Lys Val Lys Lys Gln Asn Thr Lys Gly Val
            115                 120                 125

Pro Gly Arg Val Arg Phe Leu Ile Gly Leu Leu Ile Ala Ala Leu Ala
130                 135                 140

Ala Ile Ala Ala Ala Trp Ser His Pro Pro Asp Leu Thr Leu Gln Leu
145                 150                 155                 160

Ala Met Pro Phe Phe Lys Asp Ala Leu Ile Asn Leu Gly Trp Phe Phe
                165                 170                 175

Val Pro Phe Ala Met Val Val Ile Val Gly Ala Ala Asn Ala Val Asn
                180                 185                 190

Leu Thr Asp Gly Leu Asp Gly Leu Ala Ile Met Pro Val Met Ile Ala
            195                 200                 205

Gly Thr Thr Leu Gly Val Ile Ala Tyr Val Val Gly Asn Phe Asn Leu
210                 215                 220

Thr Asp Tyr Leu Gly Val His Phe Val Pro Gly Thr Gly Glu Leu Leu
225                 230                 235                 240

Ile Phe Ser Ser Ala Leu Val Gly Gly Leu Gly Phe Leu Trp Tyr
                245                 250                 255

Asn Ala Pro Pro Ala Ala Val Phe Met Gly Asp Thr Gly Ser Leu Ala
                260                 265                 270

Leu Gly Gly Ala Leu Gly Ala Ile Ala Val Cys Thr Lys His Glu Ile
            275                 280                 285

Val Leu Ala Ile Val Gly Gly Leu Phe Val Thr Glu Ala Leu Ser Val
290                 295                 300

Ile Ile Gln Val Leu Tyr Phe Lys Arg Thr Gly Arg Arg Val Phe Leu
305                 310                 315                 320

Met Ala Pro Ile His His His Phe Glu Lys Lys Gly Trp Ala Glu Pro
                325                 330                 335

Gln Ile Val Ile Arg Phe Trp Ile Ile Ser Leu Ile Leu Ala Leu Ile
            340                 345                 350

Gly Leu Ser Thr Leu Lys Leu Arg
            355                 360

<210> SEQ ID NO 67
<211> LENGTH: 924
<212> TYPE: DNA
<213> ORGANISM: Rhodobacter sphaeroides

<400> SEQUENCE: 67
atggcgggac agtccggcag gacgttcccc agggttgctg tgctgatggg cggggcctcg     60
accgagcgcg aggtgtcgct gtcgtcgggc cattcgtgca gcgcagccct gcgggacgca    120
ggctatgagg tgacggaggt cgatgccggc cccgacctcg cccgcgtgct ggcggagctt    180
tctcccgatg cggtcttcaa cgcgctccac ggcgctgggg cgaggatggc tgccgtgcag    240
ggcctgctcg agtggctgcg cattccctac acccattccg gggtgctggc ctcggcgctg    300
```

```
gccatggaca aggcccgcgc gaaggaggtc ttcgccgcgg ccgggctgcc cgtgacccag    360
agcgtgctcg ccacgcccga ggaggtacgg gcgcgccaca tcctgccgcc gccctatgtg    420
gtcaagccca atgccgaggg ctcttcggta ggcgtctata tcgtgcacga ggatgccaac    480
ggtccgccgc agctcgcggc cgacatgccg caagacctga tggtcgagac ctatgtcccc    540
ggccgcgaac tcaccgtcac cgtgatgggc gaccgggtgc tcgcggtcac cgatatcctg    600
tccgacggct ggtacgatta cgacgccaaa taccgtcccg gcggctcgcg tcatatcgtg    660
cctgcggacc tgccggccga gatcaccgag gcctgccacg acatcgcact ccgtgcccac    720
cgcgcgctcg gttccgcgg catctcgcgc tcggacctgc gctgggacga agcgcgcggg    780 ttggcgggc tgatcctcct tgagaccaac actcagccgg gcatgacccc cacctcgctc    840
tcgcccgagc aggcggcgca ttgcggctat tccttccccg agttctgcgc ctggttggtg    900
gaggacgcct catgcagtcg ctga                                          924
```

<210> SEQ ID NO 68
<211> LENGTH: 307
<212> TYPE: PRT
<213> ORGANISM: Rhodobacter sphaeroides

<400> SEQUENCE: 68

```
Met Ala Gly Gln Ser Gly Arg Thr Phe Pro Arg Val Ala Val Leu Met
1               5                   10                  15

Gly Gly Ala Ser Thr Glu Arg Glu Val Ser Leu Ser Ser Gly His Ser
            20                  25                  30

Cys Ser Ala Ala Leu Arg Asp Ala Gly Tyr Glu Val Thr Glu Val Asp
        35                  40                  45

Ala Gly Pro Asp Leu Ala Arg Val Leu Ala Glu Leu Ser Pro Asp Ala
    50                  55                  60

Val Phe Asn Ala Leu His Gly Arg Trp Gly Glu Asp Gly Cys Val Gln
65                  70                  75                  80

Gly Leu Leu Glu Trp Leu Arg Ile Pro Tyr Thr His Ser Gly Val Leu
                85                  90                  95

Ala Ser Ala Leu Ala Met Asp Lys Ala Arg Ala Lys Glu Val Phe Ala
            100                 105                 110

Ala Ala Gly Leu Pro Val Thr Gln Ser Val Leu Ala Thr Pro Glu Glu
        115                 120                 125

Val Arg Ala Arg His Ile Leu Pro Pro Tyr Val Val Lys Pro Asn
    130                 135                 140

Ala Glu Gly Ser Ser Val Gly Val Tyr Ile Val His Glu Asp Ala Asn
145                 150                 155                 160

Gly Pro Pro Gln Leu Ala Ala Asp Met Pro Gln Asp Leu Met Val Glu
                165                 170                 175

Thr Tyr Val Pro Gly Arg Glu Leu Thr Val Thr Val Met Gly Asp Arg
            180                 185                 190

Val Leu Ala Val Thr Asp Ile Leu Ser Asp Gly Trp Tyr Asp Tyr Asp
        195                 200                 205

Ala Lys Tyr Arg Pro Gly Gly Ser Arg His Ile Val Pro Ala Asp Leu
    210                 215                 220

Pro Ala Glu Ile Thr Glu Ala Cys His Asp Ile Ala Leu Arg Ala His
225                 230                 235                 240

Arg Ala Leu Gly Cys Arg Gly Ile Ser Arg Ser Asp Leu Arg Trp Asp
                245                 250                 255
```

Glu Ala Arg Gly Leu Ala Gly Leu Ile Leu Leu Glu Thr Asn Thr Gln
            260                 265                 270

Pro Gly Met Thr Pro Thr Ser Leu Ser Pro Glu Gln Ala Ala His Cys
        275                 280                 285

Gly Tyr Ser Phe Pro Glu Phe Cys Ala Trp Leu Val Glu Asp Ala Ser
        290                 295                 300

Cys Ser Arg
305

<210> SEQ ID NO 69
<211> LENGTH: 927
<212> TYPE: DNA
<213> ORGANISM: Rhodobacter sphaeroides

<400> SEQUENCE: 69

```
atgcagtcgc tgagcttccc gccgaaccgc cgcaccccc ggctcgcgcc gccgcgccgc      60
gagaccggcc gccgcgaccc tgcgccctcg cgctgggcct atcgcgcgca gcggctctgg     120
ctcacgccca tgttccgcac ggcgctccgc gtggggctgc cgatcgtggg cgtgctgctg     180
gtggtggcgc tgatcttcgc cagcgccgac cggcgcgccg ccatggcggg cgccttcacc     240
ggcctcgtcg acagcttcca gcaacgcccc gaattcatgg taacgctgct ttcggtcgat     300
ggcgcctcgc cggaactctc agaccggatc cgggccacgc tggcgctgaa gctgccgctc     360
agctcgttcg acatcgacct gaccgccgcc cgcgcccgca tcgagagcat cgacgcggtg     420
gcgcaggccg aggtgcgggt cgctcgggc ggactgctcg aggtgcgcgt gaccgagcgc      480
gaacccgcga tcatctggcg ccggggccgcg aacctcgtgc ttctcgacgg gaccggccgc    540
cgcgtggacg atctcgcctt ccgcagcgag cggggcgatc tggcggtgat cgcgggcgag    600
ggcgccgagc gcgccgtgcc cgaggcgctc gagattctcg ccgccgcccg ccccatcctc    660
gagcggatcc gcgggctcgt gcggatgggc gagcggcgct gggacatcgt gctcgaccgc    720
gggcagcgca ttcagctgcc cgtcgaggaa cccgtggctg ccgtcgagcg gatgatcgcg    780
ctcgacgagg ccgaggacct tctggaccgc gacgtgattt ccgtcgacct gcgcatcaag    840
gaccgtccgg tgctgaggct cgcgccctac gccctgaacg ccgtccgccg cgcgcggggc    900
attgatacaa gtggaagcga cctatga                                       927
```

<210> SEQ ID NO 70
<211> LENGTH: 308
<212> TYPE: PRT
<213> ORGANISM: Rhodobacter sphaeroides

<400> SEQUENCE: 70

Met Gln Ser Leu Ser Phe Pro Pro Asn Arg Arg Thr Pro Arg Leu Ala
1               5                   10                  15

Pro Pro Arg Arg Glu Thr Gly Arg Arg Asp Pro Ala Pro Ser Arg Trp
            20                  25                  30

Ala Tyr Arg Ala Gln Arg Leu Trp Leu Thr Pro Met Phe Arg Thr Ala
        35                  40                  45

Leu Arg Val Gly Leu Pro Ile Val Gly Val Leu Val Val Ala Leu
    50                  55                  60

Ile Phe Ala Ser Ala Asp Arg Arg Ala Ala Met Ala Gly Ala Phe Thr
65                  70                  75                  80

Gly Leu Val Asp Ser Phe Gln Gln Arg Pro Glu Phe Met Val Thr Leu
                85                  90                  95

Leu Ser Val Asp Gly Ala Ser Pro Glu Leu Ser Asp Arg Ile Arg Ala

|   |   |   | 100 |   |   |   | 105 |   |   |   | 110 |   |
|---|---|---|---|---|---|---|---|---|---|---|---|---|

Thr Leu Ala Leu Lys Leu Pro Leu Ser Ser Phe Asp Ile Asp Leu Thr
    115                    120                    125

Ala Ala Arg Ala Arg Ile Glu Ser Ile Asp Ala Val Ala Gln Ala Glu
130                    135                    140

Val Arg Val Arg Ser Gly Gly Leu Leu Glu Val Arg Val Thr Glu Arg
145                    150                    155                    160

Glu Pro Ala Ile Ile Trp Arg Arg Ala Ala Asn Leu Val Leu Leu Asp
                  165                    170                    175

Gly Thr Gly Arg Arg Val Asp Asp Leu Ala Phe Arg Ser Glu Arg Gly
                  180                    185                    190

Asp Leu Ala Val Ile Ala Gly Glu Gly Ala Glu Arg Ala Val Pro Glu
                  195                    200                    205

Ala Leu Glu Ile Leu Ala Ala Ala Arg Pro Ile Leu Glu Arg Ile Arg
                  210                    215                    220

Gly Leu Val Arg Met Gly Glu Arg Arg Trp Asp Ile Val Leu Asp Arg
225                    230                    235                    240

Gly Gln Arg Ile Gln Leu Pro Val Glu Glu Pro Val Ala Ala Val Glu
                  245                    250                    255

Arg Met Ile Ala Leu Asp Glu Ala Glu Asp Leu Leu Asp Arg Asp Val
                  260                    265                    270

Ile Ser Val Asp Leu Arg Ile Lys Asp Arg Pro Val Leu Arg Leu Ala
                  275                    280                    285

Pro Tyr Ala Leu Asn Ala Val Arg Arg Ala Arg Gly Ile Asp Thr Ser
                  290                    295                    300

Gly Ser Asp Leu
305

<210> SEQ ID NO 71
<211> LENGTH: 1335
<212> TYPE: DNA
<213> ORGANISM: Rhodobacter sphaeroides

<400> SEQUENCE: 71

| | | |
|---|---|---|
| atgaccgacc tctatcagtc ccagcgcgcc atgcggaaca tgcgccgcgc cgccatgcag | 60 |
| cggggcgtga tcgcgatcct cgacgtgggc tcttccaaga tcacctgcct gatcctgcgc | 120 |
| ttcgacgggc cggaccggct cgcgcagcat gacggggtgg ggccgatggc cgggcagtcc | 180 |
| tcgttccggg tcatcggggc cgccaccacc cggtcgcgcg gggtgcattt cggcgagatc | 240 |
| tcggtgatga cgagaccga gcgcgcgatc cgcaccgcgg tgcaggcggc gcagaagatg | 300 |
| gccaacgtcc gggtggacca tgtgatcgcc tgtttcgccg gcgccgatcc gcgcagctac | 360 |
| ggcctcgcgg gcgagtggga gctgcaggat cggtcgtga ccgagcagga tgtggcccgc | 420 |
| gtgatggccg cctgcgacgt gcccgacttc ggtcagggcc gcgaggtgct gcacgcccag | 480 |
| ccggtgaact cgccctcga ccaccgcacc gggctcggcg atccgcgggg ccagatcggc | 540 |
| aaccggctgg cggtggacat gcacctgctc accgtcgagg cggacgcgat ccagaacctg | 600 |
| ctctactgca tcaagcgctg cgacctcgaa ctcgcgggga tcgcctcctc ggcctatgtc | 660 |
| tcgggcgtct cgtcgctcgt cgaggacgag caggagctgg gggccgcctg catcgacatg | 720 |
| ggcggcggtg ccacgggcct gtcgatcttc atcaagaagc acatgatctt cgcggattcg | 780 |
| gtgcggatgg gcgcgaccga tgtgacctcg acatttcca agggcctgca ggtgccgctt | 840 |
| gccaccgccg agaagatcaa gacgcggcac ggcggcgtcg tggccaccgg catggacgac | 900 |

```
cgcgagatga tcgacatcgg cgcggacacc ggcgactggg acaaggaccg ccgcaccgtc    960
agccgggccg agctgatcgg catcatgcgt ccgcgcgtcg aggagatcct cgaagaggcg   1020
cgcgcgcgtc tcgatgcggc cggtttcgag catctgccga gccagcagat cgtcatcacc   1080
gggggcggca gccagatccc gggtctcgac ggtctcgcgg cccggatcct cggccagcgg   1140
gtccgtctgg ggcgcccgct cgcgcgttca ggcctgccgc agcaggtctc cgggccgggc   1200
ttctcctcgg ccgtggggct ctgcctcttt gcggcccatc cgcaggacga atggtgggat   1260
ttcgacattc cggcagagcg ctatcccgcc cggtccctgc ggagggccat caaatggttc   1320
aaggacaact ggtaa                                                    1335
```

<210> SEQ ID NO 72
<211> LENGTH: 444
<212> TYPE: PRT
<213> ORGANISM: Rhodobacter sphaeroides

<400> SEQUENCE: 72

```
Met Thr Asp Leu Tyr Gln Ser Gln Arg Ala Met Arg Asn Met Arg Arg
1               5                   10                  15

Ala Ala Met Gln Arg Gly Val Ile Ala Ile Leu Asp Val Gly Ser Ser
            20                  25                  30

Lys Ile Thr Cys Leu Ile Leu Arg Phe Asp Gly Pro Asp Arg Leu Arg
        35                  40                  45

Glu His Asp Gly Val Gly Pro Met Ala Gly Gln Ser Ser Phe Arg Val
    50                  55                  60

Ile Gly Ala Ala Thr Thr Arg Ser Arg Gly Val His Phe Gly Glu Ile
65                  70                  75                  80

Ser Val Met Asn Glu Thr Glu Arg Ala Ile Arg Thr Ala Val Gln Ala
                85                  90                  95

Ala Gln Lys Met Ala Asn Val Arg Val Asp His Val Ile Ala Cys Phe
            100                 105                 110

Ala Gly Ala Asp Pro Arg Ser Tyr Gly Leu Ala Gly Glu Trp Glu Leu
        115                 120                 125

Gln Asp Ser Val Val Thr Glu Gln Asp Val Ala Arg Val Met Ala Ala
    130                 135                 140

Cys Asp Val Pro Asp Phe Gly Gln Gly Arg Glu Val Leu His Ala Gln
145                 150                 155                 160

Pro Val Asn Phe Ala Leu Asp His Arg Thr Gly Leu Gly Asp Pro Arg
                165                 170                 175

Gly Gln Ile Gly Asn Arg Leu Ala Val Asp Met His Leu Leu Thr Val
            180                 185                 190

Glu Ala Asp Ala Ile Gln Asn Leu Leu Tyr Cys Ile Lys Arg Cys Asp
        195                 200                 205

Leu Glu Leu Ala Gly Ile Ala Ser Ser Ala Tyr Val Ser Gly Val Ser
    210                 215                 220

Ser Leu Val Glu Asp Glu Gln Glu Leu Gly Ala Ala Cys Ile Asp Met
225                 230                 235                 240

Gly Gly Gly Ala Thr Gly Leu Ser Ile Phe Ile Lys Lys His Met Ile
                245                 250                 255

Phe Ala Asp Ser Val Arg Met Gly Gly Asp His Val Thr Ser Asp Ile
            260                 265                 270

Ser Lys Gly Leu Gln Val Pro Leu Ala Thr Ala Glu Lys Ile Lys Thr
        275                 280                 285

Arg His Gly Gly Val Val Ala Thr Gly Met Asp Asp Arg Glu Met Ile
```

```
                    290                 295                 300
Asp Ile Gly Ala Asp Thr Gly Asp Trp Asp Lys Asp Arg Arg Thr Val
305                 310                 315                 320

Ser Arg Ala Glu Leu Ile Gly Ile Met Arg Pro Arg Val Glu Glu Ile
                325                 330                 335

Leu Glu Glu Ala Arg Ala Arg Leu Asp Ala Ala Gly Phe Glu His Leu
                340                 345                 350

Pro Ser Gln Gln Ile Val Ile Thr Gly Gly Ser Gln Ile Pro Gly
        355                 360                 365

Leu Asp Gly Leu Ala Ala Arg Ile Leu Gly Gln Arg Val Arg Leu Gly
            370                 375                 380

Arg Pro Leu Arg Val Gln Gly Leu Pro Gln Gln Val Ser Gly Pro Gly
385                 390                 395                 400

Phe Ser Ser Ala Val Gly Leu Cys Leu Phe Ala Ala His Pro Gln Asp
                405                 410                 415

Glu Trp Trp Asp Phe Asp Ile Pro Ala Glu Arg Tyr Pro Ala Arg Ser
            420                 425                 430

Leu Arg Arg Ala Ile Lys Trp Phe Lys Asp Asn Trp
            435                 440

<210> SEQ ID NO 73
<211> LENGTH: 1212
<212> TYPE: DNA
<213> ORGANISM: Rhodobacter sphaeroides

<400> SEQUENCE: 73
atgacggctc tgaccagcac gcgcggccag caggatctgc cgcgctattt ctcgcaggtg      60
ttcgacgtga tgcagggact cgccacggt cggctcgact cgtgctcga cgacgggcgg      120 cgcttccggg tcgaggggca ggggccgggg ccggtcgccg aactcgacat tcatgatgcg    180
gatctcttcg cccgtctgat ccgcgagggc gacctcggct ctgcgaggc ctatctcgac      240 ggcggctggt cgacgccgga cctgcaggcc ttcatggatc tgatccatgc cgacaatgac    300
gatgtctatg acggctttcc cggtcagggg ctgctgcgcg cctacgagaa cctgcgccac    360
tggctgcgcg gcaactcgaa gcggcaggcc cgccgcaaca tcgcggccca ttacgacctc    420
ggcaacgact tctacgccct ctggctcgac gagagcatga cctattcctc ggcgctcttc    480
cggaccgggc aggagagcct cgaggaggcg cagcgggcga aatatgccag catggtcgac    540
cggatcggcg cgcagcccgg cgagcatgtg ctggagatcg gctgcggttg gggcggcttc    600
gccgaatatg cggcgcgcga gcgggggctg cgggtgacgg gcctcaccat cagccaggcg    660
cagcacgatt atgcggtcga gcggatcgcg cgggcgggcc tgtcggaccg ggtcgagatc    720
cggcttcagg actaccgcga cgagcgggc agcttcgacg gcatcgcctc gatcgagatg    780
ttcgaggcgg tgggcgagaa atactggccg gtctatttcc agaccctgcg cgagcggctg    840
aagcccgggc gcaatgccac gctgcagatc atcaccgtgc aggacaagag gtgggaggtc    900
taccggcggg gggtggattt cattcagaag tacatcttcc ccggcgggat gctgccctcg    960
cccaccgcgc tccgggtcga ggtggcgaag gcggggctgc atgtaacgga ctcggtcgag   1020 ttcgcgaga gctattccat gacgctgcgc cgctggcacg agaccttcaa cgaccgctgg   1080
gaccgggtgg cggcgctggg cttcgacgag aggttccgcc gcatgtggaa cttctatctc   1140
acctcttgcg caggctcatt cgacggcgga aactgcgacg tgacgcagat caccgtaacg   1200
cgggccgcgt aa                                                       1212
```

<210> SEQ ID NO 74
<211> LENGTH: 403
<212> TYPE: PRT
<213> ORGANISM: Rhodobacter sphaeroides

<400> SEQUENCE: 74

```
Met Thr Ala Leu Thr Ser Thr Arg Gly Gln Gln Asp Leu Pro Arg Tyr
  1               5                  10                  15

Phe Ser Gln Val Phe Asp Val Met Gln Gly Leu Arg His Gly Arg Leu
             20                  25                  30

Asp Phe Val Leu Asp Asp Gly Arg Arg Phe Arg Val Glu Gly Gln Gly
         35                  40                  45

Pro Gly Pro Val Ala Glu Leu Asp Ile His Asp Ala Asp Leu Phe Ala
 50                  55                  60

Arg Leu Ile Arg Glu Gly Asp Leu Gly Phe Cys Glu Ala Tyr Leu Asp
 65                  70                  75                  80

Gly Gly Trp Ser Thr Pro Asp Leu Gln Ala Phe Met Asp Leu Ile His
                 85                  90                  95

Ala Asp Asn Asp Asp Val Tyr Asp Gly Phe Pro Gly Gln Gly Leu Leu
            100                 105                 110

Arg Ala Tyr Glu Asn Leu Arg His Trp Leu Arg Gly Asn Ser Lys Arg
        115                 120                 125

Gln Ala Arg Arg Asn Ile Ala Ala His Tyr Asp Leu Gly Asn Asp Phe
130                 135                 140

Tyr Ala Leu Trp Leu Asp Glu Ser Met Thr Tyr Ser Ser Ala Leu Phe
145                 150                 155                 160

Arg Thr Gly Gln Glu Ser Leu Glu Glu Ala Gln Arg Ala Lys Tyr Ala
                165                 170                 175

Ser Met Val Asp Arg Ile Gly Ala Gln Pro Gly Glu His Val Leu Glu
            180                 185                 190

Ile Gly Cys Gly Trp Gly Gly Phe Ala Glu Tyr Ala Ala Arg Glu Arg
        195                 200                 205

Gly Leu Arg Val Thr Gly Leu Thr Ile Ser Gln Ala Gln His Asp Tyr
210                 215                 220

Ala Val Glu Arg Ile Ala Arg Ala Gly Leu Ser Asp Arg Val Glu Ile
225                 230                 235                 240

Arg Leu Gln Asp Tyr Arg Asp Glu Arg Gly Ser Phe Asp Gly Ile Ala
                245                 250                 255

Ser Ile Glu Met Phe Glu Ala Val Gly Glu Lys Tyr Trp Pro Val Tyr
            260                 265                 270

Phe Gln Thr Leu Arg Glu Arg Leu Lys Pro Gly Arg Asn Ala Thr Leu
        275                 280                 285

Gln Ile Ile Thr Val Gln Asp Lys Arg Trp Glu Val Tyr Arg Arg Gly
290                 295                 300

Val Asp Phe Ile Gln Lys Tyr Ile Phe Pro Gly Gly Met Leu Pro Ser
305                 310                 315                 320

Pro Thr Ala Leu Arg Val Glu Val Ala Lys Ala Gly Leu His Val Thr
                325                 330                 335

Asp Ser Val Glu Phe Gly Glu Ser Tyr Ser Met Thr Leu Arg Arg Trp
            340                 345                 350

His Glu Thr Phe Asn Asp Arg Trp Asp Arg Val Ala Ala Leu Gly Phe
        355                 360                 365

Asp Glu Arg Phe Arg Arg Met Trp Asn Phe Tyr Leu Thr Ser Cys Ala
370                 375                 380
```

```
Gly Ser Phe Asp Gly Gly Asn Cys Asp Val Thr Gln Ile Thr Val Thr
385                 390                 395                 400

Arg Ala Ala

<210> SEQ ID NO 75
<211> LENGTH: 2202
<212> TYPE: DNA
<213> ORGANISM: Rhodobacter sphaeroides

<400> SEQUENCE: 75
atgaccgatt tcaccagccg gaccgacgcg gacggggtct gcaccatcac ctgggacgtg      60
ccgggcaagt cgatgaacgt catgtcgatg gcgggatttg ccgagctcga cgggctgatc     120
gccgcggcgc tcggcgatcc gtctgtcaag ggcgtgatcc tcacctcggg caagaaggac     180
tttgccgcgg ggatggatct caatgtcatc gcccgcatga aggaggaagg cggcgacgat     240
ccggcccggg ccgtgttcga gggcgtgatg gagatgcatg ccgtcctgcg ccggatcgag     300
cgcgcgggca tggatccgaa gacgctgaag ggggcaagc catcgtggc ggccctgccc       360 ggcaccgccc tgggcctggg gctcgagctg ccgctggcct ccaccgcat catcgcggcc     420 gacaatccca aggccaagat cggcctgccc gagatcatgt ggggatcttc cccggcggc     480 ggcggcacga cgcggctcgt ccgcaggctc ggcgccatga tggcggctcc cctcctcctc     540
gagggcaagc tgaacgatcc caagggcgcc aaggccatgg tgtcgtcga cgaggtggtg     600 ccggccgatc agctgctccc gcgggcgaag gaatgggtgc tcggcgcgaa ggacgcggat     660
ctggtgaagc cgtgggacgc caagggctac aagatgcctg gcgcgcgcc ctaccatccg     720 gcgggcttca tgaccttcgt cggcgcctcg gccatggtga cgggcaagac gatgggcgtc     780
tatccggcgg ccaagggcct gctcgccgcg gtctacgagg gcgcgctcgt gcccttcgac     840
accgcgctga agatcgaggc gcgctggttc acccatgtgc tgatgaatcc ctcctcgtcg     900
gcgatgatcc ggtcgctctt catcaacaag gaggcgctgg agaagggcgc cgtccgccct     960
gccctgcccg accagtcggt ccggaagctg ggcgtgatcg gggcgggcat gatgggcgcg    1020
ggcatcgccc atgtcgcggc caatgcgggc atcgaggtc tgctgatcga cgcgacgcag    1080
gaggcggccg accgcggcaa gtcccattcg gaaggtctcc tcgacaaggg gatgaagcgg    1140
ggcaaggtct cggccgagaa gaaggccgag gtgctgggcc ggatcgccgc caccaccgac    1200
tatgcggccc tctcgggctg cgatctgatc gtcgaggcgg tgttcgagga tcccgcggtg    1260
aaggccgagg tcactcagaa ggtcgaggcc gcggtcgggc ccgactgtat cttcgcaacc    1320
aacacctcga ccctgccgat ctcggggttg gccaaggcga gccgcgatcc ggcgcagttc    1380
atcggcatcc atttcttctc gcccgtggac aagatgatgc tggtcgagat catccgcggc    1440
aaggccaccg gcgaccgcgc cgtggccaag gcgctcgatt tcgtgcgcca gatccgcaag    1500
acgcccatcg tcgtccacga tgcgcgcttc ttctacgcca accgctgcat catcccctac    1560
ctcaacgagg ggatccgcat ggtggccgaa ggcgtggcgc ccgcgctgat cgagaatgcg    1620
gcgaagctgg tggggatgcc gctcggcccc cttcagctgg tggacgaaac ctcgatcgac    1680
ctcggggtga agatcgccaa ggccacgaag gccgccctgg cgaggcccta tccggacgcg    1740
gcggtggatg cggtgatctt cccgctggcg gacgaggggc ggctcggccg caaggcgggc    1800
gcgggcttct atgcctacga cgcgccggc aagcgcgaag gtctctgcc gggcctcgcc     1860 gaccgctggc cgcaggccga ggcgcagccc gagcttgccg aggtgcagca ccggcttctc    1920
ttcgcgcagg tgctcgaggc ggtgcgcgcg ctcgaggagg gcgtgctgac cgacatccgc    1980
```

-continued

```
gagggcgacg tgggcgccat tctcggctgg ggcttcgcgc cctggtcggg cggcccgttc   2040
agctggctcg acatgatcgg cgcgccgcgc gcggtggaga tctgcgaggg gctggccgag   2100
cgtcacggca gccgcttcgc gccgccgaag ctgctggtcg agatggccgg caagggcgag   2160
agcttctacg cccgcttcgc accgcaggcc cgcgcggcct ga                      2202
```

<210> SEQ ID NO 76
<211> LENGTH: 733
<212> TYPE: PRT
<213> ORGANISM: Rhodobacter sphaeroides

<400> SEQUENCE: 76

```
Met Thr Asp Phe Thr Ser Arg Thr Asp Ala Asp Gly Val Cys Thr Ile
1               5                   10                  15

Thr Trp Asp Val Pro Gly Lys Ser Met Asn Val Met Ser Met Ala Gly
            20                  25                  30

Phe Ala Glu Leu Asp Gly Leu Ile Ala Ala Leu Gly Asp Pro Ser
        35                  40                  45

Val Lys Gly Val Ile Leu Thr Ser Gly Lys Lys Asp Phe Ala Ala Gly
    50                  55                  60

Met Asp Leu Asn Val Ile Ala Arg Met Lys Glu Glu Gly Gly Asp Asp
65                  70                  75                  80

Pro Ala Arg Ala Val Phe Glu Gly Val Met Glu Met His Ala Val Leu
                85                  90                  95

Arg Arg Ile Glu Arg Ala Gly Met Asp Pro Lys Thr Leu Lys Gly Gly
            100                 105                 110

Lys Pro Ile Val Ala Ala Leu Pro Gly Thr Ala Leu Gly Leu Gly Leu
        115                 120                 125

Glu Leu Pro Leu Ala Cys His Arg Ile Ile Ala Ala Asp Asn Pro Lys
    130                 135                 140

Ala Lys Ile Gly Leu Pro Glu Ile Met Val Gly Ile Phe Pro Gly Gly
145                 150                 155                 160

Gly Gly Thr Thr Arg Leu Val Arg Arg Leu Gly Ala Met Met Ala Ala
                165                 170                 175

Pro Leu Leu Leu Glu Gly Lys Leu Asn Asp Pro Lys Gly Ala Lys Ala
            180                 185                 190

Met Gly Val Val Asp Glu Val Val Pro Ala Asp Gln Leu Leu Pro Arg
        195                 200                 205

Ala Lys Glu Trp Val Leu Gly Ala Lys Asp Ala Asp Leu Val Lys Pro
    210                 215                 220

Trp Asp Ala Lys Gly Tyr Lys Met Pro Gly Gly Ala Pro Tyr His Pro
225                 230                 235                 240

Ala Gly Phe Met Thr Phe Val Gly Ala Ser Ala Met Val Thr Gly Lys
                245                 250                 255

Thr Met Gly Val Tyr Pro Ala Ala Lys Gly Leu Leu Ala Ala Val Tyr
            260                 265                 270

Glu Gly Ala Leu Val Pro Phe Asp Thr Ala Leu Lys Ile Glu Ala Arg
        275                 280                 285

Trp Phe Thr His Val Leu Met Asn Pro Ser Ser Ala Met Ile Arg
    290                 295                 300

Ser Leu Phe Ile Asn Lys Glu Ala Leu Glu Lys Gly Ala Val Arg Pro
305                 310                 315                 320

Ala Leu Pro Asp Gln Ser Val Arg Lys Leu Gly Val Ile Gly Ala Gly
                325                 330                 335
```

Met Met Gly Ala Gly Ile Ala His Val Ala Ala Asn Ala Gly Ile Glu
         340                 345                 350

Val Val Leu Ile Asp Ala Thr Gln Glu Ala Ala Asp Arg Gly Lys Ser
         355                 360                 365

His Ser Glu Gly Leu Leu Asp Lys Gly Met Lys Arg Gly Lys Val Ser
370                 375                 380

Ala Glu Lys Lys Ala Glu Val Leu Gly Arg Ile Ala Ala Thr Thr Asp
385                 390                 395                 400

Tyr Ala Ala Leu Ser Gly Cys Asp Leu Ile Val Glu Ala Val Phe Glu
                 405                 410                 415

Asp Pro Ala Val Lys Ala Glu Val Thr Gln Lys Val Glu Ala Ala Val
                 420                 425                 430

Gly Pro Asp Cys Ile Phe Ala Thr Asn Thr Ser Thr Leu Pro Ile Ser
                 435                 440                 445

Gly Leu Ala Lys Ala Ser Arg Asp Pro Ala Gln Phe Ile Gly Ile His
         450                 455                 460

Phe Phe Ser Pro Val Asp Lys Met Met Leu Val Glu Ile Ile Arg Gly
465                 470                 475                 480

Lys Ala Thr Gly Asp Arg Ala Val Ala Lys Ala Leu Asp Phe Val Arg
                 485                 490                 495

Gln Ile Arg Lys Thr Pro Ile Val Val His Asp Ala Arg Phe Phe Tyr
                 500                 505                 510

Ala Asn Arg Cys Ile Ile Pro Tyr Leu Asn Glu Gly Ile Arg Met Val
                 515                 520                 525

Ala Glu Gly Val Ala Pro Ala Leu Ile Glu Asn Ala Ala Lys Leu Val
         530                 535                 540

Gly Met Pro Leu Gly Pro Leu Gln Leu Val Asp Glu Thr Ser Ile Asp
545                 550                 555                 560

Leu Gly Val Lys Ile Ala Lys Ala Thr Lys Ala Ala Leu Gly Glu Ala
                 565                 570                 575

Tyr Pro Asp Ala Ala Val Asp Ala Val Ile Phe Pro Leu Ala Asp Glu
                 580                 585                 590

Gly Arg Leu Gly Arg Lys Ala Gly Ala Gly Phe Tyr Ala Tyr Asp Ala
         595                 600                 605

Ala Gly Lys Arg Glu Gly Leu Trp Pro Gly Leu Ala Asp Arg Trp Pro
610                 615                 620

Gln Ala Glu Ala Gln Pro Glu Leu Ala Glu Val Gln His Arg Leu Leu
625                 630                 635                 640

Phe Ala Gln Val Leu Glu Ala Val Arg Ala Leu Glu Glu Gly Val Leu
                 645                 650                 655

Thr Asp Ile Arg Glu Gly Asp Val Gly Ala Ile Leu Gly Trp Gly Phe
                 660                 665                 670

Ala Pro Trp Ser Gly Gly Pro Phe Ser Trp Leu Asp Met Ile Gly Ala
                 675                 680                 685

Pro Arg Ala Val Glu Ile Cys Glu Gly Leu Ala Glu Arg His Gly Ser
         690                 695                 700

Arg Phe Ala Pro Pro Lys Leu Leu Val Glu Met Ala Gly Lys Gly Glu
705                 710                 715                 720

Ser Phe Tyr Ala Arg Phe Ala Pro Gln Ala Arg Ala Ala
                 725                 730

<210> SEQ ID NO 77
<211> LENGTH: 1212

```
<212> TYPE: DNA
<213> ORGANISM: Rhodobacter sphaeroides

<400> SEQUENCE: 77
atgacggaag cctatatcta cgacgccctg cgcaccccgc gcggcaaggg ccggcccgac     60
ggcgcgctgc atgaggtgac ctcggtcgcg ctgtcggcga aggtgctgaa cgcggtcaag    120
gagcgcaacc atctcgacgg cgccgcggtc gaggatgtga tctggggcaa tgccacgcag    180
gtgggcgaac agggcggctg cctcgcgcgc tcggcggtgc tgctctcgga tctcgacgag    240
tcgatccccg gcctctcgat caaccgcttc tgtgcaagcg gatggaggc ggtgaacctc     300
gccgcgaacc aagtgcgcgc cggggcgggc gaggcctata cgcgggcgg cgtcgagatg    360
atgagccgcg tcgccatggg ctcggacggg gcggcggtgg cggcggaccc ttctctcgcc    420
atgaagacct atttcgtgcc gcagggcatc tcggccgaca tcatcgcgac cgctacggc     480
ttcagccgcg acgaggccga tgcgctggcg gtggaaagcc agaagcgcgc cgccgcggcc    540
tgggccgagg ccgcttcgc ccggtcggtc gtgccggtgc gcgaccagaa cggcgtgacg     600
atcctcgagc gcgacgaata tctgcggccc aacaccgaca tgcagtcgct gggcgcgctg    660
aagcccgcct tcaaggagat gggcgaacag atgcccgggct tcgacaagct cgcgctgatg    720
aaatatcccg agctggagcg ggtcgagcat atccaccacg ccggcaattc ctcgggcatc    780
gtggacgggg cggcggccgt gctgatcggc agccgtgcct tcggcgaggc ccatggcctg    840
cgcccgcgcg cgcgcatccg cgccaccgcg aagatcggca ccgaccctac gatcatgctg    900
acgggtccgg tgccggtgac ccagaagatc ctgcgcgagg ccgggatgca gatctcggac    960
atcgatctct tcgaggtgaa cgaggccttc gcggcggtcg tgctgcgctt ccagcaggcc   1020
ttcggcgtgg atcccgcgcg cgtgaacccg aacggcggcg ccatcgccat gggccacccg   1080
ctgggcgcga ccggcgccat catcatcggc acgctcctcg acgaactcga gcgcaccgac   1140
cgctcggtgg cctcgccac gctctgcgtg gcctcgggca tgggcgccgc caccatcatc   1200
gaacgcgtct ga                                                        1212

<210> SEQ ID NO 78
<211> LENGTH: 403
<212> TYPE: PRT
<213> ORGANISM: Rhodobacter sphaeroides

<400> SEQUENCE: 78

Met Thr Glu Ala Tyr Ile Tyr Asp Ala Leu Arg Thr Pro Arg Gly Lys
1               5                   10                  15

Gly Arg Pro Asp Gly Ala Leu His Glu Val Thr Ser Val Ala Leu Ser
            20                  25                  30

Ala Lys Val Leu Asn Ala Val Lys Glu Arg Asn His Leu Asp Gly Ala
        35                  40                  45

Ala Val Glu Asp Val Ile Trp Gly Asn Ala Thr Gln Val Gly Glu Gln
    50                  55                  60

Gly Gly Cys Leu Ala Arg Ser Ala Val Leu Leu Ser Asp Leu Asp Glu
65                  70                  75                  80

Ser Ile Pro Gly Leu Ser Ile Asn Arg Phe Cys Ala Ser Gly Met Glu
                85                  90                  95

Ala Val Asn Leu Ala Ala Asn Gln Val Arg Ala Gly Ala Gly Glu Ala
            100                 105                 110

Tyr Ile Ala Gly Gly Val Glu Met Met Ser Arg Val Ala Met Gly Ser
        115                 120                 125
```

Asp Gly Ala Ala Val Ala Ala Asp Pro Ser Leu Ala Met Lys Thr Tyr
    130                 135                 140

Phe Val Pro Gln Gly Ile Ser Ala Asp Ile Ile Ala Thr Arg Tyr Gly
145                 150                 155                 160

Phe Ser Arg Asp Glu Ala Asp Ala Leu Ala Val Glu Ser Gln Lys Arg
                165                 170                 175

Ala Ala Ala Ala Trp Ala Glu Gly Arg Phe Ala Arg Ser Val Val Pro
            180                 185                 190

Val Arg Asp Gln Asn Gly Val Thr Ile Leu Glu Arg Asp Glu Tyr Leu
        195                 200                 205

Arg Pro Asn Thr Asp Met Gln Ser Leu Gly Ala Leu Lys Pro Ala Phe
    210                 215                 220

Lys Glu Met Gly Glu Gln Met Pro Gly Phe Asp Lys Leu Ala Leu Met
225                 230                 235                 240

Lys Tyr Pro Glu Leu Glu Arg Val Glu His Ile His Ala Gly Asn
                245                 250                 255

Ser Ser Gly Ile Val Asp Gly Ala Ala Ala Val Leu Ile Gly Ser Arg
            260                 265                 270

Ala Phe Gly Glu Ala His Gly Leu Arg Pro Arg Ala Arg Ile Arg Ala
        275                 280                 285

Thr Ala Lys Ile Gly Thr Asp Pro Thr Ile Met Leu Thr Gly Pro Val
    290                 295                 300

Pro Val Thr Gln Lys Ile Leu Arg Glu Ala Gly Met Gln Ile Ser Asp
305                 310                 315                 320

Ile Asp Leu Phe Glu Val Asn Glu Ala Phe Ala Val Val Leu Arg
                325                 330                 335

Phe Gln Gln Ala Phe Gly Val Asp Pro Ala Arg Val Asn Pro Asn Gly
            340                 345                 350

Gly Ala Ile Ala Met Gly His Pro Leu Gly Ala Thr Gly Ala Ile Ile
        355                 360                 365

Ile Gly Thr Leu Leu Asp Glu Leu Glu Arg Thr Asp Arg Ser Val Gly
    370                 375                 380

Leu Ala Thr Leu Cys Val Ala Ser Gly Met Gly Ala Ala Thr Ile Ile
385                 390                 395                 400

Glu Arg Val

<210> SEQ ID NO 79
<211> LENGTH: 2316
<212> TYPE: DNA
<213> ORGANISM: Rhodobacter sphaeroides

<400> SEQUENCE: 79
gtgccatctt tttcgaccac tctcgagcaa gccatccacg gcgctctggc gcttgcgaat         60
gcccgccgtc atgaactcgc cacgctcgag cacctgttgc ttgcgctgat cgacgagccc        120
gacgcctcgc gcgtcatgaa ggcctgctcg gtcgacctcg acgagttgcg caagacgctc        180
gtcgacttca tcgacgatga tctgtccacc ctcgtgacct ctgtcgaggg ctccgaggcc        240
gtgccgacgg ccgccttcca gcgcgtgatc cagcgcgccg ccatccatgt gcaatcctcc        300
ggccggaccg aggtcacggg cgccaacgtg ctcgtcgcca tcttcgccga acgggagtcg        360
aatgccgcct atttcctgca ggagcaggac atgacccgct acgacgcggt caacttcatc        420
gcgcatggcg tggcgaagga cccgtcctat ggcgagccgc gccggtcac cggcgcggaa        480 gagcatcatg agaccccgaa ggctgaagct ggtgaggcga aggagtctgc gttgtcgaaa        540

```
tattgcgttg acctgaacgt caaggcccgc aagggcgacg tcgacccgct catcggccgc    600
gagcacgagg tcgaacgctg cattcaggtt ctctgccgcc ggcggaagaa caacccgctc    660
ctggtgggcg acccgggcgt gggcaagacg gccatcgccg aagggctcgc gcgcaagatc    720
gtcaacggcg agacgcccga catcctcgcc cgcgccacga tcttctcgct cgacatgggc    780
gcgctgctcg ccggcacccg ctaccgcggc gatttcgagg agcggctgaa ggccgtggtc    840
aaggagatgg aggatcaccc cgacgcgatc ctcttcatcg acgagatcca ccgtgatc     900
ggcgccggcg ccacctcggg cggcgcgatg gatgcctcga acctgctcaa gcccgcgctg    960
cagggcggca agctgcgctg catgggctcg accacctaca aggaatatcg tcagcatttc   1020
gagaaggacc gcgcgctcag ccgccggttc cagaagatcg acgtgaacga ccctcggtc   1080
gaggatacgg tcaagatcct gatgggcctc aagcccatt tcgaggagca tcacgacctg   1140
cgctacacgc aggacgcgat ccggaccgcg gtggaactgt ccgcgcgcta catccatgac   1200
cgcaagctgc cggacaaggc gatcgacgtg atcgacgagg ccggcgcggc ccagcacctg   1260
ctggccgaca gcaagcggcg caagactatc ggtccgcgtg agatcgaggc ggtggtggcc   1320
aagatcgccc gcatcccccc gaagagcgtc tcgaaggacg atgccgaagt gctgcgcgac   1380
ctcgagaaga ccctcaagcg ggtggtgttc ggtcaggacc gggccatcga ggccctgtcc   1440
tcggccatca gctggcgcg cgccggcctg cgcgagcccg agaagccgat cggcaactat   1500
ctcttcgcgg gcccgaccgg cgtcggcaag accgaggtgg cgaagcagct ggcaagcatc   1560
ctcggcgtgg aactgctgcg cttcgacatg tcggaatata tggagaagca cgccgtctcc   1620
cgactgatcg gcgcgcctcc gggttacgtc ggcttcgatc agggtgggat gctgaccgat   1680
ggcgtggacc agcatccgca ttgcgtgctg ctgctcgacg agatcgagaa ggcccacccg   1740
gatgtctaca acatcctgct gcaggtgatg gaccacggga aactcaccga ccacaacggc   1800
cggtcggtcg atttccgcaa cgtgatcctg atcatgacct cgaacgcagg cgcggccgag   1860
ctggccaagt ccgcgatcgg cttcggacgc gaccggcgcg agggcgagga tacgccgcc   1920
atcgagcgga ccttcacgcc cgagttccgc aaccgtctcg atgcagtcat ctccttcgcg   1980
cccctcggca aggagatcat cctgcaggtg gtcgagaagt tcgtcctcca gctcgaggcc   2040
cagctcatgg accgtggcgt gcatatcgag ctctcgccgg aagcggcggc ctggctcggc   2100
gacaagggct acgacgacaa gatgggagcg cgcccgctgg ccgcgtgat ccaggagaac   2160
atcaagaagc cgctggccga ggaactcctg ttcggccggc tggtgaaggg cggcgtcgtg   2220
aaggtcggcg tgaaggacga tacgatcgac ctgcagatcg aggaaccgaa gccgcgcctc   2280
accgggtcca gccgccgct tctgacggcc gactga                              2316
```

<210> SEQ ID NO 80
<211> LENGTH: 771
<212> TYPE: PRT
<213> ORGANISM: Rhodobacter sphaeroides

<400> SEQUENCE: 80

```
Met Pro Ser Phe Ser Thr Thr Leu Glu Gln Ala Ile His Gly Ala Leu
1               5                   10                  15
Ala Leu Ala Asn Ala Arg Arg His Glu Leu Ala Thr Leu Glu His Leu
            20                  25                  30
Leu Leu Ala Leu Ile Asp Glu Pro Asp Ala Ser Arg Val Met Lys Ala
        35                  40                  45
Cys Ser Val Asp Leu Asp Glu Leu Arg Lys Thr Leu Val Asp Phe Ile
    50                  55                  60
```

```
Asp Asp Asp Leu Ser Thr Leu Val Thr Ser Val Glu Gly Ser Glu Ala
 65                  70                  75                  80

Val Pro Thr Ala Ala Phe Gln Arg Val Ile Gln Arg Ala Ala Ile His
                 85                  90                  95

Val Gln Ser Ser Gly Arg Thr Glu Val Thr Gly Ala Asn Val Leu Val
            100                 105                 110

Ala Ile Phe Ala Glu Arg Glu Ser Asn Ala Ala Tyr Phe Leu Gln Glu
        115                 120                 125

Gln Asp Met Thr Arg Tyr Asp Ala Val Asn Phe Ile Ala His Gly Val
    130                 135                 140

Ala Lys Asp Pro Ser Tyr Gly Glu Pro Arg Pro Val Thr Gly Ala Glu
145                 150                 155                 160

Glu His His Glu Thr Pro Lys Ala Glu Ala Gly Glu Ala Lys Glu Ser
                165                 170                 175

Ala Leu Ser Lys Tyr Cys Val Asp Leu Asn Val Lys Ala Arg Lys Gly
            180                 185                 190

Asp Val Asp Pro Leu Ile Gly Arg Glu His Glu Val Glu Arg Cys Ile
        195                 200                 205

Gln Val Leu Cys Arg Arg Arg Lys Asn Asn Pro Leu Leu Val Gly Asp
    210                 215                 220

Pro Gly Val Gly Lys Thr Ala Ile Ala Glu Gly Leu Ala Arg Lys Ile
225                 230                 235                 240

Val Asn Gly Glu Thr Pro Asp Ile Leu Ala Arg Ala Thr Ile Phe Ser
                245                 250                 255

Leu Asp Met Gly Ala Leu Leu Ala Gly Thr Arg Tyr Arg Gly Asp Phe
            260                 265                 270

Glu Glu Arg Leu Lys Ala Val Val Lys Glu Met Glu Asp His Pro Asp
        275                 280                 285

Ala Ile Leu Phe Ile Asp Glu Ile His Thr Val Ile Gly Ala Gly Ala
    290                 295                 300

Thr Ser Gly Gly Ala Met Asp Ala Ser Asn Leu Leu Lys Pro Ala Leu
305                 310                 315                 320

Gln Gly Gly Lys Leu Arg Cys Met Gly Ser Thr Thr Tyr Lys Glu Tyr
                325                 330                 335

Arg Gln His Phe Glu Lys Asp Arg Ala Leu Ser Arg Arg Phe Gln Lys
            340                 345                 350

Ile Asp Val Asn Glu Pro Ser Val Glu Asp Thr Val Lys Ile Leu Met
        355                 360                 365

Gly Leu Lys Pro Tyr Phe Glu Glu His His Asp Leu Arg Tyr Thr Gln
    370                 375                 380

Asp Ala Ile Arg Thr Ala Val Glu Leu Ser Ala Arg Tyr Ile His Asp
385                 390                 395                 400

Arg Lys Leu Pro Asp Lys Ala Ile Asp Val Ile Asp Glu Ala Gly Ala
                405                 410                 415

Ala Gln His Leu Leu Ala Asp Ser Lys Arg Arg Lys Thr Ile Gly Pro
            420                 425                 430

Arg Glu Ile Glu Ala Val Val Ala Lys Ile Ala Arg Ile Pro Pro Lys
        435                 440                 445

Ser Val Ser Lys Asp Asp Ala Glu Val Leu Arg Asp Leu Glu Lys Thr
    450                 455                 460

Leu Lys Arg Val Val Phe Gly Gln Asp Arg Ala Ile Glu Ala Leu Ser
465                 470                 475                 480
```

```
Ser Ala Ile Lys Leu Ala Arg Ala Gly Leu Arg Glu Pro Glu Lys Pro
                485                 490                 495

Ile Gly Asn Tyr Leu Phe Ala Gly Pro Thr Gly Val Gly Lys Thr Glu
            500                 505                 510

Val Ala Lys Gln Leu Ala Ser Ile Leu Gly Val Glu Leu Leu Arg Phe
        515                 520                 525

Asp Met Ser Glu Tyr Met Glu Lys His Ala Val Ser Arg Leu Ile Gly
    530                 535                 540

Ala Pro Pro Gly Tyr Val Gly Phe Asp Gln Gly Met Leu Thr Asp
545                 550                 555                 560

Gly Val Asp Gln His Pro His Cys Val Leu Leu Asp Glu Ile Glu
                565                 570                 575

Lys Ala His Pro Asp Val Tyr Asn Ile Leu Leu Gln Val Met Asp His
                580                 585                 590

Gly Lys Leu Thr Asp His Asn Gly Arg Ser Val Asp Phe Arg Asn Val
            595                 600                 605

Ile Leu Ile Met Thr Ser Asn Ala Gly Ala Ala Glu Leu Ala Lys Ser
        610                 615                 620

Ala Ile Gly Phe Gly Arg Asp Arg Arg Glu Gly Glu Asp Thr Ala Ala
625                 630                 635                 640

Ile Glu Arg Thr Phe Thr Pro Glu Phe Arg Asn Arg Leu Asp Ala Val
                645                 650                 655

Ile Ser Phe Ala Pro Leu Gly Lys Glu Ile Ile Leu Gln Val Val Glu
            660                 665                 670

Lys Phe Val Leu Gln Leu Glu Ala Gln Leu Met Asp Arg Gly Val His
        675                 680                 685

Ile Glu Leu Ser Pro Glu Ala Ala Ala Trp Leu Gly Asp Lys Gly Tyr
    690                 695                 700

Asp Asp Lys Met Gly Ala Arg Pro Leu Gly Arg Val Ile Gln Glu Asn
705                 710                 715                 720

Ile Lys Lys Pro Leu Ala Glu Glu Leu Leu Phe Gly Arg Leu Val Lys
                725                 730                 735

Gly Gly Val Val Lys Val Gly Val Lys Asp Asp Thr Ile Asp Leu Gln
            740                 745                 750

Ile Glu Glu Pro Lys Pro Arg Leu Thr Gly Ser Lys Pro Pro Leu Leu
        755                 760                 765

Thr Ala Asp
    770

<210> SEQ ID NO 81
<211> LENGTH: 825
<212> TYPE: DNA
<213> ORGANISM: Rhodobacter sphaeroides

<400> SEQUENCE: 81
atggcgaacg gactgctggc tggcaagcgt gggctcatca tggggctggc gaacgacaag      60
tccatcgcct ggggcatcgc gaaatgctgc gccgaccagg gagccgagct ggccttctcc     120
tatcagggcg atgcgctgaa gaagcgcgtc gaaccgctgg ccgcctcgat cggggcgacc     180
gagatggtgg aatgcgacgt gtccgacgag gcctcgctcg accggctctt cgcgcatctg     240
aaggaggtct ggggcacgct cgacttcgtc gtccatgcca tcggcttctc ggacaagtcc     300
gagctgcgcg ccgctatgt cgacacgacg cccgcgaact tccgcatgac gatggacatt     360
tcggtctatt ccttcaccgc cgtctgccag cgcgcctgcg ccatgatgcc cgcgggcggc     420
```

```
agccttctca cgctgaccta ctacggcgcc gagaaggtga tgccgcacta caatgtgatg    480
ggaatcgcca aggccgcgct cgagacctcg gtgcagtata tcgccgagga tctgggcaag    540
gacggcatcc gcgtgaatgc gatctcggcc ggcccgatca agacgctggc cgccagcggc    600
atcggcgact ccgctacat catgaagtgg aacgagctga attcgccgct cgccgcaac     660 gtcacgcagg aagaggtggg caaggccgcg ctctatctgc tgtcggatct gggttcgggc    720
acgacgggcg aggtgctgca tgtggatgcg ggctatcacg tcgtcggcat gaaggccgtg    780
gacgcgcccg acatcgacgc cgtgaccggc cgcaaggacc actga                    825
```

<210> SEQ ID NO 82
<211> LENGTH: 274
<212> TYPE: PRT
<213> ORGANISM: Rhodobacter sphaeroides

<400> SEQUENCE: 82

```
Met Ala Asn Gly Leu Leu Ala Gly Lys Arg Gly Leu Ile Met Gly Leu
1               5                   10                  15

Ala Asn Asp Lys Ser Ile Ala Trp Gly Ile Ala Lys Cys Cys Ala Asp
                20                  25                  30

Gln Gly Ala Glu Leu Ala Phe Ser Tyr Gln Gly Asp Ala Leu Lys Lys
            35                  40                  45

Arg Val Glu Pro Leu Ala Ala Ser Ile Gly Ala Thr Glu Met Val Glu
        50                  55                  60

Cys Asp Val Ser Asp Glu Ala Ser Leu Asp Arg Leu Phe Ala His Leu
65                  70                  75                  80

Lys Glu Val Trp Gly Thr Leu Asp Phe Val Val His Ala Ile Gly Phe
                85                  90                  95

Ser Asp Lys Ser Glu Leu Arg Gly Arg Tyr Val Asp Thr Thr Pro Ala
            100                 105                 110

Asn Phe Arg Met Thr Met Asp Ile Ser Val Tyr Ser Phe Thr Ala Val
        115                 120                 125

Cys Gln Arg Ala Cys Ala Met Met Pro Ala Gly Gly Ser Leu Leu Thr
130                 135                 140

Leu Thr Tyr Tyr Gly Ala Glu Lys Val Met Pro His Tyr Asn Val Met
145                 150                 155                 160

Gly Ile Ala Lys Ala Ala Leu Glu Thr Ser Val Gln Tyr Ile Ala Glu
                165                 170                 175

Asp Leu Gly Lys Asp Gly Ile Arg Val Asn Ala Ile Ser Ala Gly Pro
            180                 185                 190

Ile Lys Thr Leu Ala Ala Ser Gly Ile Gly Asp Phe Arg Tyr Ile Met
        195                 200                 205

Lys Trp Asn Glu Leu Asn Ser Pro Leu Arg Arg Asn Val Thr Gln Glu
    210                 215                 220

Glu Val Gly Lys Ala Ala Leu Tyr Leu Leu Ser Asp Leu Gly Ser Gly
225                 230                 235                 240

Thr Thr Gly Glu Val Leu His Val Asp Ala Gly Tyr His Val Val Gly
                245                 250                 255

Met Lys Ala Val Asp Ala Pro Asp Ile Asp Ala Val Thr Gly Arg Lys
            260                 265                 270

Asp His
```

<210> SEQ ID NO 83
<211> LENGTH: 747
<212> TYPE: DNA

<213> ORGANISM: Rhodobacter sphaeroides

<400> SEQUENCE: 83

```
atgacgaaga cggcggttgt gacgggggcg gcgcgcggga tcgggcgcgc gctcgcggtg      60
gggctcgcag aggcgggcta cgatgtggcg gtgacggatc tggccgcgca ggccgacggg     120
ctggccgaga cgcgcgcgct gatcgaggcc gcggccggc gcgccttcgt cgagacggtg     180
gatgtctcgg accgggccgc ggtcgtcgcc gcgatggcgc ggatcgagga cgccgcgggc     240
gggatcgacg tgctggtgaa caatgcgggc atcctgaagc ccgcgcggct cgaggatctc     300
tcggaggccg actgggacgc gcatatggac gtgaacgtga agggcgtcct ctcctgctgt     360
caggcggtgc tgccgggaat gcgcgcgcgc aaggcggggc ggatcgtcaa catcgcctcc     420
atcgcgggcc gtcagggcgt gccgacccaa ggccattatg cggcgaccaa ggccgccgtc     480
attaccctga cgcgggtgct ggcgcaggag gccggcatgg acgggatcac cgtcaatgcc     540
atctgcccgg gcatcatcct gaccgagatg ggcaagaaca acctcggctc ggacgaggcc     600
atccgccact gggaagaggt ggccgcgctg aagcgtctcg gcgcgcccga agatatcgtg     660
gggccggtcc tgttcttcgc gggcgagcag tcggccttcg tcaccgggca ggcgctgaac     720
gtctgcggcg ggatctactt ccattag                                          747
```

<210> SEQ ID NO 84
<211> LENGTH: 248
<212> TYPE: PRT
<213> ORGANISM: Rhodobacter sphaeroides

<400> SEQUENCE: 84

```
Met Thr Lys Thr Ala Val Val Thr Gly Ala Ala Arg Gly Ile Gly Arg
1               5                   10                  15

Ala Leu Ala Val Gly Leu Ala Glu Ala Gly Tyr Asp Val Ala Val Thr
            20                  25                  30

Asp Leu Ala Ala Gln Ala Asp Gly Leu Ala Glu Thr Arg Ala Leu Ile
        35                  40                  45

Glu Ala Ala Gly Arg Arg Ala Phe Val Glu Thr Val Asp Val Ser Asp
    50                  55                  60

Arg Ala Ala Val Val Ala Ala Met Ala Arg Ile Glu Asp Ala Ala Gly
65                  70                  75                  80

Gly Ile Asp Val Leu Val Asn Asn Ala Gly Ile Leu Lys Pro Ala Arg
                85                  90                  95

Leu Glu Asp Leu Ser Glu Ala Asp Trp Asp Ala His Met Asp Val Asn
            100                 105                 110

Val Lys Gly Val Leu Ser Cys Cys Gln Ala Val Leu Pro Gly Met Arg
        115                 120                 125

Ala Arg Lys Ala Gly Arg Ile Val Asn Ile Ala Ser Ile Ala Gly Arg
    130                 135                 140

Gln Gly Val Pro Thr Gln Gly His Tyr Ala Ala Thr Lys Ala Ala Val
145                 150                 155                 160

Ile Thr Leu Thr Arg Val Leu Ala Gln Glu Ala Gly Met Asp Gly Ile
                165                 170                 175

Thr Val Asn Ala Ile Cys Pro Gly Ile Ile Leu Thr Glu Met Gly Lys
            180                 185                 190

Asn Asn Leu Gly Ser Asp Glu Ala Ile Arg His Trp Glu Glu Val Ala
        195                 200                 205

Ala Leu Lys Arg Leu Gly Ala Pro Glu Asp Ile Val Gly Pro Val Leu
    210                 215                 220
```

Phe Phe Ala Gly Glu Gln Ser Ala Phe Val Thr Gly Gln Ala Leu Asn
225                 230                 235                 240

Val Cys Gly Gly Ile Tyr Phe His
                245

<210> SEQ ID NO 85
<211> LENGTH: 738
<212> TYPE: DNA
<213> ORGANISM: Rhodobacter sphaeroides

<400> SEQUENCE: 85

```
atgttcgatc tgacgggaaa atcggcgctc atcaccggcg cttcgggcgg catcggcggc      60
ggcatcgcgc gcgcgctcca tgcggcgggg gcgacggtgg cgctctccgg cacgcggacg     120
ggaccgctcg aagagctggc ggccgagctg ggggatcgcg cccatgtgct cgcctgcaac     180
ctctcggatg cggcggccgt cgaggcgctg ccgaagcagg cggccgaggc gatgggcgcg     240
gtcgacatcc tcgtgaacaa tgcgggcatc acccgcgatc agctcgccat gcgcatgtcg     300
gacgaggatt gggagcaggt gatcgaggtg aacctgacct cgaccttccg gctctgccgc     360
ggcgtgctgc gcggcatgat gaaggcgcgc tgggggcgga tcgtcaacat cacctccatc     420
gtgggcgcga cgggcaatcc ggggcaggcc aattatgccg cctcgaaggc gggcgtcgtg     480
gccatgtcga aaagctttgc ggccgaggtg gcgagccgcg gcatcaccgt caatgcggtg     540
gcgccgggct tcatcgcgac cgcgatgacc gacaagctga cgacgagca gaaggcgcgg     600
attctgggtc aggtgccgat gggccggatg gcgcccccg acgatatcgc ggcggccgtg     660
ctctatctgg ccagtcccgc ggcgggctat gtgacggggg ccacgctcca tgtgaacggc     720
ggcatggcga tgctgtga                                                    738
```

<210> SEQ ID NO 86
<211> LENGTH: 245
<212> TYPE: PRT
<213> ORGANISM: Rhodobacter sphaeroides

<400> SEQUENCE: 86

Met Phe Asp Leu Thr Gly Lys Ser Ala Leu Ile Thr Gly Ala Ser Gly
1               5                   10                  15

Gly Ile Gly Gly Gly Ile Ala Arg Ala Leu His Ala Ala Gly Ala Thr
            20                  25                  30

Val Ala Leu Ser Gly Thr Arg Thr Gly Pro Leu Glu Glu Leu Ala Ala
        35                  40                  45

Glu Leu Gly Asp Arg Ala His Val Leu Ala Cys Asn Leu Ser Asp Ala
    50                  55                  60

Ala Ala Val Glu Ala Leu Pro Lys Gln Ala Ala Glu Ala Met Gly Ala
65                  70                  75                  80

Val Asp Ile Leu Val Asn Asn Ala Gly Ile Thr Arg Asp Gln Leu Ala
                85                  90                  95

Met Arg Met Ser Asp Glu Asp Trp Glu Gln Val Ile Glu Val Asn Leu
            100                 105                 110

Thr Ser Thr Phe Arg Leu Cys Arg Gly Val Leu Arg Gly Met Met Lys
        115                 120                 125

Ala Arg Trp Gly Arg Ile Val Asn Ile Thr Ser Ile Val Gly Ala Thr
    130                 135                 140

Gly Asn Pro Gly Gln Ala Asn Tyr Ala Ala Ser Lys Ala Gly Val Val
145                 150                 155                 160

```
Ala Met Ser Lys Ser Phe Ala Glu Val Ala Ser Arg Gly Ile Thr
            165                 170                 175

Val Asn Ala Val Ala Pro Gly Phe Ile Ala Thr Ala Met Thr Asp Lys
        180                 185                 190

Leu Asn Asp Glu Gln Lys Ala Arg Ile Leu Gly Gln Val Pro Met Gly
            195                 200                 205

Arg Met Gly Ala Pro Asp Asp Ile Ala Ala Val Leu Tyr Leu Ala
    210                 215                 220

Ser Pro Ala Ala Gly Tyr Val Thr Gly Ala Thr Leu His Val Asn Gly
225                 230                 235                 240

Gly Met Ala Met Leu
            245

<210> SEQ ID NO 87
<211> LENGTH: 1263
<212> TYPE: DNA
<213> ORGANISM: Rhodobacter sphaeroides

<400> SEQUENCE: 87
atgcgtcgag tggttgtcac ggggctgggc atggtcacgc cgctggcgtg cggcgtcgag      60
gagacctgga agcggctgct ggccgggcag tccggcgcgg gtccgatcca gcggttcgac     120
acgtccaacg tgaccacgca atatgcctgc gagatcccgg tgggcgacgg cagcgacggc     180
accttcaacg ccgacgactg gatggagccc aaggacaggc gcaaggtcga cgatttcatc     240
ctctatgcca tggccgcggc cacgcaggcg gtgaaggatt ccggctggga gccgcaatcc     300
gaggaagacc gctgccgcac gggcgtgatg atcggctcgg gcatcggcgg cctctcggcc     360
atcgccgaca cggccgtgct catcaaggaa aaggggccga agcgcgtctc gcccttcttc     420
atcccctcgg cgctcatcaa cctggcctcg ggcaggtct cgatccgctt cggctacaag     480
ggtccgaacc atgccgtcgt gaccgcctgc tcgaccggcg cccatgcgat cggcgacgcg     540
gcccggctga tccagctcgg cgatgccgac gtgatgctcg cgggcggcgc cgagagcccg     600
atctccgaga tcggcatcgc gggcttcaac gcctgcaagg cgctctcgac caagcggggc     660
aacgagcccg aggccgcctc gcggccctgg gacgccgacc gcgacggatt cgtgatgggc     720
gagggcgcgg gcgtcgtcgt gctcgaggaa tatgaacatg ccagggcgcg cggcgccaag     780
atctatgccg aggtgctggg ctacggtctt tccggcgatg cctaccacat caccgccccc     840
tcggaagacg gggacggcgg cttccgctcg atgaccatgg cgctgaagcg cgcgggcctc     900
gaaccctcgg cggtcgacta tatcaacgcc cacggcacct cgaccatggc cgacgtgatc     960
gaactcggcg cggtcgagcg gcttctgggc gaggcggcgg cggcggccac catgtcctcg    1020
accaagtcga gcatcgggca cctgctgggc gctgcgggcg cggtcgaggc gatcttctgc    1080
gtgctggcca tccgcgatca ggtggcgccg cccacgctga acctcgacaa cccggccgtg    1140
gaggcgagga tcgacctcgc acccaaggcg gcgcgcccgc gcaagatcga cgtggcgcta    1200
tcgaattcct tcggcttcgg cggcacgaac gcgtcgctgg tgctgggacg ggtcaccctcg    1260
tga                                                                  1263

<210> SEQ ID NO 88
<211> LENGTH: 420
<212> TYPE: PRT
<213> ORGANISM: Rhodobacter sphaeroides

<400> SEQUENCE: 88

Met Arg Arg Val Val Val Thr Gly Leu Gly Met Val Thr Pro Leu Ala
```

-continued

```
1               5                   10                  15
Cys Gly Val Glu Glu Thr Trp Lys Arg Leu Ala Gly Gln Ser Gly
                20                  25                  30
Ala Gly Pro Ile Gln Arg Phe Asp Thr Ser Asn Val Thr Thr Gln Tyr
                35                  40                  45
Ala Cys Glu Ile Pro Val Gly Asp Gly Ser Asp Gly Thr Phe Asn Ala
    50                  55                  60
Asp Asp Trp Met Glu Pro Lys Asp Arg Arg Lys Val Asp Asp Phe Ile
65                  70                  75                  80
Leu Tyr Ala Met Ala Ala Thr Gln Ala Val Lys Asp Ser Gly Trp
                85                  90                  95
Glu Pro Gln Ser Glu Glu Asp Arg Cys Arg Thr Gly Val Met Ile Gly
                100                 105                 110
Ser Gly Ile Gly Gly Leu Ser Ala Ile Ala Asp Thr Ala Val Leu Ile
                115                 120                 125
Lys Glu Lys Gly Pro Lys Arg Val Ser Pro Phe Phe Ile Pro Ser Ala
            130                 135                 140
Leu Ile Asn Leu Ala Ser Gly Gln Val Ser Ile Arg Phe Gly Tyr Lys
145                 150                 155                 160
Gly Pro Asn His Ala Val Val Thr Ala Cys Ser Thr Gly Ala His Ala
                165                 170                 175
Ile Gly Asp Ala Ala Arg Leu Ile Gln Leu Gly Asp Ala Asp Val Met
                180                 185                 190
Leu Ala Gly Gly Ala Glu Ser Pro Ile Ser Glu Ile Gly Ile Ala Gly
                195                 200                 205
Phe Asn Ala Cys Lys Ala Leu Ser Thr Lys Arg Gly Asn Glu Pro Glu
210                 215                 220
Ala Ala Ser Arg Pro Trp Asp Ala Asp Arg Asp Gly Phe Val Met Gly
225                 230                 235                 240
Glu Gly Ala Gly Val Val Val Leu Glu Glu Tyr Glu His Ala Arg Ala
                245                 250                 255
Arg Gly Ala Lys Ile Tyr Ala Glu Val Leu Gly Tyr Gly Leu Ser Gly
                260                 265                 270
Asp Ala Tyr His Ile Thr Ala Pro Ser Glu Asp Gly Asp Gly Gly Phe
                275                 280                 285
Arg Ser Met Thr Met Ala Leu Lys Arg Ala Gly Leu Glu Pro Ser Ala
                290                 295                 300
Val Asp Tyr Ile Asn Ala His Gly Thr Ser Thr Met Ala Asp Val Ile
305                 310                 315                 320
Glu Leu Gly Ala Val Glu Arg Leu Leu Gly Glu Ala Ala Ala Ala
                325                 330                 335
Thr Met Ser Ser Thr Lys Ser Ser Ile Gly His Leu Leu Gly Ala Ala
                340                 345                 350
Gly Ala Val Glu Ala Ile Phe Cys Val Leu Ala Ile Arg Asp Gln Val
                355                 360                 365
Ala Pro Pro Thr Leu Asn Leu Asp Asn Pro Ala Val Glu Ala Arg Ile
                370                 375                 380
Asp Leu Ala Pro Lys Ala Ala Arg Pro Arg Lys Ile Asp Val Ala Leu
385                 390                 395                 400
Ser Asn Ser Phe Gly Phe Gly Gly Thr Asn Ala Ser Leu Val Leu Gly
                405                 410                 415
Arg Val Thr Ser
            420
```

<210> SEQ ID NO 89
<211> LENGTH: 780
<212> TYPE: DNA
<213> ORGANISM: Rhodobacter sphaeroides

<400> SEQUENCE: 89

```
atggatctgg gtattcgcgg tcgccgggca ctggtctgcg cctcgtcgaa ggggctgggc      60
cttggctgtg cggcggctct ggccgaggcc ggtgtcgatc tgatgatgaa cgcgcgcggc     120
gccgaggcgc tcgaggcggc ggccgaggat ctgcggcagc ggttcggcgc gaacgtgacc     180
acggtggcgg cagacatcgt ctcggaagag gggcgggcgc gggtgctcga ggccgcgggc     240
gcggtcgaca tcctcgtgac caacgcgggc ggcccccgc ccggcctctg gtcggactgg     300
acgcgcgacg atttcatccg ggcgctcgat gccaacatgc tgacgcccat cgcgctgatg     360
accgcgctgc tgccggccat gatcgaaagc ggctggggcc gcgtcgtcaa catcacctcg     420
cagtcggtgc gcgccccgat cccggcgctc ggcctgtcga actcggcgcg cacggggctg     480
acgggctatg tggcgggcac ctcgcggcag gtggcgcagc acggtgtctg catcaacaac     540
ctgctgccgg gcatccatga caccgaccgg gccgaggcgc tcgaccgcaa tgcgatgaag     600
gcgcagggca tcacgcgcga agaggcccgc gcgcagcggg cggccagcat ccccacccgc     660
cactacggcc gggccgagga tttcggcgcc gcctgcgcct tcctctgctc cgagcatgcg     720
cgcttcatcg tgggccagaa cctgctggtc gacggcggcg gcaccaacct cacggtctga     780
```

<210> SEQ ID NO 90
<211> LENGTH: 259
<212> TYPE: PRT
<213> ORGANISM: Rhodobacter sphaeroides

<400> SEQUENCE: 90

```
Met Asp Leu Gly Ile Arg Gly Arg Arg Ala Leu Val Cys Ala Ser Ser
1               5                   10                  15

Lys Gly Leu Gly Leu Gly Cys Ala Ala Ala Leu Ala Glu Ala Gly Val
            20                  25                  30

Asp Leu Met Met Asn Ala Arg Gly Ala Glu Ala Leu Glu Ala Ala Ala
        35                  40                  45

Glu Asp Leu Arg Gln Arg Phe Gly Ala Asn Val Thr Thr Val Ala Ala
    50                  55                  60

Asp Ile Val Ser Glu Glu Gly Arg Ala Arg Val Leu Glu Ala Ala Gly
65                  70                  75                  80

Ala Val Asp Ile Leu Val Thr Asn Ala Gly Pro Pro Gly Leu
            85                  90                  95

Trp Ser Asp Trp Thr Arg Asp Asp Phe Ile Arg Ala Leu Asp Ala Asn
            100                 105                 110

Met Leu Thr Pro Ile Ala Leu Met Thr Ala Leu Leu Pro Ala Met Ile
            115                 120                 125

Glu Ser Gly Trp Gly Arg Val Val Asn Ile Thr Ser Gln Ser Val Arg
            130                 135                 140

Ala Pro Ile Pro Ala Leu Gly Leu Ser Asn Ser Ala Arg Thr Gly Leu
145                 150                 155                 160

Thr Gly Tyr Val Ala Gly Thr Ser Arg Gln Val Ala Gln His Gly Val
            165                 170                 175

Cys Ile Asn Asn Leu Leu Pro Gly Ile His Asp Thr Asp Arg Ala Glu
            180                 185                 190
```

Ala Leu Asp Arg Asn Ala Met Lys Ala Gln Gly Ile Thr Arg Glu Glu
             195                 200                 205

Ala Arg Ala Gln Arg Ala Ala Ser Ile Pro Thr Arg His Tyr Gly Arg
         210                 215                 220

Ala Glu Asp Phe Gly Ala Ala Cys Ala Phe Leu Cys Ser Glu His Ala
225                 230                 235                 240

Arg Phe Ile Val Gly Gln Asn Leu Leu Val Asp Gly Gly Thr Asn
                245                 250                 255

Leu Thr Val

<210> SEQ ID NO 91
<211> LENGTH: 1200
<212> TYPE: DNA
<213> ORGANISM: Rhodobacter sphaeroides

<400> SEQUENCE: 91

```
atgttccacc gtcccacgcg cgcaggcgcc ctttgcatga cggcgacgct gacgatcctc      60
gccgcctgca gcacttcgga cctagactgg gacctgcgcg gtcgcccccgg cgggctcagc    120 acggccgagg ccgcgcgggc ggtcagcgcc ccccgccccc gcgccgacga ccgcgggatc    180
atctcctatc cgacctatca ggtggccgtt gcccggcagg gcgagacggt cgcctcgctc    240
tcgagccgcc tcgggctcga tgccacgcag gtcgcgagct acaatgccct ctcgccgcag    300
aaccctctgc gcgccggaga gtggtcgtg ctgccgcagc gcgtggcggc ggctcccgcc    360
atgaccccgg cgcccgtcat gacggcgccc ggcgcggcga ccccggcgg catcgacgtg    420 accgccatcg ccaccagcgc cctcgaccgg cggggccctg ccaccgcgcc ggtggccgcc    480
gctcccgctc cggcccccgt gcagtctgcc gcgacagagc ctgcccgcca ccgtgtgtcg    540
cggggagaga ccgcctattc gatcgcgcgc agctacaatg tctcgcccaa ggcgctggcg    600
gactggaacg ggctcgggcc ggatctcgcg atccgcgagg ccagtatct gatgatcccg    660 accgcctctg cgcccccgcc cacggtgccc gccaatgtga ccgcggtcac ggtgcccggg    720
gcaggctcgc cgacgcccac cccgccctcg gcggccaagc cgctgcccgc cgagtcgacc    780 acgccccgcct cgaaacccgc aggccagccg gcctcgcccg acatgggcgc acagcgcacg    840
caggcctccg cctcgcggct gggattcccg gtgcagggca agatcatccg cggctatgtg    900
aagaagaaga cgacggcat cgacatctcg gcggccgtgg gcacgccggt ggcggcggcc    960
gcggacggga cggtggcggc catcacgcag gacaccgatc aggtgccgat cctcgtgatc   1020
cggcaccccg acaacctgct gacggtctat gccaatatcg acggcatcaa ggtcaccaag   1080
ggtgccagcg tgaagcgcgg acagcccatc gccgtggtgc gcgcggccga cccgcccttc   1140
gtccatttcg aggtccgcaa ggggttcgag agcgtcgatc cgatgcccta tcttcagtag   1200
```

<210> SEQ ID NO 92
<211> LENGTH: 399
<212> TYPE: PRT
<213> ORGANISM: Rhodobacter sphaeroides

<400> SEQUENCE: 92

Met Phe His Arg Pro Thr Arg Ala Gly Ala Leu Cys Met Thr Ala Thr
1               5                   10                  15

Leu Thr Ile Leu Ala Ala Cys Ser Thr Ser Asp Leu Asp Trp Asp Leu
             20                  25                  30

Arg Gly Arg Pro Gly Gly Leu Ser Thr Ala Glu Ala Ala Arg Ala Val
         35                  40                  45

Ser Ala Pro Arg Pro Arg Ala Asp Asp Arg Gly Ile Ile Ser Tyr Pro
50                  55                  60

Thr Tyr Gln Val Ala Val Ala Arg Gln Gly Glu Thr Val Ala Ser Leu
65                  70                  75                  80

Ser Ser Arg Leu Gly Leu Asp Ala Thr Gln Val Ala Ser Tyr Asn Ala
            85                  90                  95

Leu Ser Pro Gln Asn Pro Leu Arg Ala Gly Glu Val Val Leu Pro
            100                 105                 110

Gln Arg Val Ala Ala Ala Pro Ala Met Thr Pro Ala Pro Val Met Thr
            115                 120                 125

Ala Pro Gly Ala Ala Ser Pro Gly Gly Ile Asp Val Thr Ala Ile Ala
130                 135                 140

Thr Ser Ala Leu Asp Arg Ala Gly Pro Ala Thr Ala Pro Val Ala Ala
145                 150                 155                 160

Ala Pro Ala Pro Ala Pro Val Gln Ser Ala Ala Thr Glu Pro Ala Arg
                165                 170                 175

His Arg Val Ser Arg Gly Glu Thr Ala Tyr Ser Ile Ala Arg Ser Tyr
            180                 185                 190

Asn Val Ser Pro Lys Ala Leu Ala Asp Trp Asn Gly Leu Gly Pro Asp
195                 200                 205

Leu Ala Ile Arg Glu Gly Gln Tyr Leu Met Ile Pro Thr Ala Ser Ala
210                 215                 220

Pro Pro Thr Val Pro Ala Asn Val Thr Ala Val Thr Val Pro Gly
225                 230                 235                 240

Ala Gly Ser Pro Thr Pro Thr Pro Ser Ala Ala Lys Pro Leu Pro
            245                 250                 255

Ala Glu Ser Thr Thr Pro Ala Ser Lys Pro Ala Gly Gln Pro Ala Ser
            260                 265                 270

Pro Asp Met Gly Ala Gln Arg Thr Gln Ala Ser Ala Ser Arg Leu Gly
            275                 280                 285

Phe Pro Val Gln Gly Lys Ile Ile Arg Gly Tyr Val Lys Lys Lys Asn
            290                 295                 300

Asp Gly Ile Asp Ile Ser Ala Ala Val Gly Thr Pro Val Ala Ala Ala
305                 310                 315                 320

Ala Asp Gly Thr Val Ala Ala Ile Thr Gln Asp Thr Asp Gln Val Pro
                325                 330                 335

Ile Leu Val Ile Arg His Pro Asp Asn Leu Leu Thr Val Tyr Ala Asn
                340                 345                 350

Ile Asp Gly Ile Lys Val Thr Lys Gly Ala Ser Val Lys Arg Gly Gln
            355                 360                 365

Pro Ile Ala Val Val Arg Ala Ala Asp Pro Pro Phe Val His Phe Glu
370                 375                 380

Val Arg Lys Gly Phe Glu Ser Val Asp Pro Met Pro Tyr Leu Gln
385                 390                 395

<210> SEQ ID NO 93
<211> LENGTH: 660
<212> TYPE: DNA
<213> ORGANISM: Rhodobacter sphaeroides

<400> SEQUENCE: 93
atgacggcag aggcagacgg ggaggatccg gccgaacgca agatgcggtt cctgttcgcc    60
gtccgctcgc ggggcgtcac ggatgcccgc gtgctcgccg ccatggagcg gatcgaccgc   120
ggcgccttcg tccgcggcat cttcgccgac cgtgcctatg aggacatgcc gctgcccatc   180

```
gcctgcggcc agaccatcag ccagccctcg gtcgtggggc tgatgagcca ggcgctggcg    240
gtgaacccgc gcgacaaggt gctcgaggtg ggaaccggct cgggctatca ggccgccgtc    300
ctgagccagc tcgcccgccg cgtctacacc gtcgaccgtc atcgccgcct cgtgcgcgag    360
gcgaccgagg tcttccaccg cctgtccctg accaacatca ccgcgctcat tgcggacggc    420
agtttcggcc tgccggaaca ggccccgttc gaccggatcc tcgtcactgc cgcggccgag    480
gacccgcccg gccccctgtt ggcacaattg aagatcggcg tatcatggt cgtcccggtc    540 ggccagaccg atgcggtgca gaacctgatc aaggtgaccc ggctcgagca gggttacgat    600
tacgaggaac ttcgtccggt gcgcttcgtg cctctggtcg aaggcatcgg gtcggactga    660
```

<210> SEQ ID NO 94
<211> LENGTH: 219
<212> TYPE: PRT
<213> ORGANISM: Rhodobacter sphaeroides

<400> SEQUENCE: 94

Met Thr Ala Glu Ala Asp Gly Glu Asp Pro Ala Glu Arg Lys Met Arg
1               5                   10                  15

Phe Leu Phe Ala Val Arg Ser Arg Gly Val Thr Asp Ala Arg Val Leu
            20                  25                  30

Ala Ala Met Glu Arg Ile Asp Arg Gly Ala Phe Val Arg Gly Ile Phe
        35                  40                  45

Ala Asp Arg Ala Tyr Glu Asp Met Pro Leu Pro Ile Ala Cys Gly Gln
    50                  55                  60

Thr Ile Ser Gln Pro Ser Val Val Gly Leu Met Ser Gln Ala Leu Ala
65                  70                  75                  80

Val Asn Pro Arg Asp Lys Val Leu Glu Val Gly Thr Gly Ser Gly Tyr
                85                  90                  95

Gln Ala Ala Val Leu Ser Gln Leu Ala Arg Arg Val Tyr Thr Val Asp
            100                 105                 110

Arg His Arg Arg Leu Val Arg Glu Ala Thr Glu Val Phe His Arg Leu
        115                 120                 125

Ser Leu Thr Asn Ile Thr Ala Leu Ile Ala Asp Gly Ser Phe Gly Leu
    130                 135                 140

Pro Glu Gln Ala Pro Phe Asp Arg Ile Leu Val Thr Ala Ala Ala Glu
145                 150                 155                 160

Asp Pro Pro Gly Pro Leu Leu Ala Gln Leu Lys Ile Gly Gly Ile Met
                165                 170                 175

Val Val Pro Val Gly Gln Thr Asp Ala Val Gln Asn Leu Ile Lys Val
            180                 185                 190

Thr Arg Leu Glu Gln Gly Tyr Asp Tyr Glu Glu Leu Arg Pro Val Arg
        195                 200                 205

Phe Val Pro Leu Val Glu Gly Ile Gly Ser Asp
    210                 215

<210> SEQ ID NO 95
<211> LENGTH: 786
<212> TYPE: DNA
<213> ORGANISM: Rhodobacter sphaeroides

<400> SEQUENCE: 95

```
atgcgcatcc tgatcacgaa cgacgacggc atcaacgctc ccggcctcga ggtgctcgag    60
cagatcgccc tcgaactggc cggccccgag ggcgaggtct ggaccgtcgc tcccgccttc   120
```

-continued

```
gagcagtccg gcgtctcgca cgcgatcagc tacacgcatc cgatgatgat cgccaagctc      180
ggtccgcgcc gctacgcagc ggagggcagc cccgccgact gcgtgctcgc cgcgctctac      240
gacgtgctgc agggcgcccg ccccgacctc gtgctctcgg gcgtgaaccg gggcaacaac      300
tccgccgaga cgtgctcta ttccggcacg gtgggcggcg cgctcgaggc ggcgctgcag       360
ggcctgcccg ccatcgccct gtcccagttc ctcggccccg aaacggaggg gctggccgat      420
ccgttcgaat gcgcccgcac ccatggcgcg cgcatcgtac gcctcctgct cgagcgcggg      480
ctctgggacg gcgaggacta ccggctgttc tacaacgtga acttcccgcc cgtgccggct      540
gcgaacctgc gcggccaccg cgtggcggcg cagggcttcc ggcgcgacac ctccttcggg      600
gtcgagccgc acatgtcgcc ctcgggtcgc cgcttcctct ggatccgggg cggcgcccag      660
cagagcccga cgctgcccgg caccgatgcg gccgtgaacc tcgaagggtt cgtctcgatc      720
acgccgctgc gcgcggatct gactgcgcat gaccggctgg ccgagctgga ggcgctcatc      780
ggatga                                                                 786
```

<210> SEQ ID NO 96
<211> LENGTH: 261
<212> TYPE: PRT
<213> ORGANISM: Rhodobacter sphaeroides

<400> SEQUENCE: 96

```
Met Arg Ile Leu Ile Thr Asn Asp Asp Gly Ile Asn Ala Pro Gly Leu
1               5                   10                  15

Glu Val Leu Glu Gln Ile Ala Leu Glu Leu Ala Gly Pro Glu Gly Glu
            20                  25                  30

Val Trp Thr Val Ala Pro Ala Phe Glu Gln Ser Gly Val Ser His Ala
        35                  40                  45

Ile Ser Tyr Thr His Pro Met Met Ile Ala Lys Leu Gly Pro Arg Arg
    50                  55                  60

Tyr Ala Ala Glu Gly Ser Pro Ala Asp Cys Val Leu Ala Ala Leu Tyr
65                  70                  75                  80

Asp Val Leu Gln Gly Ala Arg Pro Asp Leu Val Leu Ser Gly Val Asn
                85                  90                  95

Arg Gly Asn Asn Ser Ala Glu Asn Val Leu Tyr Ser Gly Thr Val Gly
            100                 105                 110

Gly Ala Leu Glu Ala Ala Leu Gln Gly Leu Pro Ala Ile Ala Leu Ser
        115                 120                 125

Gln Phe Leu Gly Pro Glu Thr Glu Gly Leu Ala Asp Pro Phe Glu Cys
    130                 135                 140

Ala Arg Thr His Gly Ala Arg Ile Val Arg Leu Leu Glu Arg Gly
145                 150                 155                 160

Leu Trp Asp Gly Glu Asp Tyr Arg Leu Phe Tyr Asn Val Asn Phe Pro
                165                 170                 175

Pro Val Pro Ala Ala Asn Leu Arg Gly His Arg Val Ala Ala Gln Gly
            180                 185                 190

Phe Arg Arg Asp Thr Ser Phe Gly Val Glu Pro His Met Ser Pro Ser
        195                 200                 205

Gly Arg Arg Phe Leu Trp Ile Arg Gly Gly Ala Gln Gln Ser Pro Thr
    210                 215                 220

Leu Pro Gly Thr Asp Ala Ala Val Asn Leu Glu Gly Phe Val Ser Ile
225                 230                 235                 240

Thr Pro Leu Arg Ala Asp Leu Thr Ala His Asp Arg Leu Ala Glu Leu
                245                 250                 255
```

Glu Ala Leu Ile Gly
        260

<210> SEQ ID NO 97
<211> LENGTH: 972
<212> TYPE: DNA
<213> ORGANISM: Rhodobacter sphaeroides

<400> SEQUENCE: 97

```
atgacaatac gcgccgtggt gagggggcgtc gggcactatc tgcccgaccg tgtcgtcccg      60
aactccgaac tcgaggcgat cgtcgagacg accgacgaat ggatccgcac ccggtcgggc     120
atcgaacggc ggcatttcgc ggcggaggga cagacgacct ccgacctcgc cgcccgcgcg     180
gcgcgtgcag cgctcgagga cgcggggctt cagccggacg acatcgacac gctgatcgtc     240
gccacctcca cggccgatct caccttcccc tccgccgcca ccatggtgca ggcggccttg     300
ggcatgaccc gcggcttcgc cttcgacgtg caggcggtct gcgcgggctt cgtctatgcg     360
ctggccaatg ccgatgcgct gatccgctcg ggtcaggcgc agcgcgtgct cgtgatcggg     420
gccgagacct tcagccgcct gatggactgg aacgaccggg ccacctgcgt gctcttcggc     480
gatggcgcgg gcgcggtggt gctcgagggc accgagagcg ccggcacctc cgccgaccgc     540
ggcatccttg cgaccgacct gcattcggac ggccgcttca aggacctgct ctatgtcgat     600
ggcggctcct cgaccggcac cacgggccac ctgcggatgc agggacgcga ggttttccgc     660
catgccgttg agaagcttgc agaaacagcg catacggcac tggagaaggc gggcctcggc     720
gccggcgatg tcgactggat cgtgccgcat caggccaacc tgcgcatcat ctcggccacc     780
gcccagcgga tgcaggttcc gatggaccgc gtgatcctga cggtgcagga tcacggcaat     840
acctcggccg cctcgattcc cctggccctc tcggtcggca aggcacgcgg gcagatcaag     900
gaaggcgacc ttctggtcac cgaagcgatc ggcggcgggc tcgcctgggg ctcggtggtc     960
ctccgctggt ag                                                         972
```

<210> SEQ ID NO 98
<211> LENGTH: 323
<212> TYPE: PRT
<213> ORGANISM: Rhodobacter sphaeroides

<400> SEQUENCE: 98

Met Thr Ile Arg Ala Val Val Arg Gly Val Gly His Tyr Leu Pro Asp
1               5                   10                  15

Arg Val Val Pro Asn Ser Glu Leu Glu Ala Ile Val Glu Thr Thr Asp
            20                  25                  30

Glu Trp Ile Arg Thr Arg Ser Gly Ile Glu Arg Arg His Phe Ala Ala
        35                  40                  45

Glu Gly Gln Thr Thr Ser Asp Leu Ala Ala Arg Ala Ala Arg Ala Ala
    50                  55                  60

Leu Glu Asp Ala Gly Leu Gln Pro Asp Asp Ile Asp Thr Leu Ile Val
65                  70                  75                  80

Ala Thr Ser Thr Ala Asp Leu Thr Phe Pro Ser Ala Ala Thr Met Val
                85                  90                  95

Gln Ala Ala Leu Gly Met Thr Arg Gly Phe Ala Phe Asp Val Gln Ala
            100                 105                 110

Val Cys Ala Gly Phe Val Tyr Ala Leu Ala Asn Ala Asp Ala Leu Ile
        115                 120                 125

Arg Ser Gly Gln Ala Gln Arg Val Leu Val Ile Gly Ala Glu Thr Phe

```
                130                 135                 140
Ser Arg Leu Met Asp Trp Asn Asp Arg Ala Thr Cys Val Leu Phe Gly
145                 150                 155                 160

Asp Gly Ala Gly Ala Val Val Leu Glu Gly Thr Glu Ser Ala Gly Thr
                165                 170                 175

Ser Ala Asp Arg Gly Ile Leu Ala Thr Asp Leu His Ser Asp Gly Arg
                180                 185                 190

Phe Lys Asp Leu Leu Tyr Val Asp Gly Ser Ser Thr Gly Thr Thr
                195                 200                 205

Gly His Leu Arg Met Gln Gly Arg Glu Val Phe Arg His Ala Val Glu
                210                 215                 220

Lys Leu Ala Glu Thr Ala His Thr Ala Leu Glu Lys Ala Gly Leu Gly
225                 230                 235                 240

Ala Gly Asp Val Asp Trp Ile Val Pro His Gln Ala Asn Leu Arg Ile
                245                 250                 255

Ile Ser Ala Thr Ala Gln Arg Met Gln Val Pro Met Asp Arg Val Ile
                260                 265                 270

Leu Thr Val Gln Asp His Gly Asn Thr Ser Ala Ala Ser Ile Pro Leu
                275                 280                 285

Ala Leu Ser Val Gly Lys Ala Arg Gly Gln Ile Lys Glu Gly Asp Leu
                290                 295                 300

Leu Val Thr Glu Ala Ile Gly Gly Gly Leu Ala Trp Gly Ser Val Val
305                 310                 315                 320

Leu Arg Trp

<210> SEQ ID NO 99
<211> LENGTH: 468
<212> TYPE: DNA
<213> ORGANISM: Rhodobacter sphaeroides

<400> SEQUENCE: 99
atgaccgaag ccgcagaagc gacgctctcc gccgatatcc agttgatcca gcggatcatc     60
ccgcaccgtt acccgttcct gctggtggac cgggtgcgcg acatcgtccc gaacaagagc    120
gccgtcggca tcaaatgcgt cacgatgaac gagccgcagt tcacggggca cttccccggc    180
ctgccgatct cccgggcgt gcagatcatc gaggccatgg cgcagacttc ggccgtgctg    240
gtcggcgtct cgatggatct cgccgacaag ggcgccaagg tctatttcat gggcatcgac    300
ggggccaagt tccggcgcaa ggtcgtgccg ggcgacgtgc tcgagatgac cgtcaccgtg    360
aagcgcggcg cggcaaggt ctggaagttc gagggccggg cctccgtcga cggggaactg    420
gccgccgagg cggaattctc cgccatgctc gatttgccga aaggataa              468

<210> SEQ ID NO 100
<211> LENGTH: 155
<212> TYPE: PRT
<213> ORGANISM: Rhodobacter sphaeroides

<400> SEQUENCE: 100

Met Thr Glu Ala Ala Glu Ala Thr Leu Ser Ala Asp Ile Gln Leu Ile
1               5                   10                  15

Gln Arg Ile Ile Pro His Arg Tyr Pro Phe Leu Leu Val Asp Arg Val
                20                  25                  30

Arg Asp Ile Val Pro Asn Lys Ser Ala Val Gly Ile Lys Cys Val Thr
                35                  40                  45

Met Asn Glu Pro Gln Phe Thr Gly His Phe Pro Gly Leu Pro Ile Phe
```

```
            50                  55                  60
Pro Gly Val Gln Ile Ile Glu Ala Met Ala Gln Thr Ser Ala Val Leu
 65                  70                  75                  80

Val Gly Val Ser Met Asp Leu Ala Asp Lys Gly Ala Lys Val Tyr Phe
                 85                  90                  95

Met Gly Ile Asp Gly Ala Lys Phe Arg Arg Lys Val Val Pro Gly Asp
            100                 105                 110

Val Leu Glu Met Thr Val Thr Val Lys Arg Gly Gly Lys Val Trp
        115                 120                 125

Lys Phe Glu Gly Arg Ala Ser Val Asp Gly Glu Leu Ala Ala Glu Ala
    130                 135                 140

Glu Phe Ser Ala Met Leu Asp Leu Pro Lys Gly
145                 150                 155
```

<210> SEQ ID NO 101
<211> LENGTH: 933
<212> TYPE: DNA
<213> ORGANISM: Rhodobacter sphaeroides

<400> SEQUENCE: 101

```
atgatcgatg ccgtcgtgac ctgggtggat ggtgccgatc cggcccatca cgccaagcgc    60
ctgcgtcatc aggggggaggc gggcgttcat caggcggcaa ccgctccgac ccgcttcgcc   120
cattccggcg agatccgctt ctgcgtcctg tccctcctgc gcttctgccc cttcgtcgag   180
cgcatccaca tcgtcaccga cgaccagcat cccgccgtgc tggacccgat cctcgacgat   240
ccgcactggc gggaccgcat cgcggtcgtg atcaccgcg ccatctacgg cgagcatgcc   300
gatctgcttc ccgtcttctc ctcgcgctcg atcgagacga tgatccaccg gatcccgggc   360
ctcgcgccgc gcttcatcta cctcaacgac gacatcttcg tcgggcgccc gctggacgag   420
agccatttct tcgacggaga ccgggccgtc ctgcgcggcc ggatgcagcc ctttcccaat   480
ccgctcgtca cccggctgaa acgctggctg aagcgcgagc ggccgggcta caagaccgcg   540
cagcaggcgg ccgcgcggct gacgggccgg acgagcgact atttcctgac cgagcaccag   600
ccgcatccga tgcaccgcga caggcttgcc agcttctatg cgggcgatcc gcaggcgctg   660
cgccggcagg cgggccaccg ttttccgctcg gcagatcagg tctcgcccat cggcctcgcg   720
aaccatctcg agatcgaggc ccgcgccgtg atcgcgccgc cgctcgacgt gggctacatc   780
cgccccggcc gcccgaccgg cacggccctc gcccggacga tggagcggct ctgcgccaac   840
ggctatgcct cgttctgcgt ccagagtctc gacgccatgt ccgaggccga ccgccgctgc   900
gtgctggagg ggctggagcg ccattacgcc tga                                933
```

<210> SEQ ID NO 102
<211> LENGTH: 310
<212> TYPE: PRT
<213> ORGANISM: Rhodobacter sphaeroides

<400> SEQUENCE: 102

```
Met Ile Asp Ala Val Val Thr Trp Val Asp Gly Ala Asp Pro Ala His
  1               5                  10                  15

His Ala Lys Arg Leu Arg His Gln Gly Glu Ala Gly Val His Gln Ala
                 20                  25                  30

Ala Thr Ala Pro Thr Arg Phe Ala His Ser Gly Glu Ile Arg Phe Cys
             35                  40                  45

Val Leu Ser Leu Leu Arg Phe Cys Pro Phe Val Glu Arg Ile His Ile
         50                  55                  60
```

Val Thr Asp Asp Gln His Pro Ala Val Leu Asp Pro Ile Leu Asp Asp
 65                  70                  75                  80

Pro His Trp Arg Asp Arg Ile Ala Val Val Asp His Arg Ala Ile Tyr
                 85                  90                  95

Gly Glu His Ala Asp Leu Leu Pro Val Phe Ser Ser Arg Ser Ile Glu
            100                 105                 110

Thr Met Ile His Arg Ile Pro Gly Leu Ala Pro Arg Phe Ile Tyr Leu
        115                 120                 125

Asn Asp Asp Ile Phe Val Gly Arg Pro Leu Asp Glu Ser His Phe Phe
130                 135                 140

Asp Gly Asp Arg Ala Val Leu Arg Gly Arg Met Gln Pro Phe Pro Asn
145                 150                 155                 160

Pro Leu Val Thr Arg Leu Lys Arg Trp Leu Lys Arg Glu Arg Pro Gly
                165                 170                 175

Tyr Lys Thr Ala Gln Gln Ala Ala Ala Arg Leu Thr Gly Arg Thr Ser
            180                 185                 190

Asp Tyr Phe Leu Thr Glu His Gln Pro His Pro Met His Arg Asp Arg
        195                 200                 205

Leu Ala Ser Phe Tyr Ala Gly Asp Pro Gln Ala Leu Arg Arg Gln Ala
210                 215                 220

Gly His Arg Phe Arg Ser Ala Asp Gln Val Ser Pro Ile Gly Leu Ala
225                 230                 235                 240

Asn His Leu Glu Ile Glu Ala Arg Ala Val Ile Ala Pro Pro Leu Asp
                245                 250                 255

Val Gly Tyr Ile Arg Pro Gly Arg Pro Thr Gly Thr Ala Leu Ala Arg
            260                 265                 270

Thr Met Glu Arg Leu Cys Ala Asn Gly Tyr Ala Ser Phe Cys Val Gln
        275                 280                 285

Ser Leu Asp Ala Met Ser Glu Ala Asp Arg Arg Cys Val Leu Glu Gly
290                 295                 300

Leu Glu Arg His Tyr Ala
305                 310

<210> SEQ ID NO 103
<211> LENGTH: 2262
<212> TYPE: DNA
<213> ORGANISM: Rhodobacter sphaeroides

<400> SEQUENCE: 103

| | |
|---|---|
| gtgcggactg ctgtgcgcag caacacctgg atcaagctcg cgcgcctgcg caggcagcgg | 60 |
| cgattccaga cggcgatggc cttcggcctc gtcctgctgg ggccggtgct ggcgctggcg | 120 |
| accttccttg cattggggcc gatgaatcag ggggcgaatt cgccctcgct gcgattcgtg | 180 |
| ctgctggccg atctggtcta cgtcctcgcg gtggcggcgc tggtgatcgc gcggatcgcc | 240 |
| cgcatggtct cggaccggcg cagccagtcg gcgggctcgc ggctgcatct gcggctggtg | 300 |
| ggcaccttcg cggggctcgc gctcgtgccc accatcctcg tcgcggtctt cgcgatgctc | 360 |
| acggtgaacg tgggtctgga gggctggttc tctgagcggg tcggcaggt ggtgggggcc | 420 |
| tcgctcgagg cagccgaggc ctatcaggaa gagcaccgcc gcgatctgat cgaggatgcc | 480 |
| gaggcgctgg cggcctatct caacgtggcc aagcaatcga ccttcttcct gcgcgacgac | 540 |
| cagctgcggc gcttctcac gcagggacag gagaagatcc agcgcggcct gcgcgaggcc | 600 |
| ttcctgatcg atggcagcgg cgtgctccgc acccggggcg aacgcagcta tctcttcgat | 660 |

```
ttcgagcagc ccgatgccac cgacatcgag cgggcgcgcg cgggccagac ggtcctgatc      720
caggactggg ccaacaacga attccgcgcc ctcgtccatc tcacggcctt ccccgaccgc      780
ttcctctatg tctcgcgcac ggtggacggc tcgatcctga gcctgctcga cgatacgcgc      840
gagacggtgg tgctctatca tcagctggaa gccgagcgcg gcggatgct gttcgagttc       900 gggctgctct acctcggctt cgcgctgatc ctgatccttg ccgccgtctg gctggggttc      960
tggttcgccg agcggctgtc gcgccccgtg gggcggctcg caggggctgc gcagcgcgtg     1020
ggtgcgggcg atctcgacgt gcaggtgccc gaggaggagg cgacgacga gatcgcgatg     1080 ctgggccggc tcttcaacca gatgacccgg cagctgaagg ccagcgcga cgcgctgatg      1140 gacaacaacc gccagaccga gcggcggcgg cggctgttcg actcggtgct ctcctcggtc     1200
acggcggggg tgatcgggct cgacgcggtg gggcaggtcg atttcatcaa ccgcgccgcc     1260
cagcggctgc tcgaactgcc gcaggcgggc aacatgtccc tgtccaccgc cgtgccggag     1320
ttcgcggccc tcttcgcgcg gctgcgcgag acggggcgg ccgtgcagga ggagatccgc      1380
ctgatccgca agggccggat ggagagcctt ctcgtccgca tgagcccgcg cgcaacgag      1440 agcggccggc tcgaaggcta tgtggtggcc ttcgacgacg tgaccgacct cgtctcggcg     1500
cagcggatgg ccgcctgggg cgacgtgcg cggcgcatcg cgcatgagat caagaacccg      1560
ctgacgccga tccagctctc ggccgagcgg atcaagcgca agttccgccc gctcgtgggc     1620
gagcaggcgg cgatctcgga ccaatattcc gatgtcatca tccgccagac caacgatctg     1680
cgccgtatcg tggacgaatt ctcgaaattc gcccggatgc ccgagcccga ccggcgcgag     1740
gcggatctcg tgaagctcgt ccgcgacgcg gtggtgctgc aggaggcggg ccagcccgag     1800
gtgcggatcg aggcgcggct gccgtcggat ccctggccca tcgacatcga cacgaccatg     1860
atcgggcagg ccttgaccaa cctgatgaag aacgcgggcg aggcgatcga ggcccgccgc     1920
gaggcggaag gtcaggggtt cgaacccgag atccgcgtct cgcttacggt caacgaggat     1980
caggcgctgc tgcgcatcgc cgacaatggc acggggcttc cgcccgaccg gacgcggctc     2040
ttcgaaccct atgtcaccac gcgtgagaag ggcaccggcc tcggcctgcc catcgtgaag     2100
aagatcatcg aggaacatgg cggcatcctg acgctcagcg atgccgaccc cttcaccat     2160 gacggccacc gcggggccat ggccgagatc cggctgcccc gcatcctgcg cagccgggcg     2220
cgggccgcga agaccggcga ggcgagaccg gaggacacat ga                       2262
```

<210> SEQ ID NO 104
<211> LENGTH: 753
<212> TYPE: PRT
<213> ORGANISM: Rhodobacter sphaeroides

<400> SEQUENCE: 104

```
Met Arg Thr Ala Val Arg Ser Asn Thr Trp Ile Lys Leu Ala Arg Leu
1               5                   10                  15

Arg Arg Gln Arg Arg Phe Gln Thr Ala Met Ala Phe Gly Leu Val Leu
            20                  25                  30

Leu Gly Pro Val Leu Ala Leu Ala Thr Phe Leu Ala Leu Gly Pro Met
        35                  40                  45

Asn Gln Gly Ala Asn Ser Pro Ser Leu Arg Phe Val Leu Leu Ala Asp
    50                  55                  60

Leu Val Tyr Val Leu Ala Val Ala Ala Leu Val Ile Ala Arg Ile Ala
65                  70                  75                  80

Arg Met Val Ser Asp Arg Arg Ser Gln Ser Ala Gly Ser Arg Leu His
                85                  90                  95
```

```
Leu Arg Leu Val Gly Thr Phe Ala Gly Leu Ala Leu Val Pro Thr Ile
            100                 105                 110

Leu Val Ala Val Phe Ala Met Leu Thr Val Asn Val Gly Leu Glu Gly
            115                 120                 125

Trp Phe Ser Glu Arg Val Arg Gln Val Val Gly Ala Ser Leu Glu Ala
130                 135                 140

Ala Glu Ala Tyr Gln Glu Glu His Arg Arg Asp Leu Ile Glu Asp Ala
145                 150                 155                 160

Glu Ala Leu Ala Ala Tyr Leu Asn Val Ala Lys Gln Ser Thr Phe Phe
                165                 170                 175

Leu Arg Asp Asp Gln Leu Arg Pro Leu Leu Thr Gln Gly Gln Glu Lys
            180                 185                 190

Ile Gln Arg Gly Leu Arg Glu Ala Phe Leu Ile Asp Gly Ser Gly Val
            195                 200                 205

Leu Arg Thr Arg Gly Glu Arg Ser Tyr Leu Phe Asp Phe Glu Gln Pro
            210                 215                 220

Asp Ala Thr Asp Ile Glu Arg Ala Arg Ala Gly Gln Thr Val Leu Ile
225                 230                 235                 240

Gln Asp Trp Ala Asn Asn Glu Phe Arg Ala Leu Val His Leu Thr Ala
                245                 250                 255

Phe Pro Asp Arg Phe Leu Tyr Val Ser Arg Thr Val Asp Gly Ser Ile
            260                 265                 270

Leu Ser Leu Leu Asp Asp Thr Arg Glu Thr Val Val Leu Tyr His Gln
            275                 280                 285

Leu Glu Ala Glu Arg Gly Arg Met Leu Phe Glu Phe Gly Leu Leu Tyr
            290                 295                 300

Leu Gly Phe Ala Leu Ile Leu Ile Leu Ala Ala Val Trp Leu Gly Phe
305                 310                 315                 320

Trp Phe Ala Glu Arg Leu Ser Arg Pro Val Gly Arg Leu Ala Gly Ala
                325                 330                 335

Ala Gln Arg Val Gly Ala Gly Asp Leu Asp Val Gln Val Pro Glu Glu
            340                 345                 350

Glu Gly Asp Asp Glu Ile Ala Met Leu Gly Arg Leu Phe Asn Gln Met
            355                 360                 365

Thr Arg Gln Leu Lys Gly Gln Arg Asp Ala Leu Met Asp Asn Asn Arg
            370                 375                 380

Gln Thr Glu Arg Arg Arg Leu Phe Asp Ser Val Leu Ser Ser Val
385                 390                 395                 400

Thr Ala Gly Val Ile Gly Leu Asp Ala Val Gly Gln Val Asp Phe Ile
                405                 410                 415

Asn Arg Ala Ala Gln Arg Leu Leu Glu Leu Pro Gln Ala Gly Asn Met
            420                 425                 430

Ser Leu Ser Thr Ala Val Pro Glu Phe Ala Ala Leu Phe Ala Arg Leu
            435                 440                 445

Arg Glu Thr Gly Ala Ala Val Gln Glu Glu Ile Arg Leu Ile Arg Lys
            450                 455                 460

Gly Arg Met Glu Ser Leu Leu Val Arg Met Ser Pro Arg Arg Asn Glu
465                 470                 475                 480

Ser Gly Arg Leu Glu Gly Tyr Val Val Ala Phe Asp Asp Val Thr Asp
                485                 490                 495

Leu Val Ser Ala Gln Arg Met Ala Ala Trp Gly Asp Val Ala Arg Arg
            500                 505                 510
```

```
Ile Ala His Glu Ile Lys Asn Pro Leu Thr Pro Ile Gln Leu Ser Ala
515                 520                 525

Glu Arg Ile Lys Arg Lys Phe Arg Pro Leu Val Gly Glu Gln Ala Gly
530                 535                 540

Asp Leu Asp Gln Tyr Ser Asp Val Ile Ile Arg Gln Thr Asn Asp Leu
545                 550                 555                 560

Arg Arg Ile Val Asp Glu Phe Ser Lys Phe Ala Arg Met Pro Glu Pro
                565                 570                 575

Asp Arg Arg Glu Ala Asp Leu Val Lys Leu Val Arg Asp Ala Val Val
                580                 585                 590

Leu Gln Glu Ala Gly Gln Pro Glu Val Arg Ile Glu Ala Arg Leu Pro
            595                 600                 605

Ser Asp Pro Trp Pro Ile Asp Ile Asp Thr Thr Met Ile Gly Gln Ala
610                 615                 620

Leu Thr Asn Leu Met Lys Asn Ala Gly Glu Ala Ile Glu Ala Arg Arg
625                 630                 635                 640

Glu Ala Glu Gly Gln Gly Phe Gly Pro Glu Ile Arg Val Ser Leu Thr
                645                 650                 655

Val Asn Glu Asp Gln Ala Leu Leu Arg Ile Ala Asp Asn Gly Thr Gly
                660                 665                 670

Leu Pro Pro Asp Arg Thr Arg Leu Phe Glu Pro Tyr Val Thr Thr Arg
            675                 680                 685

Glu Lys Gly Thr Gly Leu Gly Leu Pro Ile Val Lys Lys Ile Ile Glu
            690                 695                 700

Glu His Gly Gly Ile Leu Thr Leu Ser Asp Ala Asp Pro Phe Thr His
705                 710                 715                 720

Asp Gly His Arg Gly Ala Met Ala Glu Ile Arg Leu Pro Arg Ile Leu
                725                 730                 735

Arg Ser Arg Ala Arg Ala Ala Lys Thr Gly Glu Ala Arg Pro Glu Asp
                740                 745                 750
Thr

<210> SEQ ID NO 105
<211> LENGTH: 1431
<212> TYPE: DNA
<213> ORGANISM: Rhodobacter sphaeroides

<400> SEQUENCE: 105
atgagcagca ttctgatcgt cgatgacgag cgcgacatcc gcgagctgat cggggacatc      60
ctgcgcgacg agggcttcca gatccgcctc gccgccaatt ccgacgagtg catggcggcg     120
gtgaatgccg agccgccggc gctgatgatc ctcgacatct ggctcaagga cagccggatg     180
gacgggatcg acatcctgaa cgcaccaag cgcgacaatc ccgacgtgcc ggtggtcatc     240
atctcggggc acggcaacat cgagatcgcg gtggcggcga tcaagcaggg cgcctacgac     300
ttcatcgaga agcccttcaa catcgaccag ctcatggtgg tggtccagcg cgcgatggag     360
acggcgcgtc tgcggcgcga aacagcgag ctgcgccggc gcgacgtctc ggcggccgag     420
atgctgggcg gctcgaccgc ctaccggctg ctgaagtcgc agctcgagaa ggtcaccaag     480
tcgaacgggc gcgtcatgct ctcagggccc gcgggcgccg ggaaagagct ggccgcgcgc     540
ttcatccacg ccaattcggg ccgggcaggg gcgcccttca tctcggtctc ctcggccacc     600
gtcgagcccg accggatgga ggaggtcctc ttcggccgcg agacggccga gcgcgggatc     660
gagcaggggc tgctcgagca ggcgcacggc ggcatcgtct atttcgacga ggtggcggac     720
```

```
atgccgctcg gcacccagtc gaagatcctg cgcgtgctga ccgaacagca attcacccgg    780
cagggcggca ccgacaaggt gcgggtcgac ctgcgggtga tctcttcgac gacgcgcgac    840
ctgcgcaccg agatcgccgc gggccgcttc cggcaggaac tttacgaccg gctgaacgtg    900
gtgccgatcg aggtgccggc gctgaccgac cggcgcgagg atattccgat gctggcccgg    960
cacttcatcg agatgttcca ccgcagtcag ggcctgccgc tgcgcagcct cacctccgag   1020
gccgaggcaa tgctccagac gatgccgtgg ccgggcaacg tgcgccagct gcgcaacgtg   1080
atcgagcggg tgctgatcct cggcgacgga tcgggcccca tcgaggcgcg cgagctgccg   1140
ggcaacgagg gcccgggcga ggaggggcgg ctgatcctcg gcggggcgct cgccacgctc   1200
ccgcttcgag aggcacgcga gctcttcgag gcgaatatc ttctcaccca gatcaaccgc   1260
ttcggcggga acatcagccg cacggcggcc tttgtcggga tggaacgctc ggccctgcac   1320
cgcaagctga agtcgctggg cgtggtgacc accgcgaagg gaggcagccg gcttgcccga   1380
atcgaggacg attacgagga cgaggaggag ccgctcgggg cgccggattg a             1431
```

<210> SEQ ID NO 106
<211> LENGTH: 476
<212> TYPE: PRT
<213> ORGANISM: Rhodobacter sphaeroides

<400> SEQUENCE: 106

```
Met Ser Ser Ile Leu Ile Val Asp Asp Glu Arg Asp Ile Arg Glu Leu
1               5                   10                  15

Ile Gly Asp Ile Leu Arg Asp Glu Gly Phe Gln Ile Arg Leu Ala Ala
            20                  25                  30

Asn Ser Asp Glu Cys Met Ala Ala Val Asn Ala Glu Pro Pro Ala Leu
        35                  40                  45

Met Ile Leu Asp Ile Trp Leu Lys Asp Ser Arg Met Asp Gly Ile Asp
    50                  55                  60

Ile Leu Lys Arg Thr Lys Arg Asp Asn Pro Asp Val Pro Val Val Ile
65                  70                  75                  80

Ile Ser Gly His Gly Asn Ile Glu Ile Ala Val Ala Ala Ile Lys Gln
                85                  90                  95

Gly Ala Tyr Asp Phe Ile Glu Lys Pro Phe Asn Ile Asp Gln Leu Met
            100                 105                 110

Val Val Val Gln Arg Ala Met Glu Thr Ala Arg Leu Arg Arg Glu Asn
        115                 120                 125

Ser Glu Leu Arg Arg Arg Asp Val Ser Ala Ala Glu Met Leu Gly Gly
    130                 135                 140

Ser Thr Ala Tyr Arg Leu Leu Lys Ser Gln Leu Glu Lys Val Thr Lys
145                 150                 155                 160

Ser Asn Gly Arg Val Met Leu Ser Gly Pro Ala Gly Ala Gly Lys Glu
                165                 170                 175

Leu Ala Ala Arg Phe Ile His Ala Asn Ser Gly Arg Ala Gly Ala Pro
            180                 185                 190

Phe Ile Ser Val Ser Ser Ala Thr Val Glu Pro Asp Arg Met Glu Glu
        195                 200                 205

Val Leu Phe Gly Arg Glu Thr Ala Glu Arg Gly Ile Glu Gln Gly Leu
    210                 215                 220

Leu Glu Gln Ala His Gly Gly Ile Val Tyr Phe Asp Glu Val Ala Asp
225                 230                 235                 240

Met Pro Leu Gly Thr Gln Ser Lys Ile Leu Arg Val Leu Thr Glu Gln
                245                 250                 255
```

```
Gln Phe Thr Arg Gln Gly Gly Thr Asp Lys Val Arg Val Asp Leu Arg
                260                 265                 270

Val Ile Ser Ser Thr Thr Arg Asp Leu Arg Thr Glu Ile Ala Ala Gly
        275                 280                 285

Arg Phe Arg Gln Glu Leu Tyr Asp Arg Leu Asn Val Val Pro Ile Glu
    290                 295                 300

Val Pro Ala Leu Thr Asp Arg Arg Glu Asp Ile Pro Met Leu Ala Arg
305                 310                 315                 320

His Phe Ile Glu Met Phe His Arg Ser Gln Gly Leu Pro Leu Arg Ser
                325                 330                 335

Leu Thr Ser Glu Ala Glu Ala Met Leu Gln Thr Met Pro Trp Pro Gly
            340                 345                 350

Asn Val Arg Gln Leu Arg Asn Val Ile Glu Arg Val Leu Ile Leu Gly
        355                 360                 365

Asp Gly Ser Gly Pro Ile Glu Ala Arg Glu Leu Pro Gly Asn Glu Gly
370                 375                 380

Pro Gly Glu Glu Gly Arg Leu Ile Leu Gly Gly Ala Leu Ala Thr Leu
385                 390                 395                 400

Pro Leu Arg Glu Ala Arg Glu Leu Phe Glu Arg Glu Tyr Leu Leu Thr
                405                 410                 415

Gln Ile Asn Arg Phe Gly Gly Asn Ile Ser Arg Thr Ala Ala Phe Val
            420                 425                 430

Gly Met Glu Arg Ser Ala Leu His Arg Lys Leu Lys Ser Leu Gly Val
        435                 440                 445

Val Thr Thr Ala Lys Gly Gly Ser Arg Leu Ala Arg Ile Glu Asp Asp
450                 455                 460

Tyr Glu Asp Glu Glu Pro Leu Gly Ala Pro Asp
465                 470                 475

<210> SEQ ID NO 107
<211> LENGTH: 1041
<212> TYPE: DNA
<213> ORGANISM: Rhodobacter sphaeroides

<400> SEQUENCE: 107
atgcaggcgc aggatgcaac tcagcttctg gagggtgtgc cgctgcccct cgtgctgatc      60
ggcccggatg agcggatccg ggcggccaac gcgccggcgc agcggctgtt cggcgccgcg     120
agcgtggcgc ggcattatgt gatggcgatg cggcagccgg cgctgctcga tgcgatcgag     180
ggcgcgatcc ggctcgatcg gccggggcgc gcgcgctaca tcatcaccgg accctcgcgg     240
gaggtgacct atcgcgcgac ggtgacgccg gtccgcatcc acggcgagag ctgcgcgctc     300
tgcgccttcg aggacatcac cgagcaggag cagatgggcg cgatccggcg cgacttcgtg     360
gcgaacgtga gccacgaact gcgcacccct ctcacggcgc tcctcggctt catcgagacg     420
ctgcagggcg ctgcgcgcga cgatcccgcg gcacggagcc ggtttctcgg catcatggcg     480
cgggaggcgg gccggatgaa ccggctggtg caggacctcc tgtcgctgag ccgggtggaa     540
tcggaagaga gggtgcggcc gaagaccccg gtggatgtga cggcggtgat cggacaggcc     600
atcgcggcgc tgcgccccat ggccgaggcc gcgggcgtcg agatccagcg tcagggcgag     660
gcggggccga tcctgctgcc gggagacccc gaccagctca cgcaggtctt tcacaacctc     720
atcgagaatg cggtgaaata cggcgcttcg ggcaagcttg tcaccgtcgg gatctcccgc     780
gatgccgagg gcctcgcgcg gctcgggccc cggtgcggga tcgaggtggt ggatcggggc     840
```

```
gaggggatcg acgccatcca tctgccgcgg ctgaccgagc ggttctaccg cgtggacaac    900
caccgctcgc gcgagaaggg cggcaccggg ctgggcctcg ccatcgtgaa gcatatcgtg    960
aaccggcacc gcggccgctt cctcatcgag agcgagctgg ggcagggcag ccgcttcatc   1020
gtgacgctgc ctctggcctg a                                             1041
```

<210> SEQ ID NO 108
<211> LENGTH: 346
<212> TYPE: PRT
<213> ORGANISM: Rhodobacter sphaeroides

<400> SEQUENCE: 108

```
Met Gln Ala Gln Asp Ala Thr Gln Leu Leu Glu Gly Val Pro Leu Pro
1               5                   10                  15

Leu Val Leu Ile Gly Pro Asp Glu Arg Ile Arg Ala Ala Asn Ala Pro
            20                  25                  30

Ala Gln Arg Leu Phe Gly Ala Ala Ser Val Ala Arg His Tyr Val Met
        35                  40                  45

Ala Met Arg Gln Pro Ala Leu Leu Asp Ala Ile Glu Gly Ala Ile Arg
    50                  55                  60

Leu Asp Arg Pro Gly Arg Ala Arg Tyr Ile Ile Thr Gly Pro Ser Arg
65                  70                  75                  80

Glu Val Thr Tyr Arg Ala Thr Val Thr Pro Val Arg Ile His Gly Glu
                85                  90                  95

Ser Cys Ala Leu Cys Ala Phe Glu Asp Ile Thr Glu Gln Glu Gln Met
            100                 105                 110

Gly Ala Ile Arg Arg Asp Phe Val Ala Asn Val Ser His Glu Leu Arg
        115                 120                 125

Thr Pro Leu Thr Ala Leu Leu Gly Phe Ile Glu Thr Leu Gln Gly Ala
    130                 135                 140

Ala Arg Asp Asp Pro Ala Ala Arg Ser Arg Phe Leu Gly Ile Met Ala
145                 150                 155                 160

Arg Glu Ala Gly Arg Met Asn Arg Leu Val Gln Asp Leu Leu Ser Leu
                165                 170                 175

Ser Arg Val Glu Ser Glu Glu Arg Val Arg Pro Lys Thr Pro Val Asp
            180                 185                 190

Val Thr Ala Val Ile Gly Gln Ala Ile Ala Ala Leu Arg Pro Met Ala
        195                 200                 205

Glu Ala Ala Gly Val Glu Ile Gln Arg Gln Gly Glu Ala Gly Pro Ile
    210                 215                 220

Leu Leu Pro Gly Asp Pro Asp Gln Leu Thr Gln Val Phe His Asn Leu
225                 230                 235                 240

Ile Glu Asn Ala Val Lys Tyr Gly Ala Ser Gly Lys Leu Val Thr Val
                245                 250                 255

Gly Ile Ser Arg Asp Ala Glu Gly Leu Ala Arg Leu Gly Pro Ala Val
            260                 265                 270

Arg Ile Glu Val Val Asp Arg Gly Glu Gly Ile Asp Ala Ile His Leu
        275                 280                 285

Pro Arg Leu Thr Glu Arg Phe Tyr Arg Val Asp Asn His Arg Ser Arg
    290                 295                 300

Glu Lys Gly Gly Thr Gly Leu Gly Leu Ala Ile Val Lys His Ile Val
305                 310                 315                 320

Asn Arg His Arg Gly Arg Phe Leu Ile Glu Ser Glu Leu Gly Gln Gly
                325                 330                 335
```

```
Ser Arg Phe Ile Val Thr Leu Pro Leu Ala
        340                 345
```

<210> SEQ ID NO 109
<211> LENGTH: 492
<212> TYPE: DNA
<213> ORGANISM: Rhodobacter sphaeroides

<400> SEQUENCE: 109

```
atgcctcttc aaccggaccc gatcgggaac ctgaacattt ctttcgaaac aaatccggcg    60
ggggcaggta tcggggtgag acgacaggac gcgagcaggc acgggcggcc ttggctgaga   120
ctggtctggg acggcgaaaa gcgggtcgca ccgctgcccg atacggcggg tccatcgcgg   180
ctgagggacg gtcccgccgc catccggctg atcgcgaccg agggcggacc tcccgggccg   240
tcctccatgg ccgagaccgg tctctcgggc ctcaccgcgc tgcttctggc cgatcttgca   300
cccgcggctg tctcggtgcc gctgatcgcg gccgattgcg acgccgtgga tcttctccac   360
cggctgcgcg gctgggcta tgcggggcgc gtgatcgtgc gctgcccgcc gctgcccgcg   420
ccggatctgg tcgagcgcga gctctcccgc catgcggcgg gcctcgccat aaacctcgtg   480
gccggggact ag                                                      492
```

<210> SEQ ID NO 110
<211> LENGTH: 163
<212> TYPE: PRT
<213> ORGANISM: Rhodobacter sphaeroides

<400> SEQUENCE: 110

```
Met Pro Leu Gln Pro Asp Pro Ile Gly Asn Leu Asn Ile Ser Phe Glu
1               5                   10                  15

Thr Asn Pro Ala Gly Ala Gly Ile Gly Val Arg Arg Gln Asp Ala Ser
            20                  25                  30

Arg His Gly Arg Pro Trp Leu Arg Leu Val Trp Asp Gly Glu Lys Arg
        35                  40                  45

Val Ala Pro Leu Pro Asp Thr Ala Gly Pro Ser Arg Leu Arg Asp Gly
    50                  55                  60

Pro Ala Ala Ile Arg Leu Ile Ala Thr Glu Gly Gly Pro Pro Gly Pro
65                  70                  75                  80

Ser Ser Met Ala Glu Thr Gly Leu Ser Gly Leu Thr Ala Leu Leu Leu
                85                  90                  95

Ala Asp Leu Ala Pro Ala Ala Val Ser Val Pro Leu Ile Ala Ala Asp
            100                 105                 110

Cys Asp Ala Val Asp Leu Leu His Arg Leu Arg Gly Leu Gly Tyr Ala
        115                 120                 125

Gly Arg Val Ile Val Arg Cys Pro Pro Leu Pro Ala Pro Asp Leu Val
    130                 135                 140

Glu Arg Glu Leu Ser Arg His Ala Ala Gly Leu Ala Ile Asn Leu Val
145                 150                 155                 160

Ala Gly Asp
```

<210> SEQ ID NO 111
<211> LENGTH: 1344
<212> TYPE: DNA
<213> ORGANISM: Rhodobacter sphaeroides

<400> SEQUENCE: 111

```
gtgctgacgc gacttcatta tcggattcac acgagcctcg aacgcatcct tccggagcgt    60
```

```
cggcttttc ttaaatccga tagcgacacg cgcttcatcc ggctccgacc cgtgacgcag    120
ctcgccgctc tcgccggcgg cacgctcctc gtaagctgga cgatcctcgc cacctccatc    180
gtgctgatgg actcggtgac cgcgggcggc acccgcgacc agacccagcg ccagcaggcg    240
ctctacgaat cccgcctcaa tgccctctcc gccgaccgcg accgccgcgc cgacgaagcc    300
gtgcgcgcgc aggagcggtt caacctcgcg ctcgccgagg tctcgaagat gcagacggcg    360
ctcctcgcca ccgaggatcg ccgcaaggaa ctcgagaccg gcatcgaggt gctgcaggac    420
acgctgatcc gcaccatcaa ggaacgcgac gacgcccgcg aggagtccga gcgcgtgacg    480
gtcgcgctgg ccgaacagac cggctcggcg cgcaccgacg gctcgcggat ggccgatgcc    540
gaggcgacgc tcgaccagct gtcctccacg ctcgcggcca ccgcccgcca gcgtgacgac    600
atggccaatg ccgtgctctt ggccaaggaa gagaccgagg aggtcctgca ggagaaggcc    660
gagcttcagg cgcgcaacga cctcatcttc ggccggctcg aggaagcggt gaccgtctcg    720
atggaaccgc tcgacaagat gttccgcgcc gcgggcctct cgaccgactc gctgctgaag    780
caggtgcgcc gcggctattc gggtcagggc ggcccactct cgaagctgac ggtctcgaca    840
atgggcggcg cgatctcac ccccgaggag cgccgcgcca acgagatcct gaacgggctc    900
gaccgcatga acctctaccg gctcgcggcc accaaggcgc ccttctcgat gccggtcaag    960
accgccttcc gctacacctc gggcttcggc gggcgcaacg acccgttcgg cgcgcggcaac   1020 cgccgccacg agggcatcga catggccggc gcgagcggca gcccgatcta ttccaccgcc   1080
gacggcgtgg tgatccaggc gggcacggcc agcggctatg caaggtcat caagatccgc   1140 cacgagttcg gcatccagac cgtctacggc cacctgtccc gaatccgggt ggagaaggga   1200
caaagggtat cgcgcggcga ccggatcggt gatatgggct caacaggccg gtccaccggc   1260
acccatcttc actatgaggt ccgcgtggac ggctcgcccg tcaacccgat gaccttcatc   1320
aaggcggcga agatgttttt ctaa                                           1344
```

<210> SEQ ID NO 112
<211> LENGTH: 447
<212> TYPE: PRT
<213> ORGANISM: Rhodobacter sphaeroides

<400> SEQUENCE: 112

```
Met Leu Thr Arg Leu His Tyr Arg Ile His Thr Ser Leu Glu Arg Ile
1               5                  10                  15

Leu Pro Glu Arg Arg Leu Phe Leu Lys Ser Asp Ser Asp Thr Arg Phe
            20                  25                  30

Ile Arg Leu Arg Pro Val Thr Gln Leu Ala Ala Leu Ala Gly Gly Thr
        35                  40                  45

Leu Leu Val Ser Trp Thr Ile Leu Ala Thr Ser Ile Val Leu Met Asp
    50                  55                  60

Ser Val Thr Ala Gly Gly Thr Arg Asp Gln Thr Gln Arg Gln Gln Ala
65                  70                  75                  80

Leu Tyr Glu Ser Arg Leu Asn Ala Leu Ser Ala Asp Arg Asp Arg Arg
                85                  90                  95

Ala Asp Glu Ala Val Arg Ala Gln Glu Arg Phe Asn Leu Ala Leu Ala
            100                 105                 110

Glu Val Ser Lys Met Gln Thr Ala Leu Leu Ala Thr Glu Asp Arg Arg
        115                 120                 125

Lys Glu Leu Glu Thr Gly Ile Glu Val Leu Gln Asp Thr Leu Ile Arg
    130                 135                 140
```

```
Thr Ile Lys Glu Arg Asp Asp Ala Arg Glu Glu Ser Glu Arg Val Thr
145                 150                 155                 160

Val Ala Leu Ala Glu Gln Thr Gly Ser Ala Arg Thr Asp Gly Ser Arg
                165                 170                 175

Met Ala Asp Ala Glu Ala Thr Leu Asp Gln Leu Ser Ser Thr Leu Ala
            180                 185                 190

Ala Thr Ala Arg Gln Arg Asp Asp Met Ala Asn Ala Val Leu Leu Ala
        195                 200                 205

Lys Glu Glu Thr Glu Glu Val Leu Gln Glu Lys Ala Glu Leu Gln Ala
    210                 215                 220

Arg Asn Asp Leu Ile Phe Gly Arg Leu Glu Glu Ala Val Thr Val Ser
225                 230                 235                 240

Met Glu Pro Leu Asp Lys Met Phe Arg Ala Ala Gly Leu Ser Thr Asp
                245                 250                 255

Ser Leu Leu Lys Gln Val Arg Arg Gly Tyr Ser Gly Gln Gly Gly Pro
            260                 265                 270

Leu Ser Lys Leu Thr Val Ser Thr Met Gly Gly Asp Leu Thr Pro
        275                 280                 285

Glu Glu Arg Arg Ala Asn Glu Ile Leu Asn Gly Leu Asp Arg Met Asn
    290                 295                 300

Leu Tyr Arg Leu Ala Ala Thr Lys Ala Pro Phe Ser Met Pro Val Lys
305                 310                 315                 320

Thr Ala Phe Arg Tyr Thr Ser Gly Phe Gly Gly Arg Asn Asp Pro Phe
                325                 330                 335

Gly Arg Gly Asn Arg Arg His Glu Gly Ile Asp Met Ala Gly Ala Ser
            340                 345                 350

Gly Ser Pro Ile Tyr Ser Thr Ala Asp Gly Val Val Ile Gln Ala Gly
        355                 360                 365

Thr Ala Ser Gly Tyr Gly Lys Val Ile Lys Ile Arg His Glu Phe Gly
    370                 375                 380

Ile Gln Thr Val Tyr Gly His Leu Ser Arg Ile Arg Val Glu Lys Gly
385                 390                 395                 400

Gln Arg Val Ser Arg Gly Asp Arg Ile Gly Asp Met Gly Ser Thr Gly
                405                 410                 415

Arg Ser Thr Gly Thr His Leu His Tyr Glu Val Arg Val Asp Gly Ser
            420                 425                 430

Pro Val Asn Pro Met Thr Phe Ile Lys Ala Ala Lys Asp Val Phe
        435                 440                 445

<210> SEQ ID NO 113
<211> LENGTH: 1173
<212> TYPE: DNA
<213> ORGANISM: Rhodobacter sphaeroides

<400> SEQUENCE: 113
atgttcgacg ataccacccc gatgatcgag cgcgtccgcg cgatccttcc ccggattgcg    60
gcgaatgcct ccagagcgga ggagatgcgc gaggtgccga aggagaacat cgacctgctc   120
aagagcaccg gcctgcaccg cgccttccag ccgaaggcct atggcgggct cgagatgccg   180
ttgccggact cgagaattg catcgcgctg atcgccaccg cctgcgggtc caccgcctgg   240
gccttctcgc tcctggccga gcacgcgcac cagatcgcgc tctattcgaa gcaattgcag   300
gacgagatct ggcaggacga tcccgacacg gtctgctcct cttcgatcgc ccttacggaa   360
aaagcccagg acgtcgaggg cggcgtccgc ttctcgggcg agttcggctg gtcgtcgggc   420
```

```
tgcgatcacg cgcaatgggc gatccttggc ttcctgcgcg acacgcccga aggcggcaag    480
gtctacagct tcgccatcct tccccgcagc gactatgaga tcaaggacac ctggttcacc    540
gccgggatgc ggggcaccgg ctcgaagacc ctcgtggtca gggacgcctt cgtgcccgag    600
caccggatcg agaccgtgcc ggcgctgatg actctgacct cggcgggcgg cggcctctat    660
cccggaagca ccacctatca tgtgcccttc atctacgtct tcgccagctg cttctccgcc    720
gtgtctctgg gcatcgcgga gcggatgatc cagctttaca ccgagcggac acggaaccgc    780
gtccgcgcct acaccggcgc caaggtgagt cagtccattc ccgcctgcat gcgtctggcg    840
gaaagcacgc atcaggtggc cgcgggccgg gccttcctcg agaagacctg ggaggacatg    900
cgcgaccacg ccgagcgccg cgtctttccg gacgagacca ggatggcctt ctggcggacc    960
aatcaggcct atgcggtgaa gatgttcgtc gctgcggtgg accggctgtt cgaagcgtcc   1020
ggcggatcgt cctggttcga cgatgccgaa gggcagcgcc tgttccgcga cgcgcacatg   1080
actgccgccc acgcctacac cgactacgac atctgcgccc agatcctcgg gcgggcgctg   1140
atggggctgg agcgggatcc ctccctgttc tga                               1173
```

<210> SEQ ID NO 114
<211> LENGTH: 390
<212> TYPE: PRT
<213> ORGANISM: Rhodobacter sphaeroides

<400> SEQUENCE: 114

```
Met Phe Asp Asp Thr Thr Pro Met Ile Glu Arg Val Arg Ala Ile Leu
1               5                   10                  15

Pro Arg Ile Ala Ala Asn Ala Ser Arg Ala Glu Glu Met Arg Glu Val
            20                  25                  30

Pro Lys Glu Asn Ile Asp Leu Leu Lys Ser Thr Gly Leu His Arg Ala
        35                  40                  45

Phe Gln Pro Lys Ala Tyr Gly Gly Leu Glu Met Pro Leu Pro Asp Phe
    50                  55                  60

Glu Asn Cys Ile Ala Leu Ile Ala Thr Ala Cys Gly Ser Thr Ala Trp
65                  70                  75                  80

Ala Phe Ser Leu Leu Ala Glu His Ala His Gln Ile Ala Leu Tyr Ser
                85                  90                  95

Lys Gln Leu Gln Asp Glu Ile Trp Gln Asp Pro Asp Thr Val Cys
            100                 105                 110

Ser Ser Ser Ile Ala Pro Tyr Gly Lys Ala Gln Asp Val Glu Gly Gly
        115                 120                 125

Val Arg Phe Ser Gly Glu Phe Gly Trp Ser Ser Gly Cys Asp His Ala
    130                 135                 140

Gln Trp Ala Ile Leu Gly Phe Leu Arg Asp Thr Pro Glu Gly Gly Lys
145                 150                 155                 160

Val Tyr Ser Phe Ala Ile Leu Pro Arg Ser Asp Tyr Glu Ile Lys Asp
                165                 170                 175

Thr Trp Phe Thr Ala Gly Met Arg Gly Thr Gly Ser Lys Thr Leu Val
            180                 185                 190

Val Arg Asp Ala Phe Val Pro Glu His Arg Ile Glu Thr Val Pro Ala
        195                 200                 205

Leu Met Thr Leu Thr Ser Ala Gly Gly Gly Leu Tyr Pro Gly Ser Thr
    210                 215                 220

Thr Tyr His Val Pro Phe Ile Tyr Val Phe Ala Ser Cys Phe Ser Ala
225                 230                 235                 240
```

Val Ser Leu Gly Ile Ala Glu Arg Met Ile Gln Leu Tyr Thr Glu Arg
            245                 250                 255

Thr Arg Asn Arg Val Arg Ala Tyr Thr Gly Ala Lys Val Ser Gln Ser
        260                 265                 270

Ile Pro Ala Cys Met Arg Leu Ala Glu Ser Thr His Gln Val Ala Ala
    275                 280                 285

Gly Arg Ala Phe Leu Glu Lys Thr Trp Glu Asp Met Arg Asp His Ala
290                 295                 300

Glu Arg Arg Val Phe Pro Asp Glu Thr Arg Met Ala Phe Trp Arg Thr
305                 310                 315                 320

Asn Gln Ala Tyr Ala Val Lys Met Phe Val Ala Val Asp Arg Leu
            325                 330                 335

Phe Glu Ala Ser Gly Gly Ser Ser Trp Phe Asp Asp Ala Glu Gly Gln
            340                 345                 350

Arg Leu Phe Arg Asp Ala His Met Thr Ala Ala His Ala Tyr Thr Asp
        355                 360                 365

Tyr Asp Ile Cys Ala Gln Ile Leu Gly Arg Ala Leu Met Gly Leu Glu
    370                 375                 380

Arg Asp Pro Ser Leu Phe
385                 390

<210> SEQ ID NO 115
<211> LENGTH: 696
<212> TYPE: DNA
<213> ORGANISM: Rhodobacter sphaeroides

<400> SEQUENCE: 115
atgagccgcg tcatcgccat caccggcacg cgcaagggca tcggccgcgc gctggccgag    60
acctatctcg cgcgcggctg gaccgtcgtc ggctgctcgc gcgatgcgag cgacctcacg   120
cacccggcct atcgccacta cacgctcgac gtggccgacg agcgggcggt cgcgggcatg   180
atgcaggatg tgccgccggac gcatggacgg ctcgacgcgc ttctgaacaa tgccggcatc   240
gcctcgatga accatgcgct gctgaccccc ggcagcacgg tcgagcgggt gttcgcgacc   300
aatgtcttcg gcaccttcct gttctgccgc gaggccgcca agctgatggg ccgccgccgc   360
accggccgga tcgtgaactt cgccaccgtg gccacgccgc tcaagctcga gggcgaggcg   420
gtctatgccg cctccaaggc gcggtcgtg tcgctgaccg aggtgctggc gcgcgagctg   480
gcgcccatgg gcatcaccgt caatgccgtg gggccgaccc cggtgcccac cgacctcgtc   540
ggcgccgtgc ccgaggagaa gatgcgcgcg ctgatcgccc ggcaggccat tccgcgctac   600
ggcaagatgg aggatgtgct caacgtctgc gacttcttcc tgcgcgacga atccgatttc   660
gtgaccggcc agacgatcta tctcggaggg gtctga                              696

<210> SEQ ID NO 116
<211> LENGTH: 231
<212> TYPE: PRT
<213> ORGANISM: Rhodobacter sphaeroides

<400> SEQUENCE: 116

Met Ser Arg Val Ile Ala Ile Thr Gly Thr Arg Lys Gly Ile Gly Arg
1               5                   10                  15

Ala Leu Ala Glu Thr Tyr Leu Ala Arg Gly Trp Thr Val Val Gly Cys
            20                  25                  30

Ser Arg Asp Ala Ser Asp Leu Thr His Pro Ala Tyr Arg His Tyr Thr
        35                  40                  45

```
Leu Asp Val Ala Asp Glu Arg Ala Val Ala Gly Met Met Gln Asp Val
 50                  55                  60
Arg Arg Thr His Gly Arg Leu Asp Ala Leu Leu Asn Asn Ala Gly Ile
 65                  70                  75                  80
Ala Ser Met Asn His Ala Leu Leu Thr Pro Gly Ser Thr Val Glu Arg
                 85                  90                  95
Val Phe Ala Thr Asn Val Phe Gly Thr Phe Leu Phe Cys Arg Glu Ala
            100                 105                 110
Ala Lys Leu Met Gly Arg Arg Thr Gly Arg Ile Val Asn Phe Ala
            115                 120                 125
Thr Val Ala Thr Pro Leu Lys Leu Glu Gly Glu Ala Val Tyr Ala Ala
130                 135                 140
Ser Lys Ala Ala Val Val Ser Leu Thr Glu Val Leu Ala Arg Glu Leu
145                 150                 155                 160
Ala Pro Met Gly Ile Thr Val Asn Ala Val Gly Pro Thr Pro Val Pro
                165                 170                 175
Thr Asp Leu Val Gly Ala Val Pro Glu Glu Lys Met Arg Ala Leu Ile
            180                 185                 190
Ala Arg Gln Ala Ile Pro Arg Tyr Gly Lys Met Glu Asp Val Leu Asn
            195                 200                 205
Val Cys Asp Phe Phe Leu Arg Asp Glu Ser Asp Phe Val Thr Gly Gln
210                 215                 220
Thr Ile Tyr Leu Gly Gly Val
225                 230

<210> SEQ ID NO 117
<211> LENGTH: 1230
<212> TYPE: DNA
<213> ORGANISM: Rhodobacter sphaeroides

<400> SEQUENCE: 117
atgcgccgcg tcgtcatcac cgggatcggc atcgtctcgc cgatcgggaa caatgccgcc      60
gaagtggaag cgagcctgcg cgccggccgc tcgggcatct ccttctcgga ggactatgcc     120
caccacggct tccgcagcca gatccacggg atgcccgatc tcgtgctcga ggaccatgtc     180
gacaagcgcg acctgcgctt catgggcgcc ggagccgcct acaacttcat cgcgatggag     240
caggcgatca aggattcggg cctcgaggcc accgaggtct cgaacccgcg caccggtctc     300
gtgatgggct cgggcgggcc gtcgacctcg aacttcttcc aggcccacaa gatcgtcatc     360
gagaagggct cgcccaagcg gatgggtccc ttcatggtga cgcgctgcat gagctcgacc     420
aactcggcct gccttgccac gcccttcaag atcaagggcg tgaactattc gatcacctcg     480
gcctgctcca cctcggccca ttgcatcggc aacggcaccg agctgatcca gatgggcaag     540
caggacatcg tcttcgccgg cggcgggaa gagctcgact ggacgctctc ctgcctcttc     600
gacgcgatgg gggccatgtc gtcgaaatac aacgatgcgc ccgagaccgc ctcgcggccg     660
ttcgacgcca cgcgcgacgg gttcgtgatc gcgggcggcg cggcgtggt cgtgctggaa     720 gagctcgagc atgcgctggc gcgcggcgcg aagatctatg ccgaagtgac cggctacggg     780
gccacctcgg acggggccga catggtggcc cgtcgggcg aaggcggcga gcggtcgatg     840
cggctggcgc tcggcacgct gcccgagggg cgccgggtcg attacatcaa cgcacacggc     900
acctcgacgc ccgcgggcga cgtgaccgag gtgcgcgcga tccggcggat cttcggcgag     960
ggcaaggttc cgccgatctc ctccaccaag tcgctcaccg ccattcgct gggggccacc    1020 ggcgtgcacg aggcgatcta ttcgatcctg atgatgcagg gcgacttcat cgcggcctcg    1080
```

```
gccaacgtga cccagctcga ccccgagatc cagccggacg agatcgccac caccctgcgc    1140
gagggggtcg agatcgactc ggtcctgtcc aacagcttcg gcttcggcgg caccaacgcc    1200
agtctgctcc tgagcaagtt caacaactga                                     1230
```

<210> SEQ ID NO 118
<211> LENGTH: 409
<212> TYPE: PRT
<213> ORGANISM: Rhodobacter sphaeroides

<400> SEQUENCE: 118

```
Met Arg Arg Val Val Ile Thr Gly Ile Gly Ile Val Ser Pro Ile Gly
1               5                   10                  15

Asn Asn Ala Ala Glu Val Glu Ala Ser Leu Arg Ala Gly Arg Ser Gly
            20                  25                  30

Ile Ser Phe Ser Glu Asp Tyr Ala His His Gly Phe Arg Ser Gln Ile
        35                  40                  45

His Gly Met Pro Asp Leu Val Leu Glu Asp His Val Asp Lys Arg Asp
    50                  55                  60

Leu Arg Phe Met Gly Ala Gly Ala Ala Tyr Asn Phe Ile Ala Met Glu
65                  70                  75                  80

Gln Ala Ile Lys Asp Ser Gly Leu Glu Ala Thr Glu Val Ser Asn Pro
                85                  90                  95

Arg Thr Gly Leu Val Met Gly Ser Gly Pro Ser Thr Ser Asn Phe
            100                 105                 110

Phe Gln Ala His Lys Ile Val Ile Glu Lys Gly Ser Pro Lys Arg Met
        115                 120                 125

Gly Pro Phe Met Val Thr Arg Cys Met Ser Ser Thr Asn Ser Ala Cys
    130                 135                 140

Leu Ala Thr Pro Phe Lys Ile Lys Gly Val Asn Tyr Ser Ile Thr Ser
145                 150                 155                 160

Ala Cys Ser Thr Ser Ala His Cys Ile Gly Asn Gly Thr Glu Leu Ile
                165                 170                 175

Gln Met Gly Lys Gln Asp Ile Val Phe Ala Gly Gly Gly Glu Glu Leu
            180                 185                 190

Asp Trp Thr Leu Ser Cys Leu Phe Asp Ala Met Gly Ala Met Ser Ser
        195                 200                 205

Lys Tyr Asn Asp Ala Pro Glu Thr Ala Ser Arg Pro Phe Asp Ala Thr
    210                 215                 220

Arg Asp Gly Phe Val Ile Ala Gly Gly Gly Val Val Leu Glu
225                 230                 235                 240

Glu Leu Glu His Ala Leu Ala Arg Gly Ala Lys Ile Tyr Ala Glu Val
                245                 250                 255

Thr Gly Tyr Gly Ala Thr Ser Asp Gly Ala Asp Met Val Ala Pro Ser
            260                 265                 270

Gly Glu Gly Gly Glu Arg Ser Met Arg Leu Ala Leu Gly Thr Leu Pro
        275                 280                 285

Glu Gly Arg Arg Val Asp Tyr Ile Asn Ala His Gly Thr Ser Thr Pro
    290                 295                 300

Ala Gly Asp Val Thr Glu Val Arg Ala Ile Arg Ile Phe Gly Glu
305                 310                 315                 320

Gly Lys Val Pro Pro Ile Ser Ser Thr Lys Ser Leu Thr Gly His Ser
                325                 330                 335

Leu Gly Ala Thr Gly Val His Glu Ala Ile Tyr Ser Ile Leu Met Met
```

```
                  340              345              350
Gln Gly Asp Phe Ile Ala Ala Ser Ala Asn Val Thr Gln Leu Asp Pro
            355                  360              365

Glu Ile Gln Pro Asp Glu Ile Ala Thr Thr Leu Arg Glu Gly Val Glu
    370                      375                  380

Ile Asp Ser Val Leu Ser Asn Ser Phe Gly Phe Gly Gly Thr Asn Ala
385                  390                  395                  400

Ser Leu Leu Leu Ser Lys Phe Asn Asn
                405
```

<210> SEQ ID NO 119
<211> LENGTH: 510
<212> TYPE: DNA
<213> ORGANISM: Rhodobacter sphaeroides

<400> SEQUENCE: 119

```
atggcggact atccgacgag cttcgacaaa gaggcgctgc tggcttgcgc gcggggcgag    60
ctcttcgggc ctggcaatgc ccagctcccg ttgccgccga tgctgatgat ggaccgcatc   120
accgacattt cggccgatgg cgggctgcat ggcaaggggc atgtcgtggc cgagttcgac   180
atccatcccg acctatggtt cttcgaatgc catttcccgg gcaatccagt catgccgggc   240
tgcctcgggc tcgacgggct ctggcagctc acgggcttca acctcggctg cgcggctgg   300 cagggccagg gcttcgcgct cggcgtgggc gaggtgaagc tctcgggcat ggtccgcccg   360
gaccgcaagc tcgtcaccta ccacgtcgat ttcacccgcg tgatcgaccg ccgcctcaag   420
atgggcgtgg cggacggccg cgtcttcgcc gatggcgaag agatctacag cgtcaaggac   480
atgaaagtcg gtctggccgc tgcggcctga                                   510
```

<210> SEQ ID NO 120
<211> LENGTH: 169
<212> TYPE: PRT
<213> ORGANISM: Rhodobacter sphaeroides

<400> SEQUENCE: 120

```
Met Ala Asp Tyr Pro Thr Ser Phe Asp Lys Glu Ala Leu Leu Ala Cys
1               5                   10                  15

Ala Arg Gly Glu Leu Phe Gly Pro Gly Asn Ala Gln Leu Pro Leu Pro
                20                  25                  30

Pro Met Leu Met Met Asp Arg Ile Thr Asp Ile Ser Ala Asp Gly Gly
            35                  40                  45

Leu His Gly Lys Gly His Val Ala Glu Phe Asp Ile His Pro Asp
        50                  55                  60

Leu Trp Phe Phe Glu Cys His Phe Pro Gly Asn Pro Val Met Pro Gly
65                  70                  75                  80

Cys Leu Gly Leu Asp Gly Leu Trp Gln Leu Thr Gly Phe Asn Leu Gly
                85                  90                  95

Trp Arg Gly Trp Gln Gly Gln Gly Phe Ala Leu Gly Val Gly Glu Val
            100                 105                 110

Lys Leu Ser Gly Met Val Arg Pro Asp Arg Lys Leu Val Thr Tyr His
        115                 120                 125

Val Asp Phe Thr Arg Val Ile Asp Arg Arg Leu Lys Met Gly Val Ala
    130                 135                 140

Asp Gly Arg Val Phe Ala Asp Gly Glu Glu Ile Tyr Ser Val Lys Asp
145                 150                 155                 160

Met Lys Val Gly Leu Ala Ala Ala Ala
```

<210> SEQ ID NO 121
<211> LENGTH: 1161
<212> TYPE: DNA
<213> ORGANISM: Rhodobacter sphaeroides

<400> SEQUENCE: 121

| | |
|---|---|
| atggcagcgg aaccgatcgt gatcgcgggg gcggcgcgga cgccgatggg cgcctttcag | 60 |
| ggtgcgctca agggccggac gggggtcgag ctcggcgcgg cggcgatctc ggccgcgctc | 120 |
| gcgcgggcgg gcctcgcccc cgaggcggtc gaggaggtcg tgatgggctg cgtgctgccc | 180 |
| gcgggcctcg ggcaggcgcc ggcgcggcag gcggctctgg gcgcggggct gccgctctcg | 240 |
| gtgccctgcg ctacgctgaa caaggtctgc ggctcgggga tgaaggccgc catggccgcg | 300 |
| catgacatga tccgggcggg cagcgcgggc atcgtcgtcg cgggcggtat ggagagcatg | 360 |
| tcgaacgcgc cctatctgct cgacaaggcg cgcggcggct accggatcgg catgggcgc | 420 |
| gtgctggacc acatgttcct cgacgggctc gaggatgcct acgaccgcgg ccgcgccatg | 480 |
| ggcaccttcg ccgaggattg cgccgaggcc taccagttca cccgcgacgc gcaggatgcc | 540 |
| tatgcgctgc cctcgctggc ccgggcgcag gcggccattg ccgaggggcg cttcgcggcc | 600 |
| gaggtggtgg cagtggacgg ggtggcggtt gacgaggccc cgggccgcgc ccgccccgag | 660 |
| aagatccccc agctcaggcc cgccttccgc gagggcggca cggtgacggc ggccaacagc | 720 |
| tcctcgatct cggacggggc ggcggcgctc gtgatcgcct cggccggcgc ggccgaggcg | 780 |
| caggggctga ccccgctcgc cacgatccgc ggccatgcaa gccatgcgca ggcgccgaac | 840 |
| cttttttacca cggcgccgat cttcgccatc gggaagcttc tcgagcggtt gggctggagc | 900 |
| gcggccgagc tcgatctctt cgagatcaac gaggctttcg cagtggtggc catggccgcg | 960 |
| atgcgcgacc tagacctgcc ccacgacaag gtcaatgtga acggcggcgc ctgcgcgctc | 1020 |
| ggccatccga tcggctgctc gggggcgcgg atcgtggtga ctttgatcga ggcgctgcgg | 1080 |
| gcgcggggat tgagacgcgg cgtggcctcg ctctgcatcg gcgcggcgga ggcgacggcg | 1140 |
| ctggcggtgg aggtgatctg a | 1161 |

<210> SEQ ID NO 122
<211> LENGTH: 386
<212> TYPE: PRT
<213> ORGANISM: Rhodobacter sphaeroides

<400> SEQUENCE: 122

Met Ala Ala Glu Pro Ile Val Ile Ala Gly Ala Ala Arg Thr Pro Met
1               5                   10                  15

Gly Ala Phe Gln Gly Ala Leu Lys Gly Arg Thr Gly Val Glu Leu Gly
                20                  25                  30

Ala Ala Ala Ile Ser Ala Ala Leu Ala Arg Ala Gly Leu Ala Pro Glu
            35                  40                  45

Ala Val Glu Glu Val Val Met Gly Cys Val Leu Pro Ala Gly Leu Gly
        50                  55                  60

Gln Ala Pro Ala Arg Gln Ala Ala Leu Gly Ala Gly Leu Pro Leu Ser
65                  70                  75                  80

Val Pro Cys Ala Thr Leu Asn Lys Val Cys Gly Ser Gly Met Lys Ala
                85                  90                  95

Ala Met Ala Ala His Asp Met Ile Arg Ala Gly Ser Ala Gly Ile Val
            100                 105                 110

Val Ala Gly Gly Met Glu Ser Met Ser Asn Ala Pro Tyr Leu Leu Asp
            115                 120                 125

Lys Ala Arg Gly Gly Tyr Arg Ile Gly His Gly Arg Val Leu Asp His
        130                 135                 140

Met Phe Leu Asp Gly Leu Glu Asp Ala Tyr Asp Arg Gly Arg Ala Met
145                 150                 155                 160

Gly Thr Phe Ala Glu Asp Cys Ala Glu Ala Tyr Gln Phe Thr Arg Asp
                165                 170                 175

Ala Gln Asp Ala Tyr Ala Leu Ala Ser Leu Ala Arg Ala Gln Ala Ala
            180                 185                 190

Ile Ala Glu Gly Arg Phe Ala Ala Glu Val Val Ala Val Asp Gly Val
        195                 200                 205

Ala Val Asp Glu Ala Pro Gly Arg Ala Arg Pro Glu Lys Ile Pro Gln
210                 215                 220

Leu Arg Pro Ala Phe Arg Glu Gly Gly Thr Val Thr Ala Ala Asn Ser
225                 230                 235                 240

Ser Ser Ile Ser Asp Gly Ala Ala Leu Val Ile Ala Ser Ala Gly
                245                 250                 255

Ala Ala Glu Ala Gln Gly Leu Thr Pro Leu Ala Thr Ile Arg Gly His
            260                 265                 270

Ala Ser His Ala Gln Ala Pro Asn Leu Phe Thr Thr Ala Pro Ile Phe
        275                 280                 285

Ala Ile Gly Lys Leu Leu Glu Arg Leu Gly Trp Ser Ala Ala Glu Val
        290                 295                 300

Asp Leu Phe Glu Ile Asn Glu Ala Phe Ala Val Val Ala Met Ala Ala
305                 310                 315                 320

Met Arg Asp Leu Asp Leu Pro His Asp Lys Val Asn Val Asn Gly Gly
                325                 330                 335

Ala Cys Ala Leu Gly His Pro Ile Gly Cys Ser Gly Ala Arg Ile Val
            340                 345                 350

Val Thr Leu Ile Glu Ala Leu Arg Ala Arg Gly Leu Arg Arg Gly Val
        355                 360                 365

Ala Ser Leu Cys Ile Gly Gly Gly Glu Ala Thr Ala Leu Ala Val Glu
370                 375                 380

Val Ile
385

<210> SEQ ID NO 123
<211> LENGTH: 693
<212> TYPE: DNA
<213> ORGANISM: Rhodobacter sphaeroides

<400> SEQUENCE: 123
atgccggatt tcctcccgt cgagccgcgc ccggcgcgcc gcttcaccga aaccgagcgt      60
caggcgctcc atgacatcat cgccgagagg cgcgacgtgc gcgacgagtt cctgccggat    120
ccggtggatc cgaggcgct gcgccgggtg ctcgaggccg cgcaccgcgc gccctcggtg    180
ggcttcatgc agccgtggaa cttcctcctg atccgcgatg ccgcgcgcag ggccgaggtc    240
cacaaggcct tccgccgcgc caacgacgag gcggcgctgc tcttcccccga ggagaagcgc    300 gacacctacc gcgcgctgaa gctgcagggc atcctgaagg cgccgctcaa catctgcgtc    360
acctgcgacc gcgaccgctg cggcgaggtg gtgctggggc ggaccccacaa tcccgagatg    420 gatctctatt cgaccgtctg cgcggtgcag aacctctggc tcgccgcgcg ggccgagggg    480
ctgggcgtgg gctgggtcag catctaccgc gaggaggagc tgcggcgat cctcggcatc    540 cccgagcgcg tcaagatcgt ggcctatctc tgcgtgggcc atgtggaccg cttctacagc    600
gcgccggaac tggccttgaa gggttggcgt cagcggctgc cgctcgacga tctgctcatg    660
gaggaaggct ggcaggccga ccgcgctttg tga    693

<210> SEQ ID NO 124
<211> LENGTH: 230
<212> TYPE: PRT
<213> ORGANISM: Rhodobacter sphaeroides

<400> SEQUENCE: 124

Met Pro Asp Phe Pro Pro Val Glu Pro Arg Pro Ala Arg Arg Phe Thr
1               5                   10                  15

Glu Thr Glu Arg Gln Ala Leu His Asp Ile Ile Ala Glu Arg Arg Asp
            20                  25                  30

Val Arg Asp Glu Phe Leu Pro Asp Pro Val Asp Pro Glu Ala Leu Arg
        35                  40                  45

Arg Val Leu Glu Ala Ala His Arg Ala Pro Ser Val Gly Phe Met Gln
    50                  55                  60

Pro Trp Asn Phe Leu Leu Ile Arg Asp Ala Ala Arg Arg Ala Glu Val
65                  70                  75                  80

His Lys Ala Phe Arg Arg Ala Asn Asp Glu Ala Ala Leu Leu Phe Pro
                85                  90                  95

Glu Glu Lys Arg Asp Thr Tyr Arg Ala Leu Lys Leu Gln Gly Ile Leu
            100                 105                 110

Lys Ala Pro Leu Asn Ile Cys Val Thr Cys Asp Arg Asp Arg Cys Gly
        115                 120                 125

Glu Val Val Leu Gly Arg Thr His Asn Pro Glu Met Asp Leu Tyr Ser
    130                 135                 140

Thr Val Cys Ala Val Gln Asn Leu Trp Leu Ala Ala Arg Ala Glu Gly
145                 150                 155                 160

Leu Gly Val Gly Trp Val Ser Ile Tyr Arg Glu Glu Leu Arg Ala
                165                 170                 175

Ile Leu Gly Ile Pro Glu Arg Val Lys Ile Val Ala Tyr Leu Cys Val
            180                 185                 190

Gly His Val Asp Arg Phe Tyr Ser Ala Pro Glu Leu Ala Leu Lys Gly
        195                 200                 205

Trp Arg Gln Arg Leu Pro Leu Asp Asp Leu Leu Met Glu Glu Gly Trp
    210                 215                 220

Gln Ala Asp Arg Ala Leu
225                 230

<210> SEQ ID NO 125
<211> LENGTH: 786
<212> TYPE: DNA
<213> ORGANISM: Rhodobacter sphaeroides

<400> SEQUENCE: 125
atggatctgg catcagagg caagacggcg ctggttctgg gcgcgggcgg gggcctcggc    60
ggcgccatcg cccgctcgct cgcccgcgag ggcgcgcggg tggcgctcgg cgacatcgac    120
ctcgccgcgg ccgaagccac cgccgaggcg atccgggccg agggcggcac ggcgctgccg    180
ctcgcctggg atctggccga cctcggcgcc atcgagacga acgtgagcct gatcgaggcc    240 gagctggggcc cggtcgacat cctcgtgaac aacacggggcg ggccgaagcc ctcgccgatc    300
gccgggcagg aggccgcgct ctggcgcgcg agcttcgagt ccatggtgct ctcggtcatc    360

```
tccatcaccg accgcgtgct gccgggcatg aaggcccgca atgggcccg catcatcacc    420 tcgacctcgt cgggcgtggt ggcgccgatc ccgaacctcg gcctgtcgaa cgcgctgcgc    480
atctcgctcg tgggctggtc gaagacgctc gcgcgcgagg tgggccgcga cggcatcacg    540
gccaacgtcg tgctgcccgg ccgcgtcgcc accaagcgca tcaccttcct cgacgagcag    600
aaggccgcgc gcgaaggccg ggccgtggcc gaagtggccg ccgagagcgt ggcctcgatc    660
ccgctcggcc gctatggtca gcccgaggaa tatggcgatg ccgtggcctt cctcgcctcg    720
gcccgcgcct cctacatcac cggcagcacc atccgcatcg acggcggcct gatcgccagc    780
gtctga                                                               786
```

<210> SEQ ID NO 126
<211> LENGTH: 261
<212> TYPE: PRT
<213> ORGANISM: Rhodobacter sphaeroides

<400> SEQUENCE: 126

```
Met Asp Leu Gly Ile Arg Gly Lys Thr Ala Leu Val Leu Gly Ala Gly
 1               5                  10                  15

Gly Gly Leu Gly Gly Ala Ile Ala Arg Ser Leu Ala Arg Glu Gly Ala
            20                  25                  30

Arg Val Ala Leu Gly Asp Ile Asp Leu Ala Ala Ala Glu Ala Thr Ala
        35                  40                  45

Glu Ala Ile Arg Ala Glu Gly Gly Thr Ala Leu Pro Leu Ala Trp Asp
    50                  55                  60

Leu Ala Asp Leu Gly Ala Ile Glu Thr Asn Val Ser Leu Ile Glu Ala
65                  70                  75                  80

Glu Leu Gly Pro Val Asp Ile Leu Val Asn Asn Thr Gly Gly Pro Lys
                85                  90                  95

Pro Ser Pro Ile Ala Gly Gln Glu Ala Ala Leu Trp Arg Ala Ser Phe
            100                 105                 110

Glu Ser Met Val Leu Ser Val Ile Ser Ile Thr Asp Arg Val Leu Pro
        115                 120                 125

Gly Met Lys Ala Arg Lys Trp Gly Arg Ile Ile Thr Ser Thr Ser Ser
    130                 135                 140

Gly Val Val Ala Pro Ile Pro Asn Leu Gly Leu Ser Asn Ala Leu Arg
145                 150                 155                 160

Ile Ser Leu Val Gly Trp Ser Lys Thr Leu Ala Arg Glu Val Gly Arg
                165                 170                 175

Asp Gly Ile Thr Ala Asn Val Val Leu Pro Gly Arg Val Ala Thr Lys
            180                 185                 190

Arg Ile Thr Phe Leu Asp Glu Gln Lys Ala Ala Arg Glu Gly Arg Ala
        195                 200                 205

Val Ala Glu Val Ala Ala Glu Ser Val Ala Ser Ile Pro Leu Gly Arg
    210                 215                 220

Tyr Gly Gln Pro Glu Glu Tyr Gly Asp Ala Val Ala Phe Leu Ala Ser
225                 230                 235                 240

Ala Arg Ala Ser Tyr Ile Thr Gly Ser Thr Ile Arg Ile Asp Gly Gly
                245                 250                 255

Leu Ile Ala Ser Val
            260
```

<210> SEQ ID NO 127
<211> LENGTH: 1092

```
<212> TYPE: DNA
<213> ORGANISM: Rhodobacter sphaeroides

<400> SEQUENCE: 127
atggctgagc tgcggggcct cgcccccggc ctgtcggtgg tgggctacgg catgtggacg      60
gcgctcgggc cggacggccc cacgacggtc gcgggcctcg acgcccggct gatcgtctcg     120
cagtcgggcg acctgcgcga gcccctgacc ggcgcggccc tcccctgctt ccggctcgcg     180
gcccagcatt ggtgggcggg gccgagcttc ctgtccgaga tgcttctgcc cgtcctcggg     240
gaatgcgccg agcagctggc cgcactgccc gcgccgctcc ggcgaccggc ctcggaggtg     300
ccggtgctga tcgccgtggc cccgtgcggg cgtcccgcac gcccggacga tctcgaggcg     360
cggctgctgg cggagctcga ggcccggctg gggccgctgc ccgaaggcag cgcggtcgtg     420
ggcgccggac gggtgggtct gccgcatctg atcgcgcggg ccgcccgaca ggcgggccgt     480 caccggtgc agatcctgat cggggtcgag agcttccttc tgcaggagat cgtcgatcac     540
tatgccgacc gtcaccggct tttgtccgag gagaacagct cgggcttcgt gccgggcgag     600
gccgcggccg cgctgatcgt ggcgccccgg ggcatggcgc cggtctggc gctgaagggc     660 ctcggcgcgg gccgcgagcc ttcgggtgca ggcggcagcc gcgatgcgcc ggtgacgggc     720
gagggcctca ccgatgcgat ccgcgcggcg ctggcggcgg ccgagatccc gctcttcgac     780
attccgatct ttctcggcga cctgaacggc gagcatttca agttcaagga ggcgatgatc     840
gccacgatgc gcctcgaccg tctgccgccc gagaatgtct cccggcggcc gcggggtcat     900
ccggaacatt ggaacgcgat cgaggggctg gagagatcg gcgcggcgct gatgcccgcg     960
cagctcggct gggccttcga ggcgtcgcgg agcggccggc tgccgcaggg ccgggcgctg    1020
gccttcgccg cgaggacga tggcgcacgg gtggcgatcg tcgccgctgc ggcaggagga    1080
cctgtccggt ga                                                       1092

<210> SEQ ID NO 128
<211> LENGTH: 363
<212> TYPE: PRT
<213> ORGANISM: Rhodobacter sphaeroides

<400> SEQUENCE: 128

Met Ala Glu Leu Arg Gly Leu Ala Pro Gly Leu Ser Val Val Gly Tyr
1               5                   10                  15

Gly Met Trp Thr Ala Leu Gly Pro Asp Gly Pro Thr Thr Val Ala Gly
                20                  25                  30

Leu Asp Ala Arg Leu Ile Val Ser Gln Ser Gly Asp Leu Arg Glu Pro
            35                  40                  45

Leu Thr Gly Ala Ala Leu Pro Cys Phe Arg Leu Ala Ala Gln His Trp
        50                  55                  60

Trp Ala Gly Pro Ser Phe Leu Ser Glu Met Leu Leu Pro Val Leu Gly
65                  70                  75                  80

Glu Cys Ala Glu Gln Leu Ala Ala Leu Pro Ala Pro Leu Arg Arg Pro
                85                  90                  95

Ala Ser Glu Val Pro Val Leu Ile Ala Val Ala Pro Cys Gly Arg Pro
            100                 105                 110

Ala Arg Pro Asp Asp Leu Glu Ala Arg Leu Leu Ala Glu Leu Glu Ala
        115                 120                 125

Arg Leu Gly Pro Leu Pro Glu Gly Ser Ala Val Val Gly Ala Gly Arg
    130                 135                 140

Val Gly Leu Pro His Leu Ile Ala Arg Ala Ala Arg Gln Ala Gly Arg
```

His Pro Val Gln Ile Leu Ile Gly Val Glu Ser Phe Leu Leu Gln Glu
145                 150                 155                 160

Ile Val Asp His Tyr Ala Asp Arg His Arg Leu Leu Ser Glu Glu Asn
            165                 170                 175

Ser Ser Gly Phe Val Pro Gly Glu Ala Ala Ala Leu Ile Val Ala
        180                 185                 190

Pro Arg Gly Met Ala Pro Gly Leu Ala Leu Lys Gly Leu Gly Ala Gly
    195                 200                 205

Arg Glu Pro Ser Gly Ala Gly Gly Ser Arg Asp Ala Pro Val Thr Gly
210                 215                 220

Glu Gly Leu Thr Asp Ala Ile Arg Ala Ala Leu Ala Ala Ala Glu Ile
225                 230                 235                 240

Pro Leu Phe Asp Ile Pro Ile Phe Leu Gly Asp Leu Asn Gly Glu His
                245                 250                 255

Phe Lys Phe Lys Glu Ala Met Ile Ala Thr Met Arg Leu Asp Arg Leu
            260                 265                 270

Pro Pro Glu Asn Val Ser Arg Arg Pro Arg Gly His Pro Glu His Trp
        275                 280                 285

Asn Ala Ile Glu Gly Leu Gly Glu Ile Gly Ala Ala Leu Met Pro Ala
    290                 295                 300

Gln Leu Gly Trp Ala Phe Glu Ala Ser Arg Ser Gly Arg Leu Pro Gln
305                 310                 315                 320

Gly Arg Ala Leu Ala Phe Ala Gly Glu Asp Asp Gly Ala Arg Val Ala
                325                 330                 335

Ile Val Ala Ala Ala Ala Gly Gly Pro Val Arg
            340                 345                 350

355                 360

<210> SEQ ID NO 129
<211> LENGTH: 1968
<212> TYPE: DNA
<213> ORGANISM: Rhodobacter sphaeroides

<400> SEQUENCE: 129
atgaccaacg acctcatccg gcgcagcgac tccgacggga tcgcgcttct gaccctcgcc      60
aacccgccgg tgaacgcgct gagcctcgcg gtgcgccaga ggctcgccgc gctgacggcc     120
gagctcgagg ccgacgagag cgtgcgcgcc gtggtgcttg cggccgaggg ccgggtcttc     180
gtcggcggcg cggacatcgc cgagttcgac cgcccgcccg aggcgccgca cctgcccgat     240
gtgatcgccg ccatcgaggc ctcgcggaag ccgtggatcg cggcgctgaa cggcgcggcc     300
ctcggcggcg gggccgagct tgcgctcggc tgccactacc ggatcttcgc ggataccgcc     360
cggctgggcc tgccggagac gagcctcggc ctcatccccg cgcgggcgg cacgcagcgc      420 ctgccgcgcc ggatcggcct tgctcccgcc atcgaggtca tcaccgccgg ccgcaccctg     480
tcggccgccg aggcgcggga ggcgggcctt cggaccggga tcgccgcggg cgagctgatc     540
cccgaggcgc tggccttcgc ccgcaccctc gacggcgccc tgccctgcc tgcctctgcg      600 gccccgctcg ccgatcccgg gcccgccttc tgggacgagg cccgcgcgcg catcgccagg     660
gcggcccgag gcaatcccgc gcccgccgcg ccctcgaag cgatccgcgc gggcgtggcg      720
gaaggcttcg ccgcgggtct ccgcgccgag cgcgagacct tcctgcggct ccgcgcttcg     780
gacgaagccg cggccctgcg ccatctcttc ttcgccgagc gtgcgcccct gcgcccggcc     840
gcccttcgcg gcatcgagcc tgtgcccctc acccgcgcag gcgtgatcgg cggcggcacg     900

-continued

```
atgggcagcg gcatcgcggc cgccctcgcc gcggccgggc tggaggtgcg tctcactgaa   960
accgggcccg agtcgctcgc ggccggcctc gagcgggtcg aggccatctt cgaggcgcag  1020
gtcaagcgcg ggctgacgga tcgggccggc gcggcggagc ggatggcccg cgtcaccggc  1080
acggtcggtc tcggggcgct ggcggactgc gatctggtga tcgaggcggt cttcgaggat  1140
ctcgccgtca agcgccgggt gttcgaagag ctggtccgtc tttgcgggcc cgaggcgatc  1200
cttgccacca acacctccta cctcgatccc gaacggatcg tggagggcct gccgcacccc  1260
caccgcttca tcgcgctgca tttcttcagc ccggcgcagg tgatgaagct gctcgagatc  1320
gtgccgctgg ccgccaccgc gccgcgcacc ctcgccaccg cgtcgctct ggcggcgcgg  1380
ctcggcaaga tcccggtaca ggcgggcaac ggcgagggtt tcatcggcaa ccgcatcctc  1440
aagcgctacc gcgccgaggc cgaggctctg ctgctcgcag gagccacccc gaccgagatc  1500
gacgaggcca tgcgcgcctt cggcctcggc atgggtccgt cgagatgca ggacatggcc  1560
gggctcgaca tcgccttccg cgcgcgggag gccgcccgcg cgctcgggca ggacctgccc  1620
gaaggccccg agaccggct ggtgcgcgca ggccgcctcg gccgcaagtc gggcggcggc  1680
tggtacgact atgcgccggg cagccgcctt ccccagccgt cgccggaggc agccgctctg  1740
atcgcgcctc tggtgacccc cggccgcgg ccgagcggca ccgagattgc cgaccgcctc  1800
atcgccgcca tggccgagga aggccaacgg atctgcgacg agggcctcgc gcagagcccc  1860
tcggacatcg atctggtcga ggtgcatggc tacggcttcc cccgtcacaa gggggggaccg  1920
atgtttcacg ccgcgcgcaa gacccgaagc cgcacgggcg agcatga              1968
```

<210> SEQ ID NO 130
<211> LENGTH: 655
<212> TYPE: PRT
<213> ORGANISM: Rhodobacter sphaeroides

<400> SEQUENCE: 130

```
Met Thr Asn Asp Leu Ile Arg Arg Ser Asp Ser Asp Gly Ile Ala Leu
1               5                   10                  15

Leu Thr Leu Ala Asn Pro Pro Val Asn Ala Leu Ser Leu Ala Val Arg
            20                  25                  30

Gln Arg Leu Ala Ala Leu Thr Ala Glu Leu Glu Ala Asp Glu Ser Val
        35                  40                  45

Arg Ala Val Val Leu Ala Ala Glu Gly Arg Val Phe Val Gly Gly Ala
    50                  55                  60

Asp Ile Ala Glu Phe Asp Arg Pro Glu Ala Pro His Leu Pro Asp
65                  70                  75                  80

Val Ile Ala Ala Ile Glu Ala Ser Arg Lys Pro Trp Ile Ala Ala Leu
                85                  90                  95

Asn Gly Ala Ala Leu Gly Gly Gly Ala Glu Leu Ala Leu Gly Cys His
            100                 105                 110

Tyr Arg Ile Phe Ala Asp Thr Ala Arg Leu Gly Leu Pro Glu Thr Ser
        115                 120                 125

Leu Gly Leu Ile Pro Gly Ala Gly Gly Thr Gln Arg Leu Pro Arg Arg
    130                 135                 140

Ile Gly Leu Ala Pro Ala Ile Glu Val Ile Thr Ala Gly Arg Thr Leu
145                 150                 155                 160

Ser Ala Ala Glu Ala Arg Glu Ala Gly Leu Ala Asp Arg Ile Ala Ala
                165                 170                 175

Gly Glu Leu Ile Pro Glu Ala Leu Ala Phe Ala Arg Thr Leu Asp Gly
            180                 185                 190
```

```
Ala Leu Pro Leu Pro Ala Ser Ala Ala Pro Leu Ala Asp Pro Gly Pro
        195                 200                 205

Ala Phe Trp Asp Glu Ala Arg Ala Arg Ile Ala Arg Ala Ala Arg Gly
    210                 215                 220

Asn Pro Ala Pro Ala Ala Ala Leu Glu Ala Ile Arg Ala Gly Val Ala
225                 230                 235                 240

Glu Gly Phe Ala Ala Gly Leu Arg Ala Glu Arg Glu Thr Phe Leu Arg
                245                 250                 255

Leu Arg Ala Ser Asp Glu Ala Ala Leu Arg His Leu Phe Phe Ala
            260                 265                 270

Glu Arg Ala Ala Leu Arg Pro Ala Ala Leu Arg Gly Ile Glu Pro Val
        275                 280                 285

Pro Leu Thr Arg Ala Gly Val Ile Gly Gly Thr Met Gly Ser Gly
        290                 295                 300

Ile Ala Ala Ala Leu Ala Ala Gly Leu Glu Val Arg Leu Thr Glu
305                 310                 315                 320

Thr Gly Pro Glu Ser Leu Ala Ala Gly Leu Glu Arg Val Glu Ala Ile
                325                 330                 335

Phe Glu Ala Gln Val Lys Arg Gly Leu Thr Asp Arg Ala Gly Ala Ala
            340                 345                 350

Glu Arg Met Ala Arg Val Thr Gly Thr Val Gly Leu Gly Ala Leu Ala
        355                 360                 365

Asp Cys Asp Leu Val Ile Glu Ala Val Phe Glu Asp Leu Ala Val Lys
    370                 375                 380

Arg Arg Val Phe Glu Glu Leu Val Arg Leu Cys Gly Pro Glu Ala Ile
385                 390                 395                 400

Leu Ala Thr Asn Thr Ser Tyr Leu Asp Pro Glu Arg Ile Val Glu Gly
                405                 410                 415

Leu Pro His Pro His Arg Phe Ile Ala Leu His Phe Phe Ser Pro Ala
            420                 425                 430

Gln Val Met Lys Leu Leu Glu Ile Val Pro Leu Ala Ala Thr Ala Pro
        435                 440                 445

Arg Thr Leu Ala Thr Gly Val Ala Leu Ala Ala Arg Leu Gly Lys Ile
    450                 455                 460

Pro Val Gln Ala Gly Asn Gly Glu Gly Phe Ile Gly Asn Arg Ile Leu
465                 470                 475                 480

Lys Arg Tyr Arg Ala Glu Ala Glu Ala Leu Leu Leu Ala Gly Ala Thr
                485                 490                 495

Pro Thr Glu Ile Asp Glu Ala Met Arg Ala Phe Gly Leu Gly Met Gly
            500                 505                 510

Pro Phe Glu Met Gln Asp Met Ala Gly Leu Asp Ile Ala Phe Arg Ala
        515                 520                 525

Arg Glu Ala Ala Arg Ala Leu Gly Gln Asp Leu Pro Glu Gly Pro Gly
    530                 535                 540

Asp Arg Leu Val Arg Ala Gly Arg Leu Gly Arg Lys Ser Gly Gly Gly
545                 550                 555                 560

Trp Tyr Asp Tyr Ala Pro Gly Ser Arg Leu Pro Gln Pro Ser Pro Glu
                565                 570                 575

Ala Ala Ala Leu Ile Ala Pro Leu Val Thr Pro Gly Pro Arg Pro Ser
            580                 585                 590

Gly Thr Glu Ile Ala Asp Arg Leu Ile Ala Ala Met Ala Glu Glu Gly
        595                 600                 605
```

```
Gln Arg Ile Cys Asp Glu Gly Leu Ala Gln Ser Pro Ser Asp Ile Asp
    610                 615                 620

Leu Val Glu Val His Gly Tyr Gly Phe Pro Arg His Lys Gly Gly Pro
625                 630                 635                 640

Met Phe His Ala Ala Arg Lys Thr Arg Ser Arg Thr Gly Gly Ala
                645                 650                 655
```

<210> SEQ ID NO 131
<211> LENGTH: 753
<212> TYPE: DNA
<213> ORGANISM: Rhodobacter sphaeroides

<400> SEQUENCE: 131

```
atgatgagca tgatcgacca cggacccgat ccgacccaga ctccgattgc cgtcggcgcc      60
atcggcggca gcggcacccg cgtcgtcgcc cgcatcctca aggggggcggg cgtcttcatg     120
gggacgaggc tgaacgagtc ggaagacaat ctggacttca ccgagcgttt ccgccatcgc     180
gaggtgctcg ctttgcccga tggggccttc gaggcgcggc tgcggcagtt cgagggcctg     240
tcgcgcgccg gcatgcgcga ggccgggcag cggcactggg gctggaaaga gcccaacacc     300
catgtggtga tcgaccggat cctcgcggcc tatccgaaga tgcgctatgt ccatctgctg     360
cgcagcgggc tcgacatggc cttctccgcc aaccagcgcc aggcgtggtt ctgggggcct     420
tacttcctcg agcgtcccgt ggccgagccg ccggggccgc gggacatgct ggcctatttc     480
tgcgcggtgc accgccggat cagcgccctg ccgaccggc cggagaaccg tggccgggtg      540
ctgttcctgc agtacgaggc gctctgcgcc cggcccgaag cggagatcgt gcggctgctg     600
gacttcctcg ggctggagcc cgcccagccc gtcgccacgc tggccgccct gatcgcgccc     660
cccgccagca tcggccggca ccgggagcac gatctgtcgg tcttcgatcc ggccgatctg     720
gcctatctca aacagaccca gcccgctccc tga                                  753
```

<210> SEQ ID NO 132
<211> LENGTH: 250
<212> TYPE: PRT
<213> ORGANISM: Rhodobacter sphaeroides

<400> SEQUENCE: 132

```
Met Met Ser Met Ile Asp His Gly Pro Asp Pro Thr Gln Thr Pro Ile
1               5                   10                  15

Ala Val Gly Ala Ile Gly Gly Ser Gly Thr Arg Val Val Ala Arg Ile
                20                  25                  30

Leu Lys Gly Ala Gly Val Phe Met Gly Thr Arg Leu Asn Glu Ser Glu
            35                  40                  45

Asp Asn Leu Asp Phe Thr Glu Arg Phe Arg His Arg Glu Val Leu Ala
        50                  55                  60

Leu Pro Asp Gly Ala Phe Glu Ala Arg Leu Arg Gln Phe Glu Gly Leu
65                  70                  75                  80

Ser Arg Ala Gly Met Arg Glu Ala Gly Gln Arg His Trp Gly Trp Lys
                85                  90                  95

Glu Pro Asn Thr His Val Val Ile Asp Arg Ile Leu Ala Ala Tyr Pro
            100                 105                 110

Lys Met Arg Tyr Val His Leu Leu Arg Ser Gly Leu Asp Met Ala Phe
        115                 120                 125

Ser Ala Asn Gln Arg Gln Ala Trp Phe Trp Gly Pro Tyr Phe Leu Glu
    130                 135                 140

Arg Pro Val Ala Glu Pro Pro Gly Pro Arg Asp Met Leu Ala Tyr Phe
```

```
                145                 150                 155                 160
Cys Ala Val His Arg Arg Ile Ser Ala Leu Ala Asp Arg Pro Glu Asn
                    165                 170                 175

Arg Gly Arg Val Leu Phe Leu Gln Tyr Glu Ala Leu Cys Ala Arg Pro
                180                 185                 190

Glu Ala Glu Ile Val Arg Leu Leu Asp Phe Leu Gly Leu Glu Pro Ala
            195                 200                 205

Gln Pro Val Ala Thr Leu Ala Ala Leu Ile Ala Pro Pro Ala Ser Ile
        210                 215                 220

Gly Arg His Arg Glu His Asp Leu Ser Val Phe Asp Pro Ala Asp Leu
225                 230                 235                 240

Ala Tyr Leu Lys Gln Thr Gln Pro Ala Pro
                245                 250

<210> SEQ ID NO 133
<211> LENGTH: 7890
<212> TYPE: DNA
<213> ORGANISM: Rhodobacter sphaeroides

<400> SEQUENCE: 133
atgccgacag tgaacctgac ctctgccctg accttctccg agggcggcgt gccgcagctc      60
gtcgacccga acatcacgat cacgggcggc ggagccttta ccgaaggcta catcgaattc     120
tcggtcagtt cgcccacggc cggcgacaac ttcagcctga ccagcgccgc caatccgctg     180
gccaacggcg cgatctcgtt cgagaacggc gacgtctatc tcgggaccgg ctcggcccgc     240
gagcggatcg gctcggtcga tgcgaccttc gacggcaggg acggccagcc gctgcgcatc     300
ctgttctcga gcccgctgcc gaacgccggc ttcgaggaag gcgaggcgaa ctggaccatc     360
cgcgacgagc aatatggcga caacggcagc gagctgaacc tcgacggcct gcagatcacg     420
ctggccaatg actcggccta cagcggcggc accggcacga ccaacgtcca ggcctccgcc     480
ggcatgacct gggacgggtc ggtgcaggat ggtgcgggcg ttgacggatc gcgcgccctc     540
tatctcggca gcggcggaaa catcgttgcg ggcgatcaga accggccggc ggctatcag     600 gtcaacggct acggctcgat ccacggcccc tatgccacca gctcggtgat caccgtcgcg     660
cagggtgact cgatctcgct cgactttcag gccgtgggca cgagcgacga ctacgaggtg     720
ttcggcttcc tgcgtcgcgt cgacgccaac ggcaacttcc tgagcaacag cgtcagcagc     780
cccgacaaca tcctgctctt cgcccagcgg ggcgatgaca ccagcgggtg gacgaccatc     840
agcaaggacg gcctgccgc aggcagctac cggttcgagt tcgtcggcgg cacctatgat     900
ggcacgggcg gcctcgcggt gggctcgaac ctctttgtcg acaacatccg cctgatctcg     960
gccacctcgg tgaacgacag catcgcccag gccatcgccc ggcaggtcgc ctaccagaac    1020
gacgccaatg atgcgccggt caccgccag atcacggtca cggccgtgga cggcaacggc    1080
atcagcggct cctcctcgaa cggcctgacc ttcgaaggcg agaacgacgc gccgagcctt    1140
gccaacacca cgctcacctc gatcgccgag acagcagcc ccgccggcca gaccatcgcc    1200
gcagccttcg cggctccctt ctcggatccc gacaacgcct attcccccac cgactcgatg    1260
gcgggcgtcg tcatcaccgg caatgcggcg accggcgccc aaggcgactg gcagtattcg    1320
accgacggcg gcaccacctg gatctcggtc ggcagcgtga cctcgcagag cgggctcgtg    1380
ctttcctcgg ccacgctgat ccgcttcgaa cccgcgctga actggaacgg cacgcccggc    1440
gcgctgacgc tccatgcgct ggacagcacc tatggcggca gcttcaccag cggcacgacg    1500
gcggtgaacc tcgacacgac cggcgccacc ggcaccggcg cgctcagcca gaacagcgcc    1560
```

```
accggctcga tcaccgtcac cccggtcaac gacgccccg tcttcaccgc ggccccggtc    1620
gcgctgacgg ttgccgacac cgaggccgtg gacacgccgg ccgcgctcac cggctcgatc    1680
tcggcctccg acctgcatgg cggtgcgccg ggcgaaggcg gcacgctcag ctacggcgtt    1740
cagggcggcg tgtcggccaa cggcttctcg gttctgacgc tgccctacgg cacgctgtcg    1800
gtgaaccagt cgaccggagc ctacagcttc ctgccgaacc ccacggcgct gaacagcctc    1860
gccgagggtg cagaggcgaa cttctccttc acgctcaccg tctcggacgg gcagggcggc    1920
acgcagaccg cgccgctcga catcaccttc accggcgcca cgacgtgcc ggtcgtcagc    1980
gcccagaccg gcacggcggt cgaggcctcg ggtctcaaca caacgtcgc cggcagcgcg    2040
gccacgggct cgctgctgac cggtccgaat gcggcgaccg atatcgacgg cgacgagatc    2100
tcggtggtgg gtgtgcgcac cggcggccag tccgagaccg gcaccgaagg cgtctggacc    2160
gacggcacga tcacgcttca gggcacctac ggcacgctga cgctgaacga ggacggcagc    2220
tggtcctacg cggccgacga tgacaacccc accgtcgacg gcctgaccgg gccgaccgac    2280
acgctggagg agaccttcac ctacaccgtg acggacgcga acggcgccac cgcgtcgcag    2340
gagctgaccg tcaccatctc gggccgcaac gacgcgctga acgtgtcgag cagcatcggc    2400
accgatatct cgacgggcga ggatgccgac acgcagatcg accttaccgg cctcgtgttc    2460
gaagaccccg atctgggctc ggaaatctac gaattcgccg tggatgcggg ccagggcacg    2520
ctctggaccg aaggtgtgga cgggctgacc gtcaccggca acggaacggg ccagctggtg    2580
ctgaccggct cggccaccgc gatttccgaa tggatcgcgg ccaacgacct gacctaccgc    2640
tcgcccgtgg aaggcagcgg cgccgacacg atcagcctct cctacagcga ggcgggcgcc    2700
gaggtccgca cggcgctcga gtccatcgac gtcgcggtgg acatgatcaa cgacccggcc    2760
gtggtcgatg tgaacggctc ggtcacgacc cagggcagcg ccggcgtggc cgaagtggct    2820
caggtcacct tcctgtcgac cggcaccgct caggtgctga atttcgacgg ggtgcagatg    2880
cagatcgcgg ccggcagcac tgccgccgag attgccgaag ccttcgcggc gcaggagttc    2940
ccgaactgga ccgtcagcct tgacggcgag ggcgggtga cgctgaccgc gaccgccacc    3000
ggcgcgcggc cggacctgac ggcggccgac ttcaccaacg gctcgggcgc cttctcgccg    3060
ctggtcgaga ccaccggcgg caccgacggc agcatcaatt tcaccgcgcg cggaccggcc    3120
atcgccatcc tgccgacgct ggaactgagc gacgtcgaca gcgcgatgat gtcgggcgcc    3180
aaggtcagca tgaccgaagg cctgttcgac aacgggttcg gcacgatcta cgaacggctc    3240
tcgctgtcg cggaggcgcg ggaattcgcg cagcagaacg gcgtgggcat cagcatcgtg    3300
acgacggccg ctgccggctc ggtcatcacc ttcaccggca tggcctcggc ggaggtctac    3360
gagaccatcc tgccgcggcgt gatctacagc aacaccaacc cgaatgcggt ggcgggcacc    3420
cgccccgtga agatcgaagt gaccgactct gacgggctcg cctcgagcct ctccagcgtc    3480
aacctgacag agggcaacac cgacatcgcc gtcggccagc gcatcttcat caacggcgtg    3540
gacagcggcc aggtcgtctc gatggtgcgc gacgccacca gcttcgtggc cagcggcccg    3600
ctggccgatc tggagccggg tgcggtgctg agcttccatg acggcagcgg tcagcagacc    3660
acggcggttt cggcgggcga cggcacggcc acgatggacg tgaacgtgat ctgggctccc    3720
gtgatcgaca tgaacggcgc cggcgcgggc gatatccacc ggacgaccta catcgagcag    3780
catgccccga tcgccatcgc gaccgccgat gcccgcatcg tcgatcagga aggtctgatc    3840
cgctcgctcg acgtcgtgct gaccaacccg ctcgacaatg tcgaaggttc ggctccggtc    3900
```

```
gaatatctcg gcatctcgaa ggcggtgctg gacgtgctgg cggcccgcgg catcaccatc    3960
ggtgcccatg acggccagtt cgacgccaac ggcaacctga ccggcgccac ctcgatcacc    4020
ttcgcggcgg ccaacggcgc cagcgccacc agcttccaga ttgcgctgcg gggcgtgacc    4080
tatgccaaca tggacgatgc cccggacacc gggacgcgga tcgtgacggc gcagggcacc    4140
gacatggacg gcaacgaggg cctgatctcg cacaccgaga tcaacccgat cgcggtgggc    4200
gacgcgccgt ggcgatcga cagcggcgtg accggctccg aagatgcggg ccatgtcttt    4260
gccgccggag acttcggctt tgccgatccg ctggatggcg gcgcgaacca gctcgcctcg    4320
atcaccatca acagcctgcc cgccacgggc acgctgctcc tgggcggggt cgcggtcgcc    4380
gtgggcaccg tggtcaccct cgcgcagctt caggccggcg cgctgaccta tcagccggtg    4440
gccaacgtga acggtgaagg ggtcgccctc g ttcgacttcc tcgtgaccga caacggcagc    4500
ctcgccaacg gcggccagac cacctcgacc gctccggcaa ccatggtgat cgacctgacg    4560
ccggtgaaca atgctccggt cctgccggaa ggcacctccg tcaccggcac cacgatcacc    4620
gaagaccagc agctgaatgc cggtgaactg gtggccgatc tggtcggcgc catgacggat    4680
gtcgatacgg gcgtgcacag cgccacgaac ggcacccagc agggcatcgc ggtttatggc    4740
gcgggctccg aagggttcgg cggcggcacc tggcagtatc gtctcgccgg cggcaccgac    4800
tggatcgacg tcaccctcga tccgggcgag gtcctgctgc tcggtgcgga cgaccgcatc    4860
cgcttctcgc cggatggcga gaacgcgacc gaggcgcagc tgtcctacta cgcctgggac    4920
ggggcgaccg gcaccgcggg caacgtggtc gcaggcatcg cggggccggg caatgcctcg    4980
aaccgtggcg gcacctcggc cttctccagc aacggcgcct ctgccacggt cgaggtgaca    5040
gctgtcaacg acgcgccgtc gatcagcatg ggcgagggca ataccttcta tgctcgcggc    5100
gaggcggtgg cgctgttctc ggacgagacg ctgcaactga ccgacccgga cgagggcgcg    5160
gcggtaagcc agattgtcat cacgctcgat ggcgagacca cggtcgacaa cgccttcggc    5220
accacctacg agacgatctt ctcggccagc ggctcgacct tcgtggccca gtcgggcacc    5280
gaactgacca tctcgggcac cggtgtggcg ggcgatccgc tcaccatctc gggggccggg    5340
tcgatggagg actaccgtga ggcgctcctc agcctgcgct acgagaacac caacccgaac    5400
gccttcgcgg gcgaccgggc gatctcggtc acggtgacgg atgagacggg ggcgggctcc    5460
gcgccgacgg acttcatcct gccggtggaa tgggcaacgg tggccgatct caacggtccg    5520
tcgggcgaag gccgcgacca ctcgatcacc tatctcgagg gcagcggcag ccaggccatc    5580
gctacggccg atgccgagat gatcgaccag gacggcaaca ccgtcgaggt cgtcatcacg    5640
ctcgaggatg cggtgaacgg ctcggccgag atgctgttcg tcgatccggc ggtcctgccg    5700
gctctggcgg cgctgaacat cgtggtcacc ggcaacggca cccacgagat ccggctgacg    5760
agcgaggagg gcgtggatcc cacgaacttc cagctggcgc tgcggccgt gcgttacgtc    5820
aacagctcga ccgcacccac cgcggcgagc cgccatgtca cggtctcctc gaccgatgcc    5880
gacggcaacc cggcgttcc ggccaccacg gtgatcggga tggagctggt gaacgacgca    5940
ccggttgcgg atctctcgat ctcctacgag gcgtccgaga cccgcaaccc gctgtcgggc    6000
gatcagctgc tgctcgacgg cacgctggac gatgccgacg gctcgggcc gaacccgccg    6060
gtcatcgaat ggctgcggga cggtgtggtg atcgcttcgg gcaacggcat gccggtctac    6120
acgctgaaac cggcggatgc aggccatgtc atcagcgccc gcatcaccta caccgacggt    6180
gaaggcaacc tcgaggtcat caacgtcgat ggccccgcca tggtcgggct gaacctcgaa    6240
ggcaccgacg gcgccgatct gctcatcggc tcgcggggcg cggacgtgat ctccggccgg    6300
```

-continued

```
atgttcaacg acacgctgat gggcggggcg ggcaacgaca gcctctacgg caacggtgac      6360
gacgaccgcc tctacgttaa cgagggcaac gacagcctct atggcgagga gggcaacgac      6420
tggctgcatg cggtcaggg cgacgacctg gtcgtgggcg cgacggcaa cgacacgctc       6480 gcgggcggtc tgggcaacga caccctgcag ggtggcgcgg caacgacac ggccagctac       6540 gaaacggcca ccgagggcgt taccgtcagc ctcgcgctgc agggcgaagg ccagttcgtg      6600
aacgcgcagg aaggcaacga cccgctgacc tcgatcgaga acctgacggg cagcaatcac     6660
gacgacacgc tgatcgggga cgagggcgac aacgtgctct cgggtctcgc gggcaacgac     6720
gtgctggtgg gcggcgcggg caatgacacg ctgctcggcg gtgccggcaa cgacatcgcc     6780
gactacgccg cggcgacggg cggggtgacg gtcaatctgg cgcgtgatgg gcaggcgcag     6840
atcatcggcg ccgatcaggg caccgatgtc ctgagctcga tcgagggtgt catcggcagc     6900
gccttcaacg acatcctgtc gggcagcgcg gtcgccaacc tcatcttcgg tggggacggt     6960
gccgacctgg ccaccggtgg cgcgggcaac gacaccatcc tcggcggcgc cggatcggac     7020
agcctctatg caaccttgg ggatgacctc ctctttggtg acgtgggcaa cgactggatc      7080
cacggcggcc agggcaacga caccgtcctc ggcggtttcg gcgacgatac gctggccggc     7140
ggcgtcggtg acgatgtggt ggatggcggc gatgggatcg acaccgtcga gttccagacc     7200
gcaaccgccg tgtcaccgt ggatctctcg ctgcagggtc aggcgcagcg catcagtgcc      7260
gaggaaggca cggatacgct gttctcgatc gagaacatcc tcggcagccg gtatgacgac     7320
cgcctgctgg gcgatgcggg ctccaacttg atcgacggca gtgccggcaa cgacactgcc     7380
atgggtcagg cgggcgagga cctcatcttc ggcggggacg gcaacgacag cctctatggc    7440
aaccaggaca cgacactct ggtcggcggc aacggcaacg actggttgca cggcggtcag     7500
ggcaacgatc tcctggtggg cgatgccggc agcgacaccc tcaacggcgg cgtgggcgac    7560
gatgtgctgg tcggggggtca gggcttcgac cttctgacgg cggcaccgg ggcggacact     7620 ttcgtcttcg gcagcctcga cagcgcggat gcggatcgga tcaccgattt cgagcagggc    7680
gtcgaccaga tcgtgatcgc cgaccagctg atgtgggcgc tggagaatgc cgagctgaac     7740
ctcgccgatc agatcgtctg gaatgccgag accggcatgc tctccatcga tctcgacgcc    7800
ggggaggcga cccgtctggt ggatcttgct cagatcgatc atgatggaac gctgaacatc     7860
acgatcgacg acttccagtt cctgcgctga                                      7890
```

<210> SEQ ID NO 134
<211> LENGTH: 2629
<212> TYPE: PRT
<213> ORGANISM: Rhodobacter sphaeroides

<400> SEQUENCE: 134

```
Met Pro Thr Val Asn Leu Thr Ser Ala Leu Thr Phe Ser Glu Gly Gly
1               5                  10                  15

Val Pro Gln Leu Val Asp Pro Asn Ile Thr Ile Thr Gly Gly Gly Ala
            20                  25                  30

Phe Thr Glu Gly Tyr Ile Glu Phe Ser Val Ser Ser Pro Thr Ala Gly
        35                  40                  45

Asp Asn Phe Ser Leu Thr Ser Ala Ala Asn Pro Leu Ala Asn Gly Ala
    50                  55                  60

Ile Ser Phe Glu Asn Gly Asp Val Tyr Leu Gly Thr Gly Ser Ala Arg
65                  70                  75                  80

Glu Arg Ile Gly Ser Val Asp Ala Thr Phe Asp Gly Gln Asp Gly Gln
```

```
                85                  90                  95
Pro Leu Arg Ile Leu Phe Ser Ser Pro Leu Pro Asn Ala Gly Phe Glu
            100                 105                 110
Glu Gly Glu Ala Asn Trp Thr Ile Arg Asp Glu Gln Tyr Gly Asp Asn
        115                 120                 125
Gly Ser Glu Leu Asn Leu Asp Gly Leu Gln Ile Thr Leu Ala Asn Asp
    130                 135                 140
Ser Ala Tyr Ser Gly Gly Thr Gly Thr Thr Asn Val Gln Ala Ser Ala
145                 150                 155                 160
Gly Met Thr Trp Asp Gly Ser Val Gln Asp Gly Ala Gly Val Asp Gly
                165                 170                 175
Ser Arg Ala Leu Tyr Leu Gly Ser Gly Gly Asn Ile Val Ala Gly Asp
            180                 185                 190
Gln Asn Pro Ala Gly Gly Tyr Gln Val Asn Gly Tyr Gly Ser Ile His
        195                 200                 205
Gly Pro Tyr Ala Thr Ser Ser Val Ile Thr Val Ala Gln Gly Asp Ser
    210                 215                 220
Ile Ser Leu Asp Phe Gln Ala Val Gly Thr Ser Asp Asp Tyr Glu Val
225                 230                 235                 240
Phe Gly Phe Leu Arg Arg Val Asp Ala Asn Gly Asn Phe Leu Ser Asn
                245                 250                 255
Ser Val Ser Ser Pro Asp Asn Ile Leu Leu Phe Ala Gln Arg Gly Asp
            260                 265                 270
Asp Thr Ser Gly Trp Thr Thr Ile Ser Lys Asp Gly Leu Pro Ala Gly
        275                 280                 285
Ser Tyr Arg Phe Glu Phe Val Gly Gly Thr Tyr Asp Gly Thr Gly Gly
    290                 295                 300
Leu Ala Val Gly Ser Asn Leu Phe Val Asp Asn Ile Arg Leu Ile Ser
305                 310                 315                 320
Ala Thr Ser Val Asn Asp Ser Ile Ala Gln Ala Ile Ala Arg Gln Val
                325                 330                 335
Ala Tyr Gln Asn Asp Ala Asn Asp Ala Pro Val Thr Arg Gln Ile Thr
            340                 345                 350
Val Thr Ala Val Asp Gly Asn Gly Ile Ser Gly Ser Ser Asn Gly
        355                 360                 365
Leu Thr Phe Glu Gly Glu Asn Asp Ala Pro Ser Leu Ala Asn Thr Thr
    370                 375                 380
Leu Thr Ser Ile Ala Glu Asp Ser Ser Pro Ala Gly Gln Thr Ile Ala
385                 390                 395                 400
Ala Ala Phe Gly Gly Ser Phe Ser Asp Pro Asp Asn Ala Tyr Ser Pro
                405                 410                 415
Thr Asp Ser Met Ala Gly Val Val Ile Thr Gly Asn Ala Ala Thr Gly
            420                 425                 430
Ala Gln Gly Asp Trp Gln Tyr Ser Thr Asp Gly Thr Thr Trp Ile
        435                 440                 445
Ser Val Gly Ser Val Thr Ser Gln Ser Gly Leu Val Leu Ser Ser Ala
    450                 455                 460
Thr Leu Ile Arg Phe Glu Pro Ala Leu Asn Trp Asn Gly Thr Pro Gly
465                 470                 475                 480
Ala Leu Thr Leu His Ala Leu Asp Ser Thr Tyr Gly Gly Ser Phe Thr
                485                 490                 495
Ser Gly Thr Thr Ala Val Asn Leu Asp Thr Thr Gly Ala Thr Gly Thr
            500                 505                 510
```

```
Gly Ala Leu Ser Gln Asn Ser Ala Thr Gly Ser Ile Thr Val Thr Pro
            515                 520                 525

Val Asn Asp Ala Pro Val Phe Thr Ala Ala Pro Val Ala Leu Thr Val
        530                 535                 540

Ala Asp Thr Glu Ala Val Asp Thr Pro Ala Ala Leu Thr Gly Ser Ile
545                 550                 555                 560

Ser Ala Ser Asp Leu His Gly Gly Ala Pro Gly Glu Gly Gly Thr Leu
                565                 570                 575

Ser Tyr Gly Val Gln Gly Gly Val Ser Ala Asn Gly Phe Ser Val Leu
                580                 585                 590

Thr Leu Pro Tyr Gly Thr Leu Ser Val Asn Gln Ser Thr Gly Ala Tyr
            595                 600                 605

Ser Phe Leu Pro Asn Pro Thr Ala Leu Asn Ser Leu Ala Glu Gly Ala
            610                 615                 620

Glu Ala Asn Phe Ser Phe Thr Leu Thr Val Ser Asp Gly Gln Gly Gly
625                 630                 635                 640

Thr Gln Thr Ala Pro Leu Asp Ile Thr Phe Thr Gly Ala Asn Asp Val
                645                 650                 655

Pro Val Val Ser Ala Gln Thr Gly Thr Ala Val Glu Ala Ser Gly Leu
                660                 665                 670

Asn Asn Asn Val Ala Gly Ser Ala Ala Thr Gly Ser Leu Leu Thr Gly
                675                 680                 685

Pro Asn Ala Ala Thr Asp Ile Asp Gly Asp Glu Ile Ser Val Val Gly
            690                 695                 700

Val Arg Thr Gly Gly Gln Ser Glu Thr Gly Thr Glu Gly Val Trp Thr
705                 710                 715                 720

Asp Gly Thr Ile Thr Leu Gln Gly Thr Tyr Gly Thr Leu Thr Leu Asn
                725                 730                 735

Glu Asp Gly Ser Trp Ser Tyr Ala Ala Asp Asp Asn Pro Thr Val
                740                 745                 750

Asp Gly Leu Thr Gly Pro Thr Asp Thr Leu Glu Glu Thr Phe Thr Tyr
            755                 760                 765

Thr Val Thr Asp Ala Asn Gly Ala Thr Ala Ser Gln Glu Leu Thr Val
        770                 775                 780

Thr Ile Ser Gly Arg Asn Asp Ala Leu Asn Val Ser Ser Ser Ile Gly
785                 790                 795                 800

Thr Asp Ile Ser Thr Gly Glu Asp Ala Asp Thr Gln Ile Asp Leu Thr
                805                 810                 815

Gly Leu Val Phe Glu Asp Pro Asp Leu Gly Ser Glu Ile Tyr Glu Phe
                820                 825                 830

Ala Val Asp Ala Gly Gln Gly Thr Leu Trp Thr Glu Gly Val Asp Gly
            835                 840                 845

Leu Thr Val Thr Gly Asn Gly Thr Gly Gln Leu Val Leu Thr Gly Ser
        850                 855                 860

Ala Thr Ala Ile Ser Glu Trp Ile Ala Ala Asn Asp Leu Thr Tyr Arg
865                 870                 875                 880

Ser Pro Val Glu Gly Ser Gly Ala Asp Thr Ile Ser Leu Ser Tyr Ser
                885                 890                 895

Glu Ala Gly Ala Glu Val Arg Thr Ala Leu Glu Ser Ile Asp Val Ala
                900                 905                 910

Val Asp Met Ile Asn Asp Pro Ala Val Val Asp Val Asn Gly Ser Val
            915                 920                 925
```

Thr Thr Gln Gly Ser Ala Gly Val Ala Glu Val Ala Gln Val Thr Phe
930               935                  940

Leu Ser Thr Gly Thr Ala Gln Val Leu Asn Phe Asp Gly Val Gln Met
945               950                  955                  960

Gln Ile Ala Ala Gly Ser Thr Ala Ala Glu Ile Ala Glu Ala Phe Ala
              965                  970                  975

Ala Gln Glu Phe Pro Asn Trp Thr Val Ser Leu Asp Gly Glu Gly Arg
              980                  985                  990

Val Thr Leu Thr Ala Thr Ala Thr Gly Ala Arg Pro Asp Leu Thr Ala
              995                 1000                 1005

Ala Asp Phe Thr Asn Gly Ser Gly Ala Phe Ser Pro Leu Val Glu
    1010                1015                1020

Thr Thr Gly Gly Thr Asp Gly Ser Ile Asn Phe Thr Ala Arg Gly
    1025                1030                1035

Pro Ala Ile Ala Ile Leu Pro Thr Leu Glu Leu Ser Asp Val Asp
    1040                1045                1050

Ser Ala Met Met Ser Gly Ala Lys Val Ser Met Thr Glu Gly Leu
    1055                1060                1065

Phe Asp Asn Gly Phe Gly Thr Ile Tyr Glu Arg Leu Ser Leu Ser
    1070                1075                1080

Ala Glu Ala Arg Glu Phe Ala Gln Gln Asn Gly Val Gly Ile Ser
    1085                1090                1095

Ile Val Thr Thr Ala Ala Ala Gly Ser Val Ile Thr Phe Thr Gly
    1100                1105                1110

Met Ala Ser Ala Glu Val Tyr Glu Thr Ile Leu Arg Gly Val Ile
    1115                1120                1125

Tyr Ser Asn Thr Asn Pro Asn Ala Val Ala Gly Thr Arg Pro Val
    1130                1135                1140

Lys Ile Glu Val Thr Asp Ser Asp Gly Leu Ala Ser Ser Leu Ser
    1145                1150                1155

Ser Val Asn Leu Thr Glu Gly Asn Thr Asp Ile Ala Val Gly Gln
    1160                1165                1170

Arg Ile Phe Ile Asn Gly Val Asp Ser Gly Gln Val Val Ser Met
    1175                1180                1185

Val Arg Asp Ala Thr Ser Phe Val Ala Ser Gly Pro Leu Ala Asp
    1190                1195                1200

Leu Glu Pro Gly Ala Val Leu Ser Phe His Asp Gly Ser Gly Gln
    1205                1210                1215

Gln Thr Thr Ala Val Ser Ala Gly Asp Gly Thr Ala Thr Met Asp
    1220                1225                1230

Val Asn Val Ile Trp Ala Pro Val Ile Asp Met Asn Gly Ala Gly
    1235                1240                1245

Ala Gly Asp Ile His Arg Thr Thr Tyr Ile Glu Gln His Ala Pro
    1250                1255                1260

Ile Ala Ile Ala Thr Ala Asp Ala Arg Ile Val Asp Gln Glu Gly
    1265                1270                1275

Leu Ile Arg Ser Leu Asp Val Val Leu Thr Asn Pro Leu Asp Asn
    1280                1285                1290

Val Glu Gly Ser Ala Pro Val Glu Tyr Leu Gly Ile Ser Lys Ala
    1295                1300                1305

Val Leu Asp Val Leu Ala Ala Arg Gly Ile Thr Ile Gly Ala His
    1310                1315                1320

Asp Gly Gln Phe Asp Ala Asn Gly Asn Leu Thr Gly Ala Thr Ser

|      |      |      | 1325 |      |      |      | 1330 |      |      |      | 1335 |      |      |
|------|------|------|------|------|------|------|------|------|------|------|------|------|------|

Ile Thr Phe Ala Ala Ala Asn Gly Ala Ser Ala Thr Ser Phe Gln
    1340                    1345                1350

Ile Ala Leu Arg Gly Val Thr Tyr Ala Asn Met Asp Asp Ala Pro
    1355                    1360                1365

Asp Thr Gly Thr Arg Ile Val Thr Ala Gln Gly Thr Asp Met Asp
    1370                    1375                1380

Gly Asn Glu Gly Leu Ile Ser His Thr Glu Ile Asn Pro Ile Ala
    1385                    1390                1395

Val Gly Asp Ala Pro Val Ala Ile Asp Ser Gly Val Thr Gly Ser
    1400                    1405                1410

Glu Asp Ala Gly His Val Phe Ala Ala Gly Asp Phe Gly Phe Ala
    1415                    1420                1425

Asp Pro Leu Asp Gly Gly Ala Asn Gln Leu Ala Ser Ile Thr Ile
    1430                    1435                1440

Asn Ser Leu Pro Ala Thr Gly Thr Leu Leu Gly Gly Val Ala
    1445                    1450                1455

Val Ala Val Gly Thr Val Val Thr Leu Ala Gln Leu Gln Ala Gly
    1460                    1465                1470

Ala Leu Thr Tyr Gln Pro Val Ala Asn Val Asn Gly Glu Gly Val
    1475                    1480                1485

Ala Ser Phe Asp Phe Leu Val Thr Asp Asn Gly Ser Leu Ala Asn
    1490                    1495                1500

Gly Gly Gln Thr Thr Ser Thr Ala Pro Ala Thr Met Val Ile Asp
    1505                    1510                1515

Leu Thr Pro Val Asn Asp Ala Pro Val Leu Pro Glu Gly Thr Ser
    1520                    1525                1530

Val Thr Gly Thr Thr Ile Thr Glu Asp Gln Gln Leu Asn Ala Gly
    1535                    1540                1545

Glu Leu Val Ala Asp Leu Val Gly Ala Met Thr Asp Val Asp Thr
    1550                    1555                1560

Gly Val His Ser Ala Thr Asn Gly Thr Gln Gln Gly Ile Ala Val
    1565                    1570                1575

Tyr Gly Ala Gly Ser Glu Gly Phe Gly Gly Thr Trp Gln Tyr
    1580                    1585                1590

Arg Leu Ala Gly Gly Thr Asp Trp Ile Asp Val Thr Leu Asp Pro
    1595                    1600                1605

Gly Glu Val Leu Leu Leu Gly Ala Asp Asp Arg Ile Arg Phe Ser
    1610                    1615                1620

Pro Asp Gly Glu Asn Ala Thr Glu Ala Gln Leu Ser Tyr Tyr Ala
    1625                    1630                1635

Trp Asp Gly Ala Thr Gly Thr Ala Gly Asn Val Val Ala Gly Ile
    1640                    1645                1650

Ala Gly Pro Gly Asn Ala Ser Asn Arg Gly Gly Thr Ser Ala Phe
    1655                    1660                1665

Ser Ser Asn Gly Ala Ser Ala Thr Val Glu Val Thr Ala Val Asn
    1670                    1675                1680

Asp Ala Pro Ser Ile Ser Met Gly Glu Gly Asn Thr Phe Tyr Ala
    1685                    1690                1695

Arg Gly Glu Ala Val Ala Leu Phe Ser Asp Glu Thr Leu Gln Leu
    1700                    1705                1710

Thr Asp Pro Asp Glu Gly Ala Ala Val Ser Gln Ile Val Ile Thr
    1715                    1720                1725

```
Leu Asp Gly Glu Thr Thr Val Asp Asn Ala Phe Gly Thr Thr Tyr
    1730            1735               1740

Glu Thr Ile Phe Ser Ala Ser Gly Ser Thr Phe Val Ala Gln Ser
    1745            1750               1755

Gly Thr Glu Leu Thr Ile Ser Gly Thr Gly Val Ala Gly Asp Pro
    1760            1765               1770

Leu Thr Ile Ser Gly Ala Gly Ser Met Glu Asp Tyr Arg Glu Ala
    1775            1780               1785

Leu Leu Ser Leu Arg Tyr Glu Asn Thr Asn Pro Asn Ala Phe Ala
    1790            1795               1800

Gly Asp Arg Ala Ile Ser Val Thr Val Thr Asp Glu Thr Gly Ala
    1805            1810               1815

Gly Ser Ala Pro Thr Asp Phe Ile Leu Pro Val Glu Trp Ala Thr
    1820            1825               1830

Val Ala Asp Leu Asn Gly Pro Ser Gly Glu Gly Arg Asp His Ser
    1835            1840               1845

Ile Thr Tyr Leu Glu Gly Ser Gly Ser Gln Ala Ile Ala Thr Ala
    1850            1855               1860

Asp Ala Glu Met Ile Asp Gln Asp Gly Asn Thr Val Glu Val Val
    1865            1870               1875

Ile Thr Leu Glu Asp Ala Val Asn Gly Ser Ala Glu Met Leu Phe
    1880            1885               1890

Val Asp Pro Ala Val Leu Pro Ala Leu Ala Ala Leu Asn Ile Val
    1895            1900               1905

Val Thr Gly Asn Gly Thr His Glu Ile Arg Leu Thr Ser Glu Glu
    1910            1915               1920

Gly Val Asp Pro Thr Asn Phe Gln Leu Ala Leu Arg Ala Val Arg
    1925            1930               1935

Tyr Val Asn Ser Ser Thr Ala Pro Thr Ala Ala Glu Arg His Val
    1940            1945               1950

Thr Val Ser Ser Thr Asp Ala Asp Gly Asn Pro Gly Val Pro Ala
    1955            1960               1965

Thr Thr Val Ile Gly Met Glu Leu Val Asn Asp Ala Pro Val Ala
    1970            1975               1980

Asp Leu Ser Ile Ser Tyr Glu Ala Ser Glu Thr Arg Asn Pro Leu
    1985            1990               1995

Ser Gly Asp Gln Leu Leu Leu Asp Gly Thr Leu Asp Asp Ala Asp
    2000            2005               2010

Gly Leu Gly Pro Asn Pro Pro Val Ile Glu Trp Leu Arg Asp Gly
    2015            2020               2025

Val Val Ile Ala Ser Gly Asn Gly Met Pro Val Tyr Thr Leu Lys
    2030            2035               2040

Pro Ala Asp Ala Gly His Val Ile Ser Ala Arg Ile Thr Tyr Thr
    2045            2050               2055

Asp Gly Glu Gly Asn Leu Glu Val Ile Asn Val Asp Gly Pro Ala
    2060            2065               2070

Met Val Gly Leu Asn Leu Glu Gly Thr Asp Gly Ala Asp Leu Leu
    2075            2080               2085

Ile Gly Ser Arg Gly Ala Asp Val Ile Ser Gly Arg Met Phe Asn
    2090            2095               2100

Asp Thr Leu Met Gly Gly Ala Gly Asn Asp Ser Leu Tyr Gly Asn
    2105            2110               2115
```

```
Gly Asp Asp Asp Arg Leu Tyr Val Asn Glu Gly Asn Asp Ser Leu
    2120                2125                2130

Tyr Gly Glu Glu Gly Asn Asp Trp Leu His Gly Gln Gly Asp
    2135                2140                2145

Asp Leu Val Val Gly Gly Asp Gly Asn Asp Thr Leu Ala Gly Gly
    2150                2155                2160

Leu Gly Asn Asp Thr Leu Gln Gly Gly Ala Gly Asn Asp Thr Ala
    2165                2170                2175

Ser Tyr Glu Thr Ala Thr Glu Gly Val Thr Val Ser Leu Ala Leu
    2180                2185                2190

Gln Gly Glu Gly Gln Phe Val Asn Ala Gln Glu Gly Asn Asp Pro
    2195                2200                2205

Leu Thr Ser Ile Glu Asn Leu Thr Gly Ser Asn His Asp Asp Thr
    2210                2215                2220

Leu Ile Gly Asp Glu Gly Asp Asn Val Leu Ser Gly Leu Ala Gly
    2225                2230                2235

Asn Asp Val Leu Val Gly Gly Ala Gly Asn Asp Thr Leu Leu Gly
    2240                2245                2250

Gly Ala Gly Asn Asp Ile Ala Asp Tyr Ala Ala Ala Thr Gly Gly
    2255                2260                2265

Val Thr Val Asn Leu Ala Arg Asp Gly Gln Ala Gln Ile Ile Gly
    2270                2275                2280

Ala Asp Gln Gly Thr Asp Val Leu Ser Ser Ile Glu Gly Val Ile
    2285                2290                2295

Gly Ser Ala Phe Asn Asp Ile Leu Ser Gly Ser Ala Val Ala Asn
    2300                2305                2310

Leu Ile Phe Gly Gly Asp Gly Ala Asp Leu Ala Thr Gly Gly Ala
    2315                2320                2325

Gly Asn Asp Thr Ile Leu Gly Gly Ala Gly Ser Asp Ser Leu Tyr
    2330                2335                2340

Gly Asn Leu Gly Asp Asp Leu Leu Phe Gly Asp Val Gly Asn Asp
    2345                2350                2355

Trp Ile His Gly Gly Gln Gly Asn Asp Thr Val Leu Gly Gly Phe
    2360                2365                2370

Gly Asp Asp Thr Leu Ala Gly Gly Val Gly Asp Asp Val Val Asp
    2375                2380                2385

Gly Gly Asp Gly Ile Asp Thr Val Glu Phe Gln Thr Ala Thr Ala
    2390                2395                2400

Gly Val Thr Val Asp Leu Ser Leu Gln Gly Gln Ala Gln Arg Ile
    2405                2410                2415

Ser Ala Glu Glu Gly Thr Asp Thr Leu Phe Ser Ile Glu Asn Ile
    2420                2425                2430

Leu Gly Ser Arg Tyr Asp Asp Arg Leu Leu Gly Asp Ala Gly Ser
    2435                2440                2445

Asn Leu Ile Asp Gly Ser Ala Gly Asn Asp Thr Ala Met Gly Gln
    2450                2455                2460

Ala Gly Glu Asp Leu Ile Phe Gly Gly Asp Gly Asn Asp Ser Leu
    2465                2470                2475

Tyr Gly Asn Gln Asp Asn Asp Thr Leu Val Gly Gly Asn Gly Asn
    2480                2485                2490

Asp Trp Leu His Gly Gly Gln Gly Asn Asp Leu Leu Val Gly Asp
    2495                2500                2505

Ala Gly Ser Asp Thr Leu Asn Gly Gly Val Gly Asp Asp Val Leu
```

| | | | | | | | | | | |
|---|---|---|---|---|---|---|---|---|---|---|
| | 2510 | | | | 2515 | | | | 2520 | |
| Val | Gly | Gly | Gln | Gly | Phe | Asp | Leu | Leu | Thr | Gly | Gly | Thr | Gly | Ala |
| 2525 | | | | | 2530 | | | | | 2535 | | | |
| Asp | Thr | Phe | Val | Phe | Gly | Ser | Leu | Asp | Ser | Ala | Asp | Ala | Asp | Arg |
| 2540 | | | | | 2545 | | | | | 2550 | | | |
| Ile | Thr | Asp | Phe | Glu | Gln | Gly | Val | Asp | Gln | Ile | Val | Ile | Ala | Asp |
| 2555 | | | | | 2560 | | | | | 2565 | | | |
| Gln | Leu | Met | Trp | Ala | Leu | Glu | Asn | Ala | Glu | Leu | Asn | Leu | Ala | Asp |
| 2570 | | | | | 2575 | | | | | 2580 | | | |
| Gln | Ile | Val | Trp | Asn | Ala | Glu | Thr | Gly | Met | Leu | Ser | Ile | Asp | Leu |
| 2585 | | | | | 2590 | | | | | 2595 | | | |
| Asp | Ala | Gly | Glu | Ala | Thr | Arg | Leu | Val | Asp | Leu | Ala | Gln | Ile | Asp |
| 2600 | | | | | 2605 | | | | | 2610 | | | |
| His | Asp | Gly | Thr | Leu | Asn | Ile | Thr | Ile | Asp | Phe | Gln | Phe | Leu | |
| 2615 | | | | | 2620 | | | | | 2625 | | | | |
| Arg | | | | | | | | | | | | | | |

<210> SEQ ID NO 135
<211> LENGTH: 6183
<212> TYPE: DNA
<213> ORGANISM: Rhodobacter sphaeroides

<400> SEQUENCE: 135

```
atgccgacag tgaacctgac ctctgccctg accttctccg agggcggcgt gccgcagctc      60
gtcgacccga acatcacgat cacgggcggc ggagccttta ccgaaggcta catcgaattc     120
tcggtcagtt cgcccacggc cggcgacaac ttcagcctga ccagcgccgc caatccgctg     180
gccaacggcg cgatctcgtt cgagaacggc gacgtctatc tcgggaccgg ctcggccgc      240
gagcggatcg gctcggtcga tgcgaccttc gacgccagg acggccagcc gctgcgcatc     300
ctgttctcga gcccgctgcc gaacgccggc ttcgaggaag cgaggcgaa ctggaccatc      360
cgcgacgagc aatatggcga caacggcagc gagctgaacc tcgacgggcct gcagatcacg     420
ctggccaatg actcggccta cagcggcggc accggcacga ccaacgtcca ggcctccgcc     480
ggcatgacct gggacgggtc ggtgcaggat ggtgcgggcg ttgacggatc gcgcgccctc     540
tatctcggca gcggcggaaa catcgttgcg ggcgatcaga acccggccgg cggctatcag     600
gtcaacggct acggctcgat ccacggcccc tatgccacca gctcggtgat caccgtcgcg     660
cagggtgact cgatctcgct cgactttcag gccgtgggca cgagcgacga ctacgaggtg     720
ttcggcttcc tgcgtcgcgt cgacgccaac ggcaacttcc tgagcaacag cgtcagcagc     780
cccgacaaca tcctgctctt cgcccagcgg ggcgatgaca ccagcgggtg gacgaccatc     840
agcaaggacg gcctgcccgc aggcagctac cggttcgagt tcgtcggcgg cacctatgat     900
ggcacgggcg gcctcgcggt gggctcgaac ctctttgtcg acaacatccg cctgatctcg     960
gccacctcgg tgaacgacag catcgcccag gccatcgccc ggcaggtcgc ctaccagaac    1020
gacgccaatg atgcgccggt caccgcgcag atcacggtca cggccgtgga cggcaacggc    1080
atcagcggct cctcctcgaa cggcctgacc ttcgaaggcg agaacgacgc gccgagcctt    1140
gccaacacca cgctcacctc gatcgccgag gacagcagcc ccgccggcca gaccatcgcc    1200
gcagccttcg gcggctcctt ctcggatccc gacaacgcct attccccac cgactcgatg    1260
gcgggcgtcg tcatcaccgg caatgcggcg accggcgccc aaggcgactg gcagtattcg    1320
accgacggcg gcaccacctg gatctcggtc ggcagcgtga cctcgcagag cgggctcgtg    1380
```

```
ctttcctcgg ccacgctgat ccgcttcgaa cccgcgctga actggaacgg cacgcccggc    1440
gcgctgacgc tccatgcgct ggacagcacc tatggcggca gcttcaccag cggcacgacg    1500
gcggtgaacc tcgacacgac cggcgccacc ggcaccggcg cgctcagcca gaacagcgcc    1560
accggctcga tcaccgtcac cccggtcaac gacgcccccg tcttcaccgc ggccccggtc    1620
gcgctgacgg ttgccgacac cgaggccgtg gacacgccgg ccgcgctcac cggctcgatc    1680
tcggcctccg acctgcatgg cggtgcgccg ggcgaaggcg gcacgctcag ctacggcgtt    1740
cagggcggcg tgtcggccaa cggcttctcg gttctgacgc tgccctacgg cacgctgtcg    1800
gtgaaccagt cgaccggagc ctacagcttc ctgccgaacc ccacggcgct gaacagcctc    1860
gccgagggtg cagaggcgaa cttctccttc acgctcaccg tctcggacgg gcagggcggc    1920
acgcagaccg cgccgctcga catcaccttc accggcgcca acgacgtgcc ggtcgtcagc    1980
gcccagaccg gcacggcggt cgaggcctcg ggtctcaaca caacgtcgc cggcagcgcg    2040
gccacgggct cgctgctgac cggtccgaat gcggcgaccg atatcgacgg cgacgagatc    2100
tcggtggtgg gtgtgcgcac cggcggccag tccgagaccg gcaccgaagg cgtctggacc    2160
gacggcacga tcacgcttca gggcacctac ggcacgctga cgctgaacga ggacggcagc    2220
tggtcctacg cggccgacga tgacaacccg accgtcgacg gctgaccgg gccgaccgac    2280
acgctggagg agaccttcac ctacaccgtg acggacgcga acggcgccac cgcgtcgcag    2340
gagctgaccg tcaccatctc gggccgcaac gacgcgctga acgtgtcgag cagcatcggc    2400
accgatatct cgacgggcga ggatgccgac acgcagatcg accttaccgg cctcgtgttc    2460
gaagaccccg atctgggctc ggaaatctac gaattcgccg tggatgcggg ccagggcacg    2520
ctctggaccg aaggtgtgga cgggctgacc gtcaccggca acggaacggg ccagctggtg    2580
ctgaccggct cggccaccgc gatttccgaa tggatcgcgg ccaacgacct gacctaccgc    2640
tcgcccgtgg aaggcagcgg cgccgacacg atcagcctct cctacagcga ggcgggcgcc    2700
gaggtccgca cggcgctcga gtccatcgac gtcgcggtgg acatgatcaa cgacccggcc    2760
gtggtcgatg tgaacggctc ggtcacgacc cagggcagcg ccggcgtggc cgaagtggct    2820
caggtcacct tcctgtcgac cggcaccgct caggtgctga atttcgacgg ggtgcagatg    2880
cagatcgcgg ccggcagcac tgccgccgag attgccgaag ccttcgcggc gcaggagttc    2940
ccgaactgga ccgtcagcct tgacggcgag ggccgggtga cgctgaccgc gaccgccacc    3000
ggcgcgcggc cggacctgac ggcggccgac ttcaccaacg gctcgggcgc cttctcgccg    3060
ctggtcgaga ccaccggcgg caccgacggc agcatcaatt tcaccgcgcg cggaccggcc    3120
atcgccatcc tgccgacgct ggaactgagc gacgtcgaca gcgcgatgat gtcgggcgcc    3180
aaggtcagca tgaccgaagg cctgttcgac aacgggttcg gcacgatcta cgaacggctc    3240
tcgctgtcgg cggaggcgcg ggaattcgcg cagcagaacg gcgtgggcat cagcatcgtg    3300
acgacgcccg ctgccggctc ggtcatcacc ttcaccggca tggcctcggc ggaggtctac    3360
gagaccatcc tgcgcggcgt gatctacagc aacaccaacc cgaatgcggt ggcgggcacc    3420
cgccccgtga agatcgaagt gaccgactct gacgggctcg cctcgagcct ctccagcgtc    3480
aacctgacag agggcaacac cgacatcgcc gtcggccagc gcatcttcat caacggcgtg    3540
gacagcggcc aggtcgtctc gatggtgcgc gacgccacca gcttcgtggc cagcggcccg    3600
ctggccgatc tggagccggg tgcggtgctg agcttccatg acggcagcgg tcagcagacc    3660
acggcggttt cggcgggcga cggcacggcc acgatggacg tgaacgtgat ctgggctccc    3720
gtgatcgaca tgaacggcgc cggcgcgggc gatatccacc ggacgaccta catcgagcag    3780
```

```
catgccccga tcgccatcgc gaccgccgat gcccgcatcg tcgatcagga aggtctgatc    3840
cgctcgctcg acgtcgtgct gaccaacccg ctcgacaatg tcgaaggttc ggctccggtc    3900
gaatatctcg gcatctcgaa ggcggtgctg gacgtgctgg cggcccgcgg catcaccatc    3960
ggtgcccatg acgccagtt cgacgccaac ggcaacctga ccggcgccac ctcgatcacc     4020
ttcgcggcgg ccaacggcgc cagcgccacc agcttccaga ttgcgctgcg gggcgtgacc    4080
tatgccaaca tggacgatgc cccggacacc gggacgcgga tcgtgacggc cagggcacc    4140 gacatggacg gcaacgaggg cctgatctcg cacaccgaga tcaacccgat cgcggtgggc    4200
gacgcgccgt tggcgatcga cagcggcgtg accggctccg aagatgcggg ccatgtcttt    4260
gccgccggag acttcggctt tgccgatccg ctggatggcg gcgcgaacca gctcgcctcg    4320
atcaccatca acagcctgcc cgccacgggc acgctgctcc tgggcggggt cgcggtcgcc    4380
gtgggcaccg tggtcaccct cgcgcagctt caggccggcg cgctgaccta tcagccggtg    4440
gccaacgtga acggtgaagg ggtcgcctcg ttcgacttcc tcgtgaccga caacggcagc    4500
ctcgccaacg gcggccagac cacctcgacc gctccggcaa ccatggtgat cgacctgacg    4560
ccggtgaacg atgctccggt cctgccggaa ggcacctccg tcaccggcac cacgatcacc    4620
gaagaccagc agctgaatgc cggtgaactg gtggccgatc tggtcggcgc catgacggat    4680
gtcgatacgg gcgtgcacag cgccacgaac ggcacccagc agggcatcgc ggtttatggc    4740
gcgggctccg aagggttcgg cggcggcacc tggcagtatc gtctcgccgg cggcaccgac    4800
tggatcgacg tcaccctcga tccgggcgag gtcctgctgc tcggtgcgga cgaccgcatc    4860
cgcttctcgc cggatggcga gaacgcgacc gaggcgcagc tgtcctacta cgcctgggac    4920
ggggcgaccg gcaccgcggg caacgtggtc gcaggcatcg cggggccggg caatgcctcg    4980
aaccgtggcg gcacctcggc cttctccagc aacggcgcct ctgccacggt cgaggtgaca    5040
gctgtcaacg acgcgccgtc gatcagcatg ggcgagggca ataccttcta tgctcgcggc    5100
gaggcggtgg cgctgttctc ggacgagacg ctgcaactga ccgacccgga cgagggcgcg    5160
gcggtaagcc agattgtcat cacgctcgat ggcgagacca cggtcgacaa cgccttcggc    5220
accacctacg agacgatctt ctcggccagc ggctcgacct tcgtgcccca gtcgggcacc    5280
gaactgacca tctcgggcac cggtgtggcg ggcgatccgc tcaccatctc ggggccggg    5340 tcgatggagg actaccgtga ggcgctcctc agcctgcgct acgagaacac caacccgaac    5400
gccttcgcgg gcgaccgggc gatctcggtc acggtgacgg atgagacggg ggcgggctcc    5460
gcgccgacgg acttcatcct gccggtggaa tgggcaacgg tggccgatct caacggtccg    5520
tcgggcgaag gccgcgacca ctcgatcacc tatctcgagg gcagcggcag ccaggccatc    5580
gctacggccg atgccgagat gatcgaccag gacggcaaca ccgtcgaggt cgtcatcacg    5640
ctcgaggatg cggtgaacgg ctcggccgag atgctgttcg tcgatccggc ggtcctgccg    5700
gctctggcgg cgctgaacat cgtggtcacc ggcaacggca cccacgagat ccggctgacg    5760
agcgaggagg gcgtggatcc cacgaacttc cagctggcgc tgcgggccgt gcgttacgtc    5820
aacagctcga ccgcacccac cgcggcggag cgccatgtca cggtctcctc gaccgatgcc    5880
gacggcaacc cgggcgttcc ggccaccacg gtgatcggga tggagctggg tgaacgacgc    5940
accggttgcg gatctctcga tctcctacga ggcgtccgag acccgcaacc cgctgtcggg    6000
cgatcagctg ctgctcgacg gcacgctgga cgatgccgac gggctcgggc cgaacccgcc    6060
ggtcatcgaa tggctgcggg acggtgtggt gatcgcttcg ggcaacggca tgccggtcta    6120
```

```
cacgctgaaa ccggcggatg caggccatgt catcagcgcc cgcatcacct acaccgacgg    6180
tga                                                                 6183
```

<210> SEQ ID NO 136
<211> LENGTH: 2060
<212> TYPE: PRT
<213> ORGANISM: Rhodobacter sphaeroides

<400> SEQUENCE: 136

```
Met Pro Thr Val Asn Leu Thr Ser Ala Leu Thr Phe Ser Glu Gly Gly
1               5                   10                  15

Val Pro Gln Leu Val Asp Pro Asn Ile Thr Ile Thr Gly Gly Gly Ala
            20                  25                  30

Phe Thr Glu Gly Tyr Ile Glu Phe Ser Val Ser Ser Pro Thr Ala Gly
        35                  40                  45

Asp Asn Phe Ser Leu Thr Ser Ala Ala Asn Pro Leu Ala Asn Gly Ala
    50                  55                  60

Ile Ser Phe Glu Asn Gly Asp Val Tyr Leu Gly Thr Gly Ser Ala Arg
65                  70                  75                  80

Glu Arg Ile Gly Ser Val Asp Ala Thr Phe Asp Gly Gln Asp Gly Gln
                85                  90                  95

Pro Leu Arg Ile Leu Phe Ser Ser Pro Leu Pro Asn Ala Gly Phe Glu
            100                 105                 110

Glu Gly Glu Ala Asn Trp Thr Ile Arg Asp Glu Gln Tyr Gly Asp Asn
        115                 120                 125

Gly Ser Glu Leu Asn Leu Asp Gly Leu Gln Ile Thr Leu Ala Asn Asp
    130                 135                 140

Ser Ala Tyr Ser Gly Gly Thr Gly Thr Thr Asn Val Gln Ala Ser Ala
145                 150                 155                 160

Gly Met Thr Trp Asp Gly Ser Val Gln Asp Gly Ala Gly Val Asp Gly
                165                 170                 175

Ser Arg Ala Leu Tyr Leu Gly Ser Gly Gly Asn Ile Val Ala Gly Asp
            180                 185                 190

Gln Asn Pro Ala Gly Gly Tyr Gln Val Asn Gly Tyr Gly Ser Ile His
        195                 200                 205

Gly Pro Tyr Ala Thr Ser Ser Val Ile Thr Val Ala Gln Gly Asp Ser
    210                 215                 220

Ile Ser Leu Asp Phe Gln Ala Val Gly Thr Ser Asp Asp Tyr Glu Val
225                 230                 235                 240

Phe Gly Phe Leu Arg Arg Val Asp Ala Asn Gly Asn Phe Leu Ser Asn
                245                 250                 255

Ser Val Ser Ser Pro Asp Asn Ile Leu Leu Phe Ala Gln Arg Gly Asp
            260                 265                 270

Asp Thr Ser Gly Trp Thr Thr Ile Ser Lys Asp Gly Leu Pro Ala Gly
        275                 280                 285

Ser Tyr Arg Phe Glu Phe Val Gly Gly Thr Tyr Asp Gly Thr Gly Gly
    290                 295                 300

Leu Ala Val Gly Ser Asn Leu Phe Val Asp Asn Ile Arg Leu Ile Ser
305                 310                 315                 320

Ala Thr Ser Val Asn Asp Ser Ile Ala Gln Ala Ile Ala Arg Gln Val
                325                 330                 335

Ala Tyr Gln Asn Asp Ala Asn Asp Ala Pro Val Thr Arg Gln Ile Thr
            340                 345                 350

Val Thr Ala Val Asp Gly Asn Gly Ile Ser Gly Ser Ser Ser Asn Gly
```

-continued

```
                 355                 360                 365
Leu Thr Phe Glu Gly Glu Asn Asp Ala Pro Ser Leu Ala Asn Thr Thr
370                 375                 380
Leu Thr Ser Ile Ala Glu Asp Ser Ser Pro Ala Gly Gln Thr Ile Ala
385                 390                 395                 400
Ala Ala Phe Gly Gly Ser Phe Ser Asp Pro Asp Asn Ala Tyr Ser Pro
                        405                 410                 415
Thr Asp Ser Met Ala Gly Val Val Ile Thr Gly Asn Ala Ala Thr Gly
                420                 425                 430
Ala Gln Gly Asp Trp Gln Tyr Ser Thr Asp Gly Gly Thr Thr Trp Ile
            435                 440                 445
Ser Val Gly Ser Val Thr Ser Gln Ser Gly Leu Val Leu Ser Ser Ala
450                 455                 460
Thr Leu Ile Arg Phe Glu Pro Ala Leu Asn Trp Asn Gly Thr Pro Gly
465                 470                 475                 480
Ala Leu Thr Leu His Ala Leu Asp Ser Thr Tyr Gly Gly Ser Phe Thr
                        485                 490                 495
Ser Gly Thr Thr Ala Val Asn Leu Asp Thr Thr Gly Ala Thr Gly Thr
                500                 505                 510
Gly Ala Leu Ser Gln Asn Ser Ala Thr Gly Ser Ile Thr Val Thr Pro
            515                 520                 525
Val Asn Asp Ala Pro Val Phe Thr Ala Ala Pro Val Ala Leu Thr Val
530                 535                 540
Ala Asp Thr Glu Ala Val Asp Thr Pro Ala Ala Leu Thr Gly Ser Ile
545                 550                 555                 560
Ser Ala Ser Asp Leu His Gly Gly Ala Pro Gly Glu Gly Gly Thr Leu
                        565                 570                 575
Ser Tyr Gly Val Gln Gly Gly Val Ser Ala Asn Gly Phe Ser Val Leu
                580                 585                 590
Thr Leu Pro Tyr Gly Thr Leu Ser Val Asn Gln Ser Thr Gly Ala Tyr
            595                 600                 605
Ser Phe Leu Pro Asn Pro Thr Ala Leu Asn Ser Leu Ala Glu Gly Ala
        610                 615                 620
Glu Ala Asn Phe Ser Phe Thr Leu Thr Val Ser Asp Gly Gln Gly Gly
625                 630                 635                 640
Thr Gln Thr Ala Pro Leu Asp Ile Thr Phe Thr Gly Ala Asn Asp Val
                        645                 650                 655
Pro Val Val Ser Ala Gln Thr Gly Thr Ala Val Glu Ala Ser Gly Leu
                660                 665                 670
Asn Asn Asn Val Ala Gly Ser Ala Thr Gly Ser Leu Leu Thr Gly
            675                 680                 685
Pro Asn Ala Ala Thr Asp Ile Asp Gly Asp Glu Ile Ser Val Val Gly
        690                 695                 700
Val Arg Thr Gly Gly Gln Ser Glu Thr Gly Thr Glu Gly Val Trp Thr
705                 710                 715                 720
Asp Gly Thr Ile Thr Leu Gln Gly Tyr Gly Thr Leu Thr Leu Asn
                        725                 730                 735
Glu Asp Gly Ser Trp Ser Tyr Ala Ala Asp Asp Asn Pro Thr Val
                740                 745                 750
Asp Gly Leu Thr Gly Pro Thr Asp Thr Leu Glu Glu Thr Phe Thr Tyr
            755                 760                 765
Thr Val Thr Asp Ala Asn Gly Ala Thr Ala Ser Gln Glu Leu Thr Val
770                 775                 780
```

```
Thr Ile Ser Gly Arg Asn Asp Ala Leu Asn Val Ser Ser Ile Gly
785                 790                 795                 800

Thr Asp Ile Ser Thr Gly Glu Asp Ala Asp Thr Gln Ile Asp Leu Thr
            805                 810                 815

Gly Leu Val Phe Glu Asp Pro Asp Leu Gly Ser Glu Ile Tyr Glu Phe
                820                 825                 830

Ala Val Asp Ala Gly Gln Gly Thr Leu Trp Thr Glu Gly Val Asp Gly
                835                 840                 845

Leu Thr Val Thr Gly Asn Gly Thr Gly Gln Leu Val Leu Thr Gly Ser
850                 855                 860

Ala Thr Ala Ile Ser Glu Trp Ile Ala Ala Asn Asp Leu Thr Tyr Arg
865                 870                 875                 880

Ser Pro Val Glu Gly Ser Gly Ala Asp Thr Ile Ser Leu Ser Tyr Ser
                885                 890                 895

Glu Ala Gly Ala Glu Val Arg Thr Ala Leu Glu Ser Ile Asp Val Ala
                900                 905                 910

Val Asp Met Ile Asn Asp Pro Ala Val Val Asp Val Asn Gly Ser Val
                915                 920                 925

Thr Thr Gln Gly Ser Ala Gly Val Ala Glu Val Ala Gln Val Thr Phe
930                 935                 940

Leu Ser Thr Gly Thr Ala Gln Val Leu Asn Phe Asp Gly Val Gln Met
945                 950                 955                 960

Gln Ile Ala Ala Gly Ser Thr Ala Ala Glu Ile Ala Glu Ala Phe Ala
                965                 970                 975

Ala Gln Glu Phe Pro Asn Trp Thr Val Ser Leu Asp Gly Glu Gly Arg
                980                 985                 990

Val Thr Leu Thr Ala Thr Ala Thr  Gly Ala Arg Pro Asp  Leu Thr Ala
                995                 1000                1005

Ala Asp  Phe Thr Asn Gly Ser  Gly Ala Phe Ser Pro  Leu Val Glu
    1010                1015                1020

Thr Thr  Gly Gly Thr Asp Gly  Ser Ile Asn Phe Thr  Ala Arg Gly
    1025                1030                1035

Pro Ala  Ile Ala Ile Leu Pro  Thr Leu Glu Leu Ser  Asp Val Asp
    1040                1045                1050

Ser Ala  Met Met Ser Gly Ala  Lys Val Ser Met Thr  Glu Gly Leu
    1055                1060                1065

Phe Asp  Asn Gly Phe Gly Thr  Ile Tyr Glu Arg Leu  Ser Leu Ser
    1070                1075                1080

Ala Glu  Ala Arg Glu Phe Ala  Gln Gln Asn Gly Val  Gly Ile Ser
    1085                1090                1095

Ile Val  Thr Thr Ala Ala Ala  Gly Ser Val Ile Thr  Phe Thr Gly
    1100                1105                1110

Met Ala  Ser Ala Glu Val Tyr  Glu Thr Ile Leu Arg  Gly Val Ile
    1115                1120                1125

Tyr Ser  Asn Thr Asn Pro Asn  Ala Val Ala Gly Thr  Arg Pro Val
    1130                1135                1140

Lys Ile  Glu Val Thr Asp Ser  Asp Gly Leu Ala Ser  Ser Leu Ser
    1145                1150                1155

Ser Val  Asn Leu Thr Glu Gly  Asn Thr Asp Ile Ala  Val Gly Gln
    1160                1165                1170

Arg Ile  Phe Ile Asn Gly Val  Asp Ser Gly Gln Val  Val Ser Met
    1175                1180                1185
```

```
Val Arg Asp Ala Thr Ser Phe Val Ala Ser Gly Pro Leu Ala Asp
    1190            1195            1200

Leu Glu Pro Gly Ala Val Leu Ser Phe His Asp Gly Ser Gly Gln
    1205            1210            1215

Gln Thr Thr Ala Val Ser Ala Gly Asp Gly Thr Ala Thr Met Asp
    1220            1225            1230

Val Asn Val Ile Trp Ala Pro Val Ile Asp Met Asn Gly Ala Gly
    1235            1240            1245

Ala Gly Asp Ile His Arg Thr Thr Tyr Ile Glu Gln His Ala Pro
    1250            1255            1260

Ile Ala Ile Ala Thr Ala Asp Ala Arg Ile Val Asp Gln Glu Gly
    1265            1270            1275

Leu Ile Arg Ser Leu Asp Val Val Leu Thr Asn Pro Leu Asp Asn
    1280            1285            1290

Val Glu Gly Ser Ala Pro Val Glu Tyr Leu Gly Ile Ser Lys Ala
    1295            1300            1305

Val Leu Asp Val Leu Ala Ala Arg Gly Ile Thr Ile Gly Ala His
    1310            1315            1320

Asp Gly Gln Phe Asp Ala Asn Gly Asn Leu Thr Gly Ala Thr Ser
    1325            1330            1335

Ile Thr Phe Ala Ala Asn Gly Ala Ser Ala Thr Ser Phe Gln
    1340            1345            1350

Ile Ala Leu Arg Gly Val Thr Tyr Ala Asn Met Asp Asp Ala Pro
    1355            1360            1365

Asp Thr Gly Thr Arg Ile Val Thr Ala Gln Gly Thr Asp Met Asp
    1370            1375            1380

Gly Asn Glu Gly Leu Ile Ser His Thr Glu Ile Asn Pro Ile Ala
    1385            1390            1395

Val Gly Asp Ala Pro Val Ala Ile Asp Ser Gly Val Thr Gly Ser
    1400            1405            1410

Glu Asp Ala Gly His Val Phe Ala Ala Gly Asp Phe Gly Phe Ala
    1415            1420            1425

Asp Pro Leu Asp Gly Gly Ala Asn Gln Leu Ala Ser Ile Thr Ile
    1430            1435            1440

Asn Ser Leu Pro Ala Thr Gly Thr Leu Leu Gly Gly Val Ala
    1445            1450            1455

Val Ala Val Gly Thr Val Val Thr Leu Ala Gln Leu Gln Ala Gly
    1460            1465            1470

Ala Leu Thr Tyr Gln Pro Val Ala Asn Val Asn Gly Glu Gly Val
    1475            1480            1485

Ala Ser Phe Asp Phe Leu Val Thr Asp Asn Gly Ser Leu Ala Asn
    1490            1495            1500

Gly Gly Gln Thr Thr Ser Thr Ala Pro Ala Thr Met Val Ile Asp
    1505            1510            1515

Leu Thr Pro Val Asn Asp Ala Pro Val Leu Pro Glu Gly Thr Ser
    1520            1525            1530

Val Thr Gly Thr Thr Ile Thr Glu Asp Gln Gln Leu Asn Ala Gly
    1535            1540            1545

Glu Leu Val Ala Asp Leu Val Gly Ala Met Thr Asp Val Asp Thr
    1550            1555            1560

Gly Val His Ser Ala Thr Asn Gly Thr Gln Gln Gly Ile Ala Val
    1565            1570            1575

Tyr Gly Ala Gly Ser Glu Gly Phe Gly Gly Gly Thr Trp Gln Tyr
```

-continued

```
            1580                1585                1590

Arg Leu Ala Gly Gly Thr Asp Trp Ile Asp Val Thr Leu Asp Pro
    1595                1600                1605

Gly Glu Val Leu Leu Leu Gly Ala Asp Asp Arg Ile Arg Phe Ser
    1610                1615                1620

Pro Asp Gly Glu Asn Ala Thr Glu Ala Gln Leu Ser Tyr Tyr Ala
    1625                1630                1635

Trp Asp Gly Ala Thr Gly Thr Ala Gly Asn Val Val Ala Gly Ile
    1640                1645                1650

Ala Gly Pro Gly Asn Ala Ser Asn Arg Gly Gly Thr Ser Ala Phe
    1655                1660                1665

Ser Ser Asn Gly Ala Ser Ala Thr Val Glu Val Thr Ala Val Asn
    1670                1675                1680

Asp Ala Pro Ser Ile Ser Met Gly Glu Gly Asn Thr Phe Tyr Ala
    1685                1690                1695

Arg Gly Glu Ala Val Ala Leu Phe Ser Asp Glu Thr Leu Gln Leu
    1700                1705                1710

Thr Asp Pro Asp Glu Gly Ala Ala Val Ser Gln Ile Val Ile Thr
    1715                1720                1725

Leu Asp Gly Glu Thr Thr Val Asp Asn Ala Phe Gly Thr Thr Tyr
    1730                1735                1740

Glu Thr Ile Phe Ser Ala Ser Gly Ser Thr Phe Val Ala Gln Ser
    1745                1750                1755

Gly Thr Glu Leu Thr Ile Ser Gly Thr Gly Val Ala Gly Asp Pro
    1760                1765                1770

Leu Thr Ile Ser Gly Ala Gly Ser Met Glu Asp Tyr Arg Glu Ala
    1775                1780                1785

Leu Leu Ser Leu Arg Tyr Glu Asn Thr Asn Pro Asn Ala Phe Ala
    1790                1795                1800

Gly Asp Arg Ala Ile Ser Val Thr Val Thr Asp Glu Thr Gly Ala
    1805                1810                1815

Gly Ser Ala Pro Thr Asp Phe Ile Leu Pro Val Glu Trp Ala Thr
    1820                1825                1830

Val Ala Asp Leu Asn Gly Pro Ser Gly Glu Gly Arg Asp His Ser
    1835                1840                1845

Ile Thr Tyr Leu Glu Gly Ser Gly Ser Gln Ala Ile Ala Thr Ala
    1850                1855                1860

Asp Ala Glu Met Ile Asp Gln Asp Gly Asn Thr Val Glu Val Val
    1865                1870                1875

Ile Thr Leu Glu Asp Ala Val Asn Gly Ser Ala Glu Met Leu Phe
    1880                1885                1890

Val Asp Pro Ala Val Leu Pro Ala Leu Ala Ala Leu Asn Ile Val
    1895                1900                1905

Val Thr Gly Asn Gly Thr His Glu Ile Arg Leu Thr Ser Glu Glu
    1910                1915                1920

Gly Val Asp Pro Thr Asn Phe Gln Leu Ala Leu Arg Ala Val Arg
    1925                1930                1935

Tyr Val Asn Ser Ser Thr Ala Pro Thr Ala Ala Glu Arg His Val
    1940                1945                1950

Thr Val Ser Ser Thr Asp Ala Asp Gly Asn Pro Gly Val Pro Ala
    1955                1960                1965

Thr Thr Val Ile Gly Met Glu Leu Gly Glu Arg Arg Thr Gly Cys
    1970                1975                1980
```

Gly Ser Leu Asp Leu Leu Arg Gly Val Arg Asp Pro Gln Pro Ala
    1985                1990                1995

Val Gly Arg Ser Ala Ala Ala Arg Arg His Ala Gly Arg Cys Arg
    2000                2005                2010

Arg Ala Arg Ala Glu Pro Ala Gly His Arg Met Ala Ala Gly Arg
    2015                2020                2025

Cys Gly Asp Arg Phe Gly Gln Arg His Ala Gly Leu His Ala Glu
    2030                2035                2040

Thr Gly Gly Cys Arg Pro Cys His Gln Arg Pro His His Leu His
    2045                2050                2055

Arg Arg
    2060

<210> SEQ ID NO 137
<211> LENGTH: 747
<212> TYPE: DNA
<213> ORGANISM: Rhodobacter sphaeroides

<400> SEQUENCE: 137
atgaaccaga tcgatctggc cggccgcgtg ccgtggtga cgggcggcgc gcaggggatc    60
gggcgcgccg tggccgagcg gctgatcgcc tcggggcgc gggtctgcct gtgggaccgc   120
gacgccgggc gggccgcggc gacggcggcc gaactgggcg ggaacagctt ctttcaggtg   180
gtggatcagg tggatttcac ggcggtaaag gccgccgccg acgccaccga agccacgggc   240
ggccggatcg acatcctgat cgccaacgcg ggcatcgccg gcagcaatgc gccggtcgcc   300
gactacccgg tcgaggaatg gcaccgcatc atcgatatca acctgaacgg tgtcttccat   360
tgctgcaagg cggtggtgcc cggcatgaag gcccacggat acgggcgcat cgtcacggtc   420
gcctcgatcg ccggcaagga aggcaatccc aatgcggccg cctattcggc ctcgaaggcc   480
ggggtcatcg cttgaccaa tcgctgggc aaggaggtcg ccggccagga tatcgccgtc   540
aattgcgtga ccccggccgc cgcccgcacg cagatcttcg accagatggc gcagagccac   600
atcgactaca tgctgtcgcg catcccgcgc ggccgctttc tggatctgga cgaggccgcg   660
gcgatgatcg cgtggctggc cagtgccgag aacagcttta ccaccggtgc cgtcttcgat   720
ctctccggcg gccgggccac ctattga                                        747

<210> SEQ ID NO 138
<211> LENGTH: 248
<212> TYPE: PRT
<213> ORGANISM: Rhodobacter sphaeroides

<400> SEQUENCE: 138

Met Asn Gln Ile Asp Leu Ala Gly Arg Val Ala Val Val Thr Gly Gly
1               5                   10                  15

Ala Gln Gly Ile Gly Arg Ala Val Ala Glu Arg Leu Ile Ala Ser Gly
            20                  25                  30

Ala Arg Val Cys Leu Trp Asp Arg Asp Ala Gly Arg Ala Ala Ala Thr
        35                  40                  45

Ala Ala Glu Leu Gly Gly Asn Ser Phe Phe Gln Val Val Asp Gln Val
    50                  55                  60

Asp Phe Thr Ala Val Lys Ala Ala Ala Asp Ala Thr Glu Ala Thr Gly
65                  70                  75                  80

Gly Arg Ile Asp Ile Leu Ile Ala Asn Ala Gly Ile Ala Gly Ser Asn
                85                  90                  95

Ala Pro Val Ala Asp Tyr Pro Val Glu Glu Trp His Arg Ile Ile Asp
            100                 105                 110

Ile Asn Leu Asn Gly Val Phe His Cys Cys Lys Ala Val Val Pro Gly
        115                 120                 125

Met Lys Ala His Gly Tyr Gly Arg Ile Val Thr Val Ala Ser Ile Ala
    130                 135                 140

Gly Lys Glu Gly Asn Pro Asn Ala Ala Ala Tyr Ser Ala Ser Lys Ala
145                 150                 155                 160

Gly Val Ile Ala Leu Thr Lys Ser Leu Gly Lys Glu Val Ala Gly Gln
                165                 170                 175

Asp Ile Ala Val Asn Cys Val Thr Pro Ala Ala Ala Arg Thr Gln Ile
            180                 185                 190

Phe Asp Gln Met Ala Gln Ser His Ile Asp Tyr Met Leu Ser Arg Ile
            195                 200                 205

Pro Arg Gly Arg Phe Leu Asp Leu Asp Glu Ala Ala Ala Met Ile Ala
    210                 215                 220

Trp Leu Ala Ser Ala Glu Asn Ser Phe Thr Thr Gly Ala Val Phe Asp
225                 230                 235                 240

Leu Ser Gly Gly Arg Ala Thr Tyr
                245

<210> SEQ ID NO 139
<211> LENGTH: 936
<212> TYPE: DNA
<213> ORGANISM: Rhodobacter sphaeroides

<400> SEQUENCE: 139
atgtcggtgg gagtgattgg aaccggcttc gtcggccggg gctgggcgat ctgccttgcc      60
cgggccggcc acgaggtccg gctgtgggat ccggcgcccg acgccgccga ggccgcccgc     120
acctatatcg ccgagatgct gccggatctg gcggccgcgg acctgctggg cggccgcgcc     180
ccggacgcgg tgctggagcg gatccgcgtc gccccggaca tggccaccgc cgtccgcggc     240
gcccgccaca ttcaggaaag cgccccgag gatctgcttc tgaagaccgc gctcttcgcc     300
gagctcgacg ctctggccga tcccggcgcg gtgatcgcaa gctcctcctc ggcgcttctg     360
ccttcggcct tcaccgaggg gctggcaggg gcggccgct gcctcgtcgc ccatccggtc      420
aatccgccgc acctcattcc gctggtcgag ctggtgccgg cgccgtggac cgacgaggag     480
acgctggccc ggaccgagac gctcatgcgc gagatcggcc agagcccggt gcggctcgag     540
cgcgaggtgg acggcttcct gctgaaccgg atccaggccg cggtgctcga cgaggccttc     600
cggctggtcg atgcgggcct cgcctcggcc gatgcggtgg atgcctgcct ccgcgacggt     660
ctggcgctgc gctgggtctt catggggccg ttcgagacca tcgacctcaa cgcgcccgag     720
ggcgtgcgcg actatgtcgc ccgctaccag ccgatgttcc gcaggctcac cgacacgatg     780
cgggaaagcg ccgactggtc cggcccggtg ctcgaccgga tcgaggccga ccgccgcgcg     840
cgcctgccgc aggaggcgct gcgcgcccgg cagatgtggc gcgaccgccg gctgatggcg     900
ctcgccgcct ccgccgcca atccctgcaa tcctag                                936

<210> SEQ ID NO 140
<211> LENGTH: 311
<212> TYPE: PRT
<213> ORGANISM: Rhodobacter sphaeroides

<400> SEQUENCE: 140

Met Ser Val Gly Val Ile Gly Thr Gly Phe Val Gly Arg Gly Trp Ala

```
    1               5                  10                 15
Ile Cys Leu Ala Arg Ala Gly His Glu Val Arg Leu Trp Asp Pro Ala
                20                 25                 30
Pro Asp Ala Ala Glu Ala Ala Arg Thr Tyr Ile Ala Glu Met Leu Pro
                35                 40                 45
Asp Leu Ala Ala Ala Asp Leu Leu Gly Gly Arg Ala Pro Asp Ala Val
    50                 55                 60
Leu Glu Arg Ile Arg Val Ala Pro Asp Met Ala Thr Ala Val Arg Gly
65                 70                 75                 80
Ala Arg His Ile Gln Glu Ser Ala Pro Glu Asp Leu Leu Leu Lys Thr
                85                 90                 95
Ala Leu Phe Ala Glu Leu Asp Ala Leu Ala Asp Pro Gly Ala Val Ile
                100                105                110
Ala Ser Ser Ser Ser Ala Leu Leu Pro Ser Ala Phe Thr Glu Gly Leu
                115                120                125
Ala Gly Ala Gly Arg Cys Leu Val Ala His Pro Val Asn Pro Pro His
                130                135                140
Leu Ile Pro Leu Val Glu Leu Val Pro Ala Pro Trp Thr Asp Glu Glu
145                150                155                160
Thr Leu Ala Arg Thr Glu Thr Leu Met Arg Glu Ile Gly Gln Ser Pro
                165                170                175
Val Arg Leu Glu Arg Glu Val Asp Gly Phe Leu Leu Asn Arg Ile Gln
                180                185                190
Ala Ala Val Leu Asp Glu Ala Phe Arg Leu Val Asp Ala Gly Leu Ala
                195                200                205
Ser Ala Asp Ala Val Asp Ala Cys Leu Arg Asp Gly Leu Ala Leu Arg
    210                215                220
Trp Val Phe Met Gly Pro Phe Glu Thr Ile Asp Leu Asn Ala Pro Glu
225                230                235                240
Gly Val Arg Asp Tyr Val Ala Arg Tyr Gln Pro Met Phe Arg Arg Leu
                245                250                255
Thr Asp Thr Met Arg Glu Ser Ala Asp Trp Ser Gly Pro Val Leu Asp
                260                265                270
Arg Ile Glu Ala Asp Arg Arg Ala Arg Leu Pro Gln Glu Ala Leu Arg
                275                280                285
Ala Arg Gln Met Trp Arg Asp Arg Leu Met Ala Leu Ala Ala Phe
                290                295                300
Arg Arg Gln Ser Leu Gln Ser
305                310

<210> SEQ ID NO 141
<211> LENGTH: 741
<212> TYPE: DNA
<213> ORGANISM: Rhodobacter sphaeroides

<400> SEQUENCE: 141
gtgaccggtg ggctcctcgt gacgggcggc agcggcgcca tcggtggcgc actctgccgg      60
atcgcggccc ggcagcaccc ggtgtgggtc ggctacggcg cggggggcgg acgggcccgg     120
gcccttgccg ccgagatcac gcaggcgggc ggacgggcca gccgctggc gctgccgctt      180 caggatcccg cagcgctcga gaccgcgctg gcagcacttc ccgagccgcc cgcgtcactc     240
gcgctctgcg cctggcccgc gcccttcgtg gcgcccttcg ggcgtcaggg cgaggatctg     300
gcgcttcagg cggcggcgct tgccggctgt cacgcgctga tcgccacggc ctggcggctc     360
```

| | | |
|---|---|---|
| tggtggcggc gcgcgggcgg cgggcatgtg ctggccgtcc tgtcggccgc gtccgagccg | 420 |
| cccgtggccc gccacatggc cgcctatgtg gcgcagaagg cggcgctgcg cgccctgctc | 480 |
| gcggcggccg ccgccgaact ggggcccgcg ggctgcggg tgagcgtggt ggccccggc | 540 |
| ttcgtcgaga cgccgatgct cggcgccttc gacccgcgcc tgctggagcg cgccggggcc | 600 |
| gacgccggag gcaggttcct gtcccctgaa cgcgtggcgc aggcgctcgt cgccgcgctc | 660 |
| gacgcaccgc ccccgccgg gacggtgcag gacattcatc tggctgagga ggtggagagc | 720 |
| gatgaaaagc aaaccgcttg a | 741 |

<210> SEQ ID NO 142
<211> LENGTH: 246
<212> TYPE: PRT
<213> ORGANISM: Rhodobacter sphaeroides

<400> SEQUENCE: 142

Met Thr Gly Gly Leu Leu Val Thr Gly Gly Ser Gly Ala Ile Gly Gly
1               5                   10                  15

Ala Leu Cys Arg Ile Ala Ala Arg Gln His Pro Val Trp Val Gly Tyr
                20                  25                  30

Gly Ala Gly Ala Gly Arg Ala Arg Ala Leu Ala Ala Glu Ile Thr Gln
            35                  40                  45

Ala Gly Gly Arg Ala Glu Pro Leu Ala Leu Pro Leu Gln Asp Pro Ala
        50                  55                  60

Ala Leu Glu Thr Ala Leu Ala Ala Leu Pro Glu Pro Pro Ala Ser Leu
65                  70                  75                  80

Ala Leu Cys Ala Trp Pro Ala Pro Phe Val Ala Pro Phe Gly Arg Gln
                85                  90                  95

Gly Glu Asp Leu Ala Leu Gln Ala Ala Ala Leu Ala Gly Cys His Ala
            100                 105                 110

Leu Ile Ala Thr Ala Trp Arg Leu Trp Trp Arg Arg Ala Gly Gly Gly
        115                 120                 125

His Val Leu Ala Val Leu Ser Ala Ala Ser Glu Pro Pro Val Ala Arg
130                 135                 140

His Met Ala Ala Tyr Val Ala Gln Lys Ala Ala Leu Arg Ala Leu Leu
145                 150                 155                 160

Ala Ala Ala Ala Ala Glu Leu Gly Pro Ala Gly Leu Arg Val Ser Val
                165                 170                 175

Val Ala Pro Gly Phe Val Glu Thr Pro Met Leu Gly Ala Phe Asp Pro
            180                 185                 190

Arg Leu Leu Glu Arg Ala Arg Ala Asp Ala Gly Gly Arg Phe Leu Ser
        195                 200                 205

Pro Glu Arg Val Ala Gln Ala Leu Val Ala Ala Leu Asp Ala Pro Pro
    210                 215                 220

Pro Ala Gly Thr Val Gln Asp Ile His Leu Ala Glu Glu Val Glu Ser
225                 230                 235                 240

Asp Glu Lys Gln Thr Ala
                245

<210> SEQ ID NO 143
<211> LENGTH: 996
<212> TYPE: DNA
<213> ORGANISM: Rhodobacter sphaeroides

<400> SEQUENCE: 143
atggccgagg ccgacaccga gcgccggccc cacatcccgg tgctgctgcg tcctcttctg     60

```
gccgcggtgg cgccggtcga gggcacatgg ctcgacggca ccttcggggc gggcggttat    120
gcgcggggtc tgctcgaggc gggcgcggac cgggtgatcg gcgtcgaccg cgatccgctc    180
gcgctgaaga tggcctccgg ctgggcgggt gactacggcg accgcctgcg cctcgtggcg    240
ggcaccttct cgcagctcga cagccatgcg ggcgcgcccc tcgacggggt ggtgctcgat    300
ctcggcgtct cctccatgca gctcgatctg gccgaacgcg gcttctcgtt ccagaaggac    360
ggcccgctcg acatgcgcat gagccaagag ggcgaaagcg cggccgatct ggtcaatacc    420
gcctccgagg agacgctggc cgacattctc tatcattatg gcgaggagcg cgcctcgcgc    480
cgcatcgccc gcgccatcgt cgaggcccgc gccgcggcgc ccatcacccg cacgctcgcg    540
ctggccgaga tcgtggcgcg ctgcctgccg cggccgaagc ccggccagat gcacccggcc    600
acccgcagct tcaggcgat ccgtatcgcg gtgaatgccg aattctcgga actggtcgag    660
gggctcgagg cggccgagcg cgcgctcagg cccggcggcc ggctcgccgt cgtcaccttc    720
cacagcctcg aggaccggat cgtgaaacgg ttcctccagc tccgctcggg cggcgagggg    780
cagggcaacc gctacgcccc cgagacgcgc gccgatgcgc cccgcttcac tcttccgctc    840
cgtcgtgcca tcagcccgga cgaggcggaa ctcgccgaga tccgcgcgc ccggtcggcc    900 cggctgcggg tgggcgtccg gacggacgcc cccgcgggaa aggtcgatcc gcaggcgctc    960
ggcaccccgc tcatcccgaa gaaaggacgc cgctga                              996
```

<210> SEQ ID NO 144
<211> LENGTH: 331
<212> TYPE: PRT
<213> ORGANISM: Rhodobacter sphaeroides

<400> SEQUENCE: 144

```
Met Ala Glu Ala Asp Thr Glu Arg Arg Pro His Ile Pro Val Leu Leu
1               5                   10                  15

Arg Pro Leu Leu Ala Ala Val Ala Pro Val Glu Gly Thr Trp Leu Asp
            20                  25                  30

Gly Thr Phe Gly Ala Gly Gly Tyr Ala Arg Gly Leu Leu Glu Ala Gly
        35                  40                  45

Ala Asp Arg Val Ile Gly Val Asp Arg Asp Pro Leu Ala Leu Lys Met
    50                  55                  60

Ala Ser Gly Trp Ala Gly Asp Tyr Gly Asp Arg Leu Arg Leu Val Ala
65                  70                  75                  80

Gly Thr Phe Ser Gln Leu Asp Ser His Ala Gly Ala Pro Leu Asp Gly
                85                  90                  95

Val Val Leu Asp Leu Gly Val Ser Ser Met Gln Leu Asp Leu Ala Glu
            100                 105                 110

Arg Gly Phe Ser Phe Gln Lys Asp Gly Pro Leu Asp Met Arg Met Ser
        115                 120                 125

Gln Glu Gly Glu Ser Ala Ala Asp Leu Val Asn Thr Ala Ser Glu Glu
    130                 135                 140

Thr Leu Ala Asp Ile Leu Tyr His Tyr Gly Glu Glu Arg Ala Ser Arg
145                 150                 155                 160

Arg Ile Ala Arg Ala Ile Val Glu Ala Arg Ala Ala Pro Ile Thr
                165                 170                 175

Arg Thr Leu Ala Leu Ala Glu Ile Val Ala Arg Cys Leu Pro Arg Pro
            180                 185                 190

Lys Pro Gly Gln Met His Pro Ala Thr Arg Ser Phe Gln Ala Ile Arg
        195                 200                 205
```

```
Ile Ala Val Asn Ala Glu Phe Ser Glu Leu Val Glu Gly Leu Glu Ala
    210                 215                 220

Ala Glu Arg Ala Leu Arg Pro Gly Gly Arg Leu Ala Val Val Thr Phe
225                 230                 235                 240

His Ser Leu Glu Asp Arg Ile Val Lys Arg Phe Leu Gln Leu Arg Ser
                245                 250                 255

Gly Gly Glu Gly Gln Gly Asn Arg Tyr Ala Pro Glu Thr Arg Ala Asp
            260                 265                 270

Ala Pro Arg Phe Thr Leu Pro Leu Arg Arg Ala Ile Ser Pro Asp Glu
        275                 280                 285

Ala Glu Leu Ala Glu Asn Pro Arg Ala Arg Ser Ala Arg Leu Arg Val
    290                 295                 300

Gly Val Arg Thr Asp Ala Pro Ala Gly Lys Val Asp Pro Gln Ala Leu
305                 310                 315                 320

Gly Thr Pro Leu Ile Pro Lys Lys Gly Arg Arg
                325                 330
```

<210> SEQ ID NO 145
<211> LENGTH: 744
<212> TYPE: DNA
<213> ORGANISM: Rhodobacter sphaeroides

<400> SEQUENCE: 145

```
atgaccggac gtctggcagg ccgcaagatc gtcatcaccg agcaggctc gggcatcggc       60
cgcgagtccg cgcgccagtt cgcgcgcgag ggggcgacgc tggcgctgat cgaccgcgac      120
gaggcggcgg cgcaggtgac ggcggacgag acgggggggcc atgtcttcgc gctcgacgtg    180
accgacgagg cggcggtcga aaccgtcgtg ggccgcgcgg cggaggcgct cggcggcatc      240
gacgggctgc tcaattcggc gggcatcctg accatgaaga ccgtggacga tatcggcgtc     300
gaggagttcc gccgggtggt ggatgtgaac ctgacgggga ccttcctcgt ctgtcaggcg    360
gcgctgccgt ggctgcgcaa ggagccgaag gccgccatcg tcaacatcgc ctcggcgcag      420
gcgctgctgc cctcgctgac cggctcggcc tatgccgcct cgaaggccgc ggtgatgatg     480
ttctcgaaga gcatcgccaa ggaacttgcc ccggcggtgc gggtgaacat catctgcccg     540
ggggccaccg agacgccgat gaccgatcag ggcgtggcgc ccgacgatgt ggcgggccgc    600
aaggcgctgg ccgcggtcta tgcgatgaac cgtctggccc agcccgagga gatcgcggcg    660
ggcatcctgt tcctgatgtc ggacgaggcc gcggccatca cgggcgtcgc gctggcgatc    720
gacaacggcc gcaccttcca ttga                                             744
```

<210> SEQ ID NO 146
<211> LENGTH: 247
<212> TYPE: PRT
<213> ORGANISM: Rhodobacter sphaeroides

<400> SEQUENCE: 146

```
Met Thr Gly Arg Leu Ala Gly Arg Lys Ile Val Ile Thr Gly Ala Gly
1               5                   10                  15

Ser Gly Ile Gly Arg Glu Ser Ala Arg Gln Phe Ala Arg Glu Gly Ala
            20                  25                  30

Thr Leu Ala Leu Ile Asp Arg Asp Glu Ala Ala Ala Gln Val Thr Ala
        35                  40                  45

Asp Glu Thr Gly Gly His Val Phe Ala Leu Asp Val Thr Asp Glu Ala
    50                  55                  60
```

```
Ala Val Glu Thr Val Val Gly Arg Ala Ala Glu Leu Gly Gly Ile
 65                  70                  75                  80

Asp Gly Leu Leu Asn Ser Ala Gly Ile Leu Thr Met Lys Thr Val Asp
                 85                  90                  95

Asp Ile Gly Val Glu Glu Phe Arg Arg Val Val Asp Val Asn Leu Thr
            100                 105                 110

Gly Thr Phe Leu Val Cys Gln Ala Ala Leu Pro Trp Leu Arg Lys Glu
        115                 120                 125

Pro Lys Ala Ala Ile Val Asn Ile Ala Ser Ala Gln Ala Leu Leu Pro
    130                 135                 140

Ser Leu Thr Gly Ser Ala Tyr Ala Ala Ser Lys Ala Ala Val Met Met
145                 150                 155                 160

Phe Ser Lys Ser Ile Ala Lys Glu Leu Ala Pro Ala Val Arg Val Asn
                165                 170                 175

Ile Ile Cys Pro Gly Ala Thr Glu Thr Pro Met Thr Asp Gln Gly Val
            180                 185                 190

Ala Pro Asp Asp Val Ala Gly Arg Lys Ala Leu Ala Ala Val Tyr Ala
        195                 200                 205

Met Asn Arg Leu Ala Gln Pro Glu Glu Ile Ala Ala Gly Ile Leu Phe
    210                 215                 220

Leu Met Ser Asp Glu Ala Ala Ile Thr Gly Val Ala Leu Ala Ile
225                 230                 235                 240

Asp Asn Gly Arg Thr Phe His
                245

<210> SEQ ID NO 147
<211> LENGTH: 1194
<212> TYPE: DNA
<213> ORGANISM: Rhodobacter sphaeroides

<400> SEQUENCE: 147
atgaaccagc agaacacgat tccgcagct cctgcggaca cgatggccga acgggcccgg      60
gccatcgccc ccctcgtgcg ggccgaggcg caggcctcgg aagagctcgg gacgatgacg     120
cccaaggtgg tgcaggccat caaggaggcg ggcctcttct ggatgctcct cgagcgcaag     180
gtgggcggcg cccaggccga catggccgat tgcatgcgcg cctgggaaga gatcgccgcc     240
gccgacgcct cggccggctg gtcgctgatg gccaactcga caggcaccgc cgttccttac     300
gcctattgca gcgaggaggc ggtggccgag atctacggcg ccccgaact gccgatcatg      360 gccgggatgc tcgggccggg cggctcggcg aaggagaccg agggcgcgct ccacggcagc     420
ggcaaatatc gcttcggcag cggctcgctg catgcgacct ggatcggcgc gggcatgttc     480
gtgatggacg agggcggcat gcgcaagctg cctgacggca gccccgtcgt gcgcgtctgc     540
tggcggccgg cctcggaggt cacgttcgac aatgaatgga acgtgctcgg cctgcgcggc     600
acgggcagcg tcgattacac gctggaggaa gccacgatcc ccgcgggctt ccaccacgag     660
cgcgcggtcc agcgcggcct gcgcgactgg cggctctacg acatcggcat cccgggcctc     720
gcctgtgcgg gccacaccgg ggtggcgctc ggcctgatgc gccgcgcgct ggaagagatc     780
acccgcatcg ccttcggcaa gaagcgcccg gcctatcaga ccgtgctggg cgaccagcag     840
gtcttccgcc acgatttcgc ctatcacgag gcgagctatc acgggcgcg cgacttcacc      900 ctgcgcttct acgccgagat ccaggagtat ctggaggcgg cggcgagct cacgcccgcc      960 atgcgcgcgc gcttccggca gaactgcatc tatgtccaca aggtcgcggc cgaggttgtg    1020
cgcttctgct acacgatggg cggctccgag gcgctgcgcg agccgagcga tctcgggcgc    1080
```

```
tgcatgcgcg acatgtatgc cgcgacccag catatcttcg tcgatacgat cgccatgcag    1140
gacatcgcgt gccgatcct cgccgaatgg agagagcagg ccgccgcgca atga           1194
```

<210> SEQ ID NO 148
<211> LENGTH: 397
<212> TYPE: PRT
<213> ORGANISM: Rhodobacter sphaeroides

<400> SEQUENCE: 148

```
Met Asn Gln Gln Asn Thr Ile Ser Ala Ala Pro Ala Asp Thr Met Ala
1               5                   10                  15

Glu Arg Ala Arg Ala Ile Ala Pro Leu Val Arg Ala Glu Ala Gln Ala
            20                  25                  30

Ser Glu Glu Leu Gly Thr Met Thr Pro Lys Val Val Gln Ala Ile Lys
        35                  40                  45

Glu Ala Gly Leu Phe Trp Met Leu Leu Glu Arg Lys Val Gly Gly Ala
    50                  55                  60

Gln Ala Asp Met Ala Asp Cys Met Arg Ala Trp Glu Glu Ile Ala Ala
65                  70                  75                  80

Ala Asp Ala Ser Ala Gly Trp Ser Leu Met Ala Asn Ser Thr Gly Thr
                85                  90                  95

Ala Val Pro Tyr Ala Tyr Cys Ser Glu Glu Val Ala Glu Ile Tyr
            100                 105                 110

Gly Gly Pro Glu Leu Pro Ile Met Ala Gly Met Leu Gly Pro Gly Gly
        115                 120                 125

Ser Ala Lys Glu Thr Glu Gly Ala Leu His Gly Ser Gly Lys Tyr Arg
    130                 135                 140

Phe Gly Ser Gly Ser Leu His Ala Thr Trp Ile Gly Ala Gly Met Phe
145                 150                 155                 160

Val Met Asp Glu Gly Gly Met Arg Lys Leu Pro Asp Gly Ser Pro Val
                165                 170                 175

Val Arg Val Cys Trp Arg Pro Ala Ser Glu Val Thr Phe Asp Asn Glu
            180                 185                 190

Trp Asn Val Leu Gly Leu Arg Gly Thr Gly Ser Val Asp Tyr Thr Leu
        195                 200                 205

Glu Glu Ala Thr Ile Pro Ala Gly Phe His His Glu Arg Ala Val Gln
    210                 215                 220

Arg Gly Leu Arg Asp Trp Arg Leu Tyr Asp Ile Gly Ile Pro Gly Leu
225                 230                 235                 240

Ala Cys Ala Gly His Thr Gly Val Ala Leu Gly Leu Met Arg Arg Ala
                245                 250                 255

Leu Glu Glu Ile Thr Arg Ile Ala Phe Gly Lys Lys Arg Pro Ala Tyr
            260                 265                 270

Gln Thr Val Leu Gly Asp Gln Gln Val Phe Arg His Asp Phe Ala Tyr
        275                 280                 285

His Glu Ala Ser Tyr His Ala Ala Arg Asp Phe Thr Leu Arg Phe Tyr
    290                 295                 300

Ala Glu Ile Gln Glu Tyr Leu Glu Ala Gly Gly Glu Leu Thr Pro Ala
305                 310                 315                 320

Met Arg Ala Arg Phe Arg Gln Asn Cys Ile Tyr Val His Lys Val Ala
                325                 330                 335

Ala Glu Val Val Arg Phe Cys Tyr Thr Met Gly Gly Ser Glu Ala Leu
            340                 345                 350
```

```
Arg Glu Pro Ser Asp Leu Gly Arg Cys Met Arg Asp Met Tyr Ala Ala
            355                 360                 365

Thr Gln His Ile Phe Val Asp Thr Ile Ala Met Gln Asp Ile Ala Val
    370                 375                 380

Pro Ile Leu Ala Glu Trp Arg Glu Gln Ala Ala Ala Gln
385                 390                 395
```

<210> SEQ ID NO 149
<211> LENGTH: 20
<212> TYPE: DNA
<213> ORGANISM: Artificial Sequence
<220> FEATURE:
<223> OTHER INFORMATION: Primer tpnRL13-2

<400> SEQUENCE: 149
cagcaacacc ttcttcacga                                            20

<210> SEQ ID NO 150
<211> LENGTH: 20
<212> TYPE: DNA
<213> ORGANISM: Artificial Sequence
<220> FEATURE:
<223> OTHER INFORMATION: Primer tpnRL17-1.

<400> SEQUENCE: 150
aacaagccag ggatgtaacg                                            20

<210> SEQ ID NO 151
<211> LENGTH: 30
<212> TYPE: DNA
<213> ORGANISM: Artificial Sequence
<220> FEATURE:
<223> OTHER INFORMATION: Primer KCL58.

<400> SEQUENCE: 151
gcattctaga cgaggcctac gattatctgc                                 30

<210> SEQ ID NO 152
<211> LENGTH: 30
<212> TYPE: DNA
<213> ORGANISM: Artificial Sequence
<220> FEATURE:
<223> OTHER INFORMATION: Primer KCL59.

<400> SEQUENCE: 152
cgataagctt gtcgggtcgt ttaccagaac                                 30

<210> SEQ ID NO 153
<211> LENGTH: 19
<212> TYPE: DNA
<213> ORGANISM: Artificial Sequence
<220> FEATURE:
<223> OTHER INFORMATION: Primer KCL60.

<400> SEQUENCE: 153
cggaccgttc tgcgaagca                                             19

<210> SEQ ID NO 154
<211> LENGTH: 20
<212> TYPE: DNA
<213> ORGANISM: Artificial Sequence
<220> FEATURE:
<223> OTHER INFORMATION: Primer KCL63.

<400> SEQUENCE: 154
ttcaggcgcc gaccgggact                    20

<210> SEQ ID NO 155
<211> LENGTH: 24
<212> TYPE: DNA
<213> ORGANISM: Artificial Sequence
<220> FEATURE:
<223> OTHER INFORMATION: Primer KCL72.

<400> SEQUENCE: 155
tatctcttcg atttcgagca gccc               24

<210> SEQ ID NO 156
<211> LENGTH: 20
<212> TYPE: DNA
<213> ORGANISM: Artificial Sequence
<220> FEATURE:
<223> OTHER INFORMATION: Primer KCL84.

<400> SEQUENCE: 156
atgttgacct cgtcggaatg                    20

<210> SEQ ID NO 157
<211> LENGTH: 20
<212> TYPE: DNA
<213> ORGANISM: Artificial Sequence
<220> FEATURE:
<223> OTHER INFORMATION: Primer KCL85.

<400> SEQUENCE: 157
gcaagaagat caccgacctc                    20

<210> SEQ ID NO 158
<211> LENGTH: 23
<212> TYPE: DNA
<213> ORGANISM: Artificial Sequence
<220> FEATURE:
<223> OTHER INFORMATION: Primer KCL86.

<400> SEQUENCE: 158
tccttgagcc agatgtcgag gat                23

<210> SEQ ID NO 159
<211> LENGTH: 24
<212> TYPE: DNA
<213> ORGANISM: Artificial Sequence
<220> FEATURE:
<223> OTHER INFORMATION: Primer KCL87.

<400> SEQUENCE: 159
aggccttgac caacctgatg aaga               24

<210> SEQ ID NO 160
<211> LENGTH: 24
<212> TYPE: DNA
<213> ORGANISM: Artificial Sequence
<220> FEATURE:
<223> OTHER INFORMATION: Primer KCL88.

<400> SEQUENCE: 160
ttccagctga tgatagagca ccac               24

<210> SEQ ID NO 161
<211> LENGTH: 24
<212> TYPE: DNA
<213> ORGANISM: Artificial Sequence

```
<220> FEATURE:
<223> OTHER INFORMATION: Primer KCL89.

<400> SEQUENCE: 161
tcaccttcgg cgctatttcg atct                                      24

<210> SEQ ID NO 162
<211> LENGTH: 19
<212> TYPE: DNA
<213> ORGANISM: Artificial Sequence
<220> FEATURE:
<223> OTHER INFORMATION: Primer KCL116.

<400> SEQUENCE: 162
gcctttgtcg ggatggaac                                            19

<210> SEQ ID NO 163
<211> LENGTH: 24
<212> TYPE: DNA
<213> ORGANISM: Artificial Sequence
<220> FEATURE:
<223> OTHER INFORMATION: Primer ChrR-UP1.

<400> SEQUENCE: 163
gcgccagcat atgagttgag tgag                                      24

<210> SEQ ID NO 164
<211> LENGTH: 20
<212> TYPE: DNA
<213> ORGANISM: Artificial Sequence
<220> FEATURE:
<223> OTHER INFORMATION: Primer ChrR-DS1.

<400> SEQUENCE: 164
cgtgaatgac aggggtcgcc                                           20
```